United States Patent
Baloglu et al.

(10) Patent No.: US 9,994,558 B2
(45) Date of Patent: Jun. 12, 2018

(54) MULTICYCLIC COMPOUNDS AND METHODS OF USING SAME

(71) Applicant: Karyopharm Therapeutics Inc., Newton, MA (US)

(72) Inventors: Erkan Baloglu, Stoneham, MA (US); Sharon Shacham, Newton, MA (US); William Senapedis, Millis, MA (US); Dilara McCauley, Arlington, MA (US); Yosef Landesman, Brookline, MA (US); Gali Golan, Mesilat Zion (IL); Ori Kalid, Pardes Hanna (IL); Sharon Shechter, Andover, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 0 days. days.

(21) Appl. No.: 15/023,269

(22) PCT Filed: Sep. 19, 2014

(86) PCT No.: PCT/US2014/056580
§ 371 (c)(1),
(2) Date: Mar. 18, 2016

(87) PCT Pub. No.: WO2015/042414
PCT Pub. Date: Mar. 26, 2015

(65) Prior Publication Data
US 2017/0096417 A1    Apr. 6, 2017

Related U.S. Application Data

(60) Provisional application No. 61/880,488, filed on Sep. 20, 2013, provisional application No. 61/904,888, filed on Nov. 15, 2013.

(51) Int. Cl.
| | |
|---|---|
| C07D 213/73 | (2006.01) |
| C07D 401/12 | (2006.01) |
| C07D 409/14 | (2006.01) |
| A61K 31/433 | (2006.01) |
| C07D 409/12 | (2006.01) |
| C07D 213/81 | (2006.01) |
| C07D 413/12 | (2006.01) |

(52) U.S. Cl.
CPC ......... *C07D 409/12* (2013.01); *C07D 213/73* (2013.01); *C07D 213/81* (2013.01); *C07D 401/12* (2013.01); *C07D 409/14* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 8,173,677 B2 | 5/2012 | Roulston et al. | |
| 8,912,184 B1 | 12/2014 | Fleischer et al. | |
| 9,856,241 B2 | 1/2018 | Baloglu et al. | |
| 2004/0186114 A1 | 9/2004 | Cirillo et al. | |
| 2008/0020413 A1 | 1/2008 | Tong et al. | |
| 2009/0124687 A1 | 5/2009 | Oishi et al. | |
| 2012/0053170 A1 | 3/2012 | Arigon et al. | |
| 2012/0329786 A1 | 12/2012 | Willardsen et al. | |
| 2013/0317027 A1 | 11/2013 | Willardsen et al. | |
| 2016/0221994 A1 | 8/2016 | Baloglu et al. | |
| 2017/0096417 A1 | 4/2017 | Baloglu et al. | |

FOREIGN PATENT DOCUMENTS

| | | |
|---|---|---|
| CN | 1152032 C | 6/2004 |
| EP | 1627873 A1 | 2/2006 |
| EP | 1798224 A1 | 6/2007 |
| EP | 2003118 A1 | 12/2008 |
| EP | 2098231 A1 | 9/2009 |
| WO | WO-97/48397 A1 | 12/1997 |
| WO | WO-97/48696 A1 | 12/1997 |
| WO | WO-99/53920 A1 | 10/1999 |
| WO | WO-03/008365 A2 | 1/2003 |
| WO | WO-03/080054 A1 | 10/2003 |
| WO | WO-2005/014566 A1 | 2/2005 |
| WO | WO-2005/097770 A1 | 10/2005 |
| WO | WO 2005/115990 A1 * | 12/2005 |
| WO | WO-2006/106326 A1 | 10/2006 |
| WO | WO-2006/116136 A1 | 11/2006 |
| WO | WO-2008/025857 A2 | 3/2008 |
| WO | WO-2008/026018 A1 | 3/2008 |
| WO | WO-2008/152097 A1 | 12/2008 |
| WO | WO-2009/072004 A2 | 6/2009 |
| WO | WO-2009/109610 A1 | 9/2009 |
| WO | WO-2011/109441 A1 | 9/2011 |
| WO | WO-2012/150952 A1 | 11/2012 |
| WO | WO-2012/177782 A1 | 12/2012 |
| WO | WO-2013/082150 A1 | 6/2013 |
| WO | WO-2014/074715 A1 | 5/2014 |
| WO | WO-2014/085607 A1 | 6/2014 |

(Continued)

OTHER PUBLICATIONS

Non-Final Office Action dated Nov. 14, 2016 for U.S. Appl. No. 14/647,662 "Substituted 2,3-Dihydrobenzofuranyl Compounds and Uses Thereof."

(Continued)

*Primary Examiner* — Zinna Northington Davis
(74) *Attorney, Agent, or Firm* — Foley Hoag LLP

(57) ABSTRACT

The invention generally relates to compounds represented by Structural Formula I: or a pharmaceutically acceptable salt thereof, wherein the variables are as defined and described herein. The invention also includes the synthesis and use of a compound of structural formula I, or a pharmaceutically acceptable salt or composition thereof, e.g., in treatment of cancer (e.g., mantle cell lymphoma), and other diseases and disorders (e.g., PAK-mediated, for example, PAK4-mediated, diseases and disorders).

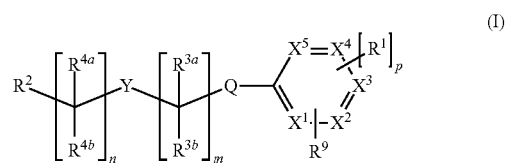

(I)

17 Claims, 1 Drawing Sheet

(56) References Cited

FOREIGN PATENT DOCUMENTS

| WO | WO-2014/111871 A1 | 7/2014 |
|---|---|---|
| WO | WO-2015/003166 A1 | 1/2015 |
| WO | WO-2015/042414 A1 | 3/2015 |
| WO | WO-2015/054060 A1 | 4/2015 |
| WO | WO-2016/100515 A1 | 6/2016 |
| WO | WO-2017/031204 A1 | 2/2017 |
| WO | WO-2017/031213 A1 | 2/2017 |
| WO | WO-2017/031323 A1 | 2/2017 |
| WO | WO-2017/117406 A1 | 7/2017 |
| WO | WO-2017/117447 A1 | 7/2017 |

OTHER PUBLICATIONS

Bhatia et al., "Autoimmunity and autoimmune disease in 6," Principles of Medical Biology, 239-263, 244 (1996).
Database Registry Chemical Abstracts, Database Accession No. 1025224-12-7, CAS Registry No. 1025224-12-7 (Jun. 4, 2008).
Database Registry Chemical Abstracts, Database Accession No. 1025516-17-9, CAS Registry No. 1025516-17-9 (Jun. 5, 2008).
Database Registry Chemical Abstracts, Database Accession No. 1060535-75-2; CAS Registry Nos. 1060535-75-2; 1060530-87-1; 1060530-87-1; 1060527-21-0; 1060504-54-2; 1060421-07-9; 1060400-89-6 (Oct. 13, 2008).
Database Registry Chemical Abstracts, Database Accession No. 1065636-94-3; CAS Registry No. 1065636 94-3 (Oct. 24, 2008).
Database Registry Chemical Abstracts, Database Accession No. 1067037-85-7; CAS Registry No. 1067037-85-7 (Oct. 27, 2008).
Database Registry Chemical Abstracts, Database Accession No. 1067055-04-2; CAS Registry No. 1067055-04-2 (Oct. 28, 2008).
Database Registry Chemical Abstracts, Database Accession No. 1069903-74-7; CAS Registry Nos. 1069646-70-3; 1069796-77-5; 1069496-70-3; 1069605-79-3 (Nov. 2, 2008).
Database Registry Chemical Abstracts, Database Accession No. 1070271-09-8; CAS Registry No. 1070271-09-08 (Nov. 3, 2008).
Database Registry Chemical Abstracts, Database Accession No. 1110694-76-2, CAS Registry No. 1110694-76-2 (Feb. 23, 2009).
Database Registry Chemical Abstracts, Database Accession No. 1110698-05-9, CAS Registry No. 1110698-05-9 (Feb. 23, 2009).
Database Registry Chemical Abstracts, Database Accession No. 1110699-54-1, CAS Registry No. 1110699-54-1 (Feb. 23, 2009).
Database Registry Chemical Abstracts, Database Accession No. 1110699-68-7, CAS Registry No. 1110699-68-7 (Feb. 23, 2009).
Database Registry Chemical Abstracts, Database Accession No. 1110701-07-9, CAS Registry No. 1110701-07-9 (Feb. 23, 2009).
Database Registry Chemical Abstracts, Database Accession No. 1110701-73-9, CAS Registry No. 1110701-73-9 (Feb. 23, 2009).
Database Registry Chemical Abstracts, Database Accession No. 1110705-13-9, CAS Registry No. 1110705-13-9 (Feb. 23, 2009).
Database Registry Chemical Abstracts, Database Accession No. 1110707-61-3, CAS Registry No. 1110707-61-3 (Feb. 23, 2009).
Database Registry Chemical Abstracts, Database Accession No. 1110708-07-0, CAS Registry No. 1110708-07-0 (Feb. 23, 2009).
Database Registry Chemical Abstracts, Database Accession No. 1110708-69-4, CAS Registry No. 1110708-69-4 (Feb. 23, 2009).
Eswaran et al., "UnPAKing the class differences among p21-activated kinases," Trends Biochem Sci, 33(8): 394-403 (2008).
Galli et al., "Medicinal chemistry of nicotinamide phosphoribosyltransferase (NAMPT) inhibitors," J Med Chem, 56:6279-96 (2013).
Giannetti et al., "Fragment-Based Identification of Amides Derived from trans-2-(Pyridin-2-yl) cyclopropanecarboxylic Acid as Potent Inhibitors of Human Nicotinamide Phosphoribosyltransferase (NAMPT)," J Med Chem, 57(3): 770-792 (2014).
Girouard et al., "Neurovascular coupling in the normal brain and in hypertension, stroke, and Alzheimer disease," J Appl Physiol, 100(1): 328-335, 332 (2006).
Guo et al., "Discovery of pyrroloaminopyrazoles as novel PAK inhibitors," J Med Chem, 55(10): 4728-4739 (2012).

Hayter et al., "Updated assessment of the prevalence, spectrum and case definition of autoimmune disease," Autoimmun Rev, 11(10): 754-765, 756 (2012).
Houtkooper et al., "Exploring the therapeutic space around NAD+," J Cell Biol, 199(2):205-9 (2012).
International Search Report and Written Opinion for International Application No. PCT/US2016/047566, "Substituted Benzofuranyl Compounds and Uses Thereof," dated Oct. 4, 2016.
International Search Report and Written Opinion for International Application No. PCT/US2016/069241, "Substituted Benzofuranyl Compounds and Uses Thereof," dated Mar. 16, 2017.
International Search Report and Written Opinion for International Application No. PCT/US2015/066098, "Cyclic Compounds and Uses Thereof," dated Mar. 16, 2016.
International Search Report and Written Opinion for International Application No. PCT/US2016/047337, "Cyclic Compounds and Uses Thereof," dated Oct. 6, 2016.
International Search Report and Written Opinion for International Application No. PCT/US2016/047358, "Cyclic Compounds and Uses Thereof," dated Oct. 26, 2016.
International Search Report for International Application No. PCT/US2013/072264, "Substituted 2,3-Dihydrobenzofuranyl Compounds and Uses Thereof"; dated May 16, 2014.
International Search Report for International Application No. PCT/US2014/045479, "Substituted Benzofuranyl and Benzoxazolyl Compounds and Uses Thereof"; dated Oct. 27, 2014.
International Search Report for International Application No. PCT/US2014/056580, "Multicyclic Compounds and Methods of Using Same"; dated Nov. 27, 2014.
Kreis et al., "PAK signalling in neuronal physiology," Cell Signal, 21: 384-393 (2009).
Ma et al., "PAK in Alzheimer disease, Huntington disease and X-linked mental retardation," Cell Logist, 2(2): 2159-2799 (2012).
Marelli et al., "Tumor targeting via integrin ligands," Front Oncol, 3: 1-12 (2013).
O'Brien et al., "Vascular cognitive impairment," Lancet Neurol, 2(2): 89-98, 96 (2003).
Sampath et al., "Inhibition of nicotinamide phosphoribosyltransferase (NAMPT) as a therapeutic strategy in cancer," Pharmacol Therapeut (2014).
Shah et al., "Current approaches in the treatment of Alzheimer's disease," Biomed & Pharmacother, 62: 199-207 (2008).
Wang et al., "Mathematical modeling in cancer drug discovery," Drug Discov Today, 19(2): 145-150 (2014).
Written Opinion of International Application No. PCT/US2013/072264, "Substituted 2,3-Dihydrobenzofuranyl Compounds and Uses Thereof"; dated May 16, 2014.
Yin et al., "Intrinsic directionality of migrating vascular smooth muscle cells is regulated by NAD+ biosynthesis," J Cell Sci, 125:5770-80 (2012).
Final Rejection for U.S. Appl. No. 14/647,662, "Substituted 2,3-Dihydrobenzofuranyl Compounds and Uses Thereof," dated Jul. 12, 2017.
Non-Final Rejection for U.S. Appl. No. 14/902,202, "Substituted Benzofuranyl and Benzoxazolyl Compounds and Uses Thereof," dated Apr. 21, 2017.
Non-Final Rejection for U.S. Appl. No. 15/023,269, "Multicyclic Compounds and Methods of Using Same," dated Jun. 23, 2017.
Notice of Allowance for U.S. Appl. No. 14/647,662, "Substituted 2,3-Dihydrobenzofuranyl Compounds and Uses Thereof," dated Nov. 24, 2017.
Notice of Allowance for U.S. Appl. No. 14/902,202, "Substituted Benzofuranyl and Benzoxazolyl Compounds and Uses Thereof," dated Aug. 29, 2017.
Restriction Requirement for U.S. Appl. No. 15/023,269, "Multicyclic Compounds and Methods of Using Same," dated Feb. 13, 2017.
International Preliminary Report on Patentability for International Application No. PCT/US14/045479 dated Jan. 5, 2016.
International Preliminary Report on Patentability for International Application No. PCT/US2013/072264 dated Jun. 2, 2015.
International Preliminary Report on Patentability for International Application No. PCT/US2015/066098 dated Jun. 20, 2017.

(56) References Cited

OTHER PUBLICATIONS

International Preliminary Report on Patentability for International Application No. PCT/US2014/056580, "Multicyclic Compounds and Methods of Using Same," dated Mar. 22, 2016.
International Search Report and Written Opinion for International Patent Application No. PCT/US2016/069303 dated May 26, 2017.
Written Opinion for International Application No. PCT/US14/045479 dated Oct. 27, 2014.
Written Opinion for International Application No. PCT/US14/056580 dated Nov. 27, 2014.

* cited by examiner

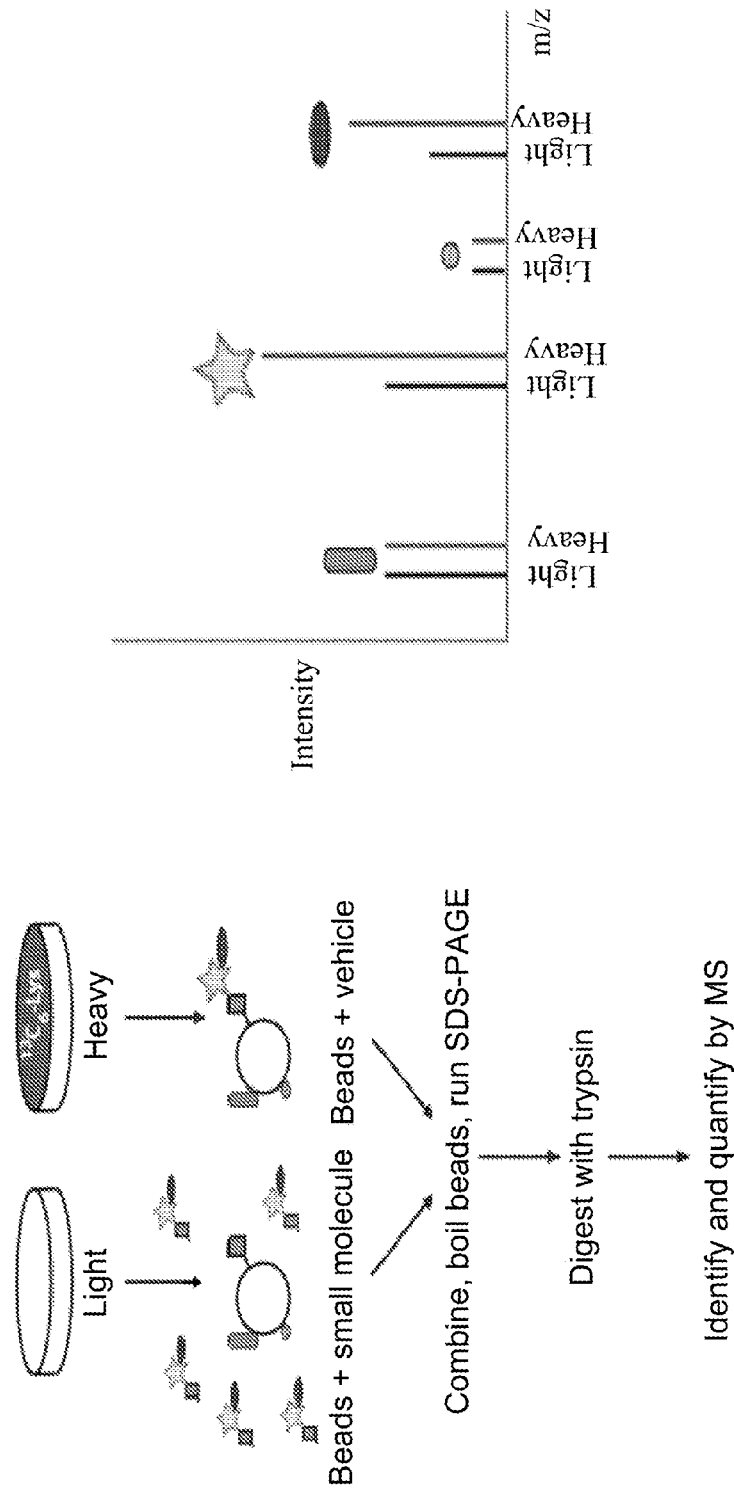

MULTICYCLIC COMPOUNDS AND METHODS OF USING SAME

RELATED APPLICATIONS

This application is the U.S. National Stage of International Application No. PCT/US2014/056580, filed Sep. 19, 2014, which designates the U.S., published in English, and claims the benefit of U.S. Provisional Application No. 61/880,488, filed on Sep. 20, 2013 and 61/904,888, filed Nov. 15, 2013. The entire teachings of the above applications are incorporated herein by reference.

BACKGROUND OF THE INVENTION

Cancer is the second most common cause of death in the United States, exceeded only by heart disease. In the United States, cancer accounts for one of every four deaths. With population growth and aging of the population, the number of new cancer patients is expected to double to 2.6 million by 2050. There is a clear need for additional drug-like compounds that are effective for the treatment of cancer.

SUMMARY OF THE INVENTION

The present invention relates to multicyclic compounds, or pharmaceutically acceptable salts or compositions thereof, useful as anti-cancer agents. In one embodiment of the invention, the compounds are represented by Structural Formula (I):

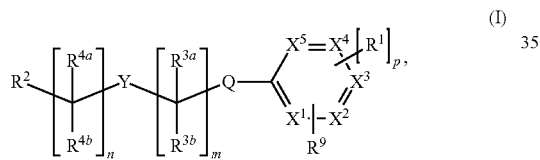

or a pharmaceutically acceptable salt thereof, wherein each variable is as defined and described herein.

Another embodiment of the invention is a pharmaceutical composition comprising a compound of the invention, or a pharmaceutically acceptable salt thereof, and a pharmaceutically acceptable carrier.

Yet another embodiment of the invention is a method for treating cancer in a subject in need thereof, the method comprising administering to the subject in need thereof a therapeutically effective amount of a compound of the invention, or a pharmaceutically acceptable salt thereof, or a composition comprising a compound of the invention, or a pharmaceutically acceptable salt thereof.

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

As such, in another embodiment, the invention is a method of treating a PAK-mediated disorder in a subject in need thereof, comprising administering to the subject in need thereof a therapeutically effective amount of a compound of the invention, or a pharmaceutically acceptable salt thereof, or a pharmaceutical composition comprising a compound of the invention, or a pharmaceutically acceptable salt thereof.

Another embodiment of the invention is use of a compound of the invention for treating cancer or a PAK-mediated disorder in a subject.

Another embodiment of the invention is use of a compound of the invention for the manufacture of a medicament for treating cancer or a PAK-mediated disorder in a subject.

Compounds of the present invention, and pharmaceutically acceptable salts and/or compositions thereof, are useful for treating a variety of cancers, such as lymphoma and, more specifically, mantle cell lymphoma.

BRIEF DESCRIPTION OF THE DRAWINGS

The foregoing will be apparent from the following more particular description of example embodiments of the invention.

FIG. 1 is a schematic representation of a SILAC experiment and shows the experimental design.

DETAILED DESCRIPTION OF THE INVENTION

A description of example embodiments of the invention follows.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

"Aliphatic" means an optionally substituted, saturated or unsaturated, branched or straight-chain monovalent hydrocarbon radical having the specified number of carbon atoms.

"Alkyl" means an optionally substituted saturated aliphatic branched or straight-chain monovalent hydrocarbon radical having the specified number of carbon atoms. Thus, "($C_1$-$C_4$) alkyl" means a radical having from 1-4 carbon atoms in a linear or branched arrangement. "($C_1$-$C_4$)alkyl" includes methyl, ethyl, propyl, isopropyl, n-butyl and tert-butyl.

"Alkenyl" means an optionally substituted aliphatic branched or straight-chain monovalent hydrocarbon radical having at least one carbon-carbon double bond and the specified number of carbon atoms. Thus, "($C_1$-$C_4$) alkenyl" means a radical having at least one carbon-carbon double bond and from 1-4 carbon atoms in a linear or branched arrangement. "($C_1$-$C_4$)alkenyl" includes —$CHCH_2$, —$CH_2CHCH_2$ and —$C(CH_3)CH_2$.

"Amino" means —$NH_2$.

As used herein, the term "dialkylamino" means (alkyl)$_2$-N—, wherein the alkyl groups, which may be the same or different, are as herein defined. Particular dialkylamino groups are (($C_1$-$C_4$)alkyl)$_2$-N—, wherein the alkyl groups may be the same or different. Exemplary dialkylamino groups include dimethylamino, diethylamino and methylethylamino.

As used herein, the term "monoalkylamino" means a radical of the formula alkyl-NH, wherein the alkyl group is as herein defined. In one aspect, a monoalkylamino is a ($C_1$-$C_6$) alkyl-amino-. Exemplary monoalkylamino groups include methylamino and ethylamino.

"Aryl" or "aromatic" means an aromatic carbocyclic ring system. An aryl moiety can be monocyclic, fused bicyclic, or polycyclic. In one embodiment, "aryl" is a 6-15 membered monocyclic or polycyclic system. Aryl systems include, but are not limited to, phenyl, naphthalenyl, fluorenyl, indenyl, azulenyl, and anthracenyl.

Monocyclic aryls are aromatic rings having the specified number of carbon atoms.

A fused bicyclic aryl has two rings which have two adjacent ring atoms in common. The first ring is a monocyclic aryl and the second ring is a monocyclic carbocyclyl or a monocyclic heterocyclyl.

Polycyclic aryls have more than two rings (e.g., three rings resulting in a tricyclic ring system) and adjacent rings have at least two ring atoms in common. The first ring is a monocyclic aryl and the remaining ring structures are monocyclic carbocyclyls or monocyclic heterocyclyls. Polycyclic ring systems include fused ring systems. A fused polycyclic ring system has at least two rings that have two adjacent ring atoms in common.

"Carbocyclyl" means a cyclic group with only ring carbon atoms. "Carbocyclyl" includes 3-15 membered saturated, partially saturated or unsaturated aliphatic cyclic hydrocarbon rings or 6-15 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remaining ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$C_3$-$C_7$ cycloalkyl" means a hydrocarbon radical of a (3-7 membered) saturated aliphatic cyclic hydrocarbon ring. A $C_3$-$C_7$ cycloalkyl includes, but is not limited to cyclopropyl, cyclobutyl, cyclopentyl, cyclohexyl and cycloheptyl.

"Hetero" refers to the replacement of at least one carbon atom member in a ring system with at least one heteroatom selected from N, S, and O. "Hetero" also refers to the replacement of at least one carbon atom member in an acyclic system. In some embodiments, a hetero ring system may have 1, 2, 3 or 4 carbon atom members replaced by a heteroatom.

"Heteroatom" refers to an atom other than carbon. Examples of heteroatoms include nitrogen, oxygen and sulfur.

"Heterocyclyl" means a cyclic 3-15 membered saturated or unsaturated aliphatic or aromatic ring wherein one or more carbon atoms in the ring are independently replaced with a heteroatom. When a heteroatom is S, it can be optionally mono- or di-oxygenated (i.e., —S(O)— or —$S(O)_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A Spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$) cycloalkyl. Alternatively, the second ring is phenyl. Example of spiro bicyclic heterocyclyl includes, but are not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heteroaryl" or "heteroaromatic ring" means a 5-15 membered monovalent heteroaromatic ring radical. A heteroaryl moiety can be monocyclic, fused bicyclic, or polycyclic. In one embodiment, a heteroaryl contains 1, 2, 3 or 4 heteroatoms independently selected from N, O, and S. Heteroaryls include, but are not limited to furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

Monocyclic heteroaryls are heteroaromatic rings having the specified number of carbon atoms.

A fused bicyclic heteroaryl has two rings which have two adjacent ring atoms in common. The first ring is a monocyclic heteroaryl and the second ring is a monocyclic carbocyclyl or a monocyclic heterocyclyl.

Polycyclic heteroaryls have more than two rings (e.g., three rings resulting in a tricyclic ring system) and adjacent rings have at least two ring atoms in common. The first ring is a monocyclic heteroaryl and the remaining ring structures are monocyclic carbocyclyls or monocyclic heterocyclyls. Polycyclic ring systems include fused ring systems. A fused polycyclic ring system has at least two rings that have two adjacent ring atoms in common.

"Halogen" and "halo" are used interchangeably herein and each refers to fluorine, chlorine, bromine, or iodine.

"Hydroxy" and "hydroxyl" are used interchangeably herein and mean —OH.

"Chloro" means —Cl.

"Fluoro" means —F.

"Cyano" means —CN.

"Sulfonate" means —$SO_2H$.

"Alkoxy" means an alkyl radical attached through an oxygen linking atom. "($C_1$-$C_6$)alkoxy" includes methoxy, ethoxy, propoxy, butoxy, pentoxy and hexoxy.

"Haloalkyl" include mono, poly, and perhaloalkyl groups, where each halogen is independently selected from fluorine, chlorine, and bromine.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

When any of $X^1$, $X^2$, $X^3$, $X^4$ and $X^5$ in the structural formulas described herein is C(H), the hydrogen of the C(H) can optionally be replaced with $R^1$ or $R^9$, in accordance with the description of values and alternative values for the variables provided herein for the structural formula. Thus, the fact that $X^1$, $X^2$, $X^3$, $X^4$ and/or $X^5$ is selected to be C(H) in a particular structure does not preclude the hydrogen of the C(H) from being substituted with $R^1$ or $R^9$, so long as the substitution is provided for in the description of values and alternative values for the variables provided herein for the structural formula.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable atom, for example, a substitutable carbon atom, of an "optionally substituted group" are independently halogen; haloalkyl;

—(CH$_2$)$_{0-4}$R° (e.g., —CH(OH)CH$_3$, —C(CH$_3$)$_2$OH); —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —(CH$_2$)$_{0-4}$C(O)NR°$_2$; —C(S)NR°$_2$; —C(O)NR°NR°$_2$; —C(S)SR°; —SC(S)SR°; —(CH$_2$)$_{0-4}$OC(O)NR°$_2$; —C(O)N(OR°)R°; —C(O)C(O)R°; —C(O)C(O)NR°$_2$; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered carbocyclyl or heterocyclyl, or, notwithstanding the definition above, two independent occurrences of R°, taken together with their intervening atom(s), form a 3-12-membered carbocyclyl or heterocyclyl, which may be substituted as defined below.

Suitable monovalent substituents on R° (or the ring formed by taking two independent occurrences of R° together with their intervening atoms), are independently halogen, haloalkyl, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include ═O and ═S.

"Heteroaryl substituent," as used herein, refers to a substituent on a heteroaryl group. Such substituents include the suitable monovalent substituents for a substitutable atom, as described above. Preferred heteroaryl substituents include halogen; —(CH$_2$)$_{0-4}$R°; —(CH$_2$)$_{0-4}$OR°; —O(CH$_2$)$_{0-4}$R°, —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —NO$_2$; —CN; —N$_3$; or —(CH$_2$)$_{0-4}$N(R°)$_2$, wherein each R° is defined above and may be substituted as defined above. Particularly preferred heteroaryl substituents include hydrogen, halogen; (C$_1$-C$_4$)alkyl; (C$_1$-C$_4$)haloalkyl; (C$_1$-C$_4$)alkoxy; (C$_1$-C$_4$)thioalkoxy; —NO$_2$; —CN; —N$_3$; or —N(R°)$_2$, wherein each R° is defined above and may be substituted as defined above.

Suitable divalent substituents on a saturated carbon atom of an "optionally substituted group" include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, and —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, and —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, and —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Pharmaceutically acceptable salts include $(C_1-C_6)$alkylhalide salts. A $(C_1-C_6)$alkylhalide salt of a compound described herein can be formed, for example, by treating a compound of Formula II (e.g., wherein q is 0) with a $(C_1-C_6)$alkylhalide salt, thereby alkylating a nitrogen atom (e.g., the nitrogen atom beta to the group $—[C(R^{4a})(R^{4b})]_n—$ in Formula II) and forming a $(C_1-C_6)$alkylhalide salt of a compound of Formula II. Examples of $(C_1-C_6)$ alkylhalide salts include methyl iodide and ethyl iodide.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a patient. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds of the Invention

A first embodiment of the invention is a compound represented by Structural Formula I:

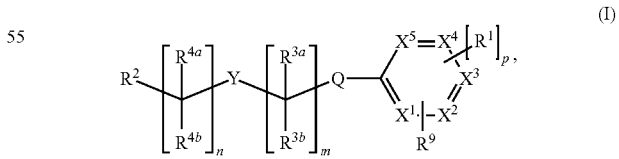

(I)

or a pharmaceutically acceptable salt thereof, wherein:
each of $X^1$, $X^2$, $X^3$, $X^4$ and $X^5$ is independently selected from C(H) and N, wherein no more than two of $X^1$, $X^2$, $X^3$, $X^4$ and $X^5$ are simultaneously N;
Y is selected from $—C(R^8)=C(R^6)—R^5—N(R^7)-*$, $—N(R^7)—R^5—C(R^6)=C(R^8)-*$, $—N(R^7)—R^5—C(R^6)(R^6)—C(R^8)(R^8)-*$, $—N(R^7)—R^5—C≡C-*$, —C(R⁸)(R⁸)—C(R⁶)(R⁶)—R⁵—N(R⁷)-* and —C≡C—R⁵—N(R⁷)-*, wherein "*" represents a portion of Y directly adjacent to —[C(R³ᵃ)(R³ᵇ)]ₘ—;

Q is selected from —O—, —S(O)₂, —NH—, and N(C₁-C₄)alkyl;

R⁵ is selected from —C(O)— and —S(O)₂—;

each R⁶ and R⁸ is independently selected from hydrogen, halo, CN, and (C₁-C₄)alkyl;

R⁷ is selected from hydrogen and (C₁-C₄)alkyl;

each R¹ is independently selected from hydroxy, halo, halo(C₁-C₄)alkyl, (C₁-C₄)alkyl, (C₁-C₄)alkoxy, carbocyclyl, heterocyclyl, cyano, sulfonate, and —S(O)₀₋₂(C₁-C₄)alkyl;

R² is aryl or heteroaryl;

each of R³ᵃ and R³ᵇ is independently selected from hydrogen, deuterium, halo, and (C₁-C₄)alkyl;

each of R⁴ᵃ and R⁴ᵇ, if present, is independently selected from hydrogen, deuterium, (C₁-C₄)alkyl, and (C₃-C₆)cycloalkyl;

R⁹ is carbocyclyl or heterocyclyl;

m is 1, 2 or 3;

n is 0 or 1; and p is 0, 1, 2 or 3, wherein:

each aryl, heteroaryl, carbocyclyl, heterocyclyl, cycloalkyl or alkyl is optionally and independently substituted.

In a first aspect of the first embodiment, n is 0. The values for the remaining variables are as defined in the first embodiment.

In a second aspect of the first embodiment, R² is optionally substituted with 1 or 2 substituents independently selected from amino, halogen, (C₁-C₄)alkyl and (C₁-C₄)haloalkyl. The values for the remaining variables are as defined in the first embodiment, or first aspect thereof.

In a third aspect of the first embodiment, R² is optionally substituted heteroaryl. The values for the remaining variables are as defined in the first embodiment, or first or second aspect thereof.

In a fourth aspect of the first embodiment, R² is optionally substituted C₅-C₆ heteroaryl having 1, 2 or 3 heteroatoms independently selected from nitrogen, oxygen and sulfur. The values for the remaining variables are as defined in the first embodiment, or first through third aspects thereof.

In a fifth aspect of the first embodiment, R² is optionally substituted pyridin-3-yl. The values for the remaining variables are as defined in the first embodiment, or first through fourth aspects thereof.

In a sixth aspect of the first embodiment, R² is selected from pyridin-3-yl and 4-aminopyridin-3-yl. The values for the remaining variables are as defined in the first embodiment, or first through fifth aspects thereof.

In a seventh aspect of the first embodiment, Q is —O—. The values for the remaining variables are as defined in the first embodiment, or first through sixth aspects thereof.

In an eighth aspect of the first embodiment, Y is —C(R⁸)=C(R⁶)—R⁵—N(R⁷)-*. The values for the remaining variables are as defined in the first embodiment, or first through seventh aspects thereof.

In a ninth aspect of the first embodiment, Y is selected from —CH=CH—C(O)—NH-* and —CH=CH—C(O)—N(CH₃)-*. The values for the remaining variables are as defined in the first embodiment, or first through eighth aspects thereof.

In a tenth aspect of the first embodiment, Y is —CH=CH—C(O)—NH-*. The values for the remaining variables are as defined in the first embodiment, or first through ninth aspects thereof.

In an eleventh aspect of the first embodiment, m is 2 or 3. The values for the remaining variables are as defined in the first embodiment, or first through tenth aspects thereof.

In a twelfth aspect of the first embodiment, m is 2. The values for the remaining variables are as defined in the first embodiment, or first through eleventh aspects thereof.

In a thirteenth aspect of the first embodiment, m is 3. The values for the remaining variables are as defined in the first embodiment, or first through twelfth aspects thereof.

In a fourteenth aspect of the first embodiment, R⁵ is —C(O)—. The values for the remaining variables are as defined in the first embodiment, or first through thirteenth aspects thereof.

In a fifteenth aspect of the first embodiment, each of R³ᵃ and R³ᵇ is independently selected from hydrogen, deuterium, fluoro and methyl. The values for the remaining variables are as defined in the first embodiment, or first through fourteenth aspects thereof.

In a sixteenth aspect of the first embodiment, each of R³ᵃ and R³ᵇ is hydrogen. The values for the remaining variables are as defined in the first embodiment, or first through fifteenth aspects thereof.

In a seventeenth aspect of the first embodiment, the portion of the compound represented by —[C(R³ᵃ)(R³ᵇ)]ₘ—, is selected from —(CH₂)₃-†, —(CH₂)₂-†, —CH₂CD₂-†*, —CH₂—C(CH₃)₂-†, —CH₂CF₂CH₂-†, and —CH₂C(CH₃)₂CH₂-†, wherein "†" represents a terminus of —[C(R³ᵃ)(R³ᵇ)]ₘ— directly adjacent to -Q-. The values for the remaining variables are as defined in the first embodiment, or first through sixteenth aspects thereof.

In an eighteenth aspect of the first embodiment, the portion of the compound represented by

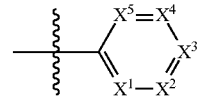

is selected from:

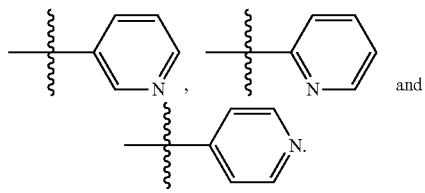

The values for the remaining variables are as defined in the first embodiment, or first through seventeenth aspects thereof.

In a nineteenth aspect of the first embodiment, each R¹, if present, is independently selected from hydroxy, halo, halo(C₁-C₄)alkyl, (C₁-C₄)alkyl and (C₁-C₄)alkoxy. The values for the remaining variables are as defined in the first embodiment, or first through eighteenth aspects thereof.

In a twentieth aspect of the first embodiment, each R¹, if present, is independently selected from halo and halo(C₁-C₄)alkyl. The values for the remaining variables are as defined in the first embodiment, or first through nineteenth aspects thereof.

In a twenty-first aspect of the first embodiment, each R¹, if present, is independently selected from fluoro, chloro, —CF₃ and —CHF₂. The values for the remaining variables are as defined in the first embodiment, or first through twentieth aspects thereof.

In a twenty-second aspect of the first embodiment, p is 0 or 1. The values for the remaining variables are as defined in the first embodiment, or first through twentieth aspects thereof.

In a twenty-third aspect of the first embodiment, p is 1. The values for the remaining variables are as defined in the first embodiment, or first through twenty-second aspects thereof.

In a twenty-fourth aspect of the first embodiment, R⁹ is optionally and independently substituted with 1, 2 or 3 substituents and is phenyl or a 5-6-membered heteroaryl having 1, 2 or 3 heteroatoms selected from nitrogen, oxygen and sulfur. The values for the remaining variables are as defined in the first embodiment, or first through twenty-third aspects thereof.

In a twenty-fifth aspect of the first embodiment, R⁹ is substituted with one or more substituents independently selected from halogen, (C₁-C₄)alkyl optionally substituted with hydroxyl, (C₂-C₄)alkenyl, (C₁-C₄)haloalkyl, —C(O)(C₁-C₄)alkyl and —C(O)NR¹¹R¹², wherein:
  R¹¹ and R¹² are each independently hydrogen, C₁-C₄ alkyl, optionally substituted carbocyclyl, or optionally substituted heterocyclyl; or
  R¹¹ and R¹² are taken together with the nitrogen atom to which they are commonly attached to form an optionally substituted heterocyclyl.
The values for the remaining variables are as defined in the first embodiment, or first through twenty-fourth aspects thereof.

In a twenty-sixth aspect of the first embodiment, R⁹ is substituted with 1 or 2 substituents independently selected from halogen; (C₁-C₄)alkyl optionally substituted with hydroxyl; (C₂-C₄)alkenyl; (C₁-C₄)haloalkyl; —C(O)(C₁-C₄)alkyl; —C(O)NR¹¹R¹², wherein R¹¹ and R¹² are taken together with the nitrogen atom to which they are commonly attached to form an optionally substituted (C₃-C₇)heterocyclyl. The values for the remaining variables are as defined in the first embodiment, or first through twenty-fifth aspects thereof.

In a twenty-seventh aspect of the first embodiment, R⁹ is substituted with one substituent selected from halogen; (C₁-C₄)alkyl optionally substituted with hydroxyl; (C₂-C₄) alkenyl; (C₁-C₄)haloalkyl; —C(O)(C₁-C₄)alkyl; —C(O)NR¹¹R¹², wherein R¹¹ and R¹² are taken together with the nitrogen atom to which they are commonly attached to form an optionally substituted (C₃-C₇)heterocyclyl; and is further optionally substituted with one substituent selected from halogen, (C₁-C₄)alkyl and (C₁-C₄)haloalkyl. The values for the remaining variables are as defined in the first embodiment, or first through twenty-sixth aspects thereof.

In a twenty-eighth aspect of the first embodiment, R⁹ is selected from phenyl, thiophenyl, pyridinyl and pyrimidinyl, and is substituted with 1 or 2 independently selected substituents. The values for the remaining variables are as defined in the first embodiment, or first through twenty-seventh aspects thereof.

In a twenty-ninth aspect of the first embodiment, R⁹ is substituted with at least one substituent independently selected from —C(O)(C₁-C₄)alkyl, —C(O)—N(R¹¹)(R¹²), hydroxy-substituted (C₁-C₄)alkyl, and (C₂-C₄)alkenyl, wherein R¹¹ and R¹² are each independently selected from (C₁-C₄)alkyl; or R¹¹ and R¹² are taken together with the nitrogen to which they are bound to form a saturated heterocyclyl comprising 0 or 1 additional heteroatoms independently selected from N, O and S, and wherein the saturated heterocyclyl is optionally substituted with 1 or 2 substituents independently selected from halogen, (C₁-C₄) alkyl and (C₁-C₄)haloalkyl. The values for the remaining variables are as defined in the first embodiment, or first through twenty-eighth aspects thereof.

In a thirtieth aspect of the first embodiment, R⁹ is selected from phenyl, thiophen-2-yl, pyridin-3-yl and pyrimidin-3-yl. The values for the remaining variables are as defined in the first embodiment, or first through twenty-ninth aspects thereof.

In a thirty-first aspect of the first embodiment, R⁹ is selected from 4-dimethylaminocarbonylphenyl, 5-acetylthiophen-2-yl, 5-(1-hydroxyethyl)thiophen-2-yl, 5-(2-hydroxypropan-2-yl)thiophen-2-yl, 5-(prop-1-en-2-yl)thiophen-2-yl, 4-(4-methylpiperazin-1-ylcarbonyl)phenyl, 4-(morpholin-4-ylcarbonyl)phenyl, 4-(3,3-difluoroazetidin-1-ylcarbonyl)phenyl, 4-(piperazin-1-ylcarbonyl)phenyl, 4-(piperidin-1-ylcarbonyl)phenyl, 4-(3,3-dimethylmorpholin-4-ylcarbonyl)phenyl, or 2-(morpholin-1-ylcarbonyl)pyrimidin-5-yl. The values for the remaining variables are as defined in the first embodiment, or first through thirtieth aspects thereof.

In a thirty-second aspect of the first embodiment, the heterocyclyl formed by R¹¹ and R¹² taken together with the nitrogen atom to which they are commonly attached is optionally substituted with 1, 2, 3 or 4 substituents independently selected from halo, halo(C₁-C₄)alkyl and (C₁-C₄) alkyl. The values for the remaining variables are as defined in the first embodiment, or first through thirty-first aspects thereof.

In a thirty-third aspect of the first embodiment, each of X¹, X², X³, X⁴ and X⁵ is C(H). The values for the remaining variables are as defined in the first embodiment, or first through thirty-second aspects thereof.

In a thirty-fourth aspect of the first embodiment, each R¹, if present, is independently selected from hydroxy, halo, halo(C₁-C₄)alkyl, (C₁-C₄)alkyl, (C₁-C₄)alkoxy and halo(C₁-C₄)alkoxy. The values for the remaining variables are as defined in the first embodiment, or first through thirty-third aspects thereof.

In a thirty-fifth aspect of the first embodiment, R⁹ is selected from 4-dimethylaminocarbonylphenyl, 5-acetylthiophen-2-yl, 5-(1-hydroxyethyl)thiophen-2-yl, 5-(2-hydroxypropan-2-yl)thiophen-2-yl, 5-(prop-1-en-2-yl)thiophen-2-yl, 4-(4-methylpiperazin-1-ylcarbonyl)phenyl, 4-(morpholin-4-ylcarbonyl)phenyl, 4-(3,3-difluoroazetidin-1-ylcarbonyl)phenyl, 4-(piperazin-1-ylcarbonyl)phenyl, 4-(piperidin-1-ylcarbonyl)phenyl, 4-(3,3-dimethylmorpholin-4-ylcarbonyl)phenyl, 2-(morpholin-1-ylcarbonyl)pyrimidin-5-yl or (4,4-difluoropiperidine-1-carbonyl)pyridin-2-yl. The values for the remaining variables are as defined in the first embodiment, or first through thirtieth aspects thereof.

A second embodiment of the invention is a compound represented by Structural Formula Ia:

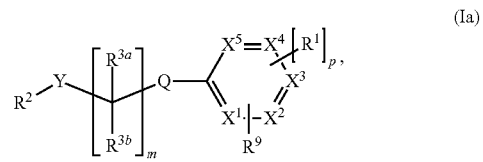

(Ia)

or a pharmaceutically acceptable salt thereof. Values and alternative values for the variables are as described in the first embodiment, or any aspect thereof.

A third embodiment of the invention is a compound represented by Structural Formula II:

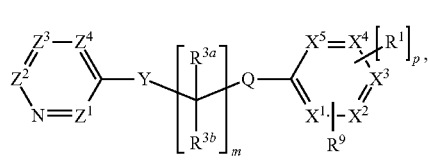
(II)

or a pharmaceutically acceptable salt thereof, wherein:
each of $Z^1$, $Z^2$, $Z^3$, and $Z^4$ is independently selected from N and $C(R^{10})$, wherein:
no more than one of $Z^1$, $Z^2$, $Z^3$ and $Z^4$ is nitrogen; and
each $R^{10}$ is independently hydrogen or a suitable heteroaryl substituent.

Values and alternative values for the remaining variables are as described in the first embodiment, or any aspect thereof.

In a first aspect of the third embodiment, the portion of the compound represented by

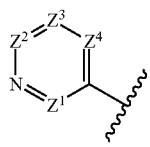

is selected from:

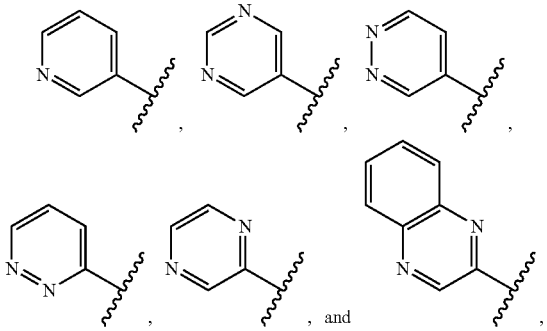
, and and is optionally further substituted. The values for the remaining variables are as defined in the first embodiment, or any aspect thereof, or the third embodiment.

A fourth embodiment of the invention is a compound represented by Structural Formula III:

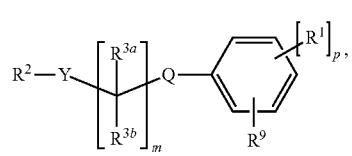
(III)

or a pharmaceutically acceptable salt thereof. Values and alternative values for the variables are as described in the first or third embodiment, or any aspect of the foregoing.

A fifth embodiment of the invention is a compound represented by Structural Formula IV or V:

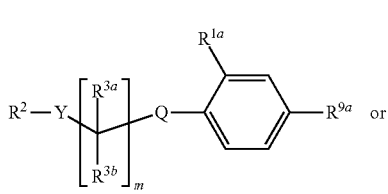
(IV)

or

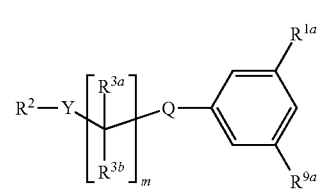
(V)

or a pharmaceutically acceptable salt thereof, wherein:
$R^{1a}$ is selected from hydrogen, hydroxyl, halogen, halo($C_1$-$C_4$)alkyl, ($C_1$-$C_4$)alkyl, ($C_1$-$C_4$)alkoxy and halo($C_1$-$C_4$)alkoxy; and
$R^{9a}$ is optionally substituted aryl or heteroaryl. Values and alternative values for the remaining variables are as described in the first or third embodiment, or any aspect of the foregoing.

In a first aspect of the fifth embodiment, $R^{1a}$ is selected from hydrogen, halogen and halo($C_1$-$C_4$)alkyl. The values for the remaining variables are as defined in the first or third embodiment, or any aspect of the foregoing, or the fifth embodiment.

In a second aspect of the fifth embodiment, $R^{1a}$ is selected from fluoro, chloro, —$CF_3$ and —$CHF_2$. The values for the remaining variables are as defined in the first or third embodiment, or any aspect of the foregoing, or the fifth embodiment, or first aspect thereof.

In a third aspect of the fifth embodiment, $R^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. The values for the remaining variables are as defined in the first or third embodiment, or any aspect of the foregoing, or the fifth embodiment, or first or second aspect thereof.

In a fourth aspect of the fifth embodiment, $R^{9a}$ is substituted with one or more substituents independently selected from halogen, ($C_1$-$C_4$)alkyl optionally substituted with hydroxyl, ($C_2$-$C_4$)alkenyl, ($C_1$-$C_4$)haloalkyl, —C(O)($C_1$-$C_4$)alkyl and —C(O)$NR^{11}R^{12}$, wherein:
$R^{11}$ and $R^{12}$ are each independently hydrogen, $C_1$-$C_4$ alkyl, optionally substituted carbocyclyl, or optionally substituted heterocyclyl; or
$R^{11}$ and $R^{12}$ are taken together with the nitrogen atom to which they are commonly attached to form an optionally substituted heterocyclyl.
The values for the remaining variables are as defined in the first or third embodiment, or any aspect of the foregoing, or the fifth embodiment, or first through third aspects thereof.

In a fifth aspect of the fifth embodiment, $R^{9a}$ is substituted with 1 or 2 substituents independently selected from halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; —C(O)$NR^{11}R^{12}$, wherein $R^{11}$ and $R^{12}$ are taken together with the nitrogen atom to which they are commonly attached to form an optionally substituted ($C_3$-$C_7$)heterocyclyl. The values for the remaining variables are as defined in the first or third embodiment, or any aspect of the foregoing, or the fifth embodiment, or first through fourth aspects thereof.

In a sixth aspect of the fifth embodiment, $R^{9a}$ is substituted with one substituent selected from halogen; $(C_1-C_4)$ alkyl optionally substituted with hydroxyl; $(C_2-C_4)$alkenyl; $(C_1-C_4)$haloalkyl; —C(O)$(C_1-C_4)$alkyl; —C(O)NR$^{11}$R$^{12}$, wherein R$^{11}$ and R$^{12}$ are taken together with the nitrogen atom to which they are commonly attached to form an optionally substituted $(C_3-C_7)$heterocyclyl; and is further optionally substituted with one substituent selected from halogen, $(C_1-C_4)$alkyl and $(C_1-C_4)$haloalkyl. The values for the remaining variables are as defined in the first or third embodiment, or any aspect of the foregoing, or the fifth embodiment, or first through fifth aspects thereof.

In a seventh aspect of the fifth embodiment, $R^{9a}$ is selected from phenyl, thiophenyl, pyridinyl and pyrimidinyl, and is substituted with 1 or 2 independently selected substituents. The values for the remaining variables are as defined in the first or third embodiment, or any aspect of the foregoing, or the fifth embodiment, or first through sixth aspects thereof.

In an eighth aspect of the fifth embodiment, $R^{9a}$ is substituted with at least one substituent independently selected from —C(O)$(C_1-C_4)$alkyl, —C(O)—N(R$^{11}$)(R$^{12}$), hydroxy-substituted $(C_1-C_4)$alkyl, and $(C_2-C_4)$alkenyl, wherein R$^{11}$ and R$^{12}$ are each independently selected from $(C_1-C_4)$alkyl; or R$^{11}$ and R$^{12}$ are taken together with the nitrogen to which they are bound to form a saturated heterocyclyl comprising 0 or 1 additional heteroatoms independently selected from N, O and S, and wherein the saturated heterocyclyl is optionally substituted with 1 or 2 substituents independently selected from halogen, $(C_1-C_4)$ alkyl and $(C_1-C_4)$haloalkyl. The values for the remaining variables are as defined in the first or third embodiment, or any aspect of the foregoing, or the fifth embodiment, or first through seventh aspects thereof.

In a ninth aspect of the fifth embodiment, $R^{9a}$ is selected from phenyl, thiophen-2-yl, pyridin-3-yl and pyrimidin-3-yl. The values for the remaining variables are as defined in the first or third embodiment, or any aspect of the foregoing, or the fifth embodiment, or first through eighth aspects thereof.

In a tenth aspect of the fifth embodiment, $R^{9a}$ is selected from 4-dimethylaminocarbonylphenyl, 5-acetylthiophen-2-yl, 5-(1-hydroxyethyl)thiophen-2-yl, 5-(2-hydroxypropan-2-yl)thiophen-2-yl, 5-(prop-1-en-2-yl)thiophen-2-yl, 4-(4-methylpiperazin-1-ylcarbonyl)phenyl, 4-(morpholin-4-ylcarbonyl)phenyl, 4-(3,3-difluoroazetidin-1-ylcarbonyl) phenyl, 4-(piperazin-1-ylcarbonyl)phenyl, 4-(piperidin-1-ylcarbonyl)phenyl, 4-(3,3-dimethylmorpholin-4-ylcarbonyl)phenyl or 2-(morpholin-1-ylcarbonyl)pyrimidin-5-yl. The values for the remaining variables are as defined in the first or third embodiment, or any aspect of the foregoing, or the fifth embodiment, or first through ninth aspects thereof.

In an eleventh aspect of the fifth embodiment, the heterocyclyl formed by R$^{11}$ and R$^{12}$ taken together with the nitrogen atom to which they are commonly attached is optionally substituted with 1, 2, 3 or 4 substituents independently selected from halo, halo$(C_1-C_4)$alkyl and $(C_1-C_4)$ alkyl. The values for the remaining variables are as defined in the first or third embodiment, or any aspect of the foregoing, or first through tenth aspects thereof.

In a twelfth aspect of the fifth embodiment, $R^{1a}$ is selected from hydrogen, hydroxyl, halogen, halo$(C_1-C_4)$alkyl, $(C_1-C_4)$alkyl and $(C_1-C_4)$alkoxy. The values for the remaining variables are as defined in the first or third embodiment, or any aspect of the foregoing, or the fifth embodiment, or first through eleventh aspects thereof.

In a thirteenth aspect of the fifth embodiment, $R^{9a}$ is selected from 4-dimethylaminocarbonylphenyl, 5-acetylthiophen-2-yl, 5-(1-hydroxyethyl)thiophen-2-yl, 5-(2-hydroxypropan-2-yl)thiophen-2-yl, 5-(prop-1-en-2-yl)thiophen-2-yl, 4-(4-methylpiperazin-1-ylcarbonyl)phenyl, 4-(morpholin-4-ylcarbonyl)phenyl, 4-(3,3-difluoroazetidin-1-ylcarbonyl)phenyl, 4-(piperazin-1-ylcarbonyl)phenyl, 4-(piperidin-1-ylcarbonyl)phenyl, 4-(3,3-dimethylmorpholin-4-ylcarbonyl)phenyl, 2-(morpholin-1-ylcarbonyl)pyrimidin-5-yl or (4,4-difluoropiperidine-1-carbonyl)pyridin-2-yl. The values for the remaining variables are as defined in the first or third embodiment, or any aspect of the foregoing, or the fifth embodiment, or first through twelfth aspects thereof.

A sixth embodiment is a compound represented by Structural Formula X:

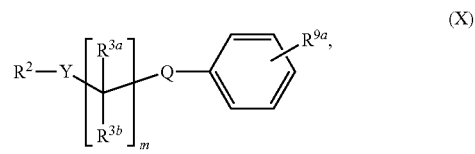

(X)

or a pharmaceutically acceptable salt thereof, wherein:

$R^{9a}$ is optionally substituted aryl or heteroaryl. Values and alternative values for the variables are as described in the first, third or fifth embodiment, or any aspect of the foregoing.

A seventh embodiment is a compound represented by Structural Formula VI or VII:

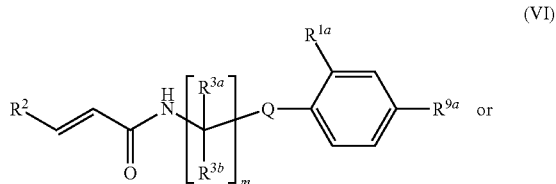

(VI)

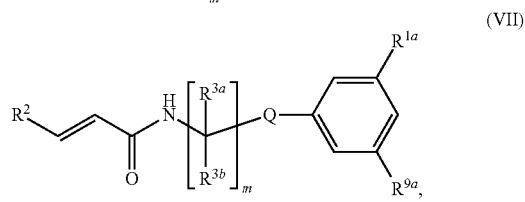

(VII)

or a pharmaceutically acceptable salt thereof. Values and alternative values for the variables are as described in the first, third or fifth embodiment, or any aspect of the foregoing.

An eighth embodiment of the invention is a compound represented by Structural Formula VIII or IX:

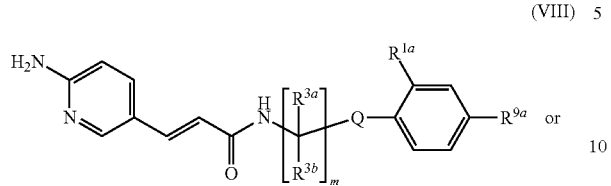

(VIII)

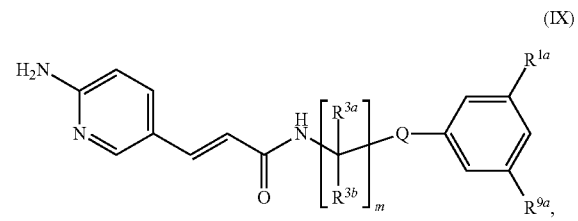

(IX)

or a pharmaceutically acceptable salt thereof. Values and alternative values for the variables are as described in the first or fifth embodiment, or any aspect of the foregoing.

A ninth embodiment of the invention is a compound represented by Structural Formula XI or XII:

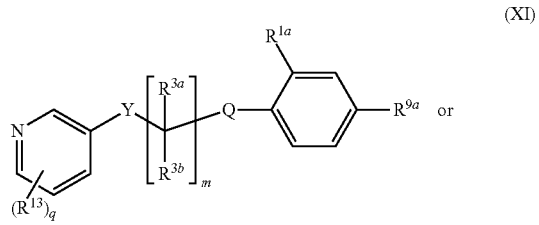

(XI)

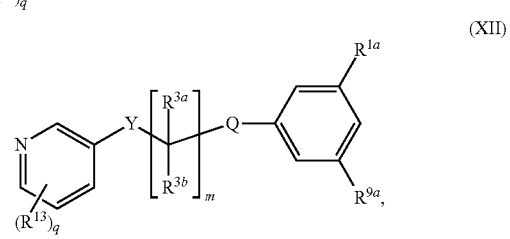

(XII)

or a pharmaceutically acceptable salt thereof, wherein:
each $R^{13}$ is independently selected from amino, halogen, $(C_1-C_4)$alkyl and $(C_1-C_4)$haloalkyl; and
q is 0, 1, 2, or 3. Values and alternative values for the remaining variables are as described in the first or fifth embodiment, or any aspect of the foregoing.

In a first aspect of the ninth embodiment, q is 0, 1 or 2. The values for the remaining variables are as defined in the first or fifth embodiment, or any aspect of the foregoing, or the ninth embodiment.

In a second aspect of the ninth embodiment, q is 1. The values for the remaining variables are as defined in the first or fifth embodiment, or any aspect of the foregoing, or the ninth embodiment, or first aspect thereof.

In a third aspect of the ninth embodiment, q is 0. The values for the remaining variables are as defined in the first or fifth embodiment, or any aspect of the foregoing, or the ninth embodiment, or first or second aspect thereof.

A tenth embodiment of the invention is a compound represented by Structural Formula XIa or XIIa:

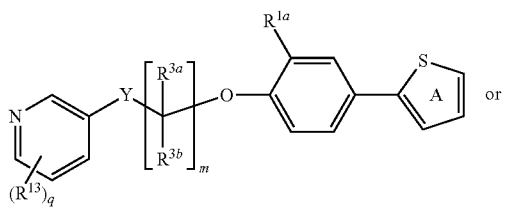

(XIa)

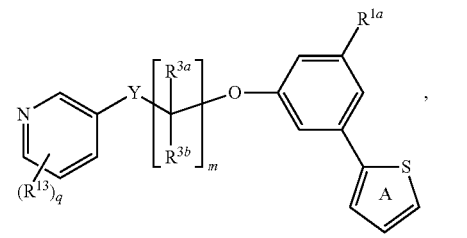

(XIIa)

or a pharmaceutically acceptable salt thereof, wherein:
Ring A is optionally and independently substituted with 1, 2 or 3 substituents. Values and alternative values for the variables are as described in the first, fifth or ninth embodiment, or any aspect of the foregoing.

In a first aspect of the tenth embodiment, Ring A is substituted with one or more substituents independently selected from halogen, $(C_1-C_4)$alkyl optionally substituted with hydroxyl, $(C_2-C_4)$alkenyl, $(C_1-C_4)$haloalkyl, —C(O)$(C_1-C_4)$alkyl and —C(O)NR$^{11}$R$^{12}$, wherein:
  $R^{11}$ and $R^{12}$ are each independently hydrogen, $C_1$-$C_4$ alkyl, optionally substituted carbocyclyl, or optionally substituted heterocyclyl; or
  $R^{11}$ and $R^{12}$ are taken together with the nitrogen atom to which they are commonly attached to form an optionally substituted heterocyclyl.

The values for the remaining variables are as defined in the first, fifth or ninth embodiment, or any aspect of the foregoing, or the tenth embodiment.

In a second aspect of the tenth embodiment, Ring A is substituted with 1 or 2 substituents independently selected from halogen; $(C_1-C_4)$alkyl optionally substituted with hydroxyl; $(C_2-C_4)$alkenyl; $(C_1-C_4)$haloalkyl; —C(O)$(C_1$-$C_4)$alkyl; —C(O)NR$^{11}$R$^{12}$, wherein $R^{11}$ and $R^{12}$ are taken together with the nitrogen atom to which they are commonly attached to form an optionally substituted $(C_3-C_7)$heterocyclyl. The values for the remaining variables are as defined in the first, fifth or ninth embodiment, or any aspect of the foregoing, or the tenth embodiment, or first aspect thereof.

In a third aspect of the tenth embodiment, Ring A is substituted with one substituent selected from halogen; $(C_1-C_4)$alkyl optionally substituted with hydroxyl; $(C_2-C_4)$alkenyl; $(C_1-C_4)$haloalkyl; —C(O)$(C_1-C_4)$alkyl; —C(O)NR$^{11}$R$^{12}$, wherein $R^{11}$ and $R^{12}$ are taken together with the nitrogen atom to which they are commonly attached to form an optionally substituted $(C_3-C_7)$heterocyclyl; and is further optionally substituted with one substituent selected from halogen, $(C_1-C_4)$alkyl and $(C_1-C_4)$haloalkyl. The values for the remaining variables are as defined in the first, fifth or ninth embodiment, or any aspect of the foregoing, or the tenth embodiment, or first or second aspect thereof.

In a fourth aspect of the tenth embodiment, Ring A is substituted with 1 or 2 independently selected substituents. The values for the remaining variables are as defined in the first, fifth or ninth embodiment, or any aspect of the foregoing, or the tenth embodiment, or first through third aspects thereof.

In a fifth aspect of the tenth embodiment, Ring A is substituted with at least one substituent independently selected from —C(O)(C$_1$-C$_4$)alkyl, —C(O)—N(R$^{11}$)(R$^{12}$), hydroxy-substituted (C$_1$-C$_4$)alkyl, and (C$_2$-C$_4$)alkenyl, wherein R$^{11}$ and R$^{12}$ are each independently selected from (C$_1$-C$_4$)alkyl; or R$^{11}$ and R$^{12}$ are taken together with the nitrogen to which they are bound to form a saturated heterocyclyl comprising 0 or 1 additional heteroatoms selected from N, O and S, and wherein the saturated heterocyclyl is optionally substituted with 1 or 2 substituents independently selected from halogen, (C$_1$-C$_4$)alkyl and (C$_1$-C$_4$)haloalkyl. The values for the remaining variables are as defined in the first, fifth or ninth embodiment, or any aspect of the foregoing, or the tenth embodiment, or first through fourth aspects thereof.

An eleventh embodiment is a compound represented by Structural Formula XIb or XIIb:

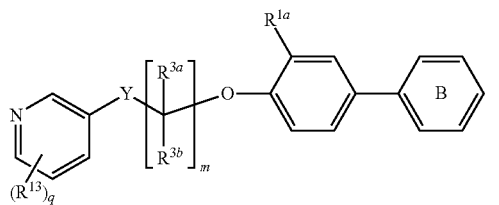

(XIb)

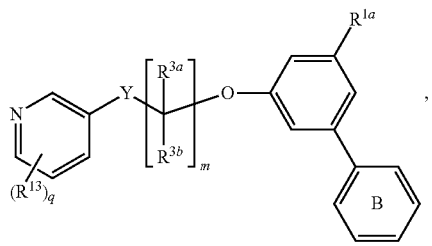

(XIIb)

or a pharmaceutically acceptable salt thereof, wherein:
Ring B is optionally and independently substituted with 1, 2 or 3 substituents. Values and alternative values for the variables are as described in the first, fifth or ninth embodiment, or any aspect of the foregoing.

In a first aspect of the eleventh embodiment, Ring B is substituted with one or more substituents independently selected from halogen, (C$_1$-C$_4$)alkyl optionally substituted with hydroxyl, (C$_2$-C$_4$)alkenyl, (C$_1$-C$_4$)haloalkyl, —C(O)(C$_1$-C$_4$)alkyl and —C(O)NR$^{11}$R$^{12}$, wherein:
  R$^{11}$ and R$^{12}$ are each independently hydrogen, C$_1$-C$_4$ alkyl, optionally substituted carbocyclyl, or optionally substituted heterocyclyl; or
  R$^{11}$ and R$^{12}$ are taken together with the nitrogen atom to which they are commonly attached to form an optionally substituted heterocyclyl.
The values for the remaining variables are as defined in the first, fifth or ninth embodiment, or any aspect of the foregoing, or the eleventh embodiment.

In a second aspect of the eleventh embodiment, Ring B is substituted with 1 or 2 substituents independently selected from halogen; (C$_1$-C$_4$)alkyl optionally substituted with hydroxyl; (C$_2$-C$_4$)alkenyl; (C$_1$-C$_4$)haloalkyl; —C(O)(C$_1$-C$_4$)alkyl; —C(O)NR$^{11}$R$^{12}$, wherein R$^{11}$ and R$^{12}$ are taken together with the nitrogen atom to which they are commonly attached to form an optionally substituted (C$_3$-C$_7$)heterocyclyl. The values for the remaining variables are as defined in the first, fifth or ninth embodiment, or any aspect of the foregoing, or the eleventh embodiment, or first aspect thereof.

In a third aspect of the eleventh embodiment, Ring B is substituted with one substituent selected from halogen; (C$_1$-C$_4$)alkyl optionally substituted with hydroxyl; (C$_2$-C$_4$)alkenyl; (C$_1$-C$_4$)haloalkyl; —C(O)(C$_1$-C$_4$)alkyl; —C(O)NR$^{11}$R$^{12}$, wherein R$^{11}$ and R$^{12}$ are taken together with the nitrogen atom to which they are commonly attached to form an optionally substituted (C$_3$-C$_7$)heterocyclyl; and is further optionally substituted with one substituent selected from halogen, (C$_1$-C$_4$)alkyl and (C$_1$-C$_4$)haloalkyl. The values for the remaining variables are as defined in the first, fifth or ninth embodiment, or any aspect of the foregoing, or the eleventh embodiment, or first or second aspect thereof.

In a fourth aspect of the eleventh embodiment, Ring B is substituted with 1 or 2 independently selected substituents. The values for the remaining variables are as defined in the first, fifth or ninth embodiment, or any aspect of the foregoing, or the eleventh embodiment, or first through third aspects thereof.

In a fifth aspect of the eleventh embodiment, Ring A is substituted with at least one substituent independently selected from —C(O)(C$_1$-C$_4$)alkyl, —C(O)—N(R$^{11}$)(R$^{12}$), hydroxy-substituted (C$_1$-C$_4$)alkyl, and (C$_2$-C$_4$)alkenyl, wherein R$^{11}$ and R$^{12}$ are each independently selected from (C$_1$-C$_4$)alkyl; or R$^{11}$ and R$^{12}$ are taken together with the nitrogen to which they are bound to form a saturated heterocyclyl comprising 0 or 1 additional heteroatoms selected from N, O and S, and wherein the saturated heterocyclyl is optionally substituted with 1 or 2 substituents independently selected from halogen, (C$_1$-C$_4$)alkyl and (C$_1$-C$_4$)haloalkyl. The values for the remaining variables are as defined in the first, fifth or ninth embodiment, or any aspect of the foregoing, or the eleventh embodiment, or first through fourth aspects thereof.

A twelfth embodiment is a compound represented by Structural Formula XIII:

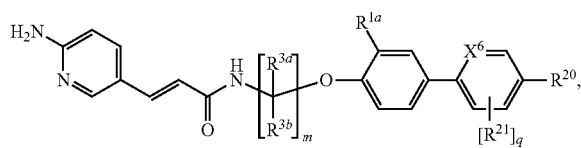

(XIII)

or a pharmaceutically acceptable salt thereof, wherein:
  X$^6$ is —N— or —C(H)—;
  R$^{20}$ is halogen, (C$_1$-C$_4$)alkyl optionally substituted with hydroxyl, (C$_2$-C$_4$)alkenyl, (C$_1$-C$_4$)haloalkyl, —C(O)(C$_1$-C$_4$)alkyl and —C(O)NR$^{11}$R$^{12}$, wherein:
    R$^{11}$ and R$^{12}$ are each independently hydrogen, C$_1$-C$_4$ alkyl, optionally substituted carbocyclyl, or optionally substituted heterocyclyl; or
    R$^{11}$ and R$^{12}$ are taken together with the nitrogen atom to which they are commonly attached to form an optionally substituted heterocyclyl;
  each R$^{21}$, if present, is independently fluoro, chloro, bromo or iodo; and
  q is 0, 1, 2, 3 or 4. Values and alternative values for the remaining variables are as described in the first through eleventh embodiments, or any aspect thereof.

In a first aspect of the twelfth embodiment, q is 0, 1 or 2. Values for the remaining variables are as described in the first through eleventh embodiments, or any aspect thereof, or the twelfth embodiment.

In a second aspect of the twelfth embodiment, $R^{21}$, for each occurrence and if present is fluoro. Values for the remaining variables are as described in the first through eleventh embodiments, or any aspect thereof, or the twelfth embodiment, or first aspect thereof.

In a third aspect of the twelfth embodiment, $R^{20}$ is —C(O)NR$^{11}$R$^{12}$, wherein $R^{11}$ and $R^{12}$ are taken together with the nitrogen atom to which they are commonly attached to form an optionally substituted ($C_3$-$C_7$)heterocyclyl having 1 or 2 heteroatoms independently selected from nitrogen, oxygen and sulfur. Values for the remaining variables are as described in the first through eleventh embodiments, or any aspect thereof, or the twelfth embodiment, or first or second aspect of the foregoing.

In a fourth aspect of the twelfth embodiment, the heterocyclyl formed by $R^{11}$ and $R^{12}$ taken together with the nitrogen atom to which they are commonly attached is optionally substituted with 1, 2, 3 or 4 substituents (e.g., 2 substituents) independently selected from halo, hydroxyl, halo($C_1$-$C_3$)alkyl, ($C_1$-$C_3$)alkyl, ($C_1$-$C_3$)alkoxy and halo($C_1$-$C_3$)alkoxy, preferably halo, for example, fluoro. Values for the remaining variables are as described in the first through eleventh embodiments, or any aspect thereof, or the twelfth embodiment, or first, second or third aspect of the foregoing.

In a fifth aspect of the twelfth embodiment, $X^6$ is —C(H)—. Values for the remaining variables are as described in the first through eleventh embodiments, or any aspect thereof, or the twelfth embodiment, or first through fourth aspects of the foregoing.

In a sixth aspect of the twelfth embodiment, $X^6$ is —N—. Values for the remaining variables are as described in the first through eleventh embodiments, or any aspect thereof, or the twelfth embodiment, or first through fifth aspects of the foregoing.

Exemplary compounds are set forth in Table 1.

Formulation and Administration

Another embodiment of the invention is a composition comprising a compound of the invention, or a pharmaceutically acceptable salt thereof, and a pharmaceutically acceptable carrier, adjuvant, or vehicle. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

The term "patient," as used herein, means an animal. In some embodiments, the animal is a mammal In certain embodiments, the patient is a veterinary patient (i.e., a non-human mammal patient). In some embodiments, the patient is a dog. In other embodiments, the patient is a human.

"Pharmaceutically or pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the invention can also be in microencapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound of the invention can be provided in an extended (or "delayed" or "sustained") release composition. This delayed-release composition comprises a compound of the invention in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

In some embodiments, pharmaceutically acceptable compositions of this invention are formulated for topical administration.

The amount of compounds of the present invention that can be combined with the carrier materials to produce a composition in a single dosage form will vary depending upon the host treated, the particular mode of administration and the activity of the compound employed. Preferably, compositions should be formulated so that a dosage of between 0.01-100 mg/kg body weight/day of the inhibitor can be administered to a patient receiving the composition.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

The pharmaceutical compositions of this invention are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agent(s) can be administered separately, as part of a multiple dose regimen, from the compounds of this invention. Alternatively, the additional agent(s) can be part of a single dosage form, mixed together with the compound of this invention in a single composition.

The compounds described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 to about 100 mg/kg of body weight or, alternatively, in a dosage ranging from about 1 mg to about 1000 mg/dose, every 4 to 120 hours, or according to the requirements of the particular drug. The methods herein contemplate administration of an effective amount of a compound of the invention, or a composition thereof, to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

Uses of Compounds and Pharmaceutically Acceptable Compositions

As used herein, "PAK-mediated" disorder or condition means any disease or other deleterious condition in which one or more p21-activated kinases (PAK) plays a role. Accordingly, another embodiment of the present invention relates to treating, for example, lessening the severity of, a PAK-mediated disorder or condition. PAK-mediated disorders include cancer, neurodegenerative diseases and immune system diseases. Specific examples of PAK-mediated disorders are set forth in detail below.

P21-activated kinases (PAKs) can be classified into two groups: group I and group II. Group I comprises PAK1, PAK2 and PAK3, and group II comprises PAK4, PAK5 and PAK6. Some embodiments of the invention relate to treating a group I PAK-mediated disorder or condition, for example, a PAK1-mediated disorder or condition, a PAK2-mediated disorder or condition, a PAK3-mediated disorder or condition or a disorder or condition mediated by a combination of PAK1, PAK2, and PAK3, for example, a disorder or condition mediated by PAK1 and PAK2, PAK1 and PAK3, PAK2 and PAK3 or PAK1, PAK2 and PAK3. Other embodiments of the invention relate to treating a group II PAK-mediated disorder or condition, for example, a PAK4-mediated disorder or condition, a PAK5-mediated disorder or condition, a PAK6-mediated disorder or condition or a disorder or condition mediated by a combination of PAK4, PAK5 and PAK6, for example, a disorder or condition mediated by PAK4 and PAK5, PAK4 and PAK6, PAK5 and PAK6 or PAK4, PAK5 and PAK6.

When "PAK" is followed by a numeral, as in "PAK4", the particular PAK isoform corresponding to that numeral is being designated. Thus, as used herein, "PAK4-mediated" disorder or condition means any disease or other deleterious condition in which PAK4 is known to play a role. Accordingly, another embodiment of the present invention relates to treating, for example, lessening the severity of, a PAK4-mediated disorder or condition. PAK4-mediated disorders include cancer, neurodegenerative diseases and immune system diseases. Specific examples of PAK4-mediated disorders are set forth in detail below.

Compounds provided by this invention are also useful as tools, for example, to study PAK modulation in biological and pathological phenomena, to study cancer or for the identification and/or comparative evaluation of PAK modulators. Accordingly, in particular embodiments, the present invention provides a method for studying an effect of a compound described herein, or a salt or composition thereof, on a sample, the method comprising contacting a sample comprising cells in culture or one or more PAKs with the compound, or the salt or composition thereof; and measuring the effect of the compound, or salt or composition thereof, on the cells or the one or more PAKs. For example, the compounds described herein can be used as a standard or control substance in binding assays (e.g., competitive binding assays) to identify or evaluate potential PAK modulators or as a discovery tool to probe the role of PAK modulation in certain disorders or conditions, such as those described herein, including cancer and PAK-mediated disorders or conditions.

Modulation, for example, modulation of one or more PAKs, can be accomplished by ligands, particularly PAK ligands, that act as, for example, agonists, partial agonists, inverse agonists, antagonists or allosteric modulators (e.g., allosteric agonists, positive allosteric modulators, negative allosteric modulators). Agonists act directly to activate a receptor, whereas antagonists act indirectly to block receptor signaling by preventing agonist activity through their association with the receptor. Allosteric modulation occurs when a ligand binds at an allosteric site of a receptor, rather than at an orthosteric binding site. Allosteric modulators can include both positive and negative modulators of orthosteric ligand-mediated activity. Without being bound by a particular theory, it is believed that the compounds described herein can bind to one or more PAKs and function as allosteric modulators.

Compounds and compositions described herein are useful for treating cancer in a subject in need thereof. Thus, in certain embodiments, the present invention provides a method for treating cancer, comprising the step of administering to a patient in need thereof a compound of the present invention, or pharmaceutically acceptable salt or composition thereof. The compounds and compositions described herein can also be administered to cells in culture, e.g., in vitro or ex vivo, or to a subject, e.g., in vivo, to treat, prevent, and/or diagnose a variety of disorders, including those described herein below.

The activity of a compound utilized in this invention as an anti-cancer agent may be assayed in vitro, in vivo or in a cell line. Detailed conditions for assaying a compound utilized in this invention as an anti-cancer agent are set forth in the Exemplification.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder). In the case of wound healing, a therapeutically effective amount is an amount that promotes healing of a wound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

As used herein, an amount of a compound effective to treat a disorder, or a "therapeutically effective amount" refers to an amount of the compound which is effective, upon single or multiple dose administration to a subject or a cell, in curing, alleviating, relieving or improving one or more symptoms of a disorder. In the case of wound healing, a therapeutically effective amount is an amount that promotes healing of a wound.

As used herein, an amount of a compound effective to prevent a disorder, or a "prophylactically effective amount" of the compound refers to an amount effective, upon single- or multiple-dose administration to the subject, in preventing or delaying the onset or recurrence of a disorder or one or more symptoms of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.).

For example, provided herein are methods of treating various cancers in mammals (including humans and non-humans), comprising administering to a patient in need thereof a compound of the invention, or a pharmaceutically acceptable salt thereof. Such cancers include hematologic malignancies (leukemias, lymphomas, myelomas, myelodysplastic and myeloproliferative syndromes) and solid tumors (carcinomas such as oral, gall bladder, prostate, breast, lung, colon, pancreatic, renal, ovarian as well as soft tissue and osteo-sarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple. In some embodiments, the present invention provides a method of treating lymphoma, specifically, mantle cell lymphoma.

In some embodiments, the present invention provides a method of treating inflammatory disorders in a patient, comprising administering to the patient a compound of the invention, or a pharmaceutically acceptable salt thereof. Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

Other disorders treatable by the compounds and compositions described herein include muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

Yet other disorders treatable by the compounds and compositions described herein include head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

Yet another disorder treatable by the compounds and compositions described herein is schizophrenia.

In further aspects, the present invention provides a use of a compound of the invention, of a pharmaceutically acceptable salt thereof, for the manufacture of a medicament for the treatment of cancer. In some embodiments, the present invention provides a use of a compound of the invention in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Further exemplary cancers include diffuse large B-cell lymphoma (DLBCL), mantle cell lymphoma (MCL) and serous and endometrioid cancer. Yet a further exemplary cancer is alveolar soft part sarcoma.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome. Yet further exemplary cancers include glioma.

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of any of the formulas described herein, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary cancer treatments include, for example, chemotherapy, targeted therapies such as antibody therapies, kinase inhibitors, immunotherapy, and hormonal therapy, and anti-angiogenic therapies. Examples of each of these treatments are provided below.

As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within a cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and tositumomab typically used in a variety of B-cell malignancies. Other exemplary antibodies include cetuximab, panitumumab, trastuzumab, alemtuzumab, bevacizumab, edrecolomab, and gemtuzumab. Exemplary fusion proteins include aflibercept and denileukin diftitox. In some embodiments, targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding a tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include permutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including O6-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versustumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, croprop-amide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

In some embodiments, the viral pathogen is selected from the group consisting of herpesviridae, flaviviridae, bunyaviridae, arenaviridae, picornaviridae, togaviridae, papovaviridae, poxviridae, respiratory viruses, hepatic viruses, and other viruses.

Exemplary herpesviridae include herpes simplex virus-1; herpes simplex virus-2; cytomegalovirus, for example, human cytomegalovirus; Varicella-Zoster virus; Epstein-Barr virus; herpes virus-6, for example, human herpes virus-6; and herpes virus-8, for example, human herpes virus-8.

Exemplary flaviviridae include Dengue virus, West Nile virus, yellow fever virus, Japanese encephalitis virus, and Powassen virus.

Exemplary bunyaviridae include Rift Valley fever virus, Punta Toro virus, LaCrosse virus, and Marporal virus.

Exemplary arenaviridae include Tacaribe virus, Pinchinde virus, Junin virus, and Lassa fever virus.

Exemplary picornaviridae include polio virus; enterovirus, for example, enterovirus-71; and Coxsackie virus, for example, Coxsackie virus B3.

Exemplary togaviridae include encephalitis virus, for example, Venezuelan equine encephalitis virus, Eastern equine encephalitis virus, and Western equine encephalitis virus; and Chikungunya virus.

Exemplary papovaviridae include BK virus, JC virus, and papillomavirus.

Exemplary poxviridae include vaccinia virus, cowpox virus, and monkeypox virus.

Exemplary respiratory viruses include SARS coronavirus; influenza A virus, for example, H1N1 virus; and respiratory syncytial virus.

Exemplary hepatic viruses include hepatitis B and hepatitis C viruses.

Exemplary other viruses include adenovirus, for example, adenovirus-5; rabies virus; measles virus; ebola virus; nipah virus; and norovirus.

Ophthalmology

Compounds and methods described herein may be used to treat or prevent an ophthalmology disorder. Exemplary ophthalmology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a compound (e.g., a CRM1 inhibitor), or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, the compounds and compositions described herein useful for wound healing are administered topically, for example, proximate to the wound site, or systemically.

More specifically, a therapeutically effective amount of a compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post surgical wound, a diabetic lesion, a pressure sore, a bedsore, and a condition or wound related to diabetes or poor circulation.

In some embodiments, the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post surgical wound, a diabetic lesion, a pressure sore, a bedsore, and a condition related to diabetes or poor circulation.

The present disclosure also relates to methods and compositions of reducing scar formation during wound healing in a subject. The compounds and compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of a compound described herein (e.g., a CRM1 inhibitor), or a pharmaceutically acceptable salt thereof.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Compounds and compositions described herein are useful as radiosensitizers. Therefore, compounds and compositions described herein can be administered in combination with radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. *Cancer Res.*, 2001; 61:2008-2014 and Goldenber, D. M. *J. Nucl. Med.*, 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, brachytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both α and β-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5$^{th}$ ed., Edited by R. C. Bast et al., July 2000, B C Decker.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations

Ac acetyl
Bn benzyl
Boc tert-butoxy carbonyl
CI Chemical ionization
mCPBA meta-chloroperoxybenzoic acid
DAST diethylaminosulfur trifluoride
DCM dichloromethane
DIPEA N,N-Diisopropyl ethylamine
DMF Dimethylformamide
DMSO dimethylsulfoxide
dppf (diphenylphosphino)ferrocene
EDCI/EDC 3-(ethyliminomethyleneamino)-N,N-dimethyl-propan-1-amine
EDTA ethylenediamine tetraacetic acid
EI electron impact ionization
equiv(s). equivalent(s)
EtOAc ethyl acetate
Et Ethyl
g gram(s)
h hour(s)
HATU (Dimethylamino)-N,N-dimethyl(3H-[1,2,3]triazolo[4,5-b]pyridin-3-yloxy)methaniminium hexafluorophosphate
HOBt 1-Hydroxybenzotriazole
LCMS liquid chromatography mass spectrometry
LRMS low resolution mass spectrometry
Me methyl
mg milligram(s)
min Minute(s)
mL milliliter(s)
Ms mesityl or mesyl
NMR Nuclear magnetic resonance
PBS phosphate-buffered saline
PEG polyethylene glycol
Ph phenyl
RT, rt, r.t. Room temperature
SDS-PAGE Sodium dodecyl sulfate-polyacrylamide gel electrophoresis
T3P Propylphosphonic anhydride (available from Archimica)
TEA triethylamine
TFA trifluoroacetic acid
THF tetrahydrofuran
$t_R$ Retention time Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

Example 1. Synthetic Methods

Synthesis of (E)-N-(2-(4-(5-acetylthiophen-2-yl)-2-chlorophenoxy)ethyl)-3-(pyridin-3-yl)acrylamide (300)

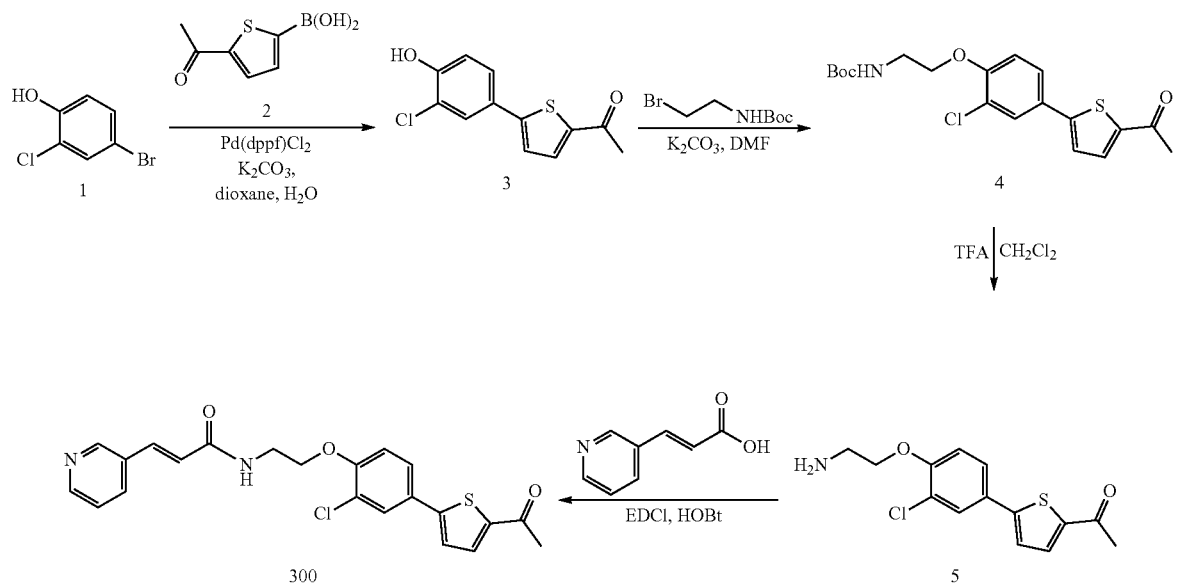

1-(5-(3-Chloro-4-hydroxyphenyl)thiophen-2-yl)ethanone (3) was synthesized using the indicated reagents according to General Procedure 1. Yield (33%). LCMS: m/z 253.1 [M+H]$^+$, $t_R$=1.64 min.

tert-Butyl 2-(4-(5-acetylthiophen-2-yl)-2-chlorophenoxy)ethylcarbamate (4) was synthesized using the indicated reagents according to General Procedure 2. DMF used as solvent. Yield (64%). LCMS: m/z 340.1 [M-55]$^+$, =1.94.

1-(5-(4-(2-Aminoethoxy)-3-chlorophenyl)thiophen-2-yl)ethanone (5) was synthesized using the indicated reagents according to General Procedure 3. Yield (100%). LCMS: m/z 296.0 [M+H]$^+$, $t_R$=1.61 min.

(E)-N-(2-(4-(5-Acetylthiophen-2-yl)-2-chlorophenoxy)ethyl)-3-(pyridin-3-yl)acrylamide (300) was synthesized according to General Procedure 4. Yield (42%). LCMS: m/z 427.1 [M+H]$^+$, $t_R$=1.68 min.

Synthesis of (E)-N-(2-(2-chloro-4-(5-(1-hydroxyethyl) thiophen-2-yl) phenoxy) ethyl)-3-(pyridin-3-yl) acrylamide (301)

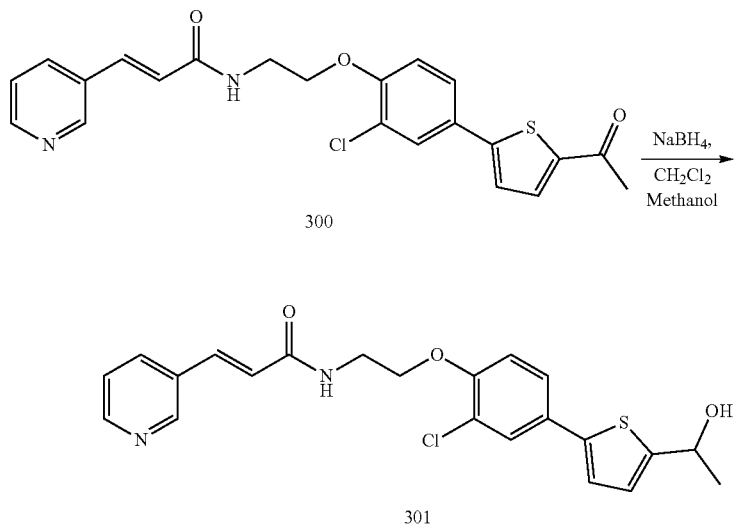 [SMILES: CC(=O)c1ccc(-c2ccc(OCCNC(=O)/C=C/c3cccnc3)c(Cl)c2)s1 ; CC(O)c1ccc(-c2ccc(OCCNC(=O)/C=C/c3cccnc3)c(Cl)c2)s1]

(E)-N-(2-(4-(5-Acetylthiophen-2-yl)-2-chlorophenoxy) ethyl)-3-(pyridin-3-yl) acrylamide (300) (0.050 g, 0.11 mmol) was dissolved in methanol:dichloromethane (1 mL:1 mL) at room temperature and the reaction mixture was cooled to 0° C. At 0° C., sodium borohydride (8.8 mg, 0.23 mmol) was added and the reaction mixture was allowed to warm to room temperature and stirred for 2 h. The reaction mixture was transferred into iced water and extracted with ethyl acetate (3×15 mL) The combined organic layers were washed with brine, dried over anhydrous $Na_2SO_4$ and concentrated under reduced pressure to give crude product, which was purified by chromatography (0-4% methanol/ dichloromethane) to obtain (E)-N-(2-(2-chloro-4-(5-(1-hydroxyethyl) thiophen-2-yl) phenoxy)ethyl)-3-(pyridin-3-yl) acrylamide (301). Yield (14%). $^1$H NMR (400 MHz, DMSO-$d_6$) δ 8.77 (s, 1H), 8.55-8.56 (m, 1H), 8.44-8.47 (t, 1H), 7.98-8.01 (m, 1H), 7.68-7.69 (d, J=2 Hz, 1H), 7.43-7.53 (m, 3H), 7.30 (s, 1H), 7.22-7.24 (d, J=8.8 Hz, 1H), 6.88-6.90 (m, 1H), 6.79-6.83 (d, J=16 Hz, 1H), 5.59-5.60 (d, J=4.8 Hz, 1H), 4.89-4.95 (m, 1H), 4.17-4.20 (t, 2H), 3.59-3.63 (t, 2H), 1.42-1.43 (d, 3H). LCMS: m/z 429.00 [M+H]$^+$, $t_R$=1.99 min.

Synthesis of (E)-N-(2-(3-(5-acetylthiophen-2-yl)-2-chlorophenoxy) ethyl)-3-(pyridin-3-yl) acrylamide (302)

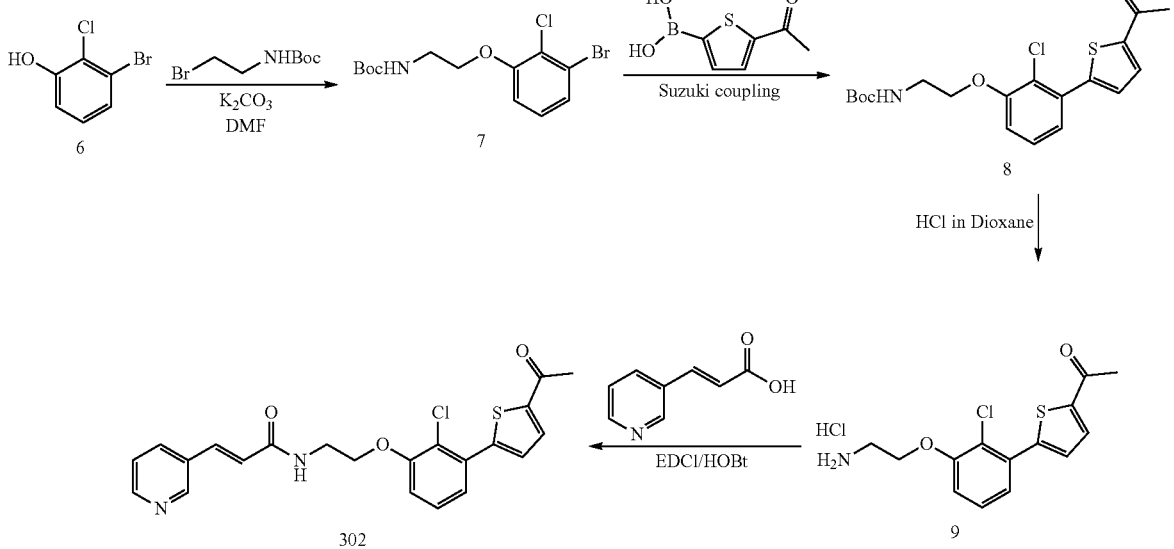

tert-Butyl 2-(3-bromo-2-chlorophenoxy) ethylcarbamate (7) was synthesized using the indicated reagents according to General Procedure 2. Yield (35%). $^1$H NMR (400 MHz, CDCl$_3$) δ 7.26-7.28 (dd, J=8 Hz, 1H), 7.08-7.29 (t, 1H), 6.88-6.90 (dd, J=8 Hz, 1H), 4.08-4.11 (t, 2H), 3.59-3.63 (q, 2H), 1.47 (s, 9H). LCMS: m/z 295.79 [M-56]$^+$, $t_R$=2.74 min.

tert-Butyl 2-(3-(5-acetylthiophen-2-yl)-2-chlorophenoxy) ethylcarbamate (8) was synthesized using General Procedure 1. Yield (30%). $^1$H NMR (400 MHz, CDCl$_3$) δ 7.70-7.71 (d, J=4 Hz, 1H), 7.38-7.39 (d, J=4 Hz 1H), 7.27-7.29 (d, J=8 Hz, 1H), 7.16-7.18 (d, J=8.8 Hz, 1H), 6.97-6.99 (d, J=8 Hz, 1H), 4.13-4.16 (t, 2H), 3.63-3.66 (q, 2H), 2.61 (s, 3H), 1.42 (s, 9H). LCMS: m/z 340.18 [M-56]$^+$, $t_R$=2.52 min.

1-(5-(3-(2-Aminoethoxy)-2-chlorophenyl) thiophen-2-yl) ethanone (9) was synthesized using the indicated reagents according to General Procedure 3. Yield (50%).

(E)-N-(2-(3-(5-Acetylthiophen-2-yl)-2-chlorophenoxy) ethyl)-3-(pyridin-3-yl) acrylamide (302) was synthesized according to General Procedure 4. Yield (15%). $^1$H NMR (400 MHz, CDCl$_3$) δ 8.77 (s, 1H), 8.60-8.61 (d, J=4 Hz, 1H), 7.83-7.85 (d, J=4 Hz, 1H), 7.71-7.72 (d, J=4 Hz, 1H), 7.66-7.69 (d, J=15.6 Hz, 1H), 7.34-7.38 (m, 2H), 7.29-7.31 (m, 2H), 7.19-7.21 (d, J=8 Hz, 1H), 7.01-7.03 (d, J=8 Hz, 1H), 6.51-6.55 (d, J=15.6 Hz, 1H), 4.24-4.26 (t, 2H), 3.91-3.94 (q, 2H), 2.61 (s, 3H). LCMS: m/z 427.10 [M+H]$^+$, $t_R$=2.0 min.

Synthesis of (E)-N-(2-(5-(5-acetylthiophen-2-yl)-2-chlorophenoxy)ethyl)-3-(pyridin-3-yl)acrylamide (303)

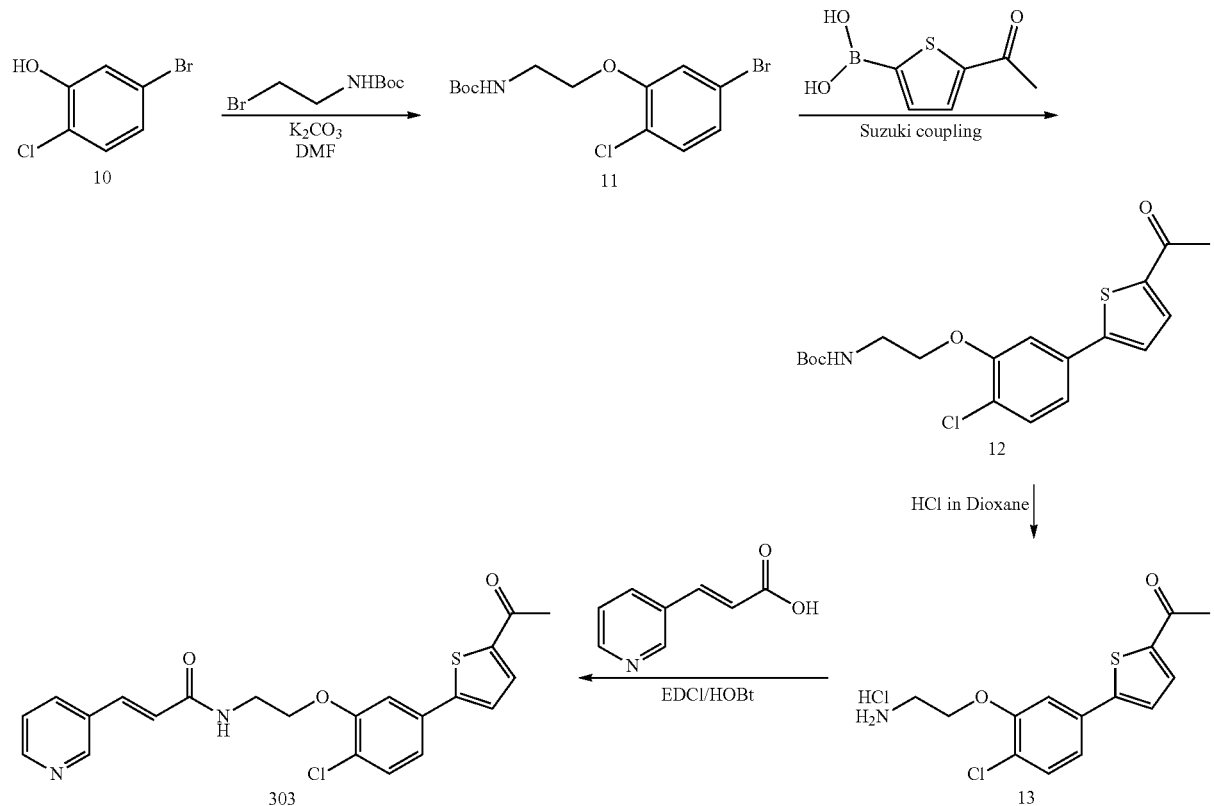

tert-Butyl 2-(5-bromo-2-chlorophenoxy)ethylcarbamate (11) was synthesized using the indicated reagents according to General Procedure 2. Yield (80%). LCMS: m/z 252.08 [M-56]$^+$, $t_R$=2.66 min.

tert-Butyl 2-(5-(5-acetylthiophen-2-yl)-2-chlorophenoxy)ethylcarbamate (12) was synthesized according to General Procedure 1. Yield (25%). LCMS: m/z 296.2[M-100]$^+$, $t_R$=2.63 min.

1-(5-(3-(2-Aminoethoxy)-4-chlorophenyl)thiophen-2-yl)ethanone hydrochloride (13) was synthesized using the indicated reagents according to General Procedure 3. Yield (75%). $^1$H NMR (400 MHz, DMSO-d$_6$) δ 8.05 (s, 2H), 7.99-8.00 (d, J=2 Hz, 1H), 7.77-7.78 (d, J=4 Hz, 1H), 7.54-7.57 (m, 2H), 7.42-7.44 (dd, J$_1$=2 Hz, J$_2$=6 Hz, 1H), 4.38-4.40 (t, J=5.2 Hz, 2H), 3.29 (bs, 2H), 2.53 (s, 3H). LCMS: m/z 296 [M-35]$^+$, $t_R$=1.81 min.

(E)-N-(2-(5-(5-Acetylthiophen-2-yl)-2-chlorophenoxy)ethyl)-3-(pyridin-3-yl)acrylamide (303) was synthesized according to General Procedure 4. Yield (65%). $^1$H NMR (400 MHz, DMSO-d$_6$) δ 8.76 (d, J=2 Hz, 1H), 8.55-8.56 (m, 1H), 8.47-8.50 (t, J=5.6 Hz, 1H), 7.96-8.0 (m, 2H), 7.78-7.79 (d, J=4 Hz, 1H), 7.37-7.56 (m, 4H), 6.82-7.36 (m, 1H), 6.78-6.82 (d, J=16 Hz, 1H), 4.28-4.31 (t, J=6 Hz, 2H), 3.62-3.64 (t, J=5.6 Hz, 2H), 2.55 (s, 3H). LCMS: m/z 427.15 [M+H]$^+$, $t_R$=2.127 min.

Synthesis of (E)-N-(2-(4-(5-acetylthiophen-2-yl)-2-chlorophenoxy) ethyl)-3-(2-chloropyridin-3-yl) acrylamide (304)

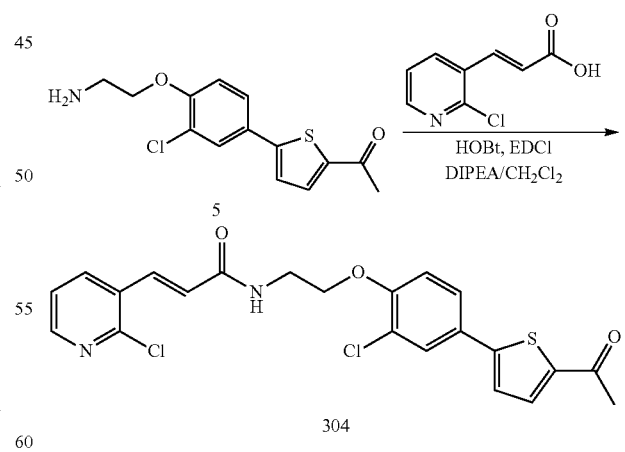

(E)-N-(2-(4-(5-Acetylthiophen-2-yl)-2-chlorophenoxy) ethyl)-3-(2-chloropyridin-3-yl) acrylamide (304) was synthesized according to General Procedure 4. Yield (48%). $^1$H NMR (400 MHz, DMSO-d$_6$) δ 8.58 (s, 1H), 8.42-8.43 (m, 1H), 8.14-8.16 (m, 1H), 7.93-7.94 (d, J=4 Hz, 1H), 7.89-7.90 (d, J=2.4 Hz, 1H), 7.64-7.72 (m, 3H), 7.50-7.53 (m, 1H), 7.29-7.31 (d, J=8.8 Hz, 1H), 6.79-6.83 (d, J=15.6 Hz, 1H), 4.22-4.25 (t, 2H), 3.62-3.65 (t, 2H), 2.54 (s, 3H). LCMS: m/z 461.07 [M+H]$^+$, $t_R$=2.35 min.

Synthesis of (E)-N-(2-(4-(5-acetylthiophen-2-yl)-2-chlorophenoxy) ethyl)-3-(2-methylpyridin-3-yl) acrylamide (305)

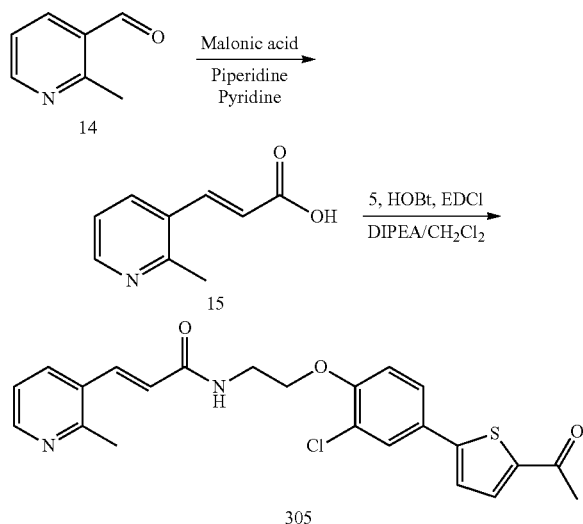

Synthesis of (E)-3-(2-methylpyridin-3-yl) acrylic acid (15)

General Procedure 5: Condensation of Aldehyde with Malonic Acid

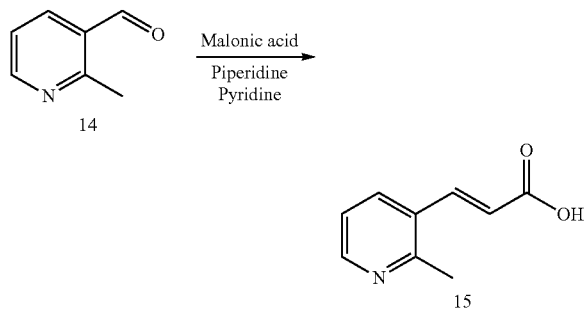

To a solution of 2-methyl-pyridine 3-carbaldehyde (14) (0.5 g, 4.1 mmol) in pyridine (2.5 mL) was added malonic acid (0.65 g, 6.1 mmol) and catalytic piperidine (0.2 mL). The reaction mixture was refluxed at 100° C. for 3 h and then concentrated under reduced pressure. The residue was diluted with water and the solid product was filtered to give (E)-3-(2-methylpyridin-3-yl) acrylic acid 15. Yield (0.47 g, 71%). $^1$H NMR (400 MHz, DMSO-d$_6$) δ 12.62 (bs, 1H), 8.45-8.46 (m, 1H), 8.09-8.11 (m, 1H), 7.51-7.91 (d, J=16 Hz, 1H), 7.27-7.30 (m, 1H), 6.51-6.55 (d, J=16 Hz, 1H), 2.58 (s, 3H).

Synthesis of (E)-N-(2-(4-(5-acetylthiophen-2-yl)-2-chlorophenoxy) ethyl)-3-(2-methylpyridin-3-yl) acrylamide (305)

(E)-N-(2-(4-(5-acetylthiophen-2-yl)-2-chlorophenoxy) ethyl)-3-(2-methylpyridin-3-yl) acrylamide (305) was synthesized using the indicated reagents according to General Procedure 4. Yield (48%). $^1$H NMR (400 MHz, DMSO-d$_6$) δ 8.48-8.51 (m, 1H), 8.42-8.44 (m, 1H), 7.93-7.94 (d, J=4 Hz, 1H), 7.88-7.90 (m, 2H), 7.69-7.72 (m, 1H), 7.62-7.66 (m, 2H), 7.29-7.31 (m, 2H), 6.36-6.67 (d, J=16 Hz, 1H), 4.22-4.24 (t, 2H), 3.60-3.64 (m, 2H), 2.57 (s, 3H), 2.54 (s, 3H). LCMS: m/z 441.16 [M+H]$^+$, $t_R$=1.94 min.

Synthesis of N-(2-(4-(5-acetylthiophen-2-yl)-2-chlorophenoxy) ethyl)-3-(pyridin-3-yl)propanamide (306)

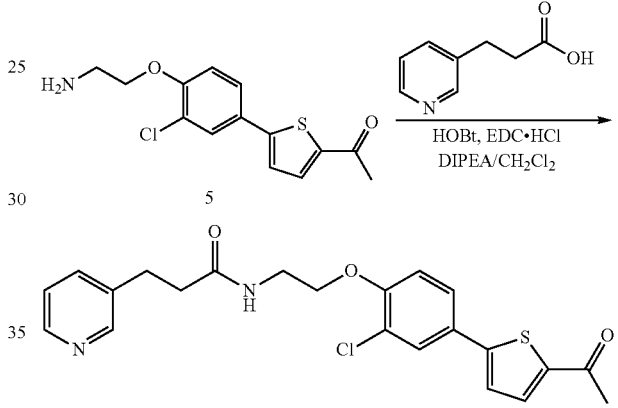

N-(2-(4-(5-Acetylthiophen-2-yl)-2-chlorophenoxy) ethyl)-3-(pyridin-3-yl)propanamide (306) was synthesized according to General Procedure 4. Yield (48%). $^1$H NMR (400 MHz, DMSO-d$_6$) δ 8.43 (s, 1H), 8.36-8.37 (m, 1H), 8.14 (t, 1H), 7.93-7.84 (d, J=4 Hz, 1H), 7.88-7.89 (d, J=2.4 Hz, 1H), 7.68-7.71 (dd, J$_1$, J$_2$=2.4 Hz, 1H), 7.64-7.65 (d, J=4 Hz, 1H), 7.60-7.62 (m, 1H), 7.25-7.27 (m, 1H), 7.22-7.24 (d, J=8.8 Hz, 1H), 4.07-4.10 (t, 2H), 3.44-3.45 (m, 2H), 2.82-2.86 (m, 2H), 2.54 (s, 3H), 2.42-2.46 (m, 2H). LCMS: m/z 429.2 [M+H]$^+$, $t_R$=1.93 min.

Synthesis of (E)-N-(2-(4-(5-acetylthiophen-2-yl)-2-chlorophenoxy) ethyl)-3-(3,5-dimethylisoxazol-4-yl) acrylamide (307)

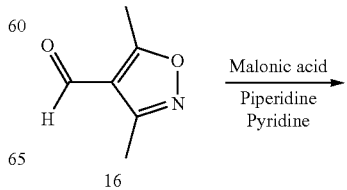

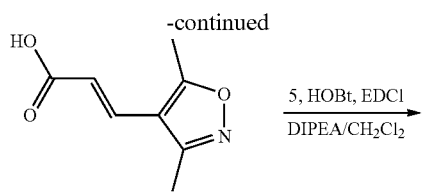

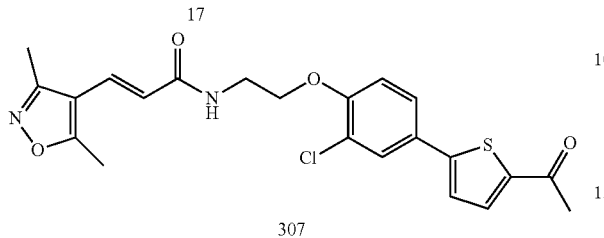
307

(E)-3-(3,5-Dimethylisoxazol-4-yl)acrylic acid (17) was synthesized using the indicated reagents according to General Procedure 5. Yield (71%). $^1$H NMR (400 MHz, DMSO-$d_6$) δ 12.48 (s, 1H), 7.63-7.40 (d, J=16.4 Hz, 1H), 6.13-6.17 (d, J=16.4 Hz, 1H), 2.51 (s, 3H), 2.34 (s, 3H).

(E)-N-(2-(4-(5-Acetylthiophen-2-yl)-2-chlorophenoxy)ethyl)-3-(3,5-dimethylisoxazol-4-yl)acrylamide (307) was synthesized using the indicated reagents according to General Procedure 4. Yield (48%). $^1$H NMR (400 MHz, DMSO-$d_6$) δ 8.40-8.43 (t, 1H), 7.93-7.94 (d, J=4 Hz, 1H), 7.89-7.90 (d, J=2.4 Hz, 1H), 7.69-7.71 (m, 1H), 7.64-7.65 (d, J=4 Hz, 1H), 7.28-7.30 (d, J=8.8 Hz, 1H), 7.21-7.25 (d, J=16 Hz, 1H), 6.46-6.50 (d, J=16 Hz, 1H), 4.19-4.22 (t, 2H), 3.58-3.62 (m, 2H), 2.53 (s, 3H), 2.49 (s, 3H), 2.33 (s, 3H). LCMS: m/z 445.16 [M+H]$^+$, $t_R$=2.31 min.

Synthesis of (E)-N-(2-(4-(5-acetylthiophen-2-yl)-2-chlorophenoxy) ethyl)-3-(6-aminopyridin-3-yl)acrylamide (308)

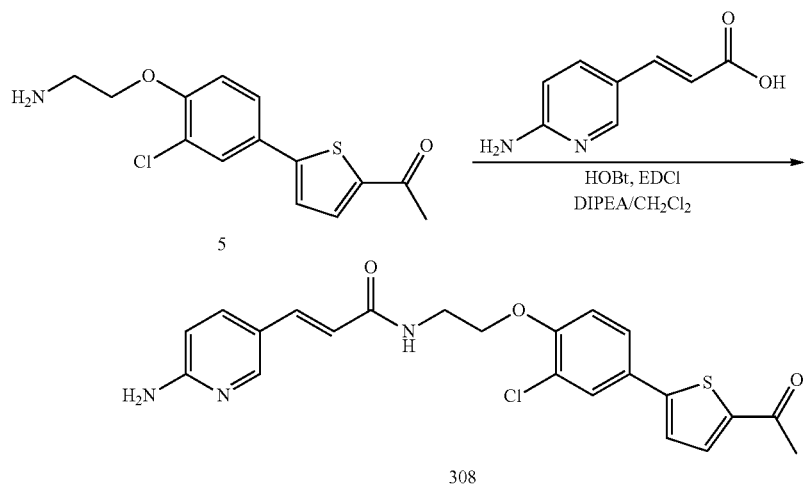
308

(E)-N-(2-(4-(5-Acetylthiophen-2-yl)-2-chlorophenoxy)ethyl)-3-(6-aminopyridin-3-yl) acrylamide (308) was synthesized using the indicated reagents according to General Procedure 4. Yield (30%). $^1$H NMR (400 MHz, DMSO-$d_6$) δ 8.20-8.23 (t, 1H), 8.07-8.08 (d, J=2 Hz, 1H), 7.93-7.94 (d, J=4 Hz, 1H), 7.88-7.89 (d, J=2.4 Hz, 1H), 7.62-7.71 (m, 3H), 7.33 (s, 1H), 7.28-7.30 (d, J=8 Hz, 1H), 6.56 (bs, 2H), 6.50-6.52 (d, J=9 Hz, 1H), 6.39-6.43 (d, J=16 Hz, 1H), 4.18-4.21 (t, 2H), 3.56-3.60 (m, 2H), 2.53 (s, 3H). LCMS: m/z 442.21 [M+H]$^+$, $t_R$=1.92 min.

Synthesis of N-(2-(4-(5-acetylthiophen-2-yl)-2-chlorophenoxy)ethyl)-3-(pyridin-3-yl)propiolamide (309)

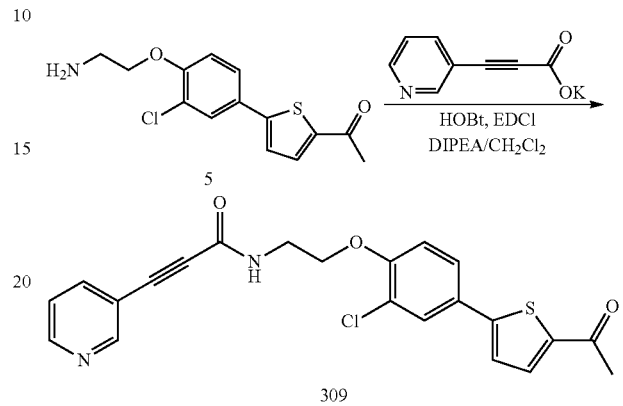
309

1-(5-(4-(2-Aminoethoxy)-3-chlorophenyl)thiophen-2-yl)ethanone 5 (0.2 g, 0.67 mmol) was dissolved in DMF (2 mL) at room temperature. The reaction mixture was cooled to 0° C. and potassium 3-(pyridin-3-yl)propiolate (0.25 g, 0.13 mmol), HOBt (0.18 g, 0.13 mmol), and EDCI (0.51 g, 0.13 mmol) were added followed by dropwise addition of DIPEA (0.46 mL, 2.7 mmol). The reaction mixture was allowed to warm to room temperature and stirred for 2 h. The reaction mixture was transferred into iced water and extracted with ethyl acetate (3×50 mL). The combined organic layers were washed with brine and dried over anhydrous Na$_2$SO$_4$. The organic layer was concentrated under reduced pressure to give the crude product, which was purified by chromatography (0-10% MeOH in CH$_2$Cl$_2$) to yield N-(2-(4-(5-acetylthiophen-2-yl)-2-chlorophenoxy)ethyl)-3-(pyridine-3-yl)propiolamide (309). (Yield: 0.06 g, 21%). $^1$H NMR (400 MHz, DMSO-$d_6$) δ 9.16 (s, 1H), 8.77 (s, 1H), 8.67 (d, J=3.6 Hz, 1H), 8.02 (d, J=8 Hz, 1H), 7.93 (d, J=3.6 Hz, 1H), 7.90 (s, 1H), 7.71 (d, J=6.8 Hz, 1H), 7.65 (s, 1H), 7.53-7.49 (m, 1H), 7.27 (d, J=8.4 Hz, 1H), 4.27-4.20 (m, 2H), 3.60-3.58 (m, 2H), 2.54 (s, 3H). LCMS: m/z 424.9 [M–H]⁺, $t_R$=5.96 min.

Synthesis of (E)-N-(2-(4-(5-acetylthiophen-2-yl)-2-chlorophenoxy)ethyl)-3-(pyridazin-3-yl)acrylamide (310)

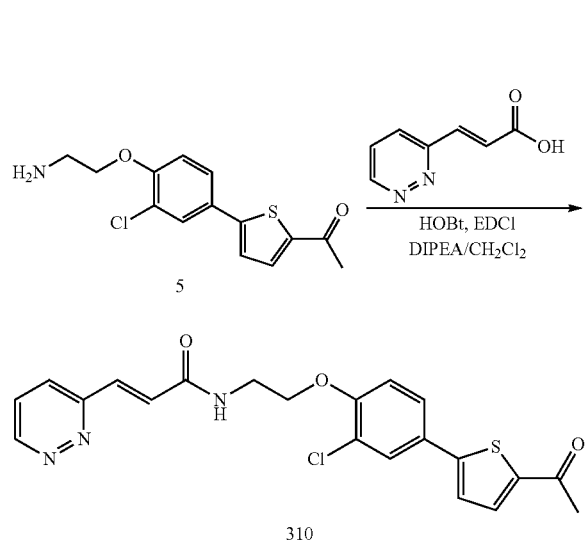

(E)-N-(2-(4-(5-Acetylthiophen-2-yl)-2-chlorophenoxy) ethyl)-3-(pyridazin-3-yl)acrylamide (310) was synthesized using the indicated reagents according to General Procedure 4. Yield (45%). ¹H NMR (400 MHz, DMSO-d₆) δ 9.18-9.20 (d, J=6.4 Hz, 1H), 8.69-8.72 (m, 1H), 7.92-7.94 (m, 2H), 7.89-7.90 (d, J=2.4 Hz, 1H), 7.69-7.77 (m, 2H), 7.60-7.65 (m, 2H), 7.29-7.31 (d, J=8.8 Hz, 1H), 7.24-7.28 (d, J=16 Hz, 1H), 4.23-4.26 (t, 2H), 3.62-3.66 (m, 2H), 2.53 (s, 3H). LCMS: m/z 429.2 [M+H]⁺, $t_R$=1.93 min.

Synthesis of (E)-N-(2-(4-(5-acetylthiophen-2-yl)-2-chlorophenoxy)ethyl)-N-methyl-3-(pyridin-3-yl)acrylamide (311)

Synthesis of tert-butyl 2-(4-bromo-2-chlorophenoxy)ethylcarbamate (18)

General Procedure 2: Alkylation

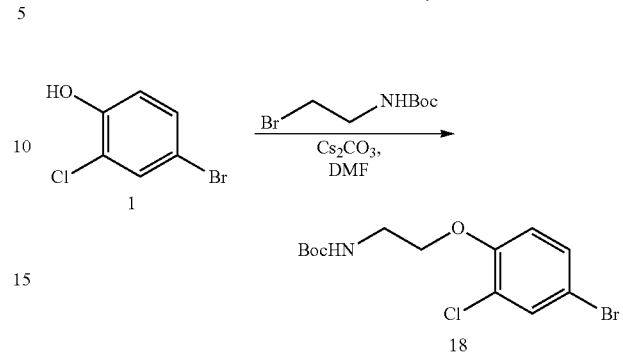

4-Bromo-2-chlorophenol (1) (10.0 g, 48.19 mmol) was dissolved in DMF (100 mL) at room temperature. tert-Butyl 2-bromoethylcarbamate (26.05 g, 120.48 mmol) and Cs₂CO₃ (39.25 g, 120.48 mmol) were added at room temperature and heated at 120° C. for 2 h. The reaction mixture was cooled to room temperature, transferred into iced water and extracted with ethyl acetate (3×350 mL). The combined organic layers were washed with brine and dried over anhydrous Na₂SO₄. The organic layer was concentrated under reduced pressure to give tert-butyl 2-(4-bromo-2-chlorophenoxy)ethylcarbamate (18), which was used in the next step without further purification. LCMS: m/z 295.79 [M-56]⁺, $t_R$=2.57 min.

Synthesis of tert-butyl 2-(4-bromo-2-chlorophenoxy)ethyl(methyl)carbamate (19)

tert-Butyl 2-(4-bromo-2-chlorophenoxy)ethylcarbamate (18) (0.4 g, 0.57 mmol) was dissolved in THF (5 mL) at room temperature. The reaction mixture was cooled to 0° C. and sodium hydride (60% in mineral oil) (0.05 g, 0.68 mmol) was added. After stirring for 2 h, methyl iodide (0.14 g, 0.85 mmol) was added dropwise. The reaction mixture was allowed to warm to room temperature and stirred for 18 h. The reaction mixture was transferred into iced water and

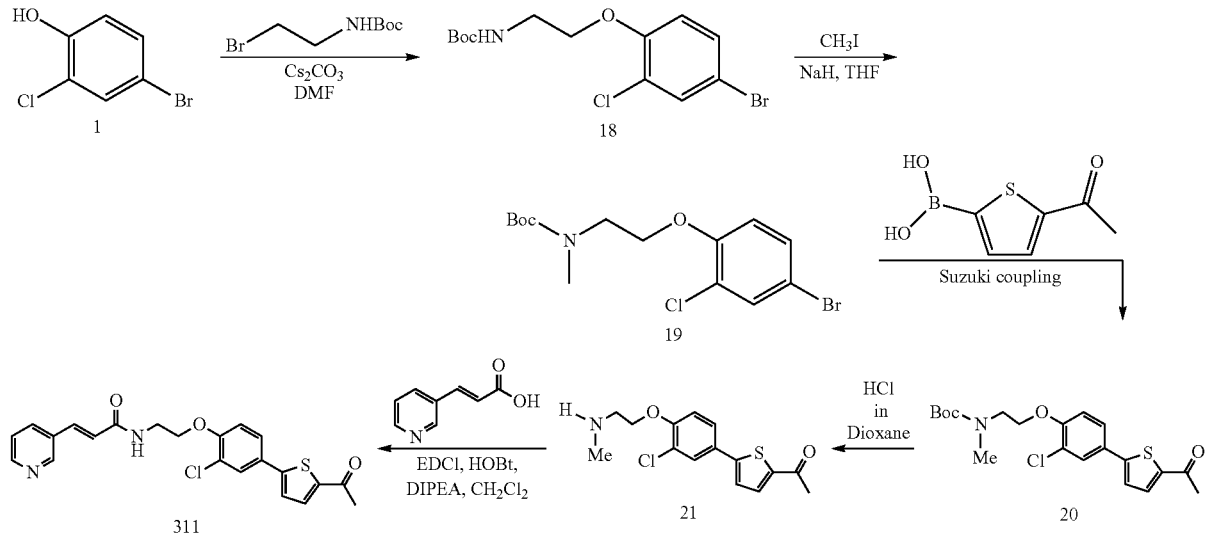

extracted with ethyl acetate (3×25 mL). The combined organic layers were washed with brine and dried over anhydrous Na$_2$SO$_4$. The organic layer was concentrated under reduced pressure to give crude tert-butyl 2-(4-bromo-2-chlorophenoxy)ethyl(methyl)carbamate (19), which was used in the next step without further purification. LCMS: m/z 308.12 [M-56]$^+$, $t_R$=2.5 min.

Synthesis of tert-butyl 2-(4-(5-acetylthiophen-2-yl)-2-chlorophenoxy) ethyl (methyl) carbamate (20)

General Procedure 1: Cross-Coupling

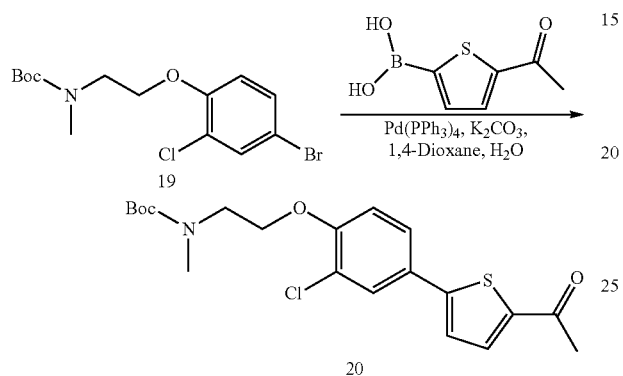

tert-Butyl 2-(4-bromo-2-chlorophenoxy)ethyl(methyl) carbamate (19) (0.2 g, 0.48 mmol) was dissolved in 1,4-dioxane (3 mL) at room temperature and degassed with N$_2$ gas for 5 min. Tetrakis(triphenylphosphine)palladium (0) (0.05 g, 20 mol %) and 5-acetyl thiophene-2-boronic acid (0.13 g, 0.82 mmol) were added at room temperature and stirred for 5 min. A degassed solution of K$_2$CO$_3$ (0.15 g, 1.09 mmol) in water (0.5 mL) was added, and the reaction mixture was irradiated under microwave for 30 min at 90° C. The reaction mixture was transferred into iced water and extracted with ethyl acetate (3×50 mL). The combined organic layers were washed with brine, dried over anhydrous Na$_2$SO$_4$ and concentrated under reduced pressure to give crude compound, which was purified by silica gel chromatography (0-50% ethyl acetate/n-hexane) to obtain tert-butyl 2-(4-(5-acetylthiophen-2-yl)-2-chlorophenoxy) ethyl (methyl) carbamate (20). (Yield: 0.05 g, 23%). $^1$H NMR (400 MHz, CDCl$_3$) δ 7.67 (bs, 1H), 7.66 (d, J=4 Hz, 1H), 7.53-7.50 (m, 1H), 7.24 (d, J=4 Hz, 1H), 6.97 (d, J=8.0 Hz, 1H), 4.23-4.11 (m, 2H), 3.69-3.61 (m, 2H), 3.07 (s, 3H), 2.58 (s, 3H), 1.44 (s, 9H).

Synthesis of 1-(5-(3-chloro-4-(2-(methylamino) ethoxy)phenyl)thiophen-2-yl)ethanone hydrochloride (21)

General Procedure 3: Boc Deprotection

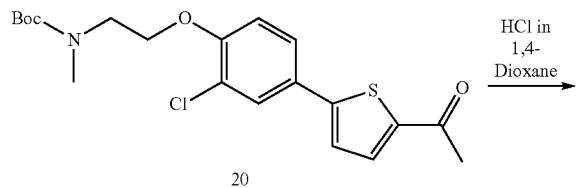

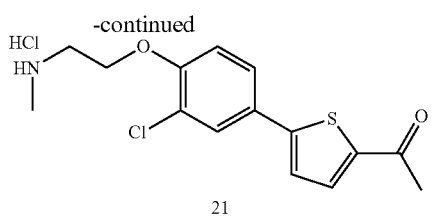

tert-Butyl 2-(4-(5-acetylthiophen-2-yl)-2-chlorophenoxy) ethyl(methyl)carbamate (20) (0.03 g, 0.08 mmol) was dissolved in dichloromethane (1 mL) at room temperature. The reaction mixture was cooled to 0° C. and HCl in dioxane (0.5 mL) was added dropwise. The reaction mixture was allowed to warm to room temperature and stirred for 3 h. The reaction mixture was concentrated under reduced pressure to give crude of 1-(5-(3-chloro-4-(2-(methylamino)ethoxy) phenyl)thiophen-2-yl) ethanone hydrochloride (21) which was used in the next step without further purification.

Synthesis of (E)-N-(2-(4-(5-acetylthiophen-2-yl)-2-chlorophenoxy)ethyl)-N-methyl-3-(pyridin-3-yl) acrylamide (311)

General Procedure 4: Amide Coupling

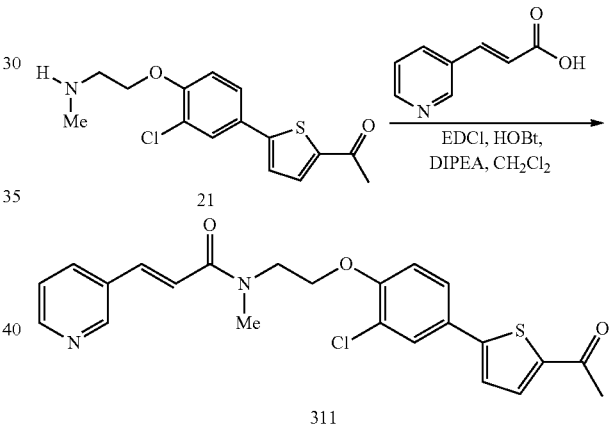

1-(5-(3-Chloro-4-(2-(methylamino)ethoxy)phenyl)thiophen-2-yl)ethanone hydrochloride (21) (0.03 g, 0.09 mmol) was dissolved in dichloromethane (5 mL). The reaction mixture was cooled to 0° C. and (E)-3-(pyridin-3-yl) acrylic acid (0.017 g, 0.011 mmol), EDCI (0.022 g, 0.013 mmol), and HOBt (0.018 g, 0.013 mmol) were added followed by DIPEA (0.03 mL, 0.193 mmol). The reaction mixture was allowed to warm to room temperature and stirred for 8 h. The reaction mixture was transferred into iced water and extracted with ethyl acetate (3×25 mL). The combined organic layers were washed with brine, dried over anhydrous Na$_2$SO$_4$ and concentrated under reduced pressure to give crude product, which was purified by silica gel chromatography (0-5% MeOH in CH$_2$Cl$_2$) to obtain (E)-N-(2-(4-(5-acetylthiophen-2-yl)-2-chlorophenoxy)ethyl)-N-methyl-3-(pyridin-3-yl)acrylamide (311). (Yield: 0.01 g, 23%). $^1$H NMR (400 MHz, DMSO-d$_6$) δ 8.82 (s, 1H), 8.53 (d, J=3.6 Hz, 1H), 8.04 (bs, 1H), 7.84 (d, J=4 Hz, 1H), 7.78 (s, 1H), 7.65 (dd, J$_1$, J$_2$=2.4 Hz, 1H), 7.48-7.53 (m, 2H), 7.37-7.40 (m, 1H), 7.26-7.32 (m, 2H), 4.33-4.36 (m, 2H), 3.92 (bs, 2H), 3.03 (s, 3H), 2.53 (s, 3H). LCMS: m/z 441.17 [M+H]$^+$, $t_R$=2.57 min.

Synthesis of (E)-N-(2-(2-(5-acetylthiophen-2-yl)phenoxy)ethyl)-3-(pyridin-3-yl)acrylamide (312)

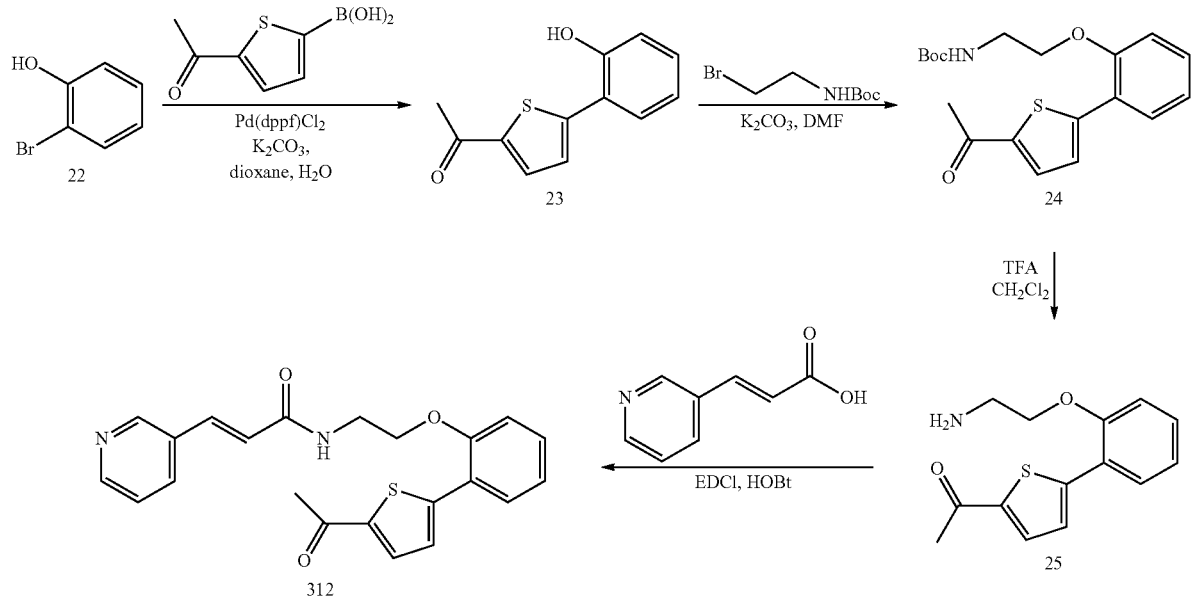

1-(5-(2-Hydroxyphenyl)thiophen-2-yl)ethanone (23) was synthesized using the indicated reagents according to General Procedure 1. Yield (47%). LCMS: m/z 219.0 [M+H]+, $t_R$=1.66 min.

tert-Butyl 2-(2-(5-acetylthiophen-2-yl)phenoxy)ethylcarbamate (24) was synthesized using the indicated reagents according to General Procedure 2. Yield (60%). LCMS: m/z 306.1 [M-55]+, $t_R$=1.90 min.

1-(5-(2-(2-Aminoethoxy)phenyl)thiophen-2-yl)ethanone (25) was synthesized according to General Procedure 3. Yield (100%). LCMS: m/z 262.1 [M+H]+, $t_R$=1.57 min.

(E)-N-(2-(2-(5-Acetylthiophen-2-yl)phenoxy)ethyl)-3-(pyridin-3-yl)acrylamide (312) was synthesized using General Procedure 4. Yield (22%). $^1$H NMR (400 MHz, CD$_3$OD): δ 9.00 (s, 1H), 8.73 (d, J=4.8 Hz, 1H), 8.61 (d, J=8.0 Hz, 1H), 7.94-7.91 (m, 1H), 7.82-7.78 (m, 2H), 7.66-7.61 (m, 2H), 7.39-7.36 (m, 1H), 7.19 (d, J=8.0 Hz, 1H), 7.10-7.06 (m, 1H), 6.97 (d, J=15.6 Hz, 1H), 4.37 (t, J=5.2 Hz, 2H), 3.84 (s, J=5.2 Hz, 2H), 2.53 (s, 3H). LCMS: m/z 393.2 [M+H]+; $t_R$=1.64 min.

Synthesis of (E)-3-(6-aminopyridin-3-yl)-N-(2-(3-chloro-4'-(4-methylpiperazine-1-carbonyl)biphenyl-4-yloxy)ethyl)acrylamide (313)

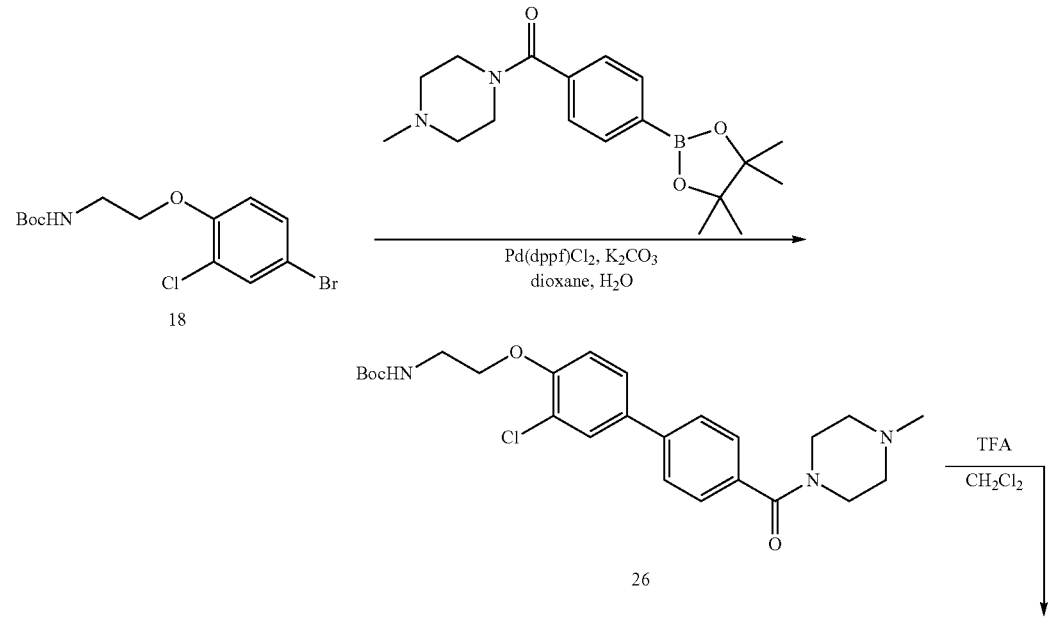

71 72

-continued

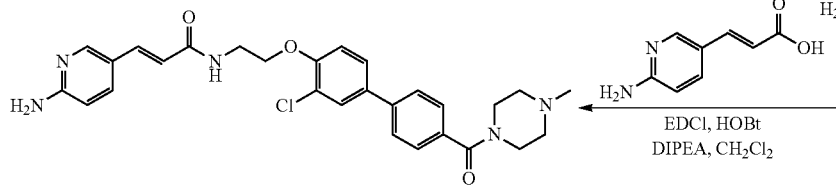 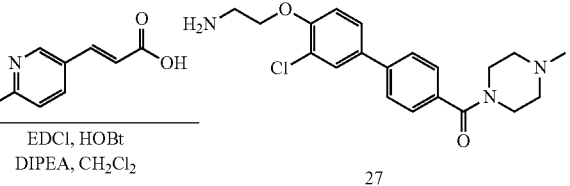

tert-Butyl 2-(3-chloro-4'-(4-methylpiperazine-1-carbonyl)biphenyl-4-yloxy)ethylcarbamate (26) was synthesized using the indicated reagents according to General Procedure 1. Yield (69%). LCMS: m/z 474.0 [M+H]$^+$; $t_R$=1.778 min.

(4'-(2-Aminoethoxy)-3'-chlorobiphenyl-4-yl)(4-methylpiperazin-1-yl)methanone (27) was synthesized using the indicated reagents according to General Procedure 3. Yield (100%). LCMS: m/z 374.0 [M+H]$^+$; $t_R$=1.42 min.

(E)-3-(6-Aminopyridin-3-yl)-N-(2-(3-chloro-4'-(4-methylpiperazine-1-carbonyl)biphenyl-4-yloxy)ethyl)acrylamide (313) was synthesized using the indicated reagents according to General Procedure 4. Yield (37%). $^1$H NMR (400 MHz, DMSO-d$_6$) δ 8.19 (t, J=5.6 Hz, 1H), 8.07 (d, J=2.2 Hz, 1H), 7.80 (d, J=2.3 Hz, 1H), 7.73 (d, J=8.2 Hz, 2H), 7.66 (dd, J=2.1 Hz, J=8.6 Hz, 1H), 7.61 (dd, J=2.3 Hz, J=8.8 Hz, 1H), 7.45 (d, J=8.3 Hz, 2H), 7.31 (dd, J=4.0 Hz, J=12.8 Hz, 2H), 6.39-6.48 (m, 4H), 4.20 (t, J=5.6 Hz, 2H), 3.54-3.61 (m, 4H), 3.36-3.39 (m, 2H), 2.26-2.33 (m, 4H), 2.20 (s, 3H). LCMS: m/z 520.3 [M+H]$^+$; $t_R$=1.51 min.

Synthesis of (E)-3-(6-aminopyridin-3-yl)-N-(2-(3-chloro-3'-methyl-4'-(morpholine-4-carbonyl)biphenyl-4-yloxy)ethyl)acrylamide (314)

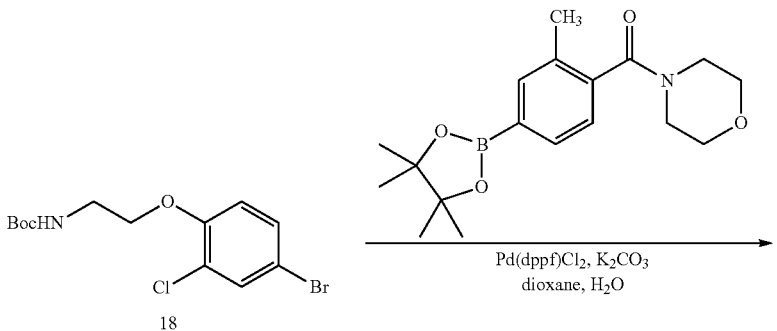

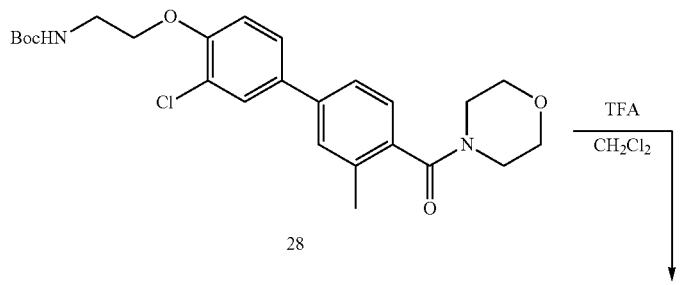

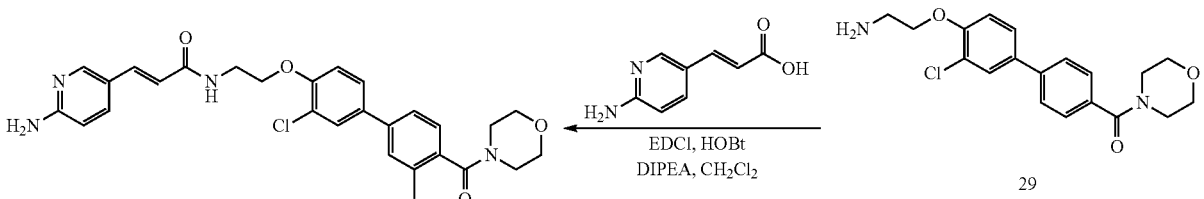

tert-Butyl 2-(3-chloro-3'-methyl-4'-(morpholine-4-carbonyl)biphenyl-4-yloxy)ethylcarbamate (28) was synthesized using the indicated reagents according to General Procedure 1. Yield (63%). LCMS: m/z 475.2 [M+H]$^+$, $t_R$=1.77 min.

(4'-(2-Aminoethoxy)-3'-chloro-3-methylbiphenyl-4-yl)(morpholino)methanone (29) was synthesized using the indicated reagents according to General Procedure 3. Yield (100%). LCMS: m/z 375.2 [M+H]$^+$, $t_R$=1.14 min.

(E)-3-(6-Aminopyridin-3-yl)-N-(2-(3-chloro-3'-methyl-4'-(morpholine-4-carbonyl)biphenyl-4-yloxy)ethyl)acrylamide (314) was synthesized using the indicated reagents according to General Procedure 4. Yield (15%). $^1$H NMR (400 MHz, DMSO-d$_6$) 8.21 (dd, J=2.0 Hz, J=9.6 Hz, 1H), 8.04 (s, 1H), 7.68 (d, J=2.0 Hz, 1H), 7.58-7.43 (m, 4H), 7.28 (d, J=7.6 Hz, 1H), 7.20 (d, J=7.6 Hz, 1H), 7.07 (d, J=9.6 Hz, 1H), 6.66 (d, J=15.6 Hz, 1H), 4.27 (t, J=5.2 Hz, 2H), 3.82-3.77 (m, 8H), 3.65-3.59 (m, 2H), 2.38 (s, 3H). LCMS: m/z 521.0 [M+H]$^+$, $t_R$=1.30 min.

Synthesis of (E)-N-(2-(2-chloro-4-(5-(2-hydroxypropan-2-yl)thiophen-2-yl)phenoxy)ethyl)-3-(pyridin-3-yl)acrylamide (320) and (E)-N-(2-(2-chloro-4-(5-(prop-1-en-2-yl)thiophen-2-yl)phenoxy)ethyl)-3-(pyridin-3-yl)acrylamide (315)

General Procedure 6: Addition of MeMgBr to Ketone (E)-N-(2-(4-(5-Acetylthiophen-2-yl)-2-chlorophenoxy)ethyl)-3-(pyridin-3-yl)acrylamide (300) (60 mg, 0.14 mmol) was dissolved in THF (5 mL) and CH$_3$MgBr (1M in THF) (0.42 mL, 0.42 mmol) was added at 0° C. The reaction mixture was stirred at room temperature for 3 h. NaHCO$_3$ aqueous solution was added to the reaction mixture and extracted with dichloromethane (15 mL×3). The combined organic layers were washed with brine, dried over anhydrous Na$_2$SO$_4$, and concentrated under reduced pressure to give the crude product, which was purified by preparative-HPLC to give (E)-N-(2-(2-chloro-4-(5-(2-hydroxypropan-2-yl)thiophen-2-yl)phenoxy)ethyl)-3-(pyridin-3-yl)acrylamide (320) (yield: 8 mg, 13%) and (E)-N-(2-(2-chloro-4-(5-(prop-1-en-2-yl)thiophen-2-yl)phenoxy)ethyl)-3-(pyridin-3-yl)acrylamide (315).

Data for (320): $^1$H NMR (400 MHz, CD$_3$OD): δ 8.72 (d, J=2.0 Hz, 1H), 8.52 (dd, J=1.2 Hz, J=4.8 Hz, 1H), 8.07-8.04 (m, 1H), 7.61-7.57 (m, 2H), 7.49-7.46 (m, 2H), 7.12-7.10 (m, 2H), 6.90 (d, J=3.6 Hz, 1H), 6.81 (d, J=15.6 Hz, 1H), 4.23 (t, J=5.6 Hz, 2H), 3.77 (t, J=5.6 Hz, 2H), 1.63 (s, 6H). LCMS: m/z 425.0 [M-17]$^+$; $t_R$=1.49 min.

Data for (315): $^1$H NMR (400 MHz, CD$_3$OD): δ 8.73 (s, 1H), 8.53 (d, J=4.8 Hz, 1H), 8.07 (d, J=8.0 Hz, 1H), 7.64-7.47 (m, 4H), 7.20-7.13 (m, 2H), 7.04 (d, J=3.6 Hz, 1H), 6.81 (d, J=16.0 Hz, 1H), 5.38 (s, 1H), 4.98 (s, 1H), 4.25 (t, J=5.6 Hz, 2H), 3.78 (t, J=5.6 Hz, 2H), 2.15 (s, 3H). LCMS: m/z 425.1 [M+H]$^+$; $t_R$=1.96 min.

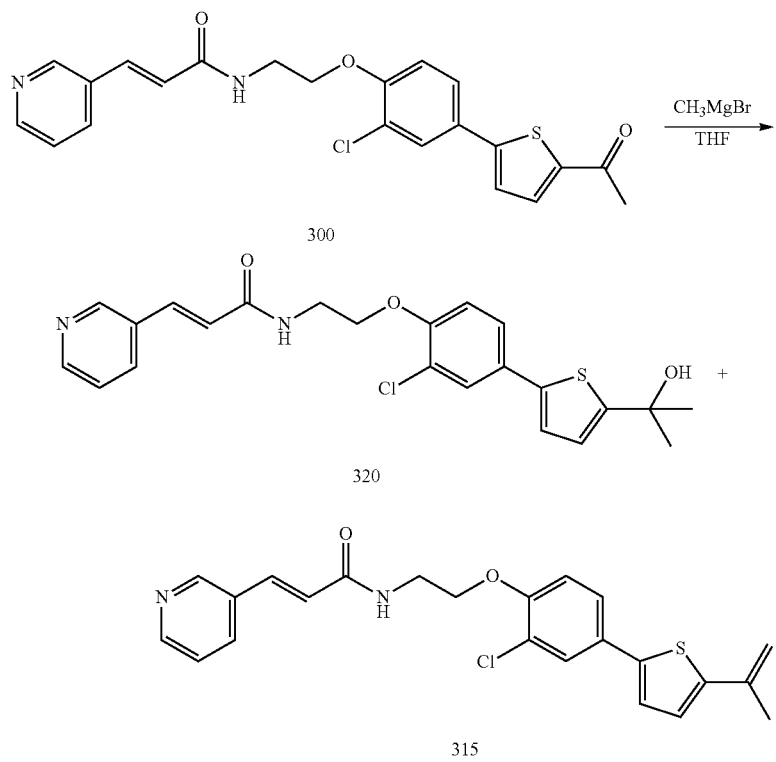

Synthesis of (E)-3-(6-aminopyridin-3-yl)-N-(2-(3-chloro-4'-(morpholine-4-carbonyl)biphenyl-4-yloxy)ethyl)acrylamide (316)

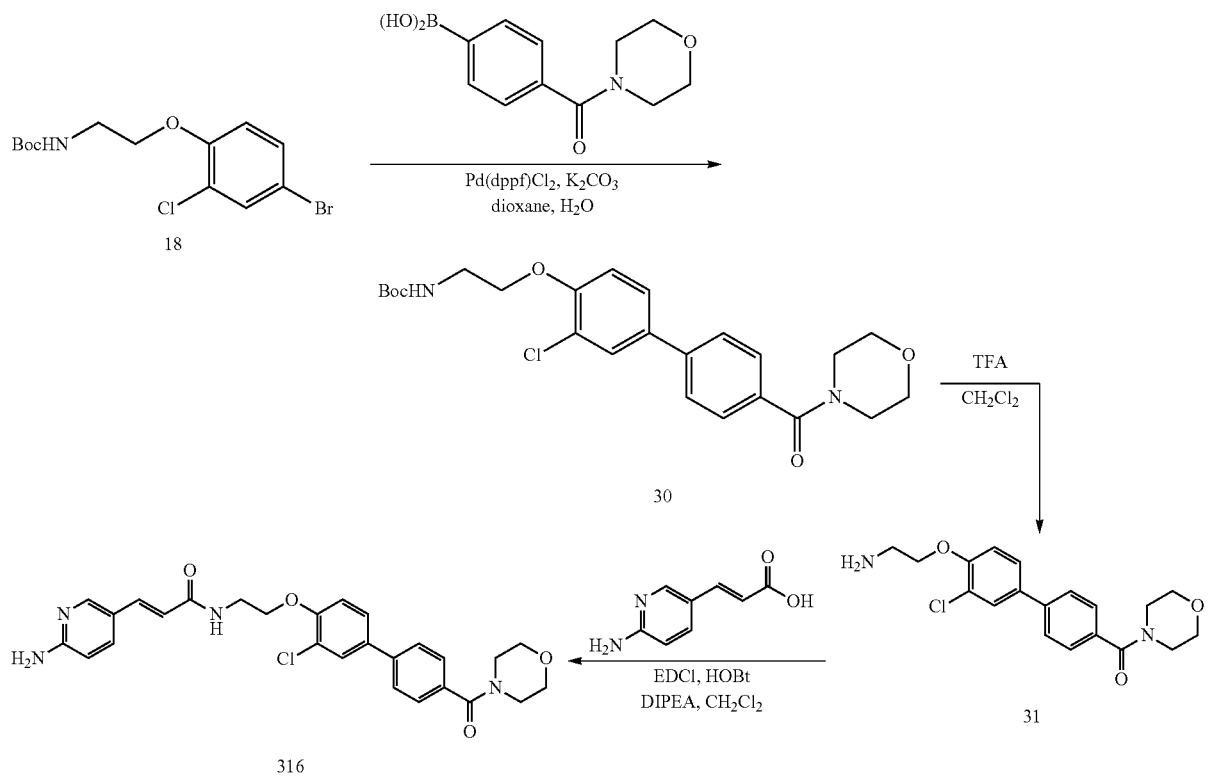

tert-Butyl 2-(3-chloro-4'-(morpholine-4-carbonyl)biphenyl-4-yloxy)ethylcarbamate (30) was synthesized using the indicated reagents according to General Procedure 1. Yield (57%). LCMS: m/z 461.1 [M+H]$^+$, $t_R$=1.79 min.

(4'-(2-Aminoethoxy)-3'-chlorobiphenyl-4-yl)(morpholino)methanone (31) was synthesized using the indicated reagents according to General Procedure 3. Yield (73%). LCMS: m/z 361.0 [M+H]$^+$, $t_R$=1.21 min.

(E)-3-(6-Aminopyridin-3-yl)-N-(2-(3-chloro-4'-(morpholine-4-carbonyl)biphenyl-4-yloxy)ethyl) acrylamide (316) was synthesized using the indicated reagents according to General Procedure 4. Yield (54%). $^1$H NMR (400 MHz, CD$_3$OD) δ 7.93-7.57 (m, 6H), 7.49-7.10 (m, 5H), 6.51 (d, J=9.2 Hz, 1H), 6.36 (d, J=16 Hz, 1H), 4.16-4.13 (m, 2H), 3.66-3.53 (m, 12H). LCMS: m/z 507.2 [M+H]$^+$, $t_R$=1.52 min.

Synthesis of (E)-3-(6-aminopyridin-3-yl)-N-(2-(3-chloro-3'-(morpholine-4-carbonyl)biphenyl-4-yloxy)ethyl)acrylamide (317)

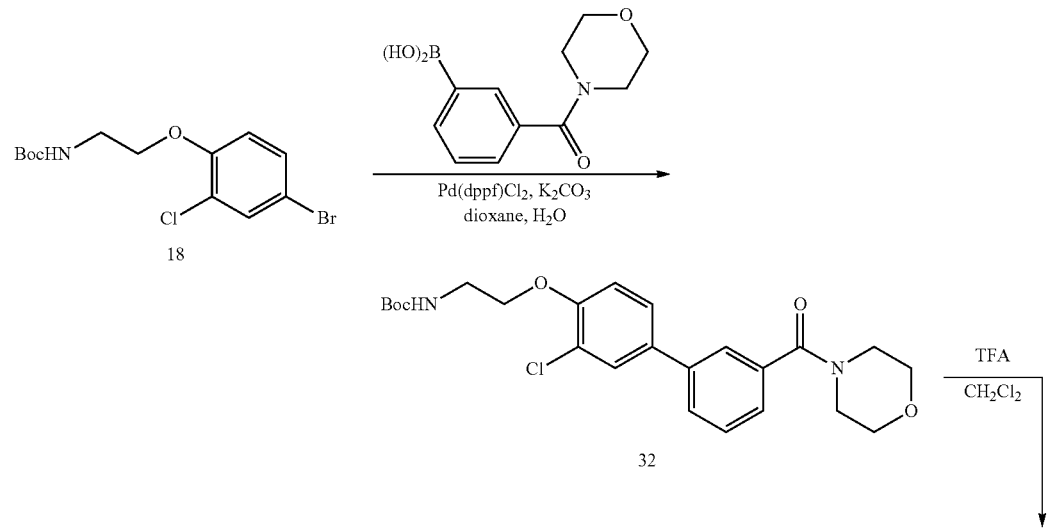

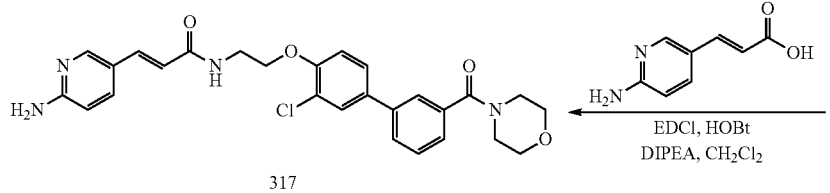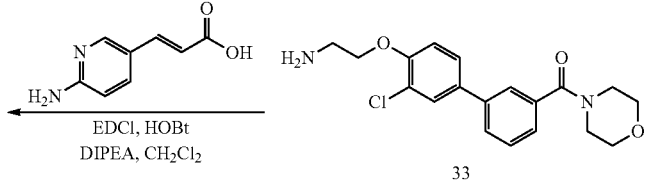

tert-Butyl 2-(3-3'-(morpholine-4-carbonyl)biphenyl-4-yloxy)ethylcarbamate (32) was synthesized using the indicated reagents according to General Procedure 1. Yield (48%). LCMS: m/z 461.1 [M+H]$^+$, $t_R$=1.80 min.

(4'-(2-Aminoethoxy)-3'-chlorobiphenyl-3-yl)(morpholino)methanone (33) was synthesized using the indicated reagents according to General Procedure 3. Yield (68%). LCMS: m/z 361.0 [M+H]$^+$, $t_R$=1.22 min.

(E)-3-(6-Aminopyridin-3-yl)-N-(2-(3-chloro-3'-(morpholine-4-carbonyl)biphenyl-4-yloxy)ethyl)acrylamide (317) was synthesized using the indicated reagents according to General Procedure 4. Yield (30%). $^1$H NMR (400 MHz, DMSO-d$_6$) δ 8.25-8.08 (m, 2H), 7.99-7.30 (m, 9H), 6.43 (s, 2H), 4.19 (s, 2H), 3.59-3.18 (m, 12H). LCMS: m/z 507.2 [M+H]$^+$, $t_R$=1.57 min.

Synthesis of (E)-3-(6-aminopyridin-3-yl)-N-(2-(3-chloro-4'-(3,3-difluoroazetidine-1-carbonyl)biphenyl-4-yloxy)ethyl)acrylamide (318)

tert-Butyl (2-((3-chloro-4'-(3,3-difluoroazetidine-1-carbonyl)-[1,1'-biphenyl]-4-yl)oxy)ethyl)carbamate (34) was synthesized using the indicated reagents according to General Procedure 1. Yield (39%). LCMS: m/z 489.1 [M+Na]$^+$; $t_R$=1.81 min.

(4'-(2-Aminoethoxy)-3'-chloro-[1,1'-biphenyl]-4-yl)(3,3-difluoroazetidin-1-yl)methanone (35) was synthesized using the indicated reagents according to General Procedure 3. Yield (100%). LCMS: m/z 367.0 [M+H]$^+$; $t_R$=0.71 min.

(E)-3-(6-Aminopyridin-3-yl)-N-(2-(3-chloro-4'-(3,3-difluoroazetidine-1-carbonyl)biphenyl-4-yloxy)ethyl)acrylamide (318) was synthesized using the indicated reagents according to General Procedure 4. Yield (40 mg, 52%). $^1$H NMR (400 MHz, CD$_3$OD) δ 8.19 (dd, J=8.0 Hz, J=12.0 Hz, 1H), 8.04 (s, 1H), 7.79-7.71 (m, 5H), 7.62 (dd, J=2.0 Hz, J=8.0 Hz, 1H), 7.46 (d, J=16.0 Hz, 1H), 7.23 (d, J=8.0 Hz, 1H), 7.05 (d, J=8.0 Hz, 1H), 6.65 (d, J=8.0 Hz, 1H), 4.75 (s, 2H), 4.57 (s, 2H), 4.29-4.27 (m, 2H), 3.80-3.77 (m, 2H). LCMS: m/z 513.1 [M+H]$^+$, $t_R$=1.35 min.

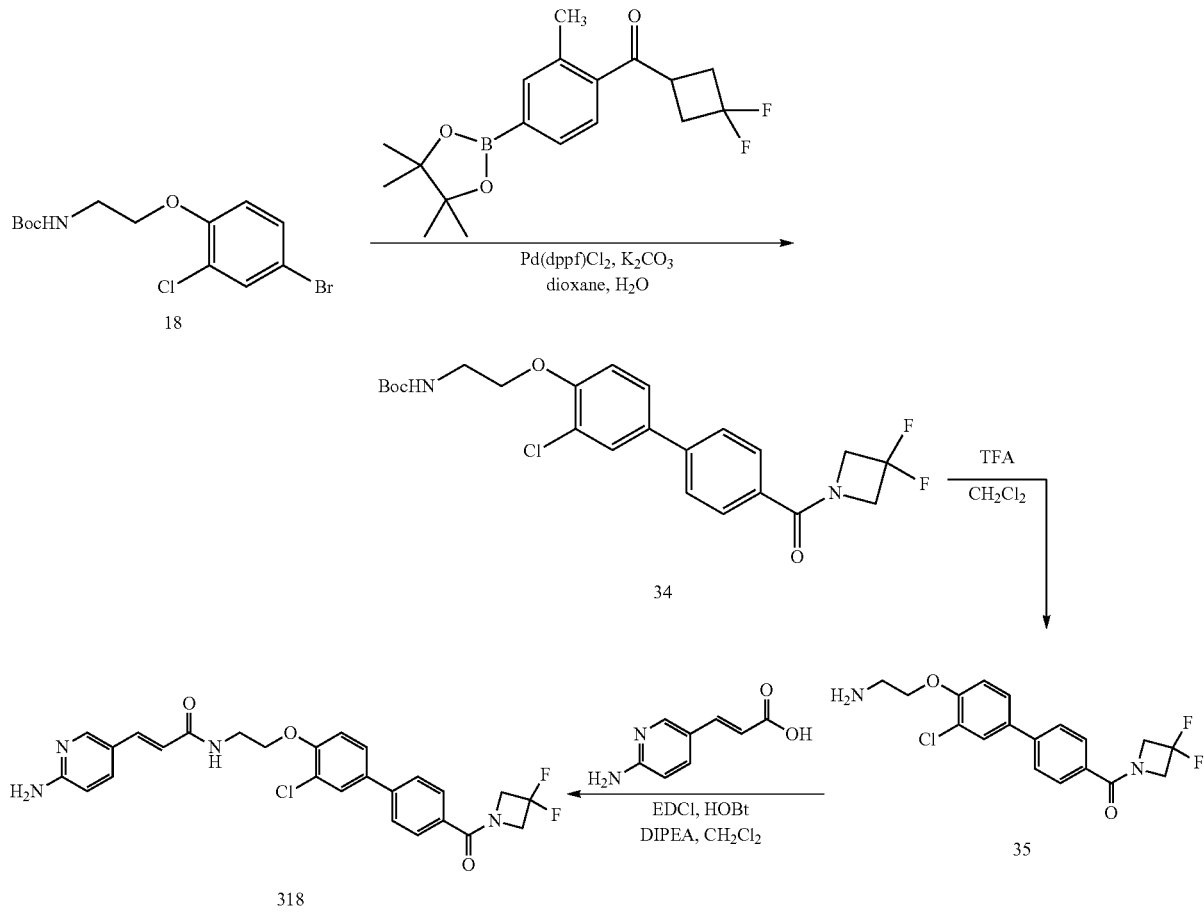

Synthesis of (E)-3-(6-aminopyridin-3-yl)-N-(2-(2-chloro-4-(5-(2-hydroxypropan-2-yl)thiophen-2-yl)phenoxy)ethyl)acrylamide (319)

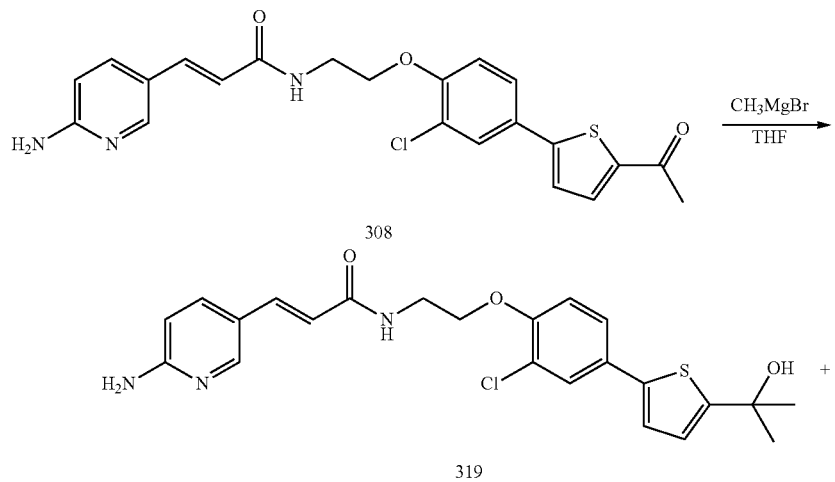

(E)-3-(6-Aminopyridin-3-yl)-N-(2-(2-chloro-4-(5-(2-hydroxypropan-2-yl)thiophen-2-yl)phenoxy)ethyl)acrylamide (319) was synthesized according to General Procedure 6. Yield (10%). $^1$H NMR (400 MHz, CD$_3$OD): δ 8.05 (d, J=2.0 Hz, 1H), 7.74 (dd, J=2.0 Hz, J=9.2 Hz, 1H), 7.61 (d, J=2.0 Hz, 1H), 7.50-7.42 (m, 2H), 7.14-7.12 (m, 2H), 6.91 (d, J=3.6 Hz, 1H), 6.60 (d, J=8.4 Hz, 1H), 6.47 (d, J=16.0 Hz, 1H), 4.22 (t, J=5.6 Hz, 2H), 3.74 (t, J=5.6 Hz, 2H), 1.62 (s, 6H). LCMS: m/z 458.1 [M+H]$^+$, $t_R$=1.63 min.

Synthesis of (E)-3-(6-aminopyridin-3-yl)-N-(2-(2-chloro-4-(6-(morpholine-4-carbonyl)pyridin-3-yl)phenoxy)ethyl)acrylamide (321)

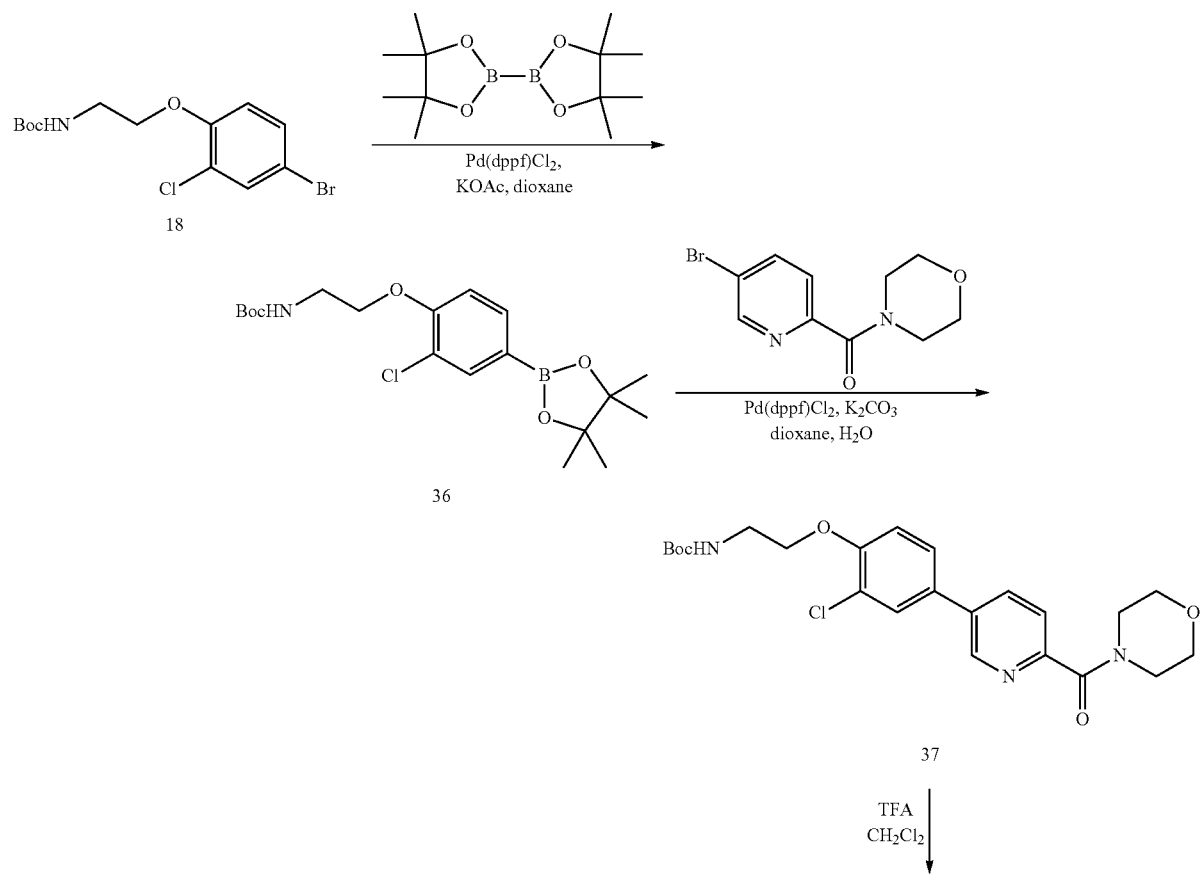

-continued

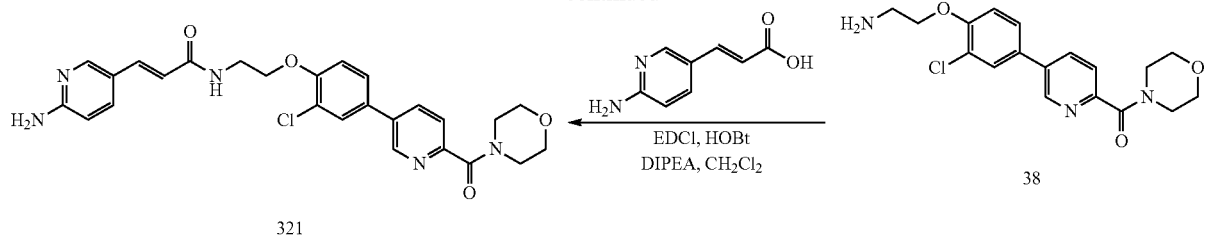

321 tert-Butyl 2-(4-bromo-2-chlorophenoxy)ethylcarbamate (18) (350 mg, 1 mmol) was dissolved in dioxane (30 mL) and degassed for 5 min. Pd(dppf)$_2$Cl$_2$ (70 mg, 0.1 mmol), KOAc (194 mg, 2 mmol) and 4,4,4',4',5,5,5',5'-octamethyl-2,2'-bi(1,3,2-dioxaborolane) (304 mg, 1.2 mmol) were added. After stirring at room temperature for 5 min, the reaction mixture was heated at 80° C. for 3 h. The reaction mixture was transferred into water and extracted with ethyl acetate (50 mL×3). The combined organic layers were washed with brine, dried over anhydrous Na$_2$SO$_4$, and concentrated under reduced pressure to give the crude product, which was purified by chromatography (0-40% ethyl acetate/n-hexane) to give tert-butyl 2-(2-chloro-4-(4,4,5,5-tetramethyl-1,3,2-dioxaborolan-2-yl)phenoxy)ethylcarbamate. Yield (300 mg, 71%). LCMS: m/z 342.1 [M-55]$^+$, t$_R$=2.09 min.

tert-Butyl 2-(2-chloro-4-(6-(morpholine-4-carbonyl)pyridin-3-yl)phenoxy)ethylcarbamate (37) was synthesized using the indicated reagents according to General Procedure 1. (Yield: 51%). LCMS: m/z 462.1 [M+H]$^+$, t$_R$=1.70 min.

(5-(4-(2-Aminoethoxy)-3-chlorophenyl)pyridin-2-yl)(morpholino)methanone (38) was synthesized using the indicated reagents according to General Procedure 3. (Yield: 48%) LCMS: m/z 362.0 [M+H]$^+$, t$_R$=1.13 min.

(E)-3-(6-Aminopyridin-3-yl)-N-(2-(2-chloro-4-(6-(morpholine-4-carbonyl)pyridin-3-yl)phenoxy)ethyl)acrylamide (321) was using the indicated reagents according to General Procedure 4. Yield (19%). $^1$H NMR (400 MHz, CD$_3$OD): δ 8.84 (d, J=2.0 Hz, 1H), 8.17 (dd, J=2.4 Hz, J=8.4 Hz, 1H), 8.05 (d, J=2.4 Hz, 1H), 7.80-7.70 (m, 4H), 7.45 (d, J=15.6 Hz, 1H), 7.27 (d, J=8.8 Hz, 1H), 6.60 (d, J=8.8 Hz, 1H), 6.47 (d, J=15.6 Hz, 1H), 4.28-4.26 (m, 2H), 3.81-3.59 (m, 10H). LCMS: m/z 508.1 [M+H]$^+$, t$_R$=1.30 min.

Synthesis of (E)-N-(2-(4-(5-acetylthiophen-2-yl)-2-chlorophenylamino)ethyl)-3-(pyridin-3-yl)acrylamide (322)

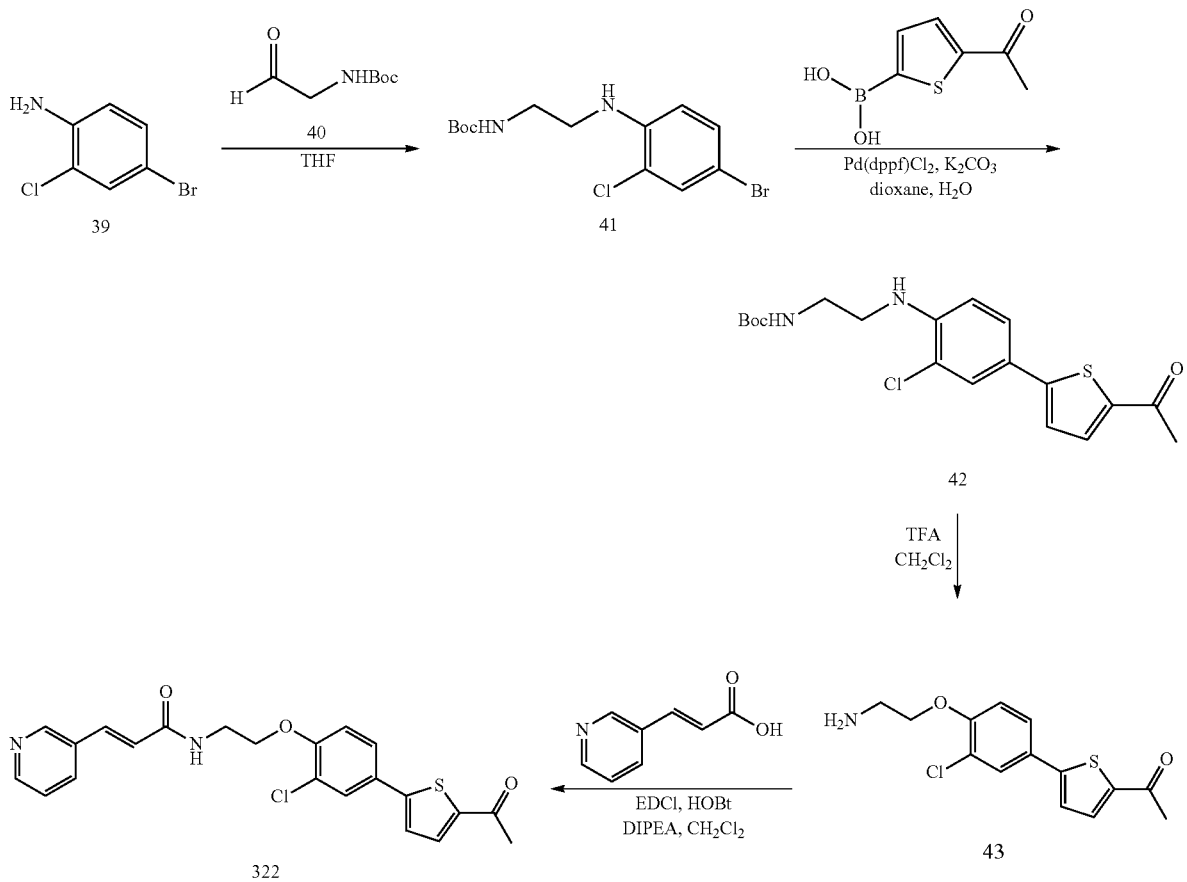

4-Bromo-2-chloroaniline (500 mg, 2.44 mmol), tert-butyl 2-oxoethylcarbamate (388 mg, 2.44 mmol) was dissolved in dry tetrahydrofuran (5 mL) To this mixture was added titanium(IV) isopropoxide (1039 mg, 3.66 mmol). After stirring at room temperature for 3 h, sodium cyanoborohydride (307 mg, 4.81 mmol) was added and the reaction mixture was stirred overnight. The reaction mixture was quenched with water (15 mL) and extracted with EtOAc (10 mL×3). The organic layers were combined, dried over anhydrous $Na_2SO_4$, and concentrated to give the crude product, which was purified by silica gel chromatography (10% EtOAc/petroleum ether) to give tert-butyl 2-(4-bromo-2-chlorophenylamino)ethylcarbamate (41) as a white solid. Yield (84 mg, 10%). LCMS: m/z 349.7 [M+H]$^+$; $t_R$=1.92 min.

tert-Butyl 2-(4-(5-acetylthiophen-2-yl)-2-chlorophenylamino)ethylcarbamate (42) was synthesized using the indicated reagents according to General Procedure 1. Yield (53%). LCMS: m/z 395.0 [M+H]$^+$, $t_R$=1.88 min.

1-(5-(4-(2-Aminoethylamino)-3-chlorophenyl)thiophen-2-yl)ethanone (43) was synthesized using the indicated reagents according to General Procedure 3. Yield (67%). LCMS: m/z 295.0 [M+H]$^+$, $t_R$=1.26 min.

(E)-N-(2-(4-(5-acetylthiophen-2-yl)-2-chlorophenylamino)ethyl)-3-(pyridin-3-yl)acrylamide (322) was synthesized according to General Procedure 4. Yield (35%). $^1$H NMR (400 MHz, CD$_3$OD): δ 8.73 (s, 1H), 8.53 (d, J=3.6 Hz, 1H), 8.07 (d, J=6.4 Hz, 1H), 7.81 (d, J=4.0 Hz, 1H), 7.64 (d, J=2 Hz, 1H), 7.61-7.47 (m, 3H), 7.32 (d, J=4.0 Hz, 1H), 6.90 (d, J=8.4 Hz, 1H), 6.75 (d, J=16 Hz, 1H), 3.60 (t, J=6.8 Hz, 2H), 3.49 (t, J=5.6 Hz, 2H), 2.56 (s, 3H). LCMS: m/z 426.0 [M+H]$^+$, $t_R$=1.68 min.

Synthesis of (E)-N-(2-(4-(5-acetylthiophen-2-yl)-2-chlorophenoxy)-2-methylpropyl)-3-(pyridin-3-yl) acrylamide (323)

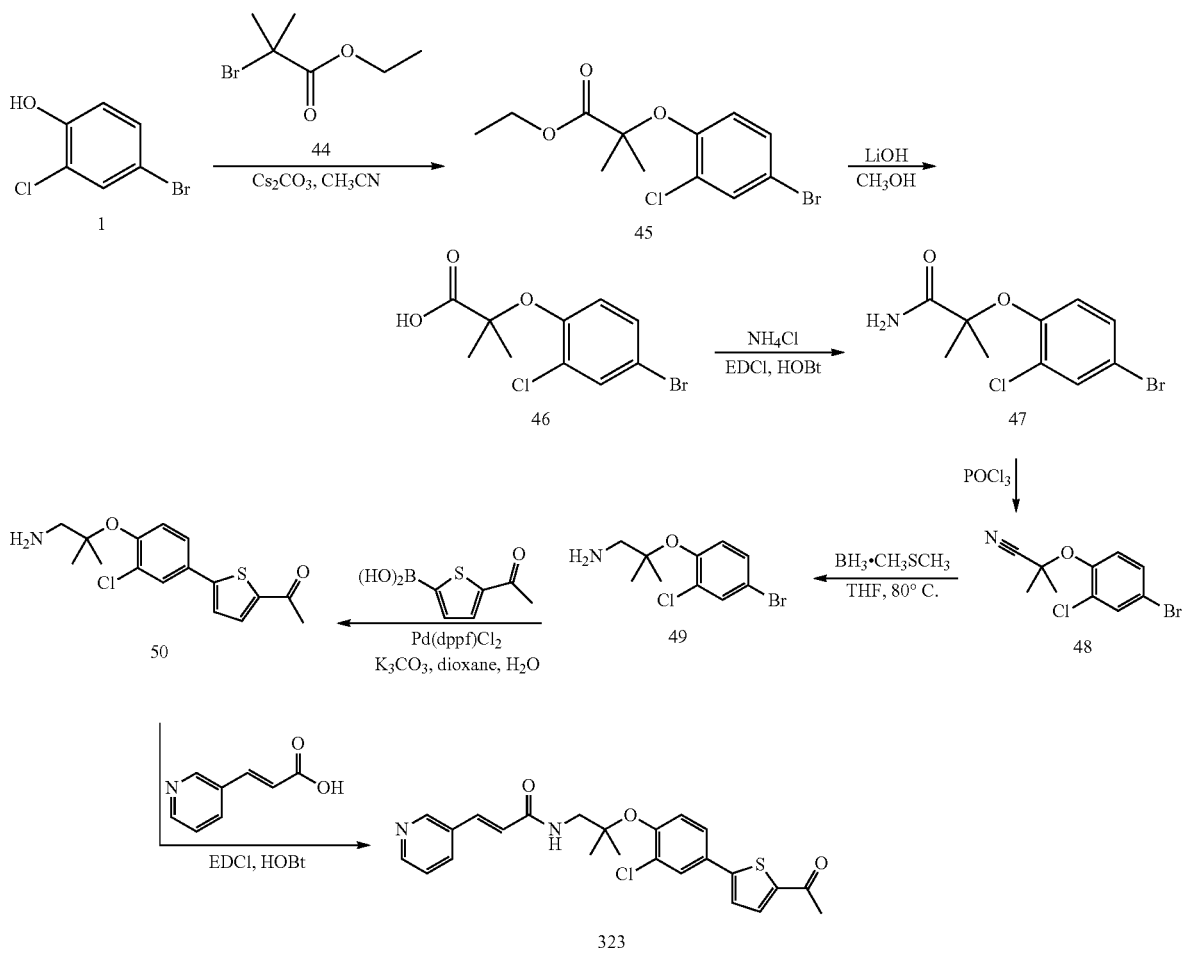

4-Bromo-2-chlorophenol (1) (8.00 g, 38.85 mmol) was dissolved in acetonitrile (30 mL). $Cs_2CO_3$ (25.10 g, 77.70 mmol) and ethyl 2-bromo-2-methylpropanoate (44) (7.54 g, 38.85 mmol) were added at 25° C., and the reaction mixture was stirred at 60° C. for 12 h. The reaction mixture was concentrated under reduced pressure and transferred into water (50 mL) and extracted with ethyl acetate (50 mL×3). The combined organic layers were washed with brine, dried over anhydrous $Na_2SO_4$, and concentrated under reduced pressure to give the crude product, which was purified by silica gel chromatography (2-5% EtOAc/petroleum ether) to give ethyl 2-(4-bromo-2-chlorophenoxy)-2-methylpropanoate (45). Yield (10.8 g, 87%). LCMS: m/z 321.0 [M+H]$^+$; $t_R$=1.11 min.

Lithium hydroxide (1.38 g, 30.00 mmol) was added to a mixture of ethyl 2-(4-bromo-2-chlorophenoxy)-2-methylpropanoate (45) (6.40 g, 20.00 mmol) in MeOH (32 mL) and H$_2$O (8 mL) at 25° C. After 4 h, the reaction mixture was transferred into water (50 mL), neutralized with dilute HCl (to pH~3) and extracted with ethyl acetate (50 mL×3). The combined organic layers were washed with saturated sodium bicarbonate solution and brine, dried over anhydrous Na$_2$SO$_4$ and concentrated under reduced pressure to obtain 2-(4-bromo-2-chlorophenoxy)-2-methylpropanoic acid (46). Yield (5.4 g, 93%). LCMS: m/z 293.0 [M+H]$^+$; t$_R$=2.55 min.

2-(4-Bromo-2-chlorophenoxy)-2-methylpropanoic acid (46) (5.40 g, 18.49 mmol) was dissolved in DMF (20 mL). Ammonium hydrochloride (1.96 g, 36.98 mmol), EDCI (5.27 g, 27.74 mmol) and HOBt (3.74 g, 27.74 mmol) were added. DIPEA (4.77 g, 36.98 mmol) was added drop wise and the reaction mixture was heated at 50° C. for 12 h. The reaction mixture was transferred into water (40 mL) and extracted with EtOAc (50 mL×3). The combined organic layers were washed with brine, dried over anhydrous Na$_2$SO$_4$ and concentrated under reduced pressure to give crude product, which was purified by silica gel chromatography (10-20% EtOAc/petroleum ether) to give 2-(4-bromo-2-chlorophenoxy)-2-methylpropanamide (47). Yield (4.05 g, 75%). LCMS: m/z 292.0 [M+H]$^+$; t$_R$=0.91 min.

2-(4-Bromo-2-chlorophenoxy)-2-methylpropanamide (47) (4.05 g, 13.92 mmol) was dissolved in phosphoryl chloride (30 mL). The reaction mixture was stirred at 80° C. for 12 h. The reaction mixture was concentrated under reduced pressure and transferred into ice water and extracted with ethyl acetate (30 mL×3). The combined organic layers were washed with brine, dried over anhydrous Na$_2$SO$_4$, and the solvents were removed under reduced pressure to give crude product, which was purified by silica gel chromatography (2-5% EtOAc/petroleum ether) to give 2-(4-bromo-2-chlorophenoxy)-2-methylpropanenitrile 6. Yield (3.60 g, 95%). LCMS: t$_R$=1.92 min.

2-(4-Bromo-2-chlorophenoxy)-2-methylpropanenitrile (48) (3.60 g, 13.18 mmol) was dissolved in THF (15 mL) and borane dimethyl sulfide complex (13.18 mL, 2 M, 26.36 mmol) was added to this reaction mixture at room temperature under nitrogen atmosphere. After stirring at 80° C. for 12 h, the reaction mixture was transferred into water and extracted with ethyl acetate (30 mL×3). The combined organic layers were washed with brine, dried over anhydrous Na$_2$SO$_4$, and concentrated under reduced pressure to give the crude product, which was purified by silica gel chromatography (5-10% EtOAc/petroleum ether) to give 2-(4-bromo-2-chlorophenoxy)-2-methylpropanenitrile (49). Yield (2.80 g, 77%). LCMS: m/z 278.0 [M+H]$^+$; t$_R$=1.31 min.

A mixture of 2-(4-bromo-2-chlorophenoxy)-2-methylpropan-1-amine (49) (230 mg, 0.83 mmol), 5-acetylthiophen-2-ylboronic acid (141 mg, 0.83 mmol), Pd(dppf)Cl$_2$ (60 mg, 0.083 mmol) and K$_2$CO$_3$ (229 mg, 1.66 mmol) in dioxane (10 mL) and H$_2$O (1 mL) was stirred at 85° C. under nitrogen atmosphere for 3 h. The reaction mixture was extracted with EtOAc (30 mL×3). The combined organic layers were washed with brine, dried over anhydrous Na$_2$SO$_4$, concentrated under reduced pressure to give the crude product, which was purified by silica gel chromatography (20% EtOAc/petroleum ether) to give 1-(5-(4-(1-amino-2-methylpropan-2-yloxy)-3-chlorophenyl)thiophen-2-yl)ethanone (50). Yield (22 mg, 8%). LCMS: m/z 324.1 [M+H]$^+$; t$_R$=1.29 min.

1-(5-(4-(1-Amino-2-methylpropan-2-yloxy)-3-chlorophenyl)thiophen-2-yl)ethanone (50) (22 mg, 0.068 mmol) was dissolved in DMF (5 mL) and cooled to 0° C. (E)-3-(pyridin-3-yl)acrylic acid (10 mg, 0.068 mmol), EDCl (26 mg, 0.14 mmol) and HOBt (19 mg, 0.14 mmol) were added to this reaction mixture. DIPEA (18 mg, 0.14 mmol) was added dropwise. The reaction mixture was warmed to room temperature and stirred further for 4 h. The reaction mixture was transferred into water (20 mL) and extracted with EtOAc (25 mL×3). The combined organic layers were washed with brine, dried over anhydrous Na$_2$SO$_4$ and concentrated under reduced pressure to give crude product, which was purified by preparative HPLC to give (E)-N-(2-(4-(5-acetylthiophen-2-yl)-2-chlorophenoxy)-2-methylpropyl)-3-(pyridin-3-yl)acrylamide (323). Yield (7 mg, 23%). $^1$H NMR (400 MHz, CD$_3$OD) δ 8.98 (s, 1H), 8.74 (s, 1H), 8.58 (d, J=8.4 Hz, 1H), 7.92-7.81 (m, 3H), 7.71-7.62 (m, 2H), 7.48 (d, J=2.0 Hz, 1H), 7.35 (d, J=8.4 Hz, 1H), 7.06 (d, J=16 Hz, 1H), 3.72 (s, 2H), 2.58 (s, 3H), 1.43 (s, 6H). LCMS: m/z 455.1 [M+H]$^+$; t$_R$=1.55 min.

Synthesis of (E)-4'-(2-(3-(6-aminopyridin-3-yl)acrylamido)ethoxy)-3'-chloro-N,N-dimethylbiphenyl-4-carboxamide (325)

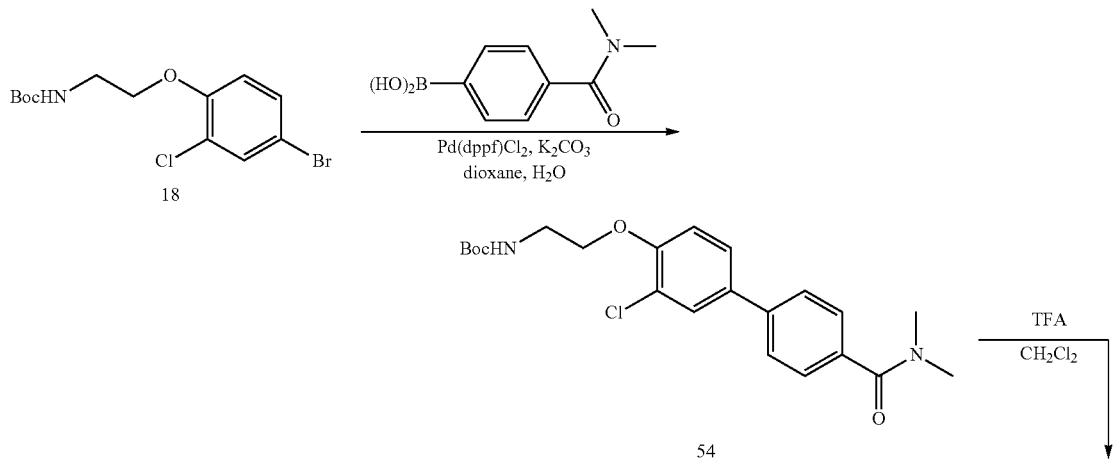

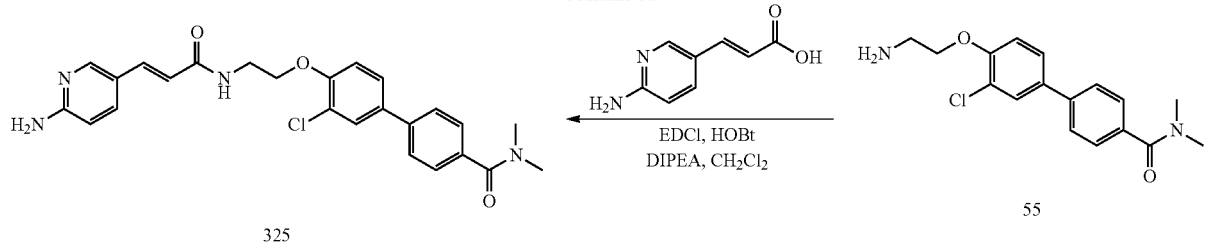

tert-Butyl 2-(3-chloro-4'-(dimethylcarbamoyl)biphenyl-4-yloxy)ethylcarbamate (54) was synthesized using the indicated reagents according to General Procedure 1. Yield (60%). LCMS: m/z 419.1 [M+H]$^+$, $t_R$=1.81 min.

4'-(2-Aminoethoxy)-3'-chloro-N,N-dimethylbiphenyl-4-carboxamide (55) was synthesized using the indicated reagents according to General Procedure 3. Yield (59%). LCMS: m/z 319.0 [M+H]$^+$, $t_R$=0.67 min.

(E)-4'-(2-(3-(6-Aminopyridin-3-yl)acrylamido)ethoxy)-3'-chloro-N,N-dimethylbiphenyl-4-carboxamide (325) was synthesized using the indicated reagents according to General Procedure 4. Yield (23%). $^1$H NMR (400 MHz, DMSO-$d_6$) δ 8.21-8.08 (m, 2H), 7.80-7.60 (m, 5H), 7.48-7.30 (m, 4H), 6.49-6.42 (m, 4H), 4.20-4.13 (m, 2H), 3.56 (s, 2H), 2.99 (s, 3H), 2.96 (s, 3H). LCMS: m/z 465.1 [M+H]$^+$, $t_R$=1.53 min.

Synthesis of (E)-3-(6-aminopyridin-3-yl)-N-(2-(3-chloro-4'-(piperazine-1-carbonyl)biphenyl-4-yloxy)ethyl)acrylamide (326)

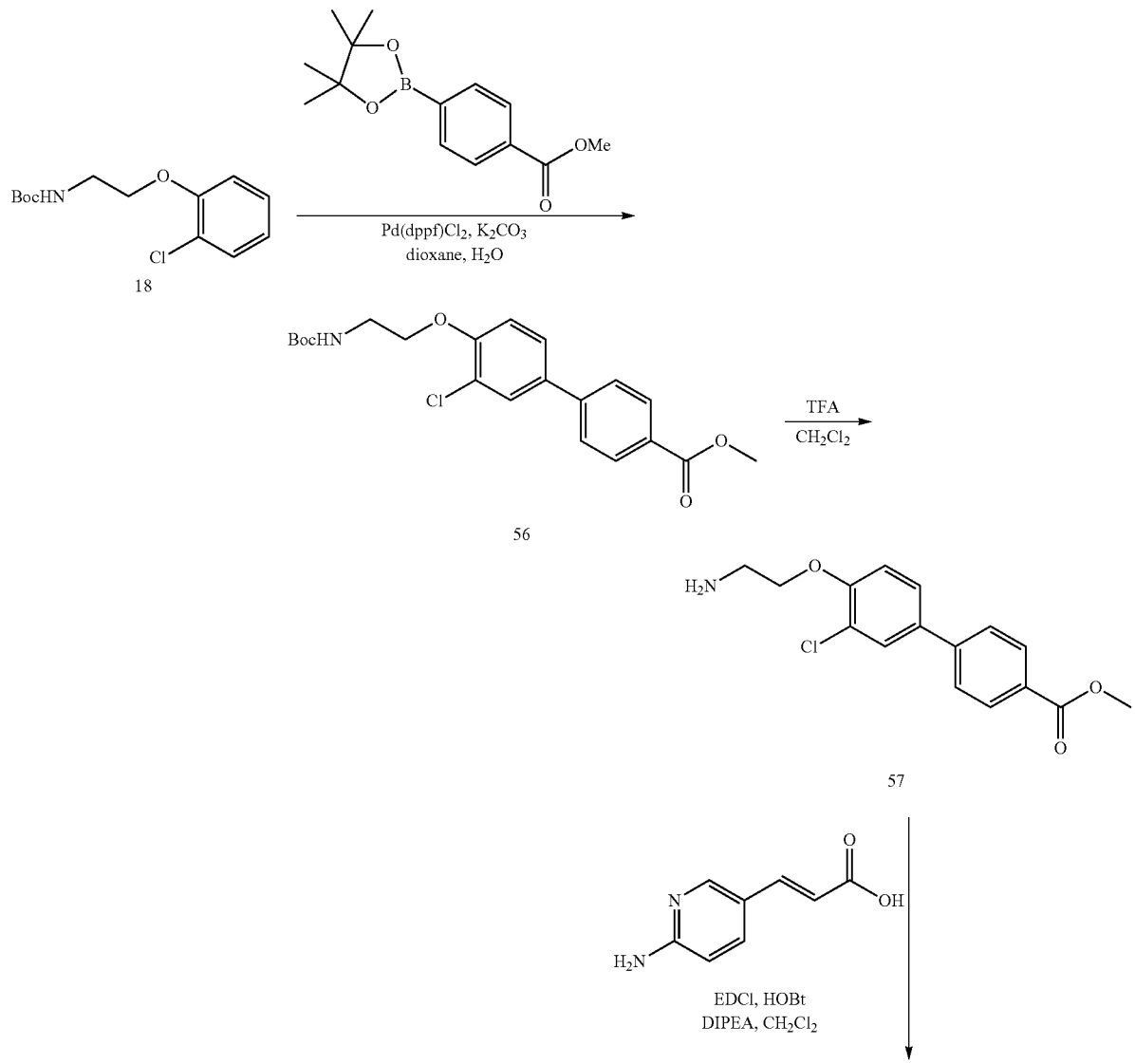

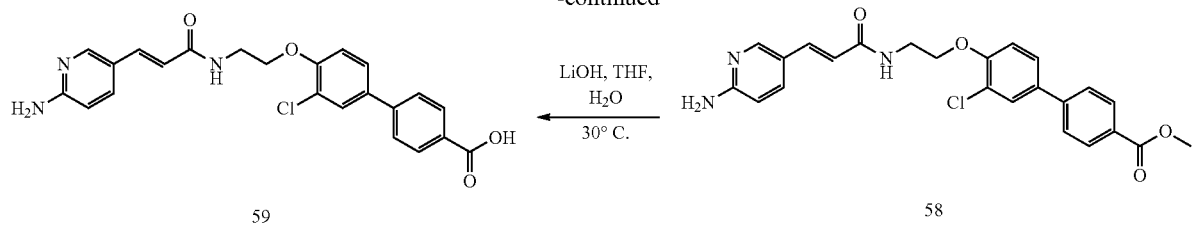

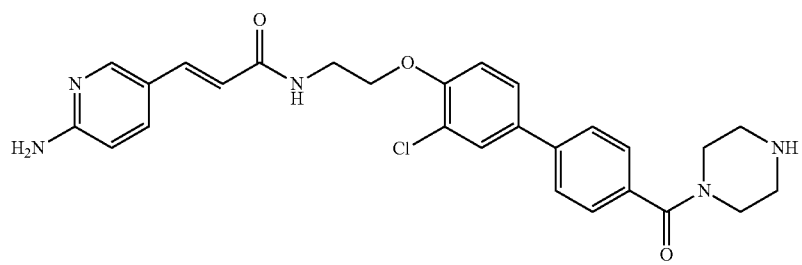

4'-(2-(tert-Butoxycarbonylamino)ethoxy)-3'-chlorobiphenyl-4-carboxylate (56) was synthesized using the indicated reagents according to General Procedure 1. Yield (74%). LCMS: m/z 406.1 [M+H]$^+$; $t_R$=2.0 min.

Methyl 4'-(2-aminoethoxy)-3'-chlorobiphenyl-4-carboxylate (57) was synthesized using the indicated reagents according to General Procedure 3. Yield (68%). LCMS: m/z 306.0 [M+H]$^+$; $t_R$=1.694 min.

(E)-Methyl 4'-(2-(3-(6-aminopyridin-3-yl)acrylamido)ethoxy)-3'-chlorobiphenyl-4-carboxylate (58) was synthesized using the indicated reagents according to General Procedure 4. Yield (78%). LCMS: m/z 452.7 [M+H]$^+$; $t_R$=1.365 min.

(E)-4'-(2-(3-(6-Aminopyridin-3-yl)acrylamido)ethoxy)-3'-chlorobiphenyl-4-carboxylic acid (59): (E)-methyl 4'-(2-(3-(6-aminopyridin-3-yl)acrylamido)ethoxy)-3'-chlorobiphenyl-4-carboxylate (58) (450 mg, 0.99 mmol) was dissolved in THF (3 mL), LiOH (95 mg, 1.99 mmol) and water (1 mL) was added to this mixture. The mixture was stirred at room temperature for 2 h. 1N HCl solution was added to the reaction mixture to adjust the pH to 6. The precipitated product, (E)-4'-(2-(3-(6-aminopyridin-3-yl)acrylamido)ethoxy)-3'-chlorobiphenyl-4-carboxylic acid, was collected by filtration. Yield (327 mg, 75%). LCMS: m/z 438.0 [M+H]$^+$; $t_R$=0.727 min.

(E)-3-(6-Aminopyridin-3-yl)-N-(2-(3-chloro-4'-(piperazine-1-carbonyl) biphenyl-4-yloxy)ethyl)acrylamide (326) was synthesized using the indicated reagents according to General Procedure 4. Yield (16%). $^1$H NMR (400 MHz, DMSO-d$_6$) δ 8.20 (t, J=5.6 Hz, 1H), 8.07 (d, J=2.1 Hz, 1H), 7.80 (d, J=2.1 Hz, 1H), 7.72 (d, J=8.1 Hz, 2H), 7.66 (dd, J=2.2 Hz, J=8.4 Hz, 1H), 7.61 (dd, J=2.0 Hz, J=8.7 Hz, 1H), 7.44 (d, J=8.2 Hz, 2H), 7.30-7.33 (m, 2H), 6.39-6.49 (m, 4H), 4.20 (t, J=5.6 Hz, 2H), 3.55-3.59 (m, 4H), 2.68-2.70 (m, 4H), 1.24 (s, 1H). LCMS: m/z 506.1 [M+H]$^+$; $t_R$=1.389 min.

Synthesis of (Z)—N-(2-(4-(5-acetylthiophen-2-yl)-2-chlorophenoxy)ethyl)-3-(pyridin-3-yl)acrylamide (327)

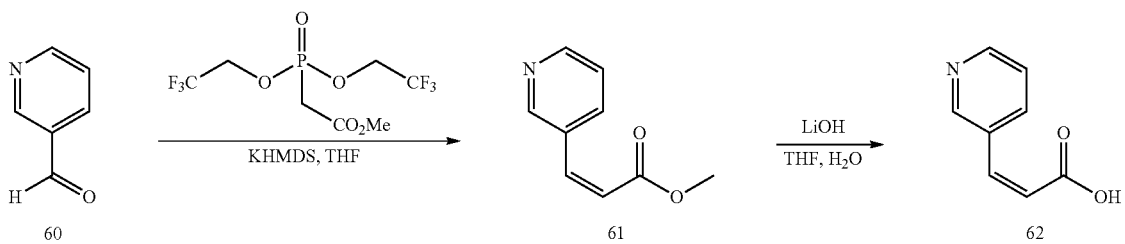

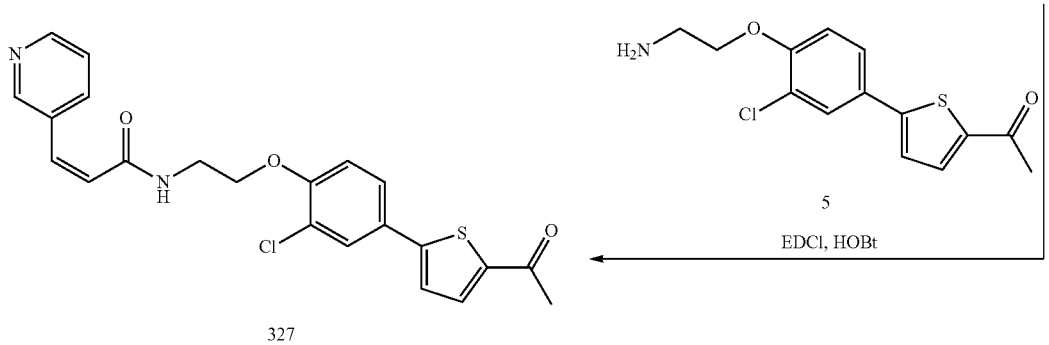

A solution of methyl 2-(bis(2,2,2-trifluoroethoxy)phosphoryl)acetate (3.27 g, 10.28 mmol) and tris(2-(2-methoxyethoxy)ethyl)amine (3.32 g, 10.28 mmol) in dry tetrahydrofuran (30 ml) was cooled to −78° C. Potassium hexamethyldisilazide (KHMDS) (2M in THF), 19.6 mL, 9.8 mmol) was added to the solution under nitrogen atmosphere. After stirring for 0.5 h, a solution of nicotinaldehyde (60) (1 g, 9.34 mmol) in dry tetrahydrofuran (5 mL) was added and the reaction mixture was maintained at −78° C. for 4 h. The mixture was quenched with aqueous ammonium chloride solution (20 mL) and extracted with EtOAc (20 mL×3). The organic layers was dried over anhydrous $Na_2SO_4$, and concentrated under reduced pressure to give the crude product, which was purified by silica gel chromatography (33% EtOAc/petroleum ether) to give (Z)-methyl 3-(pyridin-3-yl)acrylate (61) as a yellow solid. Yield (800 mg, 53%). LCMS: m/z 164.7 [M+H]$^+$; $t_R$=1.45 min.

(Z)-methyl 3-(pyridin-3-yl)acrylate (300 mg, 1.84 mmol) was dissolved in tetrahydrofuran (5 mL). Lithium hydroxide (93 mg, 2.2 mmol) and water (1 mL) were added and the reaction mixture was stirred at room temperature for 5 h. The mixture was acidified with 3N hydrogen chloride until the pH was 7, and then it was concentrated to give crude product (Z)-3-(pyridin-3-yl) acrylic acid (62), which was used directly in next step without further purification. Yield (200 mg, 73%). LCMS: m/z 150[M+H]$^+$; $t_R$=0.41 min.

(Z)—N-(2-(4-(5-Acetylthiophen-2-yl)-2-chlorophenoxy)ethyl)-3-(pyridin-3-yl)acrylamide (327) was synthesized using the indicated reagents according to General Procedure 4. Yield (13%). $^1$H NMR (400 MHz, DMSO-d$_6$) δ 8.70 (d, J=1.6 Hz, 1H), 8.50 (t, J=4.8 Hz, 1H), 8.45-8.43 (dd, J=1.2 Hz, J=4.8 Hz, 1H), 8.13 (d, J=8 Hz, 1H), 7.93 (d, J=3.6 Hz, 1H), 7.88 (d, J=2.4 Hz, 1H), 7.70-7.68 (dd, J=2.4 Hz, J=8.8 Hz, 1H), 7.64 (d, J=4.0 Hz, 1H), 7.32-7.25 (m, 2H), 6.76 (d, J=12.8 Hz, 1H), 6.18 (d, J=12.4 Hz, 1H), 4.18 (t, 0.1=5.6 Hz, 2H), 3.57-3.53 (m, 2H), 2.50 (s, 3H). LCMS: m/z 427.7 [M+H]$^+$, $t_R$=1.37 min.

Synthesis of (E)-3-(6-aminopyridin-3-yl)-N-(2-(2-chloro-4-(2-(morpholine-4-carbonyl) pyrimidin-5-yl)phenoxy)ethyl)acrylamide (328)

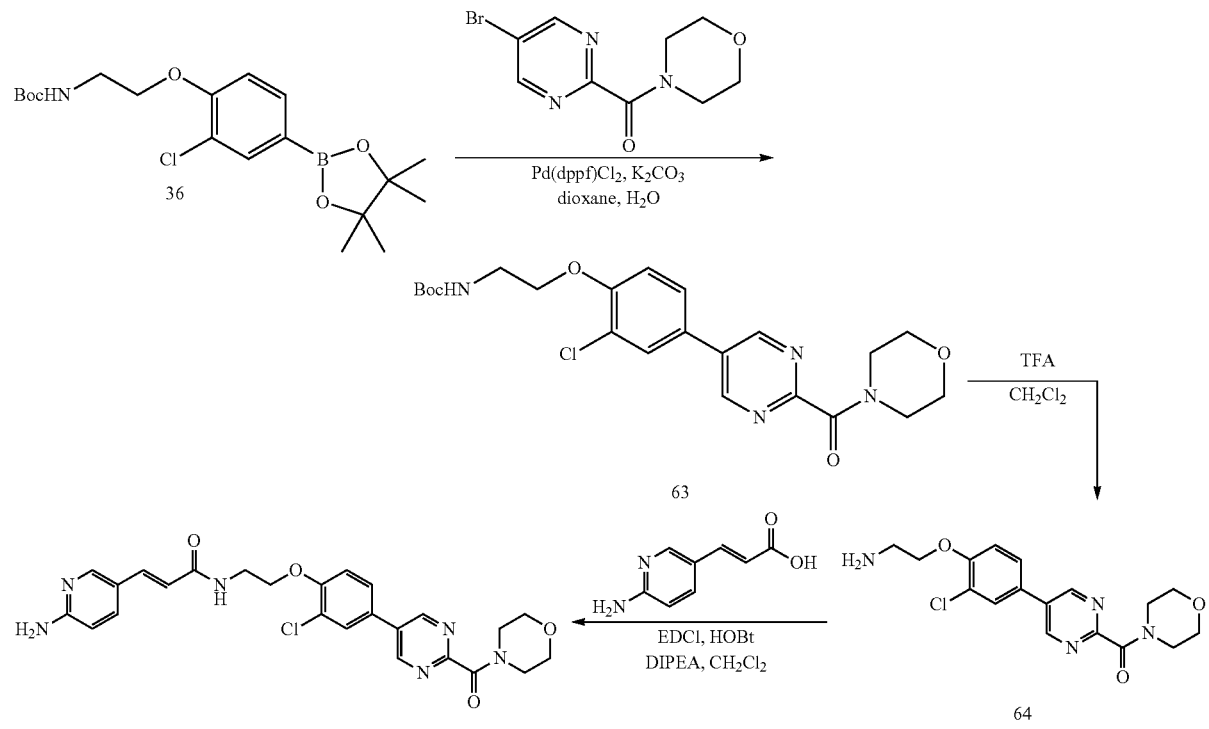

tert-Butyl 2-(2-chloro-4-(2-(morpholine-4-carbonyl)pyrimidin-5-yl)phenoxy)ethylcarbamate (63) was synthesized using the indicated reagents according to General Procedure 1. Yield (22%). LCMS: m/z 463.1 [M+H]+, $t_R$=1.65 min.

(5-(4-(2-Aminoethoxy)-3-chlorophenyl)pyrimidin-2-yl)(morpholino)methanone (64) was synthesized using the indicated reagents according to General Procedure 3. LCMS: m/z 363.1 [M+H]+, $t_R$=1.10 min.

(E)-3-(6-Aminopyridin-3-yl)-N-(2-(2-chloro-4-(2-(morpholine-4-carbonyl)pyrimidin-5-yl)phenoxy)ethyl)acrylamide (328) was synthesized using the indicated reagents according to General Procedure 4. Yield (19%). $^1$H NMR (400 MHz, CD$_3$OD): δ 9.13 (s, 2H), 8.04 (s, 1H), 7.88 (d, J=2.4 Hz, 1H), 7.75-7.70 (m, 2H), 7.45 (d, J=15.6 Hz, 1H), 7.30 (d, J=8.8 Hz, 1H), 6.60 (d, J=8.8 Hz, 1H), 6.46 (d, J=15.6 Hz, 1H), 4.29 (t, J=5.2 Hz, 2H), 3.82-3.76 (m, 6H), 3.69 (t, J=5.6 Hz, 2H), 3.45 (t, J=5.6 Hz, 2H). LCMS: m/z 509.2 [M+H]+, $t_R$=1.39 min.

Synthesis of (E)-3-(6-aminopyridin-3-yl)-N-(2-(3-chloro-4'-(piperidine-1-carbonyl)biphenyl-4-yloxy)ethyl)acrylamide (329)

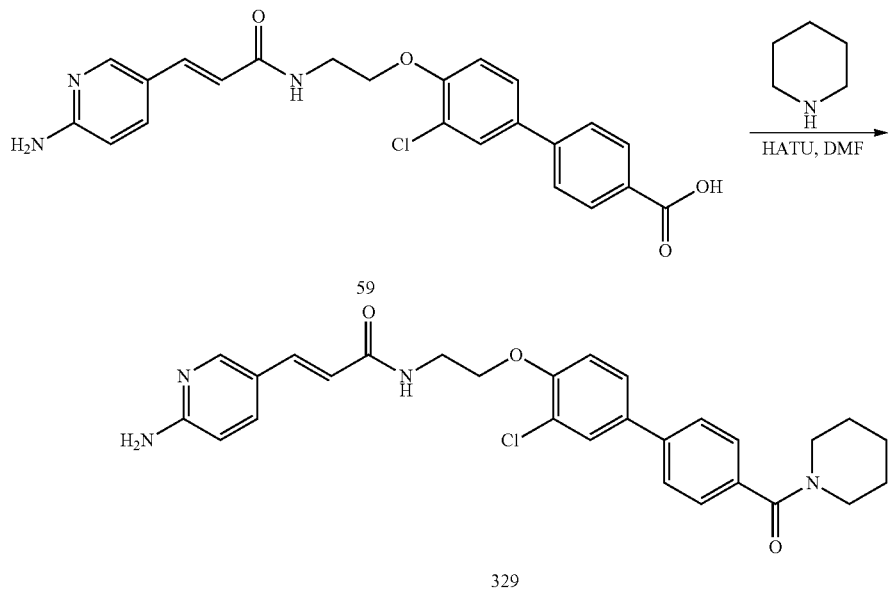

(E)-4'-(2-(3-(6-Aminopyridin-3-yl)acrylamido)ethoxy)-3'-chlorobiphenyl-4-carboxylic acid (59) (50 mg, 0.11 mmol) was dissolved in DMF (2 mL). Piperidine (10 mg, 0.11 mmol) and HATU (62 mg, 0.165 mmol) were added. The reaction mixture was stirred at room temperature for 2 h. The crude mixture was purified by preparative-HPLC to give (E)-3-(6-aminopyridin-3-yl)-N-(2-(3-chloro-4'-(piperidine-1-carbonyl)biphenyl-4-yloxy)ethyl)acrylamide (329). Yield (9 mg, 15% yield). $^1$H NMR (400 MHz, DMSO-d$_6$) δ 8.19 (t, J=5.6 Hz, 1H), 8.07 (d, J=2.1 Hz, 1H), 7.80 (d, J=2.2 Hz, 1H), 7.77 (d, J=8.4 Hz, 2H), 7.66 (dd, J=2.2 Hz, J=8.7 Hz, 1H), 7.61 (dd, J=2.0 Hz, J=9.0 Hz, 1H), 7.43 (d, J=8.2 Hz, 2H), 7.31 (dd, J=4.2 Hz, J=13.1 Hz, 2H), 6.39-6.48 (m, 4H), 4.20 (t, 2H), 3.55-3.59 (m, 4H), 1.46-4.62 (m, 6H). LCMS: m/z 505.2 [M+H]+; $t_R$=1.654 min.

Synthesis of (E)-N-(2-(6-(5-acetylthiophen-2-yl)-2-chloropyridin-3-yloxy)ethyl)-3-(6-aminopyridin-3-yl)acrylamide (330)

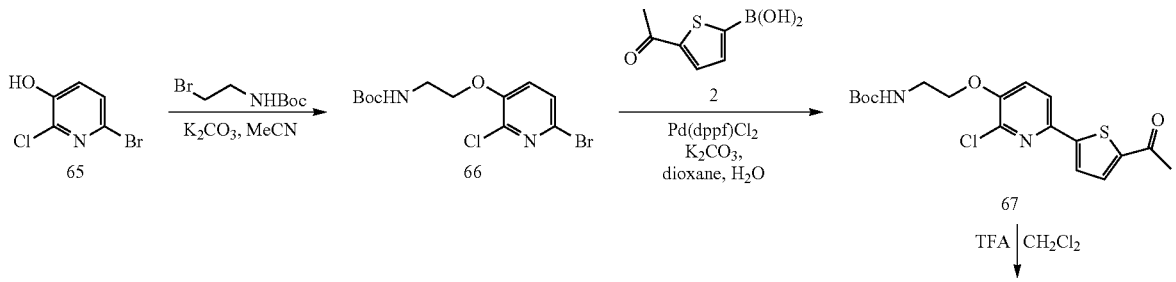

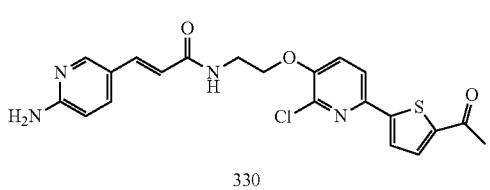

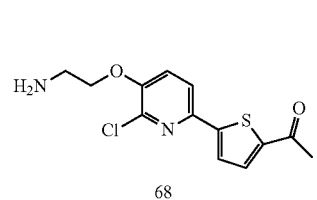

tert-Butyl 2-(6-bromo-2-chloropyridin-3-yloxy)ethylcarbamate (66) was synthesized using the indicated reagents according to General Procedure 2. Yield (86%). LCMS: m/z 350.9 [M+H]$^+$, $t_R$=1.85 min.

tert-Butyl 2-(6-(5-acetylthiophen-2-yl)-2-chloropyridin-3-yloxy)ethylcarbamate (67) was synthesized using the indicated reagents according to General Procedure 1. Yield (50%). LCMS: m/z 397.0 [M+H]$^+$, $t_R$=1.85 min.

1-(5-(5-(2-Aminoethoxy)-6-chloropyridin-2-yl) thiophen-2-yl) ethanone (68) was synthesized using the indicated reagents according to General Procedure 3. Yield (77%). LCMS: m/z 297.0 [M+H]$^+$, $t_R$=1.24 min.

(E)-N-(2-(6-(5-Acetylthiophen-2-yl)-2-chloropyridin-3-yloxy)ethyl)-3-(6-aminopyridin-3-yl)acrylamide (330) was synthesized using the indicated reagents according to General Procedure 4. Yield (42%). $^1$H NMR (400 MHz, DMSO-$d_6$) δ 8.40-8.04 (m, 6H), 7.83-7.75 (m, 3H), 7.39 (d, J=15.6 Hz, 1H), 6.96 (d, J=9.2 Hz, 1H), 6.58 (d, J=16.0 Hz, 1H), 4.27 (t, J=5.4 Hz, 2H), 3.61-3.59 (m, 2H), 2.54 (s, 3H). LCMS: m/z 443.0 [M+H]$^+$, $t_R$=1.37 min.

Synthesis of (E)-N-(2-(5-(5-acetylthiophen-2-yl)-3-chloropyridin-2-yloxy)ethyl)-3-(6-aminopyridin-3-yl)acrylamide (331)

tert-Butyl 2-(5-bromo-3-chloropyridin-2-yloxy)ethylcarbamate (70) was synthesized using the indicated reagents according to General Procedure 2. Yield (66%) LCMS: m/z 373.0 [M+Na]$^+$; $t_R$=1.62 min.

tert-Butyl 2-(5-(5-acetylthiophen-2-yl)-3-chloropyridin-2-yloxy)ethylcarbamate (71) was synthesized using the indicated reagents according to General Procedure 1. Yield (48%). LCMS: m/z 341.1 [M-55]$^+$; $t_R$=1.60 min.

1-(5-(6-(2-Aminoethoxy)-5-chloropyridin-3-yl)thiophen-2-yl)ethanone (72) was synthesized using the indicated reagents according to General Procedure 3. Yield (100%). LCMS: m/z 297.0 [M+H]$^+$; $t_R$=1.15 min.

(E)-N-(2-(5-(5-Acetylthiophen-2-yl)-3-chloropyridin-2-yloxy)ethyl)-3-(6-aminopyridin-3-yl)acrylamide (331) was synthesized using the indicated reagents according to General Procedure 4. Yield (50%). $^1$H NMR (400 MHz, CD$_3$OD) δ 8.14 (s, 1H), 8.11 (d, J=9.2 Hz, 1H), 7.98 (s, 1H), 7.93 (s, 1H), 7.76 (d, J=4.0 Hz, 1H), 7.37-7.33 (m, 2H), 6.99 (d, J=9.6 Hz, 1H), 6.50 (d, J=16 Hz, 1H), 4.31 (s, 2H), 3.74 (s, 2H), 2.52 (s, 3H). LCMS: m/z 443.0 [M+H]$^+$; $t_R$=1.41 min.

Synthesis of (E)-3-(6-aminopyridin-3-yl)-N-(2-(5-chloro-4'-(3,3-difluoroazetidine-1-carbonyl)biphenyl-3-yloxy)ethyl)acrylamide (332)

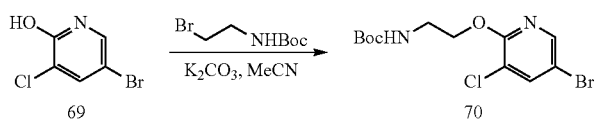

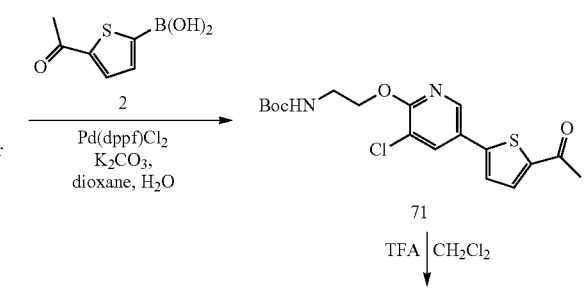

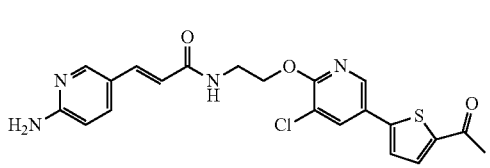

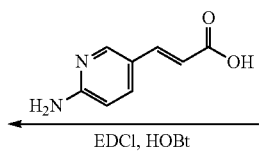

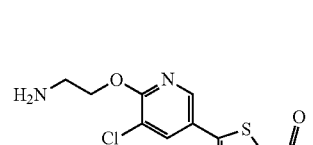

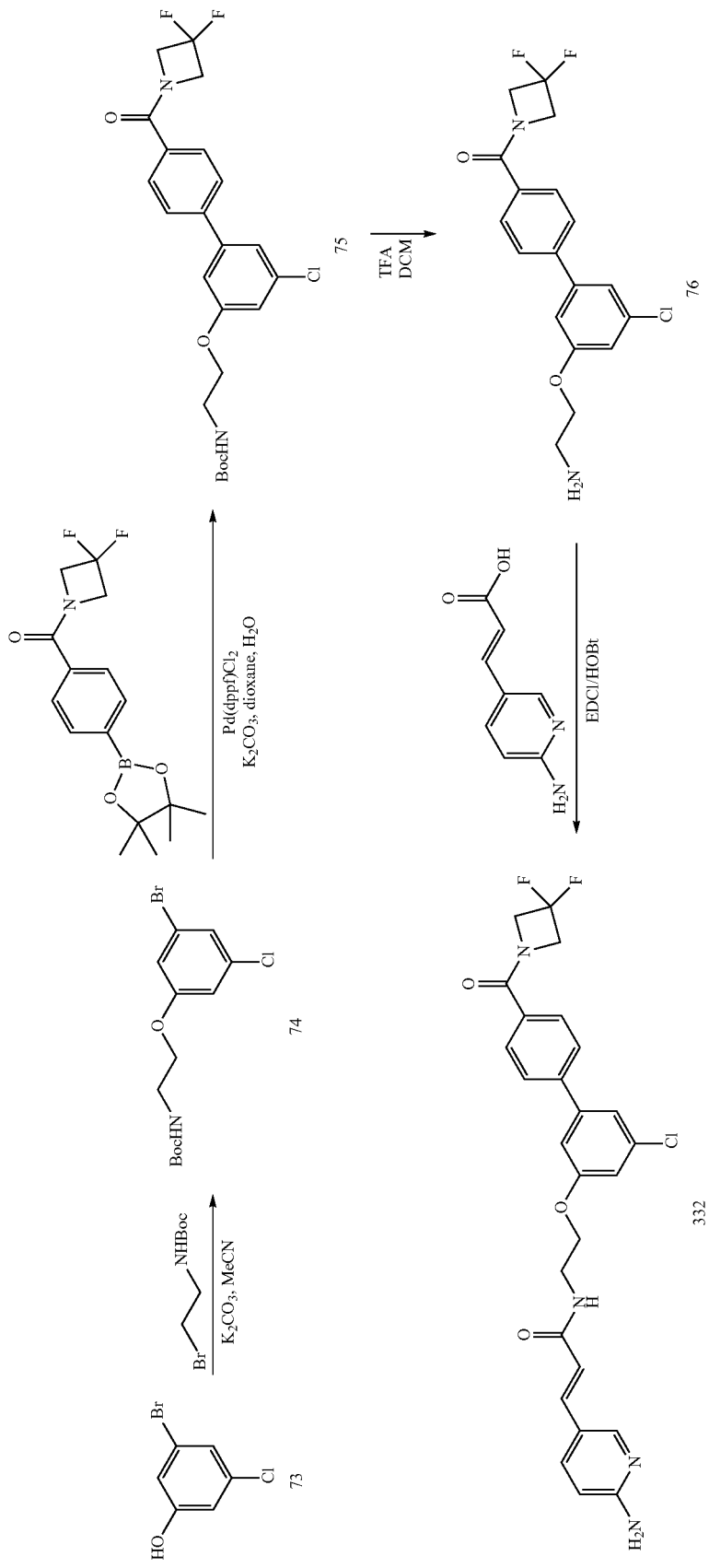

tert-Butyl 2-(3-bromo-5-chlorophenoxy)ethylcarbamate (74) was synthesized using the indicated reagents according to General Procedure 2. Yield (81%). LCMS: m/z 295.9 [M-55]$^+$, $t_R$=2.05 min.

tert-Butyl 2-(5-chloro-4'-(3,3-difluoroazetidine-1-carbonyl)biphenyl-3-yloxy)ethylcarbamate (75) was synthesized using the indicated reagents according to General Procedure 1. Yield (75%). LCMS: m/z 411.0 [M-55]$^+$.

(3'-(2-Aminoethoxy)-5'-chlorobiphenyl-4-yl)(3,3-difluoroazetidin-1-yl)methanone (76) was synthesized using the indicated reagents according to General Procedure 3. Yield (100%). LCMS: m/z 367.0 [M+H]$^+$; $t_R$=1.63 min.

(E)-3-(6-Aminopyridin-3-yl)-N-(2-(5-chloro-4'-(3,3-difluoroazetidine-1-carbonyl)biphenyl-3-yloxy)ethyl)acrylamide (332) was synthesized using the indicated reagents according to General Procedure 4. Yield (22%). $^1$H NMR (400 MHz, CD$_3$OD) δ 8.03 (s, 1H), 7.81-7.70 (m, 5H), 7.44 (d, J=15.6 Hz, 1H), 7.27 (s, 1H), 7.19 (s, 1H), 7.05 (s, 1H), 6.59 (d, J=8.4 Hz, 1H), 6.44 (d, J=15.6 Hz, 1H), 4.75-4.57 (m, 4H), 4.21-4.19 (m, 2H), 3.73-3.72 (m, 2H). LCMS: m/z 513.2 [M+H]$^+$, $t_R$=1.70 min.

Synthesis of (E)-3-(6-aminopyridin-3-yl)-N-(2-(3-chloro-4'-(3,3-difluoroazetidine-1-carbonyl)biphenyl-4-yloxy)-2-methylpropyl)acrylamide (333)

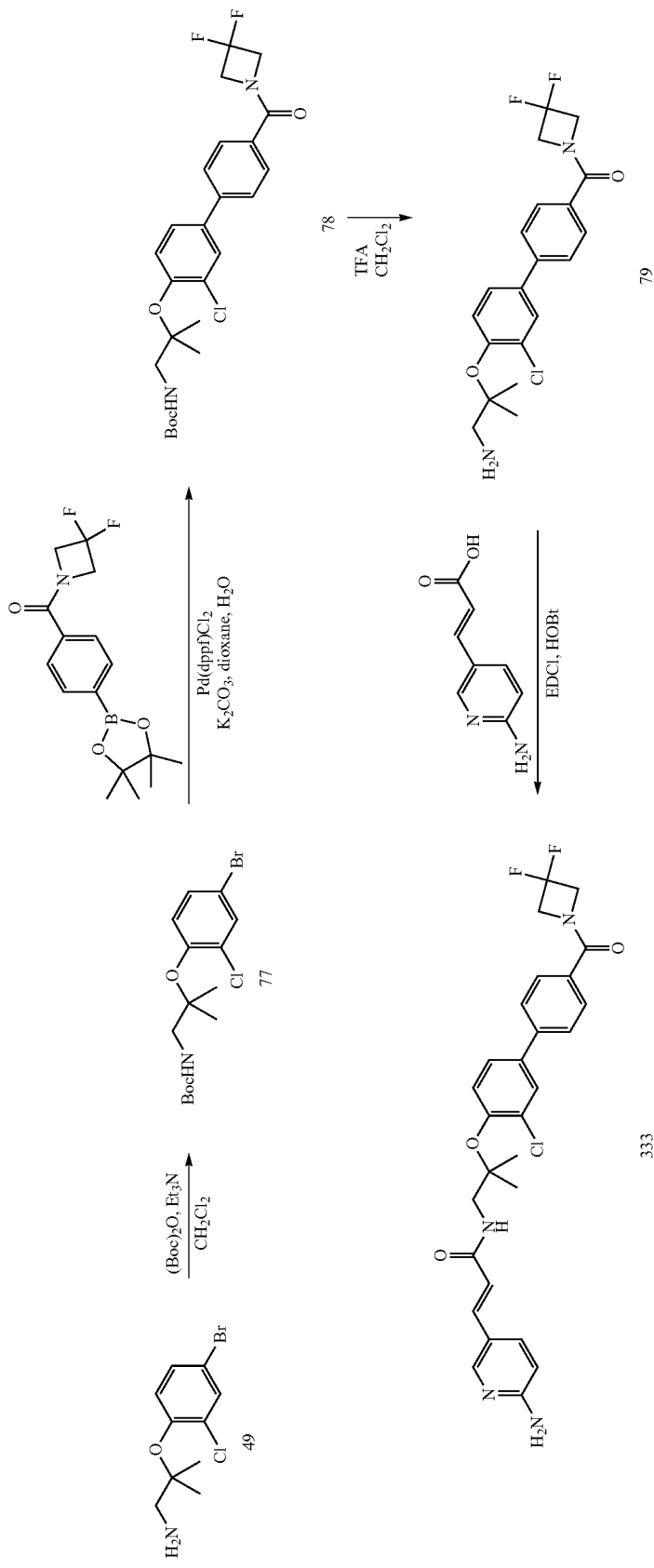

2-(4-Bromo-2-chlorophenoxy)-2-methylpropan-1-amine (49) (1.00 g, 3.61 mmol) was dissolved in dichloromethane (20 mL) and di-tert-butyl dicarbonate (0.87 g, 3.97 mmol) was added at 0° C. Triethylamine (0.55 g, 5.42 mmol) was added and the reaction mixture was stirred at room temperature for 4 h. The reaction mixture was transferred into iced water and extracted with dichloromethane (30 mL×3). The combined organic layers were washed with brine, dried over anhydrous $Na_2SO_4$, and concentrated under reduced pressure to give the crude product, which was purified by silica gel chromatography (5-10% EtOAc/petroleum ether) to give tert-butyl 2-(4-bromo-2-chlorophenoxy)-2-methylpropylcarbamate (77). Yield (420 mg, 30%). LCMS: m/z 400.1 $[M+Na]^+$; $t_R$=2.07 min.

A mixture of tert-butyl 2-(4-bromo-2-chlorophenoxy)-2-methylpropylcarbamate (77) (420 mg, 1.11 mmol), (3,3-difluoroazetidin-1-yl)(4-(4,4,5,5-tetramethyl-1,3,2-dioxaborolan-2-yl)phenyl)methanone (359 mg, 1.11 mmol), $Pd(dppf)Cl_2$ (81 mg, 0.11 mmol) and $K_2CO_3$ (306 mg, 2.22 mmol) in dioxane (10 mL) and water (1 mL) was stirred at 85° C. under nitrogen atmosphere for 3 h. The mixture was extracted with EtOAc (30 mL×3). The combined organic layers were washed with brine, dried over anhydrous $Na_2SO_4$, and the solvents were removed under reduced pressure to give the crude product, which was purified by silica gel chromatography (20% EtOAc/petroleum ether) to give tert-butyl 2-(3-chloro-4'-(3,3-difluoroazetidine-1-carbonyl)biphenyl-4-yloxy)ethylcarbamate (78) as a white solid. (Yield: 180 mg, 34%). LCMS: m/z 439.1 $[M-55]^+$; $t_R$=1.91 min.

tert-Butyl 2-(3-chloro-4'-(3,3-difluoroazetidine-1-carbonyl)biphenyl-4-yloxy)-2-methylpropylcarbamate (78) (100 mg, 0.20 mmol) was dissolved in $CH_2Cl_2$ (5 mL) TFA (1 mL) was added at 0° C. The reaction mixture was stirred at room temperature for 2 h, and concentrated under reduced pressure to give crude (4'-(1-amino-2-methylpropan-2-yloxy)-3'-chlorobiphenyl-4-yl)(3,3-difluoroazetidin-1-yl)methanone (79), which was used without further purification in the next step. Yield (100%). LCMS: m/z 395.1 $[M+H]^+$; $t_R$=1.29 min.

(4'-(1-Amino-2-methylpropan-2-yloxy)-3'-chlorobiphenyl-4-yl)(3,3-difluoroazetidin-1-yl)methanone (79) (crude product from previous step, 0.20 mmol) was dissolved in DMF (5 mL) and (E)-3-(6-aminopyridin-3-yl)acrylic acid (33 mg, 0.20 mmol) was added at 0° C. EDCl (76 mg, 0.40 mmol) and HOBt (54 mg, 0.40 mmol) were added to this reaction mixture at 0° C. DIPEA (52 mg, 0.40 mmol) was added dropwise. The reaction mixture was allowed to warm to room temperature and stirred further for 4 h. The reaction mixture was transferred into water (20 mL) and extracted with EtOAc (25 mL×3). The combined organic layers were washed with brine, dried over anhydrous $Na_2SO_4$ and concentrated under reduced pressure to give crude product, which was purified by preparative-HPLC to afford (E)-3-(6-aminopyridin-3-yl)-N-(2-(3-chloro-4'-(3,3-difluoroazetidine-1-carbonyl)biphenyl-4-yloxy)-2-methylpropyl)acrylamide (333). Yield (50 mg, 46%). $^1$H NMR (400 MHz, $CD_3OD$) δ 8.35 (s, 1H), 8.24 (dd, J=2.0 Hz, J=9.6 Hz, 1H), 8.06 (s, 1H), 7.81-7.74 (m, 5H), 7.60 (dd, J=2.0 Hz, J=8.4 Hz, 1H), 7.49 (d, J=15.6 Hz, 1H), 7.37 (d, J=8.4 Hz, 1H), 7.08 (d, J=9.2 Hz, 1H), 6.77 (d, J=15.6 Hz, 1H), 4.76 (s, 2H), 4.58 (s, 2H), 3.71 (s, 2H) 1.42 (s, 6H). LCMS: m/z 541.2 $[M+H]^+$; $t_R$=1.39 min.

Synthesis of (E)-3-(6-aminopyridin-3-yl)-N-(2-(3-chloro-4'-(3,3-difluoroazetidine-1-carbonyl)biphenyl-4-yloxy)ethyl)-N-methylacrylamide (334)

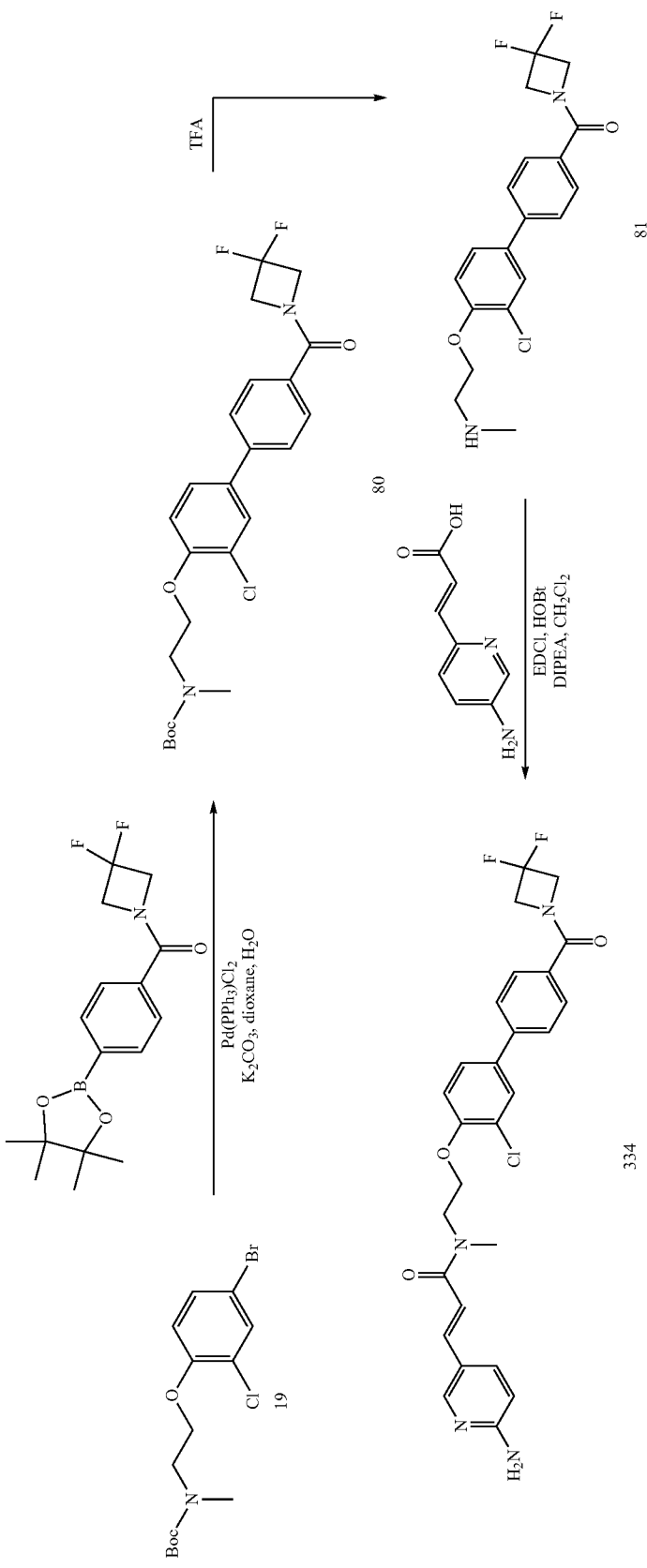

tert-Butyl 2-(3-chloro-4'-(3,3-difluoroazetidine-1-carbonyl)biphenyl-4-yloxy)ethyl (methyl)carbamate (80) was synthesized using the indicated reagents according to General Procedure 1. Yield (76%). LCMS: m/z 481.0 [M+H]$^+$, $t_R$=1.97 min.

(3'-Chloro-4'-(2-(methylamino)ethoxy)biphenyl-4-yl)(3,3-difluoroazetidin-1-yl)methanone (81) was synthesized using the indicated reagents according to General Procedure 3. Yield (100%). LCMS: m/z 381.0 [M+H]$^+$, $t_R$=1.32 min.

(E)-3-(6-Aminopyridin-3-yl)-N-(2-(3-chloro-4'-(3,3-difluoroazetidine-1-carbonyl)biphenyl-4-yloxy)ethyl)-N-methylacrylamide (334) was synthesized using the indicated reagents according to General Procedure 4. Yield (18%). $^1$H NMR (400 MHz, CD$_3$OD): δ 8.05 (d, J=12.8 Hz, 1H), 7.82-7.59 (m, 8H), 7.25-7.21 (m, 1H), 7.04-6.94 (m, 1H), 6.62-6.50 (m, 1H), 4.77-4.62 (m, 2H), 4.62-4.57 (m, 2H), 4.39-4.34 (m, 2H), 4.06-3.95 (m, 2H), 3.36-3.18 (m, 3H). LCMS: m/z 527.2 [M+H]$^+$, $t_R$=1.67 min.

Synthesis of (E)-3-(6-aminopyridin-3-yl)-N-(2-(3-chloro-4'-(3,3-dimethylmorpholine-4-carbonyl)biphenyl-4-yloxy)ethyl)acrylamide (335)

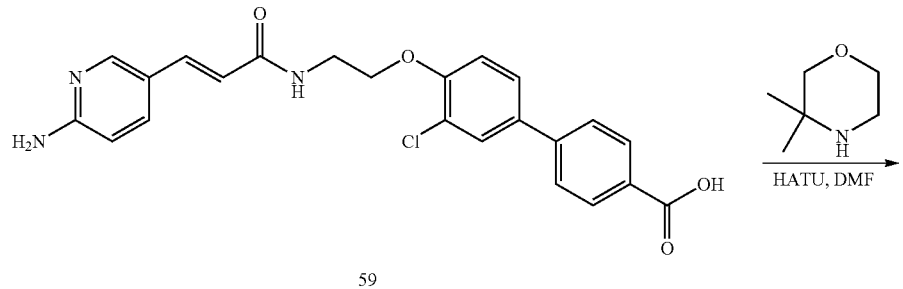

59

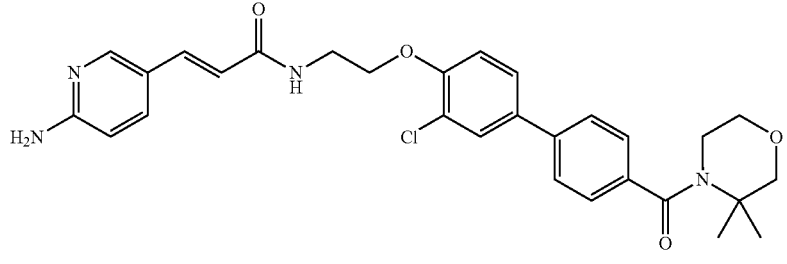

335

(E)-3-(6-Aminopyridin-3-yl)-N-(2-(3-chloro-4'-(3,3-dimethylmorpholine-4-carbonyl) biphenyl-4-yloxy)ethyl)acrylamide (335) was synthesized using the indicated reagents according to General Procedure 4. Yield (21%). $^1$H NMR (400 MHz, DMSO-d$_6$) δ 8.38 (t, J=5.6 Hz, 1H), 8.17 (d, J=1.5 Hz, 1H), 8.06 (d, J=8.7 Hz, 2H), 7.79 (d, J=2.4 Hz, 1H), 7.72 (d, J=8.2 Hz, 3H), 7.66 (dd, J=2.3 Hz, J=8.6 Hz, 1H), 7.48 (d, J=8.3 Hz, 2H), 7.40 (d, J=15.7 Hz, 1H), 7.30 (d, J=8.6 Hz, 1H), 6.95 (d, J 9.3 Hz, 1H), 6.58 (d, J=15.7 Hz, 1H), 4.21 (t, J=5.6 Hz, 2H), 3.60-3.69 (m, 6H), 3.28-3.31 (m, 2H), 1.42 (s, 6H). LCMS: m/z 535.1 [M+H]$^+$; $t_R$=1.453 min.

Synthesis of (E)-3-(6-aminopyridin-3-yl)-N-(3-(3-chloro-4'-(3,3-difluoroazetidine-1-carbonyl)biphenyl-4-yloxy)propyl)acrylamide (336)

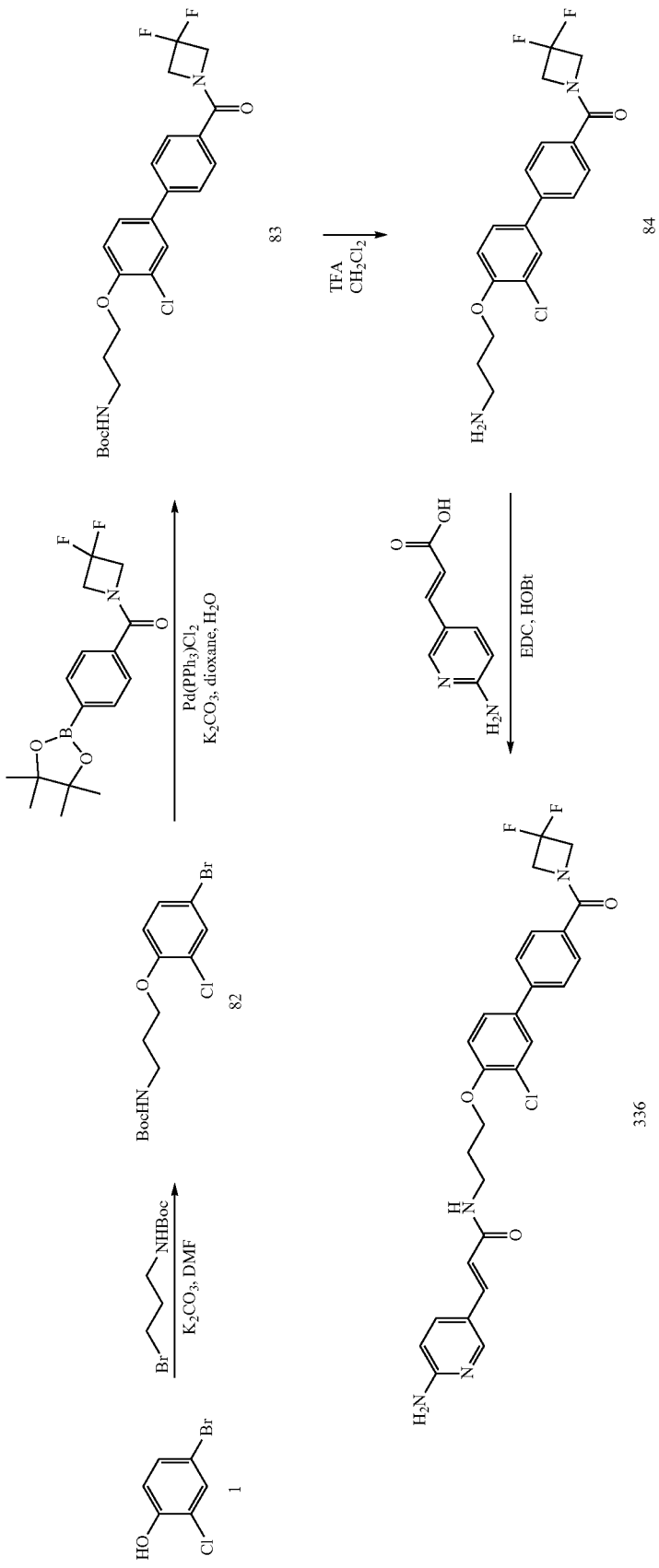

tert-Butyl 3-(4-bromo-2-chlorophenoxy)propylcarbamate (82) was synthesized using the indicated reagents according to General Procedure 2. Yield (71%). LCMS: m/z 309.0 [M-55]$^+$, t$_R$=2.06 min.

tert-Butyl 3-(3-chloro-4'-(3,3-difluoroazetidine-1-carbonyl)biphenyl-4-yloxy)propylcarbamate (83) was synthesized using the indicated reagents according to General Procedure 1. Yield (65%). LCMS: m/z 425.1 [M-55]$^+$; t$_R$=1.95 min.

(4'-(3-Aminopropoxy)-3'-chlorobiphenyl-4-yl)(3,3-difluoroazetidin-1-yl)methanone (84) was synthesized using the indicated reagents according to General Procedure 3. Yield (100%). LCMS: m/z 381.1 [M+H]$^+$; t$_R$=1.59 min.

(E)-3-(6-Aminopyridin-3-yl)-N-(3-(3-chloro-4'-(3,3-difluoroazetidine-1-carbonyl)biphenyl-4-yloxy)propyl)acrylamide (336) was synthesized using the indicated reagents according to General Procedure 4. Yield (13%). $^1$H NMR (400 MHz, CD$_3$OD): δ 8.04 (s, 1H), 7.79-7.71 (m, 6H), 7.60 (dd, J=2.4 Hz, J=8.4 Hz, 1H), 7.41 (d, J=15.6 Hz, 1H), 7.20 (d, J=8.8 Hz, 1H), 6.60 (d, J=8.8 Hz, 1H), 6.42 (d, J=15.6 Hz, 1H), 4.77 (s, 2H), 4.59 (s, 2H), 4.22 (t, J=5.6 Hz, 2H), 3.57 (t, J=5.6 Hz, 2H), 2.13 (t, J=6.0 Hz, 2H). LCMS: m/z 527.0 [M+H]$^+$; t$_R$=1.53 min.

Synthesis of (E)-3-(6-aminopyridin-3-yl)-N-(2-(3-chloro-4'-(3,3-difluoroazetidine-1-carbonyl)biphenyl-4-ylsulfonyl)ethyl)acrylamide (337)

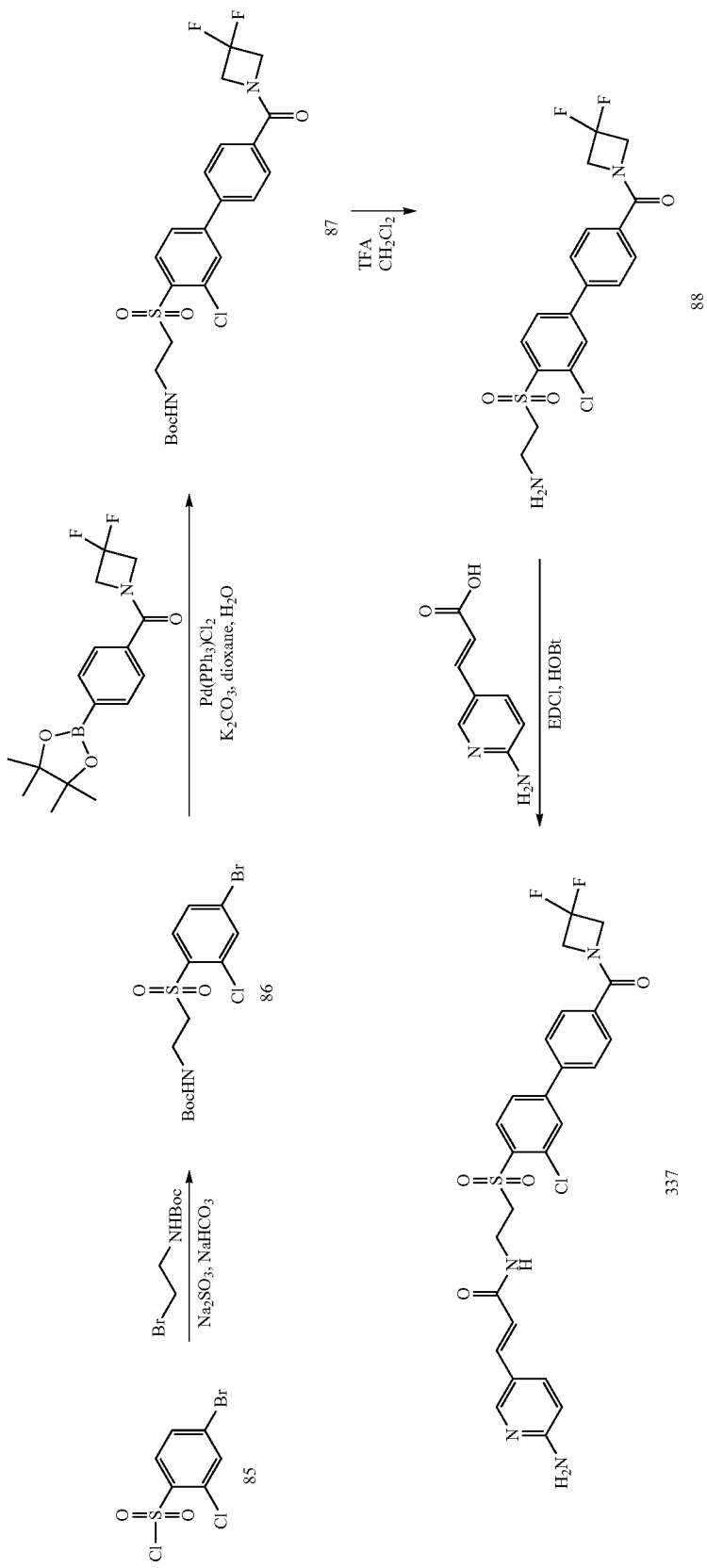

A solution of 4-bromo-2-chlorobenzene-1-sulfonyl chloride (85) (1.16 g, 4 mmol), sodium sulfite (1.01 g, 8 mmol) and sodium bicarbonate (672 mg, 8 mmol) in water (8 mL) was stirred at 100° C. for 1.5 h. The reaction mixture was cooled to 50° C. and tetrabutylammonium bromide (1.29 g, 4 mmol) and tert-butyl 2-bromoethylcarbamate (2.8 g, 12 mmol) were added and heated at 70° C. for further 3 h. The reaction mixture was cooled to room temperature, transferred into water (20 mL) and extracted with $CH_2Cl_2$ (25 mL×3). The combined organic layers were washed with brine, dried over anhydrous $Na_2SO_4$ and concentrated under reduced pressure to give crude product, which was purified by silica gel column chromatography (20% EtOAc/petroleum ether) to give tert-butyl 2-(4-bromo-2-chlorophenylsulfonyl)ethylcarbamate (86) as a white solid (260 mg, yield: 16.3%). LCMS: m/z 422.0 $[M+H]^+$, $t_R$=1.70 min.

tert-Butyl 2-(3-chloro-4'-(3,3-difluoroazetidine-1-carbonyl)biphenyl-4-ylsulfonyl)ethylcarbamate (87) was synthesized using the indicated reagents according to General Procedure 1. Yield (36%). LCMS: m/z 537.0 $[M+Na]^+$, = 1.76 min.

tert-butyl 2-(3-chloro-4'-(3,3-difluoroazetidine-1-carbonyl)biphenyl-4-ylsulfonyl)ethylcarbamate (87) (120 mg, 0.23 mmol) was dissolved in $CH_2Cl_2$ (5 mL). TFA (1 mL) was added at 0° C. The reaction mixture was stirred at room temperature for 2 h, and concentrated under reduced pressure to give the crude product, which was purified by preparative-HPLC to give (4'-(2-aminoethylsulfonyl)-3'-chlorobiphenyl-4-yl)(3,3-difluoroazetidin-1-yl)methanone (88). Yield (30 mg, 31%). LCMS: m/z 415.1 $[M+H]^+$; $t_R$=1.23 min.

(E)-3-(6-Aminopyridin-3-yl)-N-(2-(3-chloro-4'-(3,3-difluoroazetidine-1-carbonyl)biphenyl-4-ylsulfonyl)ethyl) acrylamide (337) was synthesized using the indicated reagents according to General Procedure 4. Yield (38%). $^1$H NMR (400 MHz, $CD_3OD$) δ 8.20 (d, J=8.4 Hz, 1H), 7.90-7.81 (m, 3H), 7.69 (d, J=8.4 Hz, 2H), 7.63 (d, J=8.4 Hz, 2H), 7.45 (dd, J=2.4 Hz, J=8.8 Hz, 1H), 7.12 (d, J=15.6 Hz, 1H), 6.42 (d, J=8.8 Hz, 1H), 5.91 (d, J=15.6 Hz, 1H), 4.77 (s, 2H), 4.59 (s, 2H), 3.91 (t, J=5.2 Hz, 2H), 3.69 (t, J=5.2 Hz, 2H). LCMS: m/z 561.0 $[M+H]^+$, $t_R$=1.37 min.

Synthesis of (E)-3-(6-aminopyridin-3-yl)-N-(2-(4'-(3,3-difluoroazetidine-1-carbonyl)-3-(trifluoromethyl)biphenyl-4-yloxy)ethyl)acrylamide (338)

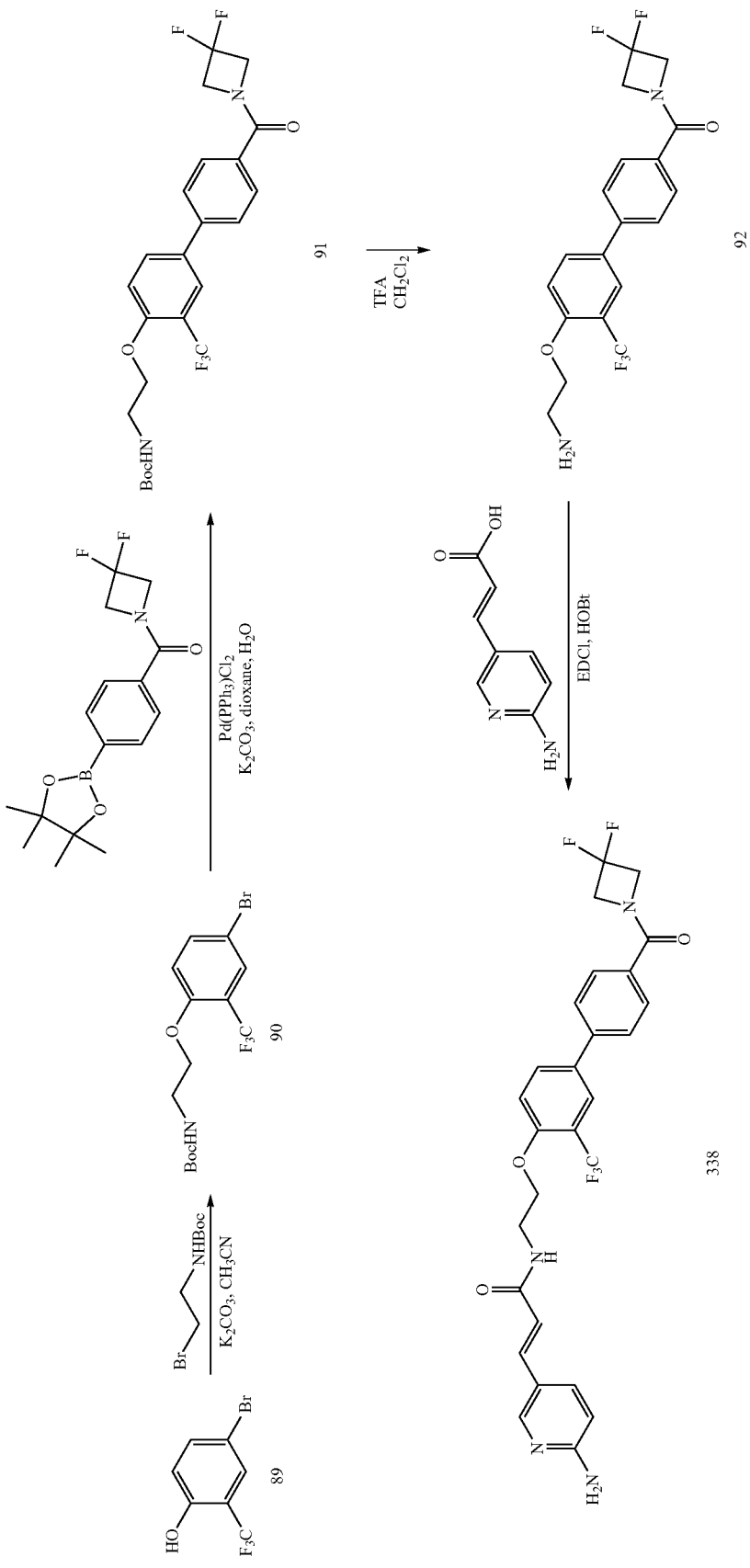

tert-Butyl 2-(4-bromo-2-(trifluoromethyl)phenoxy)ethylcarbamate (90) was synthesized using the indicated reagents according to General Procedure 2. Yield (65%). LCMS: m/z 408.0 [M+Na]$^+$, $t_R$=1.95 min.

tert-Butyl 2-(4'-(3,3-difluoroazetidine-1-carbonyl)-3-(trifluoromethyl)biphenyl-4-yloxy)ethylcarbamate (91) was synthesized using the indicated reagents according to General Procedure 1. Yield (73%). LCMS: m/z 523.1 [M+Na]$^+$, $t_R$=1.83 min.

(4'-(2-Aminoethoxy)-3'-(trifluoromethyl)biphenyl-4-yl)(3,3-difluoroazetidin-1-yl)methanone (92) was synthesized using the indicated reagents according to General Procedure 3. Yield (100%). LCMS: m/z 401.1 [M+H]$^+$; $t_R$=1.31 min.

(E)-3-(6-Aminopyridin-3-yl)-N-(2-(4'-(3,3-difluoroazetidine-1-carbonyl)-3-(trifluoromethyl)biphenyl-4-yloxy)ethyl)acrylamide (338) was synthesized using General Procedure 4. Yield (41%). $^1$H NMR (400 MHz, DMSO-d$_6$) δ 8.29 (t, J=5.6 Hz, 1H), 8.17 (d, J=2.0 Hz, 1H), 8.07-7.99 (m, 3H), 7.91 (d, J=2.0 Hz, 1H), 7.82-7.76 (m, 4H), 7.45-7.37 (m, 2H), 6.92 (d, J=9.6 Hz, 1H), 6.54 (d, J=16.0 Hz, 1H), 4.85-4.76 (m, 4H), 4.27 (t, J=5.6 Hz, 2H), 3.61-3.56 (m, 2H). LCMS: m/z 547.2 [M+H]$^+$, $t_R$=1.39 min.

Synthesis of (E)-3-(6-aminopyridin-3-yl)-N-(2-(4'-(morpholine-4-carbonyl)-3-(trifluoromethyl)biphenyl-4-yloxy)ethyl)acrylamide (339)

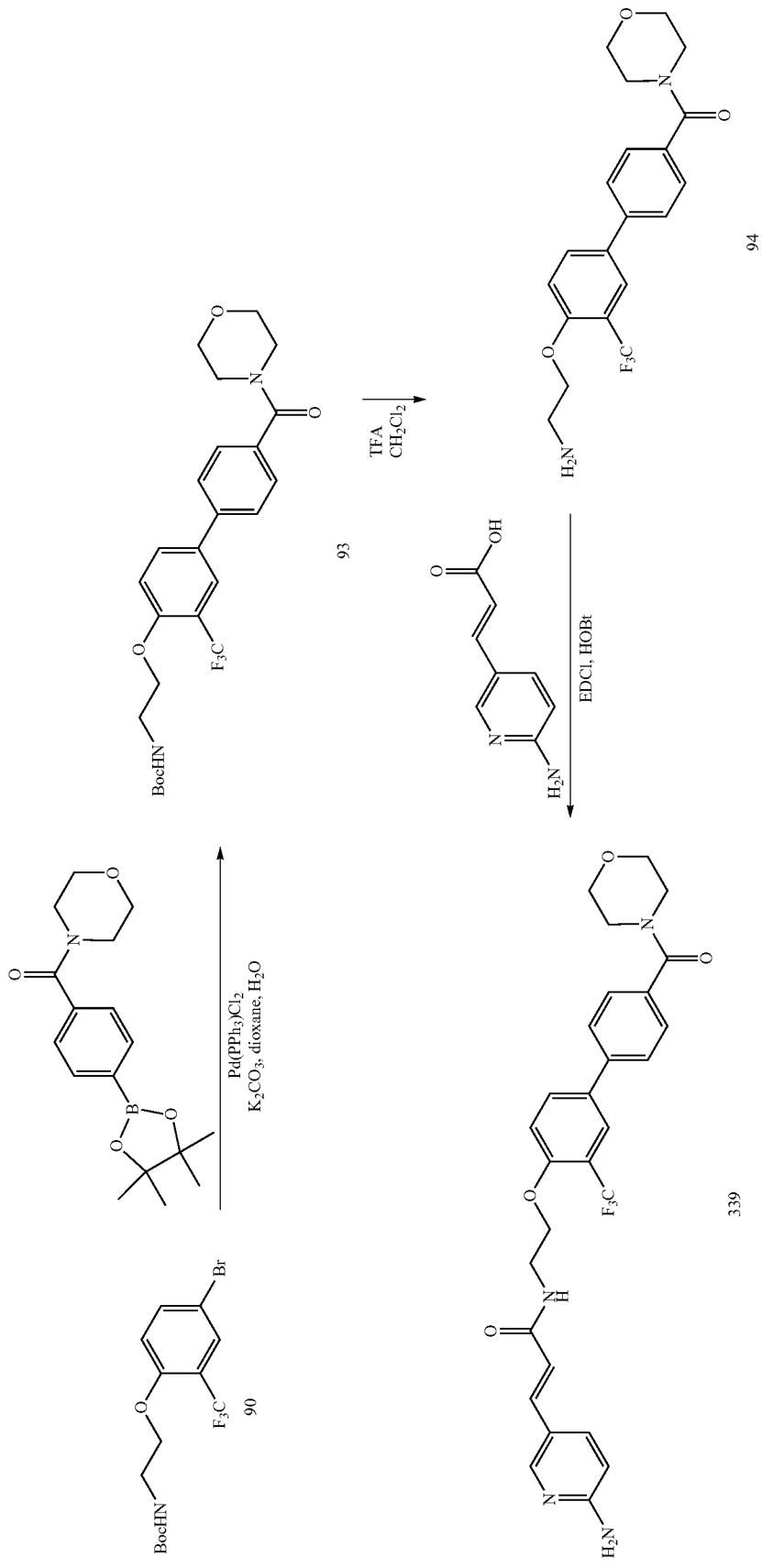

tert-Butyl 2-(4'-(morpholine-4-carbonyl)-3-(trifluoromethyl)biphenyl-4-yloxy)ethylcarbamate (93) was synthesized using the indicated reagents according to General Procedure 1. Yield (62%). LCMS: m/z 494.8 [M+H]$^+$, $t_R$=1.78 min.

(4'-(2-Aminoethoxy)-3'-(trifluoromethyl)biphenyl-4-yl)(morpholino)methanone (94) was synthesized using the indicated reagents according to General Procedure 3. Yield (100%). LCMS: m/z 394.9 [M+H]$^+$; $t_R$=1.154 min.

(E)-3-(6-Aminopyridin-3-yl)-N-(2-(4'-(morpholine-4-carbonyl)-3-(trifluoromethyl)biphenyl-4-yloxy)ethyl)acrylamide (339) was synthesized using the indicated reagents according to General Procedure 4. Yield (69%). $^1$H NMR (400 MHz, DMSO-d$_6$) δ 8.29 (t, J=5.6 Hz, 1H), 8.18 (d, J=1.6 Hz, 1H), 8.07-7.96 (m, 4H), 7.88 (d, J=2.0 Hz, 1H), 7.76 (d, J=8.4 Hz, 2H), 7.50 (d, J=8.4 Hz, 2H), 7.44-7.37 (m, 2H), 6.94 (d, J=9.2 Hz, 1H), 6.55 (d, J=15.6 Hz, 1H), 4.27 (t, J=5.6 Hz, 2H), 3.62-3.38 (m, 10H). LCMS: m/z 540.8 [M+H]$^+$, $t_R$=1.225 min.

Synthesis of (E)-3-(6-aminopyridin-3-yl)-N-(2-(6-fluoro-4'-(morpholine-4-carbonyl)biphenyl-3-yloxy)-2-methylpropyl)acrylamide (340)

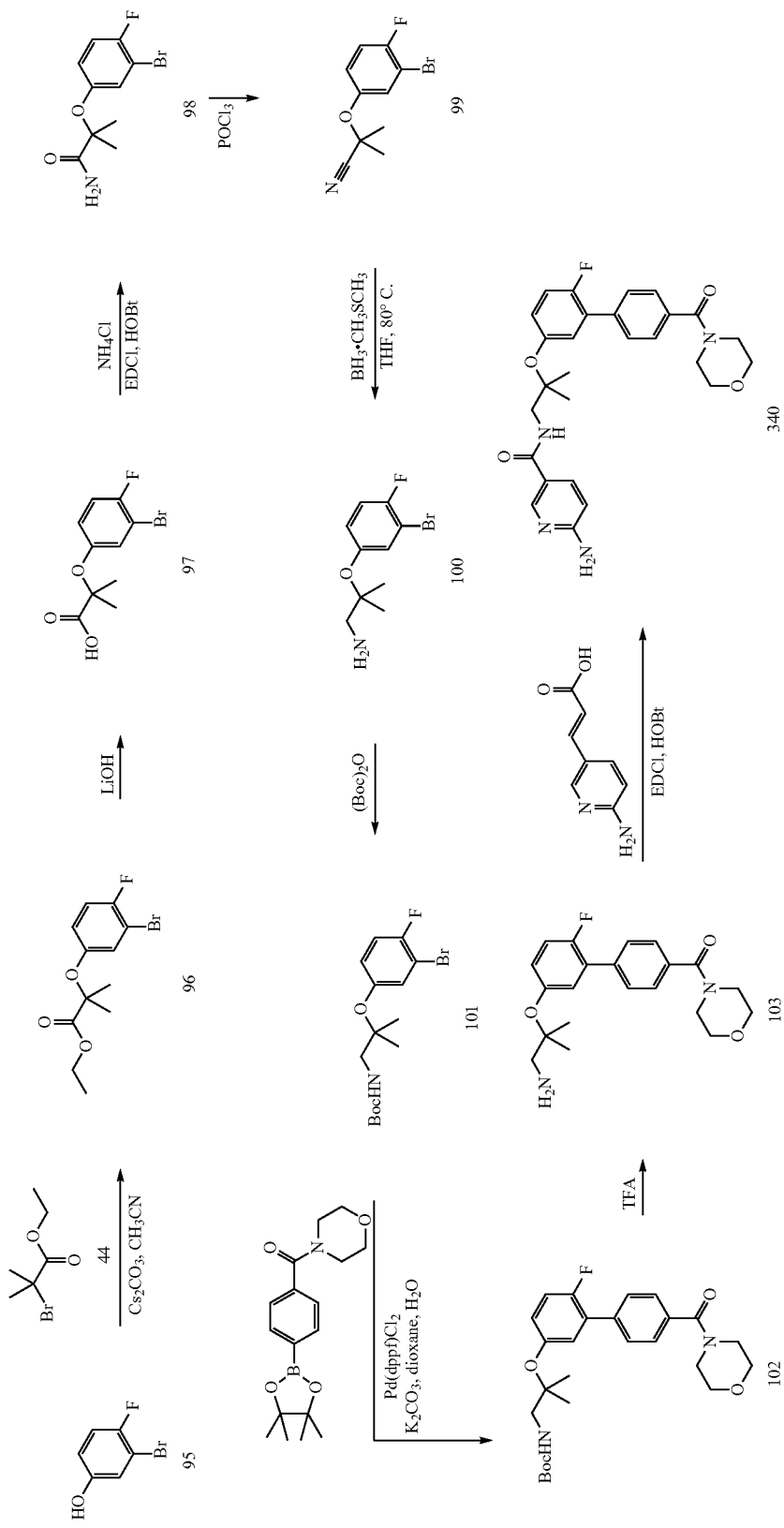

3-Bromo-4-fluorophenol (95) (10.00 g, 52.3 mmol) was dissolved in acetonitrile (150 mL). $Cs_2CO_3$ (34 g, 104.6 mmol) and ethyl 2-bromo-2-methylpropanoate (44) (10.2 g, 52.3 mmol) were added at 25° C. and the reaction mixture was stirred at 60° C. for 12 h. The reaction mixture was concentrated under reduced pressure, transferred into water and extracted with ethyl acetate (50 mL×3). The combined organic layers were washed with brine, dried over anhydrous $Na_2SO_4$, and the solvents were removed under reduced pressure to give the crude product, which was purified by silica gel chromatography (2-5% EtOAc/petroleum ether) to give ethyl 2-(3-bromo-4-fluorophenoxy)-2-methylpropanoate (96). Yield (13 g, 82%). LCMS: m/z 304.9 $[M+H]^+$; $t_R$=2.20 min.

Lithium hydroxide (2.04 g, 49.9 mmol) was added to a mixture of ethyl 2-(3-bromo-4-fluorophenoxy)-2-methylpropanoate (96) (12.7 g, 41.6 mmol) in MeOH (50 mL) and $H_2O$ (10 mL) at 25° C. The reaction mixture was stirred at 25° C. for 4 h. The reaction mixture was transferred into water, neutralized with dilute HCl (to pH~3) and extracted with ethyl acetate (50 mL×3). The combined organic layers were washed with saturated sodium bicarbonate solution, brine, dried over anhydrous $Na_2SO_4$ and concentrated under reduced pressure to obtain 2-(3-bromo-4-fluorophenoxy)-2-methylpropanoic acid (97). Yield (11 g, 96%). LCMS: m/z 277.0 $[M+H]^+$; $t_R$=1.92 min.

2-(3-Bromo-4-fluorophenoxy)-2-methylpropanoic acid (97) (11 g, 39.7 mmol) was dissolved in DMF (120 mL), and ammonium hydrochloride (2.1 g, 39.7 mmol) and EDCl (11.4 g, 59.5 mmol) and HOBt (8 g, 59.5 mmol) were added to this reaction mixture at 25° C. followed by DIPEA (10.2 g, 79.4 mmol). The reaction mixture was stirred at 50° C. for 12 h. The reaction mixture was transferred into water (40 mL) and extracted with EtOAc (50 mL×3). The combined organic layers were washed with brine, dried over anhydrous $Na_2SO_4$ and concentrated under reduced pressure to give crude product, which was purified by silica gel chromatography (30-50% EtOAc/petroleum ether) to give 2-(3-bromo-4-fluorophenoxy)-2-methylpropanamide (98). Yield (7 g, 64%). LCMS: m/z 277.9 $[M+H]^+$; $t_R$=1.63 min.

2-(3-Bromo-4-fluorophenoxy)-2-methylpropanamide (98) (4 g, 14.5 mmol) was dissolved in phosphoryl trichloride (10 mL). The reaction mixture was stirred at 80° C. for 12 h. The reaction mixture was evaporated and transferred into ice water and extracted with ethyl acetate (30 mL×3). The combined organic layers were washed with brine, dried over anhydrous $Na_2SO_4$, and the solvents were removed under reduced pressure to give the crude product, which was purified by silica gel chromatography (2-5% EtOAc/petroleum ether) to give 2-(3-bromo-4-fluorophenoxy)-2-methylpropanenitrile (99). Yield (1.7 g, 45%). LCMS: m/z 258.9 $[M+H]^+$; $t_R$=1.89 min.

2-(3-Bromo-4-fluorophenoxy)-2-methylpropanenitrile (99) (1 g, 3.8 mmol) was dissolved in THF (15 mL) and borane dimethyl sulfide complex (3.8 mL, 2M, 7.6 mmol) was added to this reaction mixture at room temperature under nitrogen atmosphere. The reaction mixture was stirred at 80° C. for 12 h. The reaction mixture was transferred into water and extracted with ethyl acetate (30 mL×3). The combined organic layers were washed with brine, dried over anhydrous $Na_2SO_4$, and the solvents were removed under reduced pressure to give the crude product, which was purified by reversed phase column chromatography to give 2-(3-bromo-4-fluorophenoxy)-2-methylpropan-1-amine (100). Yield (300 mg, 30%). LCMS: m/z 264.0 $[M+H]^+$; $t_R$=1.67 min.

2-(3-Bromo-4-fluorophenoxy)-2-methylpropan-1-amine (100) (300 mg, 1.14 mmol) was dissolved in dichloromethane (20 mL) and di-tert-butyl dicarbonate (296 mg, 1.36 mmol) was added at 0° C. Triethylamine (173 mg, 1.71 mmol) was added and the reaction mixture was stirred at room temperature for 4 h. The reaction mixture was transferred into iced water and extracted with dichloromethane (30 mL×3). The combined organic layers were washed with brine, dried over anhydrous $Na_2SO_4$, and concentrated under reduced pressure to give tert-butyl 2-(3-bromo-4-fluorophenoxy)-2-methylpropylcarbamate (101). Yield (415 mg, 100%). LCMS: m/z 386.0 $[M+Na]^+$; $t_R$=1.31 min.

A mixture of tert-butyl 2-(3-bromo-4-fluorophenoxy)-2-methylpropylcarbamate (101) (415 mg, 1.15 mmol), morpholino(4-(4,4,5,5-tetramethyl-1,3,2-dioxaborolan-2-yl)phenyl)methanone (434 mg, 1.37 mmol), $Pd(dppf)Cl_2$ (84 mg, 0.115 mmol) and $K_2CO_3$ (317 mg, 2.3 mmol) in dioxane (40 mL) and $H_2O$ (10 mL) was stirred at 85° C. under nitrogen atmosphere for 3 h. The mixture was extracted with EtOAc (30 mL×3). The combined organic layers were washed with brine, dried over anhydrous $Na_2SO_4$, and the solvents were removed under reduced pressure to give the crude product, which was purified by silica gel chromatography (20% EtOAc/petroleum ether) to give tert-butyl 2-(6-fluoro-4'-(morpholine-4-carbonyl)biphenyl-3-yloxy)-2-methylpropylcarbamate (102). Yield (400 mg, 74%). LCMS: m/z 495.1 $[M+Na]^+$; $t_R$=1.84 min.

tert-Butyl 2-(6-fluoro-4'-(morpholine-4-carbonyl)biphenyl-3-yloxy)-2-methylpropylcarbamate (102) (200 mg, 0.42 mmol) was dissolved in $CH_2Cl_2$ (5 mL). TFA (1 mL) was added at 0° C. The reaction mixture was stirred at room temperature for 2 h, and concentrated under reduced pressure to give crude (5'-(1-amino-2-methylpropan-2-yloxy)-2'-fluorobiphenyl-4-yl)(morpholino)methanone (103), which was used without further purification in the next step. Yield (100%). LCMS: m/z 373.1 $[M+H]^+$; $t_R$=1.31 min.

(5'-(1-Amino-2-methylpropan-2-yloxy)-2'-fluorobiphenyl-4-yl)(morpholino)methanone (103) (157 mg, 0.42 mmol) was dissolved in DMF (5 mL) and (E)-3-(pyridin-3-yl)acrylic acid (69 mg, 0.42 mmol) was added at 0° C. EDCl (121 mg, 0.63 mmol) and HOBt (85 mg, 0.63 mmol) were added to this reaction mixture at 0° C. followed by DIPEA (108 mg, 0.84 mmol). The reaction mixture was allowed to warm to room temperature and stirred further for 4 h. The reaction mixture was transferred into water (20 mL) and extracted with EtOAc (25 mL×3). The combined organic layers were washed with brine, dried over anhydrous $Na_2SO_4$ and concentrated under reduced pressure to give crude product, which was purified by preparative HPLC to afford (E)-3-(6-aminopyridin-3-yl)-N-(2-(6-fluoro-4'-(morpholine-4-carbonyl)biphenyl-3-yloxy)-2-methylpropyl)acrylamide (340). Yield (16 mg, 7%). $^1$H NMR (400 MHz, $CD_3OD$) δ 8.21 (dd, J=2 Hz, J=9.2 Hz, 1H), 8.04 (d, J=2.4 Hz, 1H), 7.65 (t, J=1.2 Hz, 2H), 7.54 (d, J=8 Hz, 2H), 7.47 (d, J=15.6 Hz, 1H), 7.19-7.06 (m, 4H), 6.77 (d, J=15.6 Hz, 1H), 3.81-3.50 (m, 10H), 1.33 (s, 6H). LCMS: m/z 519.3 $[M+H]^+$; $t_R$=1.58 min.

Synthesis of (E)-3-(6-aminopyridin-3-yl)-N-(2,2-dideutero-2-(3-chloro-4'-(morpholine-4-carbonyl)biphenyl-4-yloxy)ethyl)acrylamide (342)

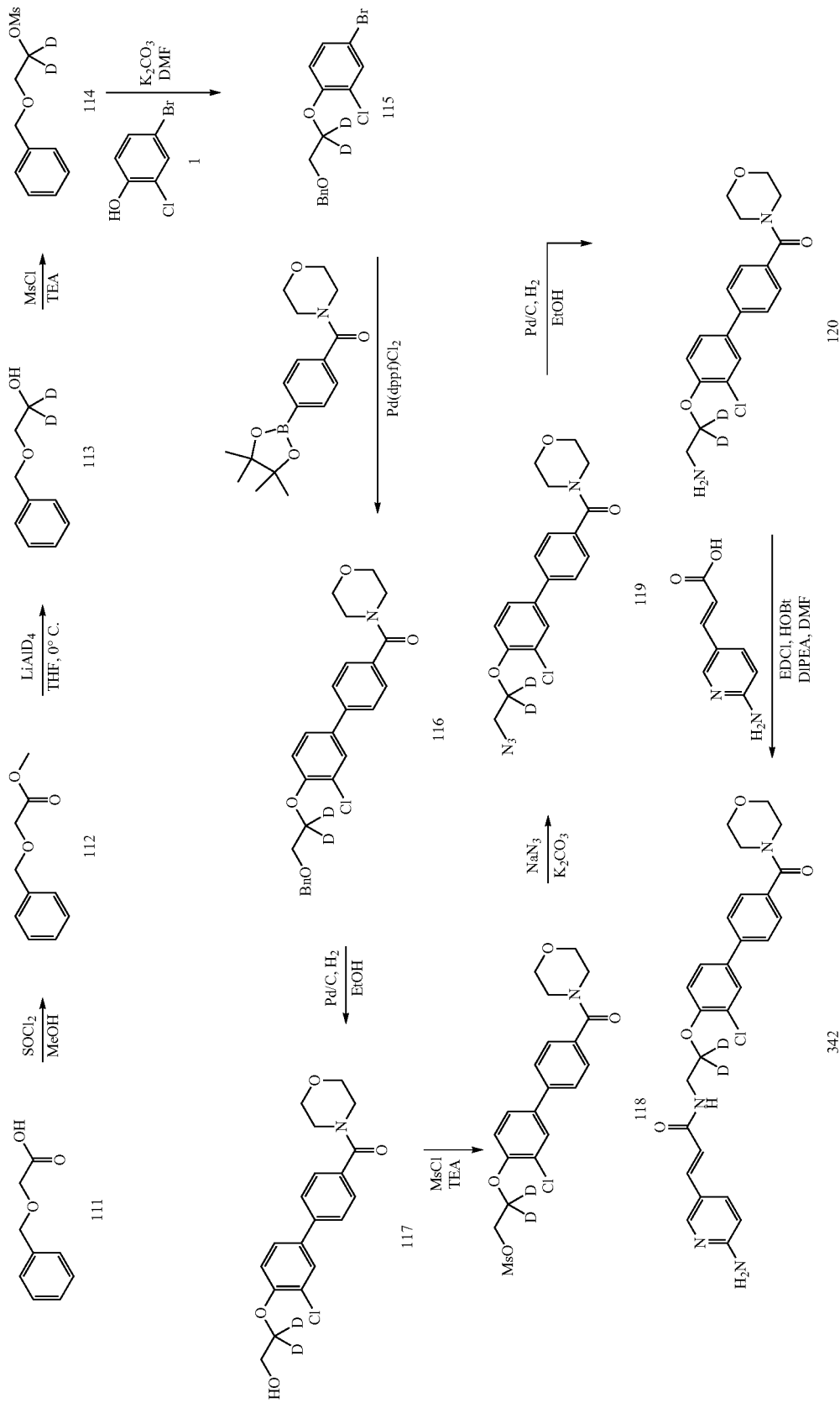

Thionyl chloride (17.2 g) was added to methanol (100 mL) at 0° C. After stirring for 1 h, 2-(benzyloxy)acetic acid (111) (8.0 g, 48.2 mmol) was added. The mixture was stirred at 60° C. for 3 h, and concentrated to give methyl 2-(benzyloxy)acetate (112) (Yield 7.8 g, 90%), which was used in the next step without further purification. LCMS: m/z 181.1 [M+H]$^+$; $t_R$=0.84 min.

Methyl 2-(benzyloxy)acetate (112) (5.5 g, 30.6 mmol) was dissolved in THF (30 mL). LiAlD$_4$ (1.4 g, 35 mmol) was added at 0° C. and the reaction mixture was stirred for 3 h. Water (1.4 mL) was added to quench the reaction. 10% aqueous NaOH solution (2.8 mL) and water (4.2 mL) were added. The mixture was filtered through a pad of CELITE®, and the precipitate was washed with THF. The filtrate was dried over anhydrous Na$_2$SO$_4$, and concentrated to give crude product, which was purified by silica gel chromatography (30% EtOAc/petroleum ether) to obtain 2-(benzyloxy)-1,1-dideuteroethanol (113) Yield (3.4 g, 74%). LCMS: m/z 177.1 [M+Na]$^+$; $t_R$=1.40 min.

Synthesis of 2-(benzyloxy)-1,1-dideuteroethyl methanesulfonate (114)

General Procedure 7: Mesylation of Alcohol

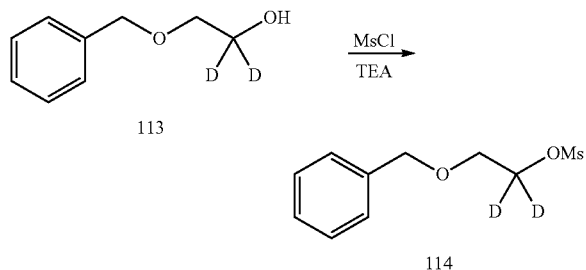

2-(Benzyloxy)-1,1-dideuteroethanol (113) (300 mg, 1.95 mmol) was dissolved in dichloromethane (10 mL). Methane sulfonyl chloride (222 mg, 1.95 mmol) and triethylamine (394 g, 3.9 mmol) were added at 0° C. and the reaction mixture was allowed to warm to room temperature and stirred for 4 h. The reaction mixture was transferred into iced water and extracted with dichloromethane (50 mL×3). The combined organic layers were washed with brine, dried over anhydrous Na$_2$SO$_4$, and concentrated under reduced pressure to give 2-(benzyloxy)-1,1-dideuteroethyl methanesulfonate (114), which was used in the next step without further purification. Yield (365 mg). LCMS: m/z 255.0 [M+Na]$^+$, $t_R$=1.84 min.

Synthesis of 1-(2-(benzyloxy)-1,1-dideuteroethoxy)-4-bromo-2-chlorobenzene (115)

General Procedure 8: Alkylation with Mesylate

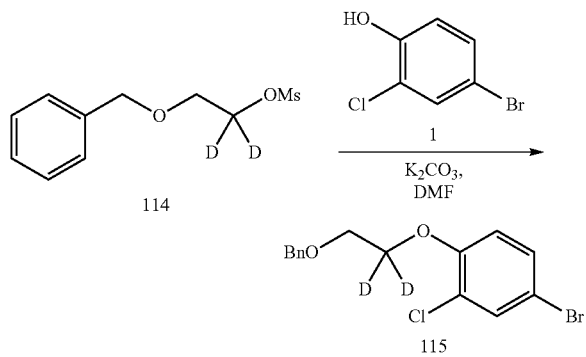

2-(Benzyloxy)-1,1-dideuteroethyl methanesulfonate (114) (232 mg, 1.0 mmol) was dissolved in acetonitrile (10 mL) K$_2$CO$_3$ (276 mg, 2.0 mmol) and 4-bromo-2-chlorophenol (1) (207 mg, 1.0 mmol) were added at 25° C. and the reaction mixture was stirred at 25° C. for 10 h. The reaction mixture was transferred into iced water and extracted with ethyl acetate (30 mL×3). The combined organic layers were washed with brine, dried over anhydrous Na$_2$SO$_4$, and concentrated under reduced pressure to give crude product, which was purified by silica gel chromatography (20% EtOAc/petroleum ether) to obtain 1-(2-(benzyloxy)-1,1-dideuteroethoxy)-4-bromo-2-chlorobenzene (115). Yield (200 mg, 70%). LCMS: m/z 365.0 [M+Na]$^+$, $t_R$=2.03 min.

Synthesis of (4'-(2-(benzyloxy)-1,1-dideuteroethoxy)-3'-chlorobiphenyl-4-yl)(morpholino)methanone (116)

A mixture of 1-(2-(benzyloxy)-1,1-dideuteroethoxy)-4-bromo-2-chlorobenzene (115) (68 mg, 0.2 mmol), morpholino(4-(4,4,5,5-tetramethyl-1,3,2-dioxaborolan-2-yl)phenyl)methanone (63 mg, 0.2 mmol), Pd(dppf)Cl$_2$ (16.3 mg, 0.02 mmol) and K$_2$CO$_3$ (55 mg, 0.4 mmol) in dioxane (10 mL) and H$_2$O (1 mL) was stirred at 85° C. under nitrogen atmosphere for 3 h. The mixture was extracted with EtOAc (20 mL×3). The combined organic layers were washed with brine, dried over anhydrous Na$_2$SO$_4$, and the solvents were removed under reduced pressure to give crude product, which was purified by silica gel chromatography (20% EtOAc/petroleum ether) to give (4'-(2-(benzyloxy)-1,1-dideuteroethoxy)-3'-chlorobiphenyl-4-yl)(morpholino)methanone (116). Yield (45 mg, 50%). LCMS: m/z 454.1 [M+H]$^+$; $t_R$=1.90 min.

Synthesis of (3'-chloro-4'-(1,1-dideutero-2-hydroxyethoxy)biphenyl-4-yl)(morpholino)methanone (117)

General Procedure 9: Hydrogenation

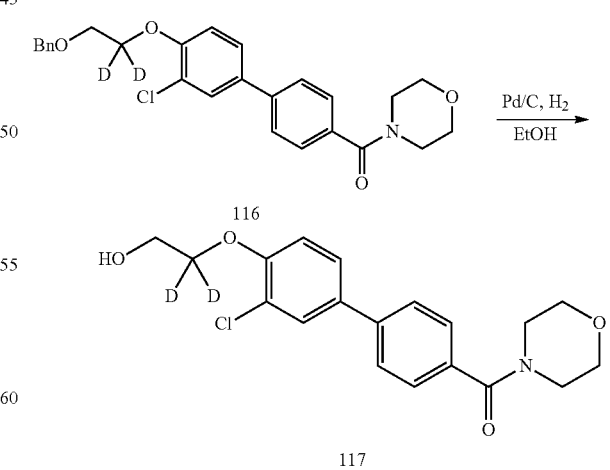

A solution of (4'-(2-(benzyloxy)-1,1-dideuteroethoxy)-3'-chlorobiphenyl-4-yl)(morpholino)methanone (116) (45.3 mg, 0.1 mmol) and 10% Pd/C (dry) (10 mg) in ethanol (10 mL) was stirred under hydrogen atmosphere (1 atm) at room temperature for 1 h. The reaction mixture was filtered and the filtrate was concentrated under reduced pressure to give (3'-chloro-4'-(1,1-dideutero-2-hydroxyethoxy)biphenyl-4-yl)(morpholino)methanone (117) (30 mg), which was used without further purification in the next step. LCMS: m/z 364.0 [M+H]⁺, $t_R$=1.50 min.

2,2-Dideutero-2-(3-chloro-4'-(morpholine-4-carbonyl)biphenyl-4-yloxy)ethyl methanesulfonate (118) was synthesized using General Procedure 7. Yield (60%). LCMS: m/z 442.0.0 [M+H]⁺; $t_R$=1.62 min.

Synthesis of (4'-(2-azido-1,1-dideuteroethoxy)-3'-chlorobiphenyl-4-yl)(morpholino)methanone (119)

General Procedure 10: Displacement of Mesylate with Azide

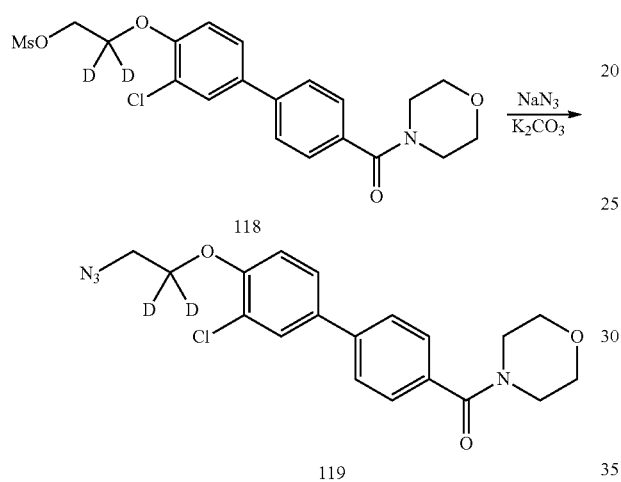

2,2-Dideutero-2-(3-chloro-4'-(morpholine-4-carbonyl)biphenyl-4-yloxy)ethyl methanesulfonate (118) (50 mg, 0.11 mmol) was dissolved DMF (10 mL) K₂CO₃ (276 mg, 2.0 mmol) and sodium azide (14 mg, 0.22 mmol) were added at 25° C. and the reaction mixture was stirred at 80° C. for 4 h. The reaction mixture was transferred into iced water and extracted with ethyl acetate (30 mL×3). The combined organic layers were washed with brine, dried over anhydrous Na₂SO₄, and concentrated under reduced pressure to give crude product, which was purified by silica gel chromatography (30% EtOAc/petroleum ether) to obtain (4'-(2-azido-1,1-dideuteroethoxy)-3'-chlorobiphenyl-4-yl)(morpholino)methanone (119). Yield (22 mg, 85%). LCMS: m/z 389.0 [M+H]⁺, $t_R$ 1.77 min.

Synthesis of (4'-(2-amino-1,1-dideuteroethoxy)-3'-chlorobiphenyl-4-yl)(morpholino)methanone (120)

General Procedure 11: Reduction of Azide

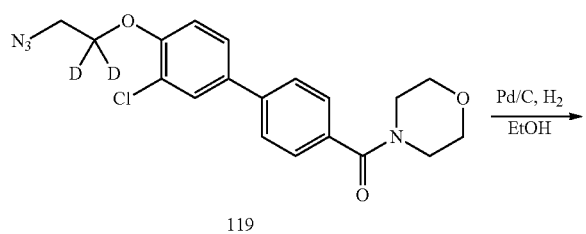

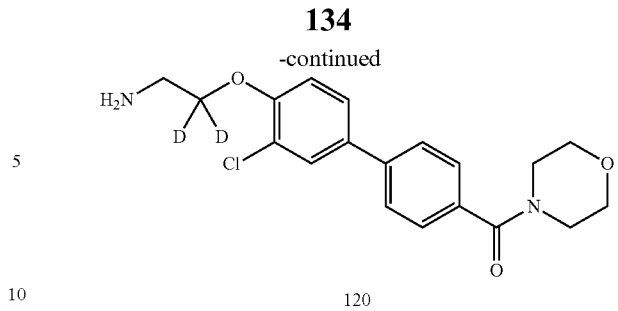

A mixture of (4'-(2-Azido-1,1-dideuteroethoxy)-3'-chlorobiphenyl-4-yl)(morpholino)methanone (119) (120 mg, 0.31 mmol) and 10% Pd/C (dry) (10 mg) in ethanol (10 mL) was stirred under hydrogen atmosphere (1 atm) at room temperature for 1 h. The reaction mixture was filtered and the filtrate was concentrated under reduced pressure to give (4'-(2-amino-1,1-dideuteroethoxy)-3'-chlorobiphenyl-4-yl) (morpholino)methanone (120) (80 mg), which was used without further purification in the next step. LCMS: m/z 363.0 [M+H]⁺, $t_R$=1.24 min.

Synthesis of methyl 2-((E)-3-(6-aminopyridin-3-yl)-N-(2,2-dideutero-2-(3-chloro-4'-(morpholine-4-carbonyl)biphenyl-4-yloxy)ethyl)acrylamide (342)

(4'-(2-Amino-1,1-dideuteroethoxy)-3'-chlorobiphenyl-4-yl)(morpholino)methanone (120) (80 mg, 0.22 mmol) was dissolved in DMF (5 mL) and (E)-3-(6-aminopyridin-3-yl) acrylic acid (38 mg, 0.22 mmol) was added at room temperature. EDCI (42 mg, 0.22 mmol) and HOBt (30 mg, 0.30 mmol) were added to this reaction mixture at room temperature followed by dropwise addition of DIPEA (57 mg, 0.44 mmol). The reaction mixture was allowed to warm to room temperature and stirred further for 4 h. The reaction mixture was transferred into water (20 mL) and extracted with EtOAc (25 mL×3). The combined organic layers were washed with brine, dried over anhydrous Na₂SO₄ and concentrated under reduced pressure to give crude product, which was purified by preparative HPLC to afford 2-((E)-3-(6-aminopyridin-3-yl)-N-(2,2-dideutero-2-(3-chloro-4'-(morpholine-4-carbonyl)biphenyl-4-yloxy)ethyl)acrylamide (342). Yield (60 mg, 54%). ¹H NMR (400 MHz, DMSO-d₆) 8.20-8.07 (m, 2H), 7.80-7.59 (m, 5H), 7.49-7.29 (m, 4H), 6.48-6.38 (m, 4H), 3.68-3.34 (m, 10H). LCMS: m/z 509.1 [M+H]⁺, $t_R$=1.34 min.

Synthesis of (E)-3-(6-aminopyridin-3-yl)-N-(2,2-dideutero-2-(6-fluoro-4'-(morpholine-4-carbonyl)biphenyl-3-yloxy)ethyl)acrylamide (343)

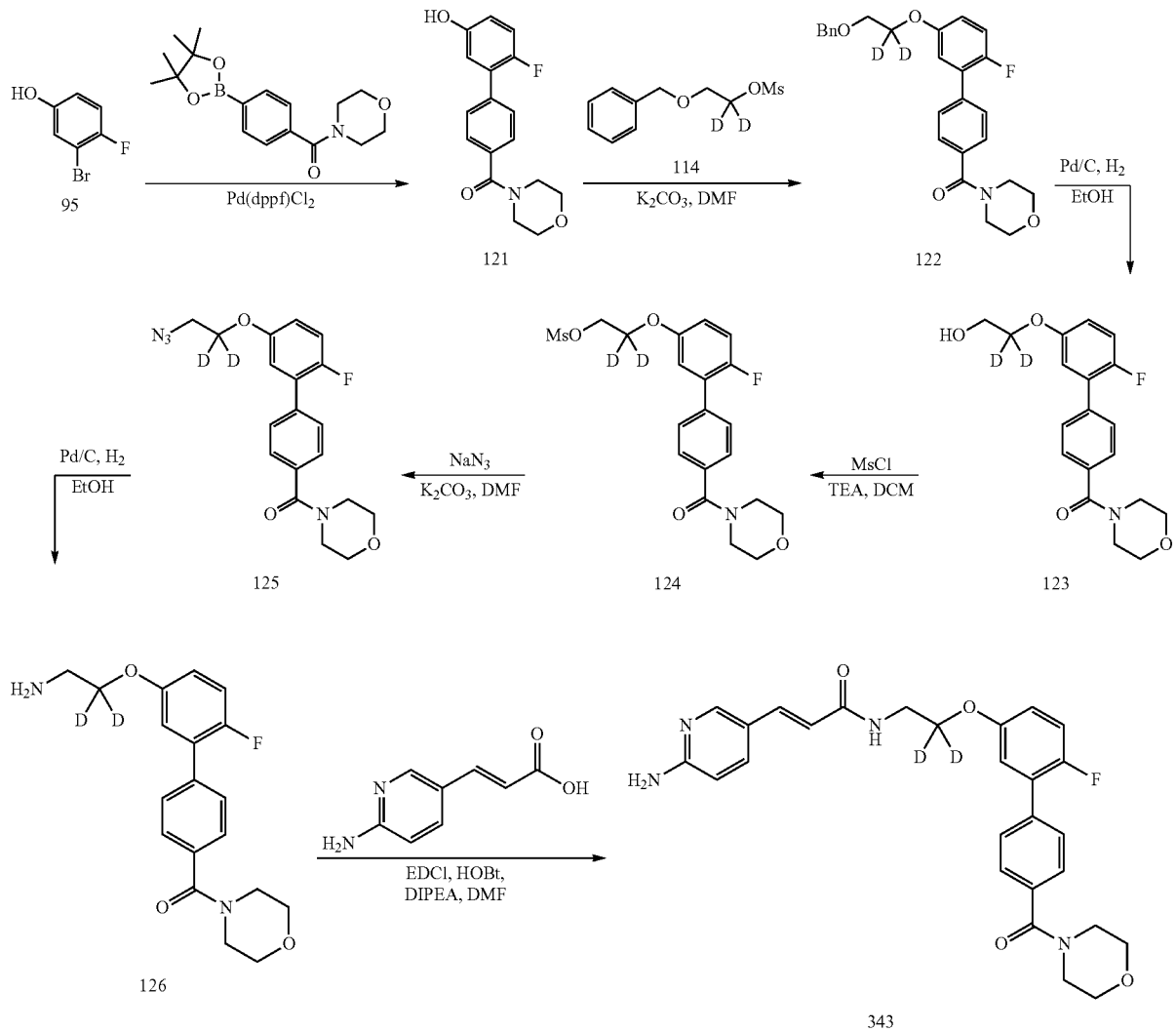

(2'-Fluoro-5'-hydroxybiphenyl-4-yl)(morpholino)methanone (121) was synthesized using the indicated reagents according to General Procedure 1. Yield (53%). LCMS: m/z 302.0[M+H]⁺; t$_R$=1.48 min.

(5'-(2-(Benzyloxy)-1,1-dideuteroethoxy)-2'-fluorobiphenyl-4-yl)(morpholino)methanone (122) was synthesized using the indicated reagents according to General Procedure 8. Yield (71%). LCMS: m/z 438.1[M+H]⁺; t$_R$=1.86 min.

(5'-(1,1-Dideutero-2-hydroxyethoxy)-2'-fluorobiphenyl-4-yl)(morpholino)methanone (123) was synthesized according to General Procedure 9. Yield (86%). LCMS: m/z 348.1 [M+H]⁺; t$_R$=1.47 min.

2-((6-Fluoro-4'-(morpholine-4-carbonyl)-[1,1'-biphenyl]-3-yl)oxy)ethyl-2,2-d2 methanesulfonate (124) was synthesized according to General Procedure 7. Yield (76%). LCMS: m/z 426.0[M+H]⁺; t$_R$=1.59 min.

(5'-(2-Azido-1,1-dideuteroethoxy)-2'-fluorobiphenyl-4-yl)(morpholino)methanone (125) was synthesized according to General Procedure 10. Yield (74%). LCMS: m/z 373.2 [M+H]⁺; t$_R$=1.76 min.

(5'-(2-Aminoethoxy-1,1-d2)-2'-fluoro-[1,1'-biphenyl]-4-yl)(morpholino)methanone (126) was synthesized using according to General Procedure 11. Yield (74%). LCMS: m/z 347.2 [M+H]⁺; t$_R$=1.76 min.

(E)-3-(6-Aminopyridin-3-yl)-N-(2,2-dideutero-2-(6-fluoro-4'-(morpholine-4-carbonyl)biphenyl-3-yloxy)ethyl)acrylamide (343) was synthesized using the indicated reagents according to General Procedure 4. Yield (57%). ¹H NMR (400 MHz, DMSO-d$_6$) 8.20-8.06 (m, 2H), 7.65-7.49 (m, 5H), 7.31-7.00 (m, 4H), 6.48-6.37 (m, 4H), 3.62-3.37 (m, 10H). LCMS: m/z 493.2 [M+H]⁺; t$_R$=1.61 min.

Synthesis of (E)-3-(6-aminopyridin-3-yl)-N-(2-(5-chloro-4'-(morpholine-4-carbonyl)biphenyl-3-yloxy)ethyl)acrylamide (344)

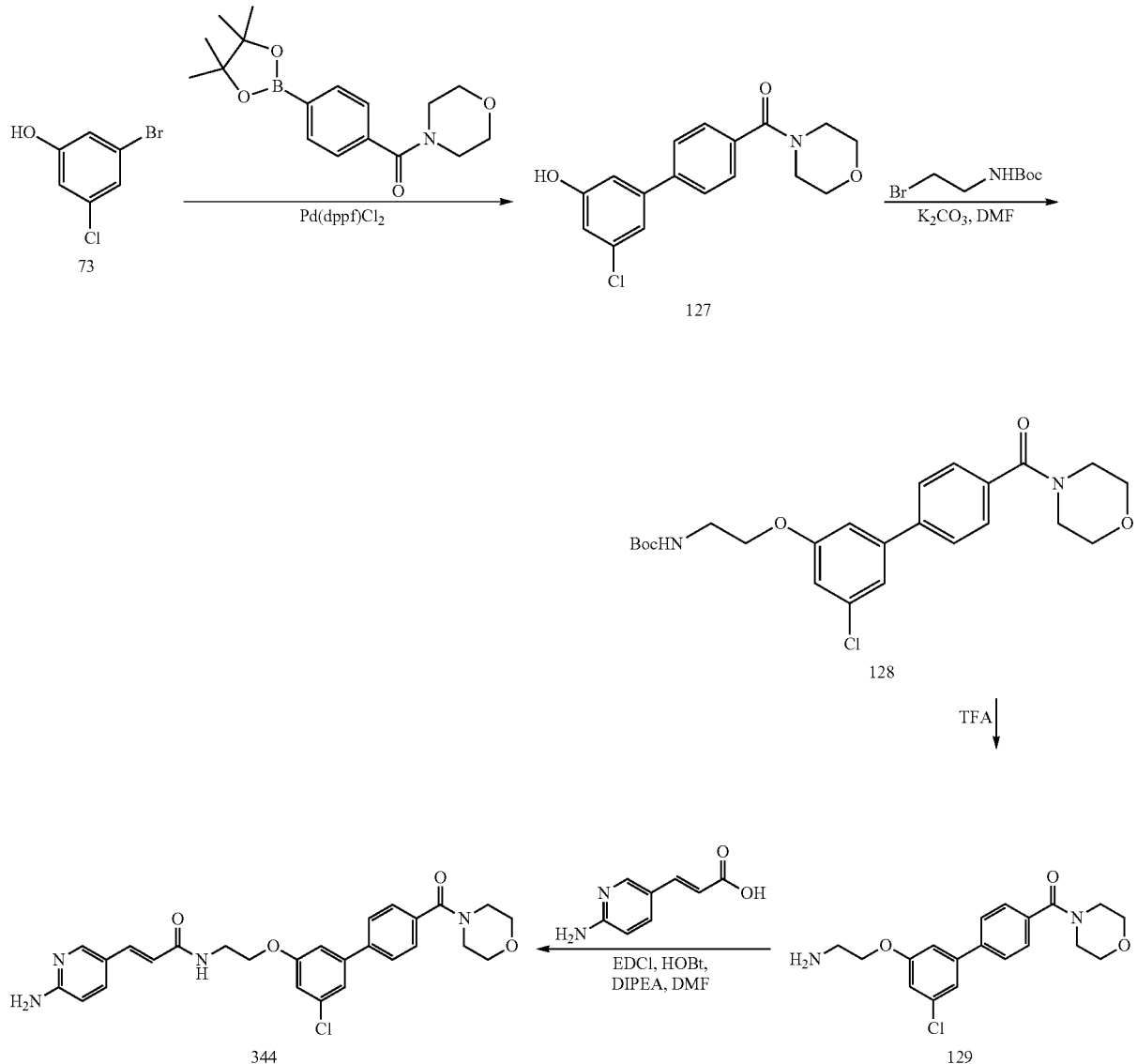

(3'-Chloro-5'-hydroxybiphenyl-4-yl)(morpholino)methanone (127) was synthesized using the indicated reagents according to General Procedure 1. Yield (600 mg, 49%). LCMS: m/z 318.0 [M+H]$^+$; $t_R$=1.07 min.

tert-Butyl 2-(5-chloro-4'-(morpholine-4-carbonyl)biphenyl-3-yloxy)ethylcarbamate (128) was synthesized using the indicated reagents according to General Procedure 2. Yield (200 mg, 92%). LCMS: m/z 405.0 [M-55]$^+$, $t_R$=1.84 min.

(3'-(2-Aminoethoxy)-5'-chlorobiphenyl-4-yl)(morpholino)methanone (129) was synthesized using the indicated reagents according to General Procedure 3. Yield (100%). LCMS: m/z 361.0 [M+H]$^+$; $t_R$=1.31 min.

(E)-3-(6-Aminopyridin-3-yl)-N-(2-(5-chloro-4'-(morpholine-4-carbonyl)biphenyl-3-yloxy)ethyl)acrylamide (344) was synthesized using the indicated reagents according to General Procedure 4. Yield (70 mg, 31%). $^1$H NMR (400 MHz, CD$_3$OD) δ 8.16 (dd, J=2.0 Hz, J=9.2 Hz, 1H), 8.02 (d, J=2.0 Hz, 1H), 7.72 (dd, J=1.6 Hz, J=6.4 Hz, 2H), 7.53 (dd, J=1.6 Hz, J=6.4 Hz, 2H), 7.43 (d, J=15.6 Hz, 1H), 7.26 (t, J=1.6 Hz, 1H), 7.05-7.02 (m, 2H), 6.62 (d, J=15.6 Hz, 1H), 4.21 (t, J=5.2 Hz, 2H), 3.78-3.51 (m, 10H). LCMS: m/z 507.1 [M+H]$^+$, $t_R$=1.43 min.

Synthesis of (E)-3-(6-aminopyridin-3-yl)-N-(3-(5-chloro-4'-(morpholine-4-carbonyl)biphenyl-3-yloxy)propyl)acrylamide (345)

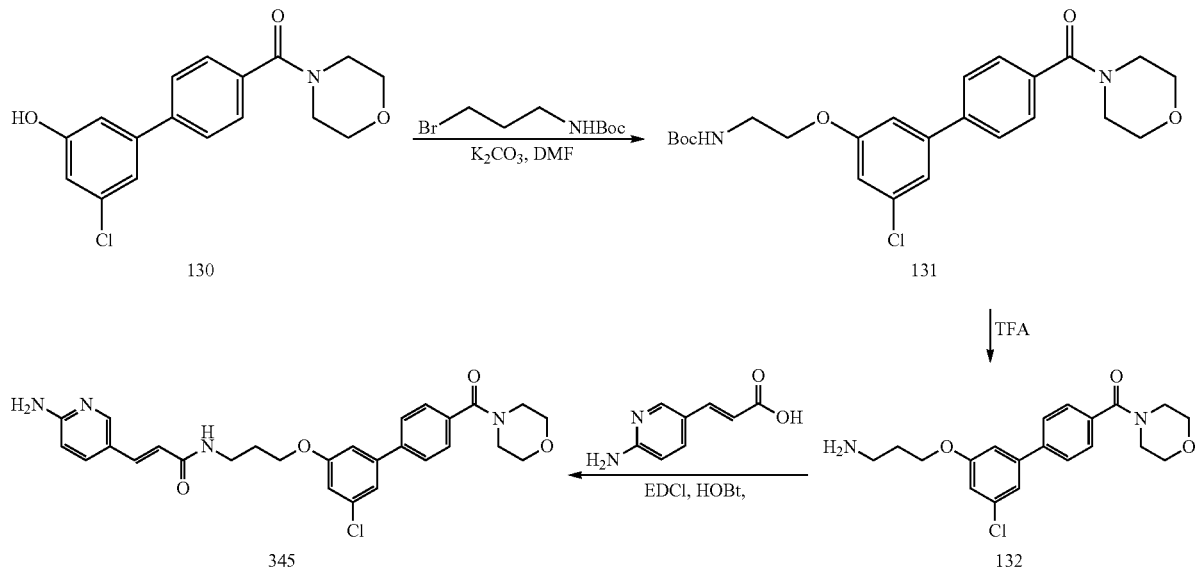

tert-Butyl 3-(5-chloro-4'-(morpholine-4-carbonyl)biphenyl-3-yloxy)propylcarbamate (131) was synthesized using the indicated reagents according to General Procedure 2. Yield (89%). LCMS: m/z 419.0 [M-55]$^+$; $t_R$=1.88 min.

(3'-(3-Aminopropoxy)-5'-chlorobiphenyl-4-yl)(morpholino)methanone (132) was synthesized using the indicated reagents according to General Procedure 3. Yield (100%). LCMS: m/z 375.0 [M+H]$^+$; $t_R$=1.36 min.

(E)-3-(6-Aminopyridin-3-yl)-N-(3-(5-chloro-4'-(morpholine-4-carbonyl)biphenyl-3-yloxy)propyl)acrylamide (345) was synthesized using the indicated reagents according to General Procedure 4. Yield (23%). $^1$H NMR (400 MHz, CD$_3$OD) δ 8.17 (dd, J=2.0 Hz, J=9.2 Hz, 1H), 7.99 (d, J=2.0 Hz, 1H), 7.71 (d, J=8.4 Hz, 2H), 7.52 (dd, J=1.6 Hz, J=6.4 Hz, 2H), 7.39 (d, J=16 Hz, 1H), 7.24 (t, J=5.6 Hz, 1H), 7.14 (t, J=2 Hz, 1H), 7.06-7.00 (m, 2H), 6.58 (d, J=16 Hz, 1H), 4.15 (t, J=6 Hz, 2H), 3.78-3.51 (m, 10H), 2.11-2.05 (m, 2H. LCMS: m/z 521.0 [M+H]$^+$, $t_R$=1.48 min.

Synthesis of (E)-3-(6-aminopyridin-3-yl)-N-(3-(5-chloro-4'-(morpholine-4-carbonyl)biphenyl-2-yloxy)propyl)acrylamide (346)

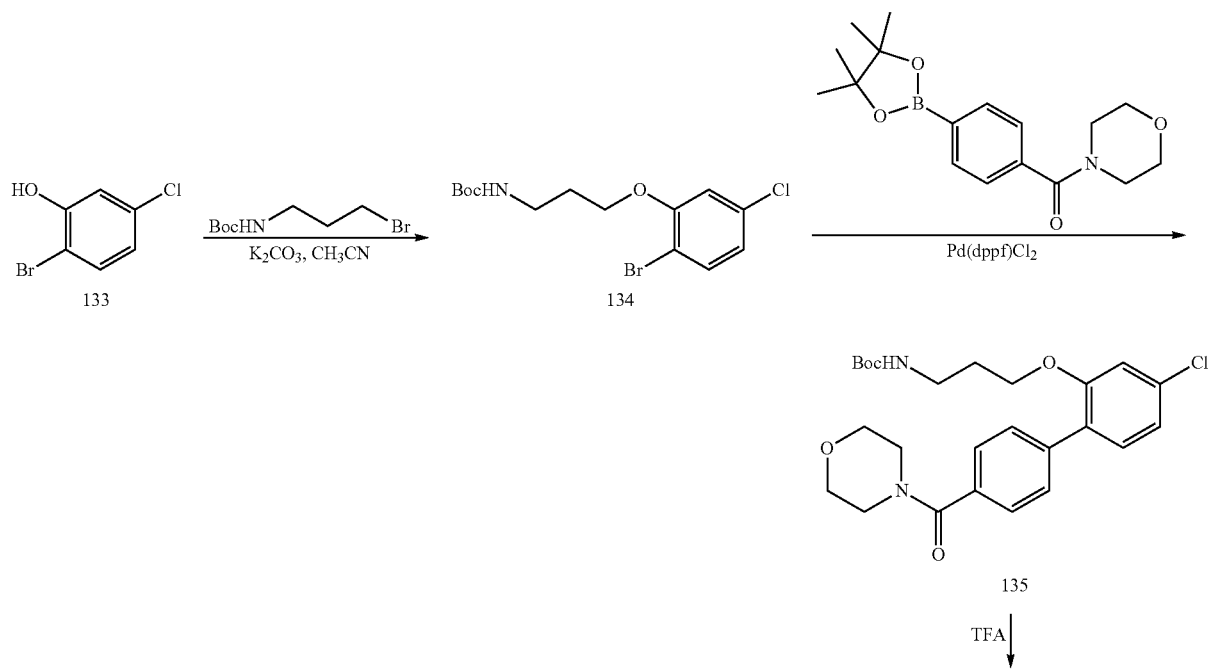

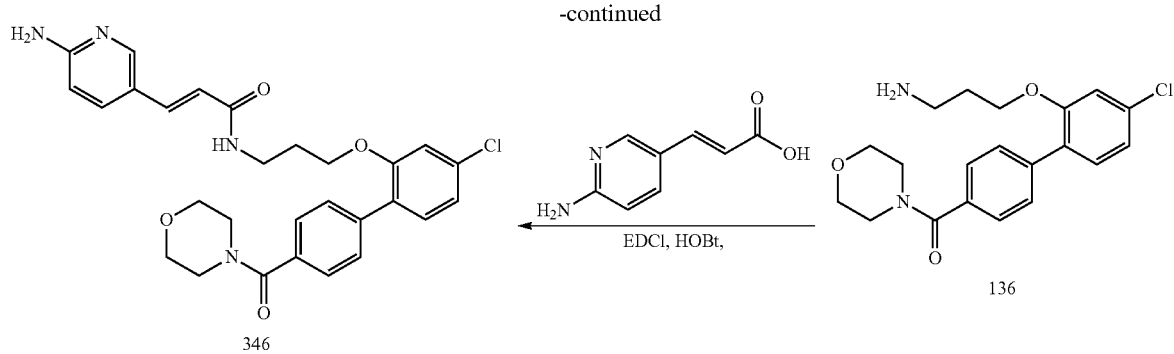

tert-Butyl 3-(2-bromo-4-chlorophenoxy)propylcarbamate (134) was synthesized using the indicated reagents according to General Procedure 2. Yield (80%). LCMS: m/z 386 [M+H]$^+$, t$_R$=1.97 min.

tert-Butyl 3-(5-chloro-4'-(morpholine-4-carbonyl)biphenyl-2-yloxy)propylcarbamate (135) was synthesized using the indicated reagents according to General Procedure 1. Yield (54%). LCMS: m/z: 497 [M+Na]$^+$, t$_R$=1.84 min.

(2'-(3-Aminopropoxy)-5'-chlorobiphenyl-4-yl)(morpholino)methanone (136) was synthesized using the indicated reagents according to General Procedure 3. Yield (88.6%). LCMS: m/z 375 [M+H]$^+$; t$_R$=1.23 min.

(E)-3-(6-aminopyridin-3-yl)-N-(3-(5-chloro-4'-(morpholine-4-carbonyl)biphenyl-2-yloxy)propyl)acrylamide (346) was synthesized using General Procedure 4. Yield (67%). $^1$H NMR (400 MHz, MeOD-d$_6$) δ 8.18-8.15 (dd, J=9.6 Hz, J=2.4 Hz, 1H), 8.03 (s, 1H), 7.65 (d, J=8.0 Hz, 2H), 7.50 (d, J=8.0 Hz, 2H), 7.41-7.31 (m, 2H), 7.14-7.03 (m, 3H), 6.51 (d, J=15.6 Hz, 1H), 4.09 (t, J=6.0 Hz, 2H), 3.78-3.40 (m, 10H), 1.99 (t, J=6.0 Hz, 2H). LCMS: m/z 520 [M+H]$^+$, t$_R$=1.28 min.

Synthesis of (E)-3-(6-aminopyridin-3-yl)-N-(2-(5-chloro-4'-(morpholine-4-carbonyl)biphenyl-3-yloxy)-2-methylpropyl)acrylamide (347)

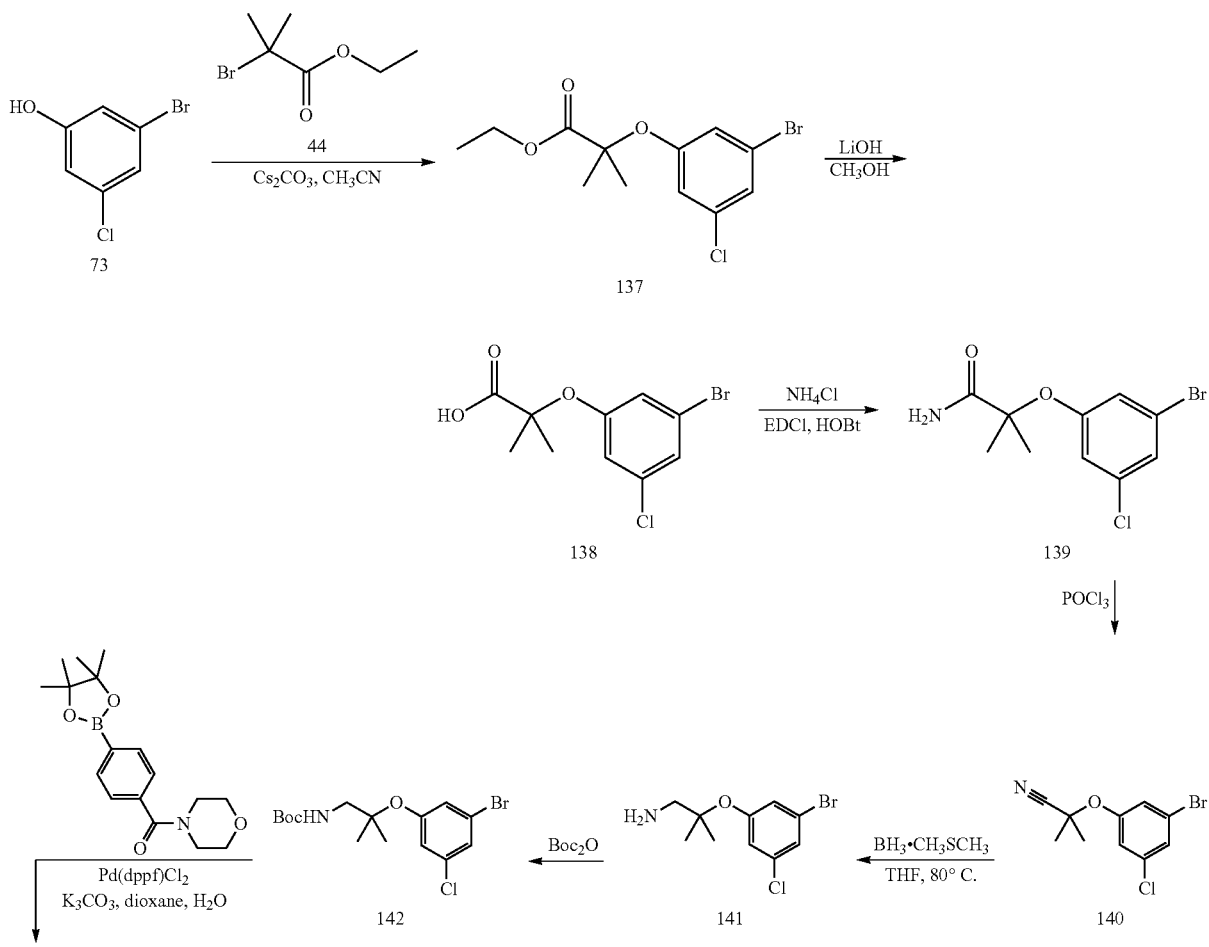

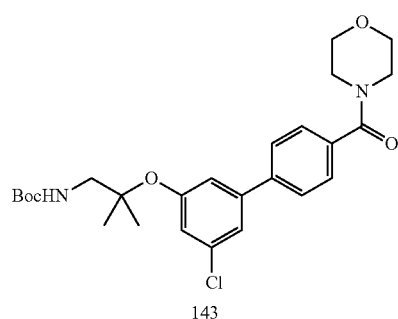
143

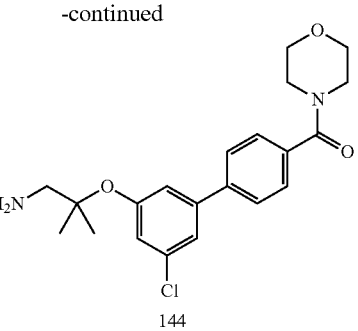
144

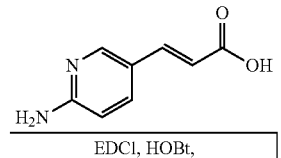

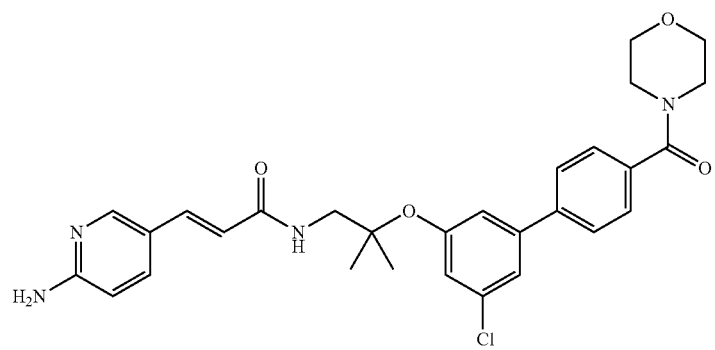
347

Ethyl 2-(3-bromo-5-chlorophenoxy)-2-methylpropanoate (137) was synthesized in accordance with the procedure used to synthesize intermediate (45). Yield (90%). LCMS: m/z 322.0 [M+H]$^+$, $t_R$=2.12 min.

2-(3-Bromo-5-chlorophenoxy)-2-methylpropanoic acid (138) was synthesized in accordance with the procedure used to synthesize intermediate (46). Yield (93%). LCMS: m/z 294.9 [M+H]$^+$, $t_R$=1.85 min.

2-(3-Bromo-5-chlorophenoxy)-2-methylpropanamide (139) was synthesized in accordance with the procedure used to synthesize intermediate (47). Yield (64%). LCMS: m/z 293.0 [M+H]$^+$, $t_R$=1.77 min.

2-(3-Bromo-5-chlorophenoxy)-2-methylpropanenitrile (140) was synthesized in accordance with the procedure used to synthesize intermediate (48). Yield (80%).

2-(3-Bromo-5-chlorophenoxy)-2-methylpropan-1-amine (141) was synthesized in accordance with the procedure used to synthesize intermediate (49). Yield (53%). LCMS: m/z 279.9 [M+H]$^+$, $t_R$=1.35 min.

tert-Butyl 2-(3-bromo-5-chlorophenoxy)-2-methylpropylcarbamate (142) was synthesized in accordance with the procedure used to synthesize intermediate (108). Yield (100%). LCMS: m/z 401.9 [M+Na]$^+$, $t_R$=2.13 min.

tert-Butyl 2-(5-chloro-4'-(morpholine-4-carbonyl)biphenyl-3-yloxy)-2-methylpropylcarbamate (143) was synthesized using the indicated reagents according to General Procedure 1. Yield (76%). LCMS: m/z 511.1 [M+H]$^+$, $t_R$=1.20 min.

(3'-(1-Amino-2-methylpropan-2-yloxy)-5'-chlorobiphenyl-4-yl)(morpholino)methanone (144) was synthesized using the indicated reagents according to General Procedure 3. Yield (100%). LCMS: m/z 389.2 [M+H]$^+$, $t_R$=1.64 min.

(E)-3-(6-Aminopyridin-3-yl)-N-(2-(5-chloro-4'-(morpholine-4-carbonyl)biphenyl-3-yloxy)-2-methylpropyl)acrylamide (347) was synthesized using the indicated reagents according to General Procedure 4. $^1$H NMR (400 MHz, CD$_3$OD) δ 8.22 (d, J=9.2 Hz, 1H), 8.04 (d, J=2 Hz, 1H), 7.72 (d, J=8 Hz, 2H), 7.55-7.45 (m, 4H), 7.27 (t, J=1.2 Hz, 1H), 7.14 (d, J=2 Hz, 1H), 7.08 (d, J=9.6 Hz, 1H), 6.77 (d, J=15.6 Hz, 1H), 3.78-3.51 (m, 10H), 1.38 (s, 6H). LCMS: m/z 535.3 [M+H]$^+$; $t_R$=1.64 min.

Synthesis of (E)-3-(6-aminopyridin-3-yl)-N-(3-(3-chloro-4'-(morpholine-4-carbonyl)biphenyl-4-yloxy)propyl)acrylamide (348)

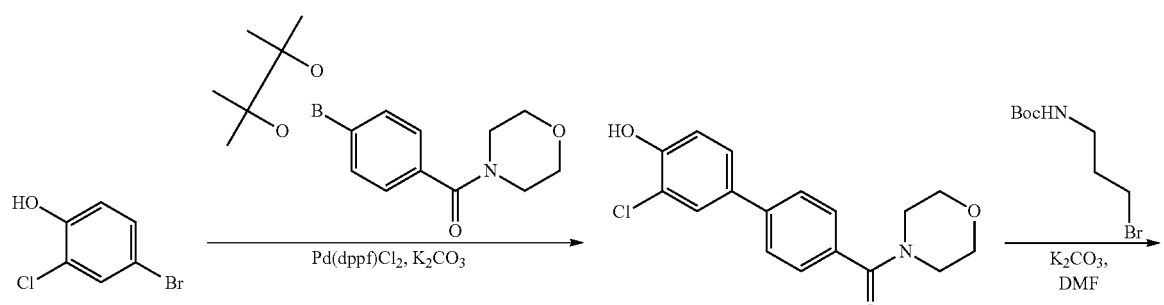
145

-continued

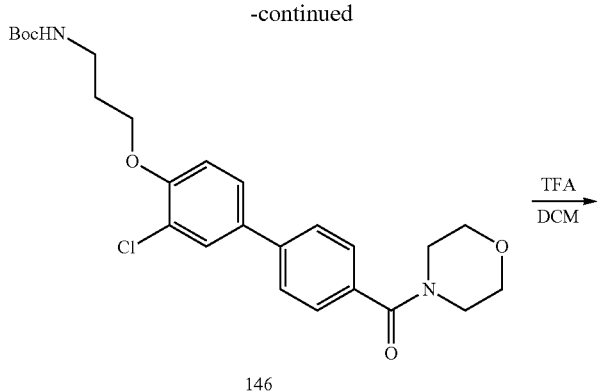

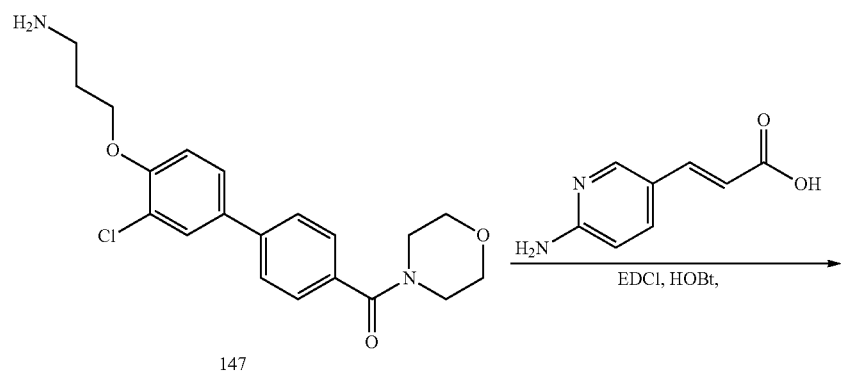

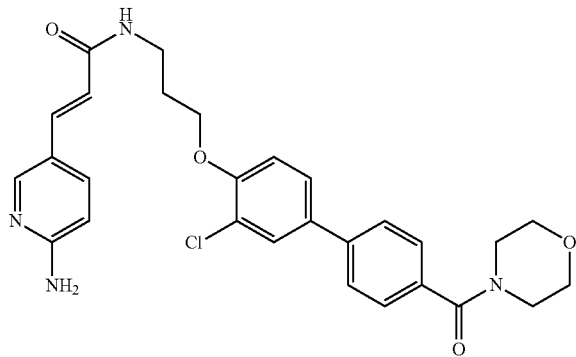

(3'-Chloro-4'-hydroxybiphenyl-4-yl)(morpholino)methanone 145 was synthesized using the indicated reagents according to General Procedure 1. Yield (56%). LCMS: m/z 318.0 [M+H]⁺; $t_R$=1.52 min.

tert-Butyl 3-(3-chloro-4'-(morpholine-4-carbonyl)biphenyl-4-yloxy)propylcarbamate 146 was synthesized in accordance with the procedure used to synthesize intermediate (45). Yield (84%). LCMS: m/z 497.0 [M+Na]⁺; $t_R$=1.20 min.

(4'-(3-Aminopropoxy)-3'-chlorobiphenyl-4-yl)(morpholino)methanone 147 was synthesized using the indicated reagents according to General Procedure 3. Yield (100%). LCMS: m/z 375.1 [M+H]⁺; $t_R$=0.91 min.

(E)-3-(6-aminopyridin-3-yl)-N-(3-(3-chloro-4'-(morpholine-4-carbonyl)biphenyl-4-yloxy)propyl)acrylamide 348 was synthesized using the indicated reagents according to General Procedure 4. Yield (18%). ¹H NMR (400 MHz, CD₃OD) δ 8.19 (dd, J=2.4 Hz, J=9.6 Hz, 1H), 8.02 (d, J=2.0 Hz, 1H), 7.70-7.68 (m, 3H), 7.58 (dd, J=2.4 Hz, J=8.8 Hz, 1H), 7.52 (dd, J=2.0 Hz, J=6.8 Hz, 2H), 7.41 (d, J=15.6 Hz, 1H), 7.19 (d, J=8.4 Hz, 1H), 7.06 (d, J=9.6 Hz, 1H), 6.59 (d, J=16 Hz, 1H), 4.21 (t, J=6 Hz, 2H), 3.78-3.57 (m, 10H), 2.13 (t, J=6 Hz, 2H). LCMS: m/z 521.1 [M+H]⁺, $t_R$=1.38 min.

Synthesis of (E)-3-(6-aminopyridin-3-yl)-N-(3-(3-chloro-4'-(morpholine-4-carbonyl)biphenyl-4-yloxy)-2,2-difluoropropyl)acrylamide (349)
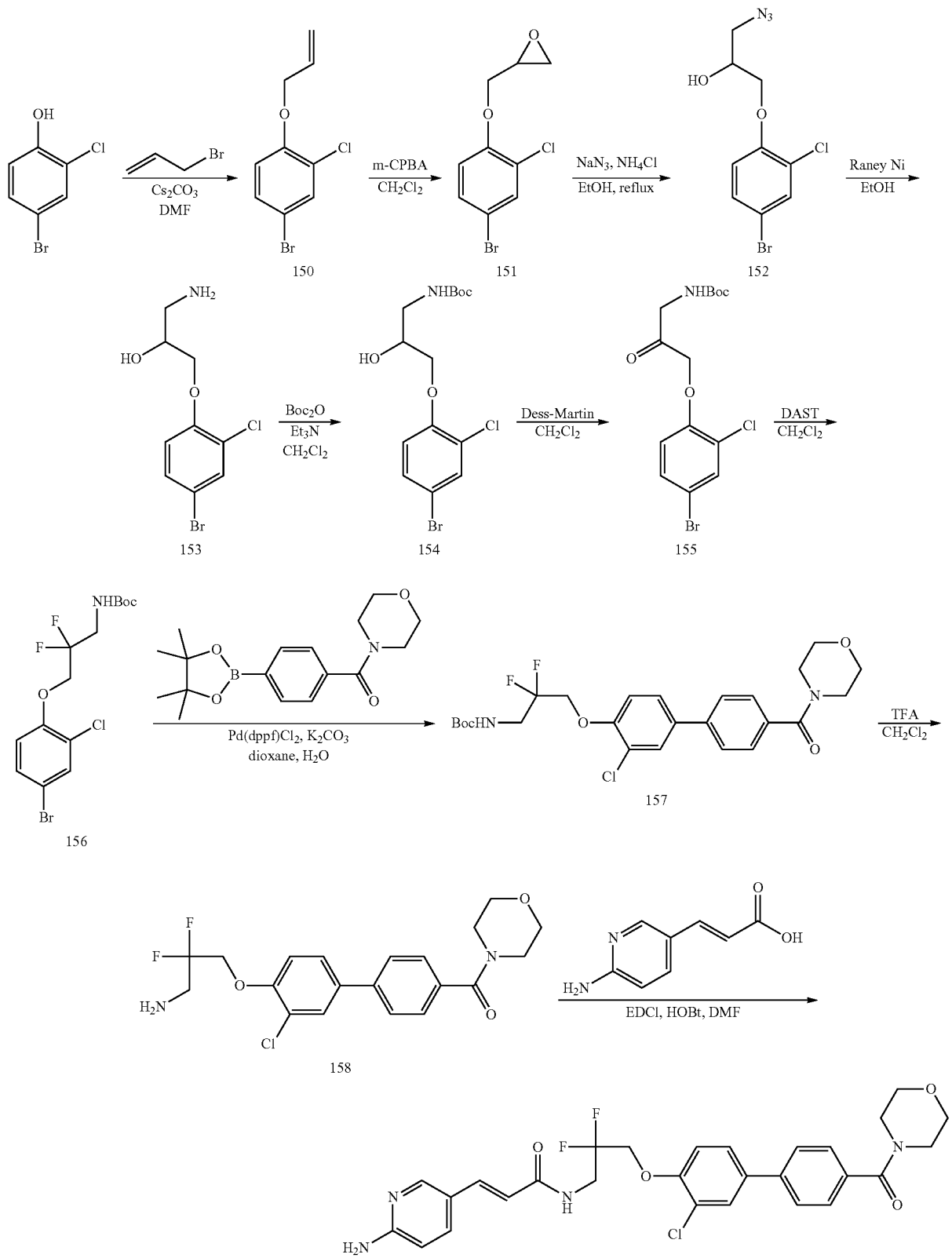

4-Bromo-2-chlorophenol 1 (5 g, 24.15 mmol) was dissolved in DMF (20 mL). $Cs_2CO_3$ (15.69 g, 48.30 mmol) and allyl bromide (3.47 g, 28.98 mmol) were added at 25° C. and the reaction mixture was stirred at 60° C. for 4 h. The reaction mixture was transferred into iced water and extracted with ethyl acetate (50 mL×3). The combined organic layers were washed with brine, dried over anhydrous $Na_2SO_4$, and concentrated under reduced pressure to give 11.2 g of 1-(allyloxy)-4-bromo-2-chlorobenzene 150, which was used in the next step without further purification.

1-(Allyloxy)-4-bromo-2-chlorobenzene 150 (11.2 g, 45.52 mmol) was dissolved in dichloromethane (30 mL). m-CPBA (15.6 g, 91.05 mmol) was added at 0° C. and the reaction mixture was stirred at room temperature for 3 days. The reaction mixture was diluted with dichloromethane (100 mL) and washed with saturated sodium bicarbonate solution and saturated sodium thiosulphate solution, followed by brine, dried over anhydrous $Na_2SO_4$, and concentrated under reduced pressure to give crude product. The residue was purified by silica gel chromatography to give 8.6 g 2-((4-bromo-2-chlorophenoxy)methyl)oxirane 151 (72% yield). LCMS: m/z 284.7 $[M+Na]^+$, $t_R$=1.81 min.

To a stirred solution of 2-((4-bromo-2-chlorophenoxy) methyl)oxirane 151 (456 mg, 1.74 mmol) in ethanol (20 ml) was added sodium azide (226 mg, 3.48 mmol) and ammonium chloride (94 mg, 1.74 mmol). The reaction mixture was stirred at reflux, overnight. After completion, the residue was treated with EtOAc and $H_2O$. The organic layer was separated; the aqueous layer was extracted with EtOAc (20 ml×3). The combined organic layers were washed with $H_2O$ and brine, dried over $Na_2SO_4$ and concentrated under reduced pressure. The residue was purified by silica gel chromatography (5 to 10% EtOAc/petroleum ether) to give 416 mg of 1-azido-3-(4-bromo-2-chlorophenoxy)propan-2-ol 152 (78% yield).

1-Azido-3-(4-bromo-2-chlorophenoxy)propan-2-ol 152 (366 mg, 1.20 mmol) was dissolved in ethanol (10 mL). Raney Ni (200 mg, wet) was added and hydrogen gas was purged. The mixture was stirred at room temperature for 30 min. The reaction mixture was filtered and the filtrate was concentrated under reduced pressure to give 272 mg 1-amino-3-(4-bromo-2-chlorophenoxy)propan-2-ol 153, which was used without further purification in the next step. LCMS: m/z 279.9 $[M+H]^+$; $t_R$=1.19 min.

1-Amino-3-(4-bromo-2-chlorophenoxy)propan-2-ol 153 (3.1 g, 11.04 mmol) was dissolved in dichloromethane (20 mL). Di-tert-butyl dicarbonate (3.6 g, 16.56 mmol) and triethylamine (1.67 g, 16.56 mmol) were added at 0° C. The reaction mixture was stirred at room temperature for 4 h. The reaction mixture was transferred into iced water and extracted with dichloromethane (50 mL×3). The combined organic layers were washed with brine, dried over anhydrous $Na_2SO_4$, and concentrated under reduced pressure to give tert-butyl 3-(4-bromo-2-chlorophenoxy)-2-hydroxypropylcarbamate 154, which was used without further purification in the next step. LCMS: m/z 401.7 [M+Na]+, $t_R$=1.83 min.

tert-Butyl 3-(4-bromo-2-chlorophenoxy)-2-hydroxypropylcarbamate 154 (2.8 g, 7.38 mmol) was dissolved in dichloromethane (40 mL). Dess-Martin reagent (4.7 g, 11.08 mmol) was added to the mixture and the mixture was stirred for 12 h. After completion, the reaction mixture was filtered and the filtrate was concentrated to get crude product, which was purified by silica gel chromatography (5 to 10% EtOAc/petroleum ether) to obtain 1.3 g tert-butyl 3-(4-bromo-2-chlorophenoxy)-2-oxopropylcarbamate 155 (46% yield). LCMS: m/z 323.9 $[M-55]^+$, $t_R$=2.04 min.

tert-Butyl 3-(4-bromo-2-chlorophenoxy)-2-oxopropylcarbamate 155 (125 mg, 0.33 mmol) was dissolved in dichloromethane (10 mL). DAST (107 mg, 0.66 mmol) was added at −78° C. The reaction mixture was stirred at −78° C. for 1 h, then allowed to warm to room temperature and stirred overnight. The reaction was quenched with saturated sodium bicarbonate solution; the mixture was extracted with dichloromethane (20 mL×3). The combined organic layers were washed with brine, dried over anhydrous $Na_2SO_4$, and the solvents were removed under reduced pressure to give crude product, which was purified by reverse phase HPLC (TFA condition) to give 38 mg tert-butyl 3-(4-bromo-2-chlorophenoxy)-2,2-difluoropropylcarbamate 156 (yield: 29%). LCMS: m/z 305.0 [M-55]+, $t_R$=1.87 min.

A mixture of tert-butyl 3-(4-bromo-2-chlorophenoxy)-2,2-difluoropropylcarbamate 156 (150 mg, 0.38 mmol), morpholino(4-(4,4,5,5-tetramethyl-1,3,2-dioxaborolan-2-yl) phenyl)methanone (119 mg, 0.38 mmol), $Pd(dppf)Cl_2$ (29 mg, 0.038 mmol) and $K_2CO_3$ (103 mg, 0.75 mmol) in 15 mL of dioxane and 3 mL of $H_2O$ was stirred at 80° C. under nitrogen atmosphere for 3 h. The mixture was extracted with EtOAc (20 mL×3). The combined organic layers were washed with brine, dried over anhydrous $Na_2SO_4$, and the solvents were removed under reduced pressure to give crude product, which was purified by silica gel chromatography (20 to 50% EtOAc/petroleum ether) to give 110 mg tert-butyl 3-(3-chloro-4'-(morpholine-4-carbonyl)biphenyl-4-yloxy)-2,2-difluoropropylcarbamate 157 (yield: 58%). LCMS: m/z 510.8 $[M+H]^+$; $t_R$=1.77 min.

tert-Butyl 3-(3-chloro-4'-(morpholine-4-carbonyl)biphenyl-4-yloxy)-2,2-difluoropropylcarbamate 157 (110 mg, 0.22 mmol) was dissolved in $CH_2Cl_2$ (15 mL). TFA (3 mL) was added at 0° C. The reaction mixture was stirred at room temperature for 2 h, and concentrated under reduced pressure to give crude (4'-(3-amino-2,2-difluoropropoxy)-3'-chlorobiphenyl-4-yl)(morpholino)methanone 158, which was used without further purification in the next step. Yield (100%). LCMS: m/z 411.1 $[M+H]^+$; $t_R$=0.84 min.

(4'-(3-Amino-2,2-difluoropropoxy)-3'-chlorobiphenyl-4-yl)(morpholino)methanone 158 (88 mg, 0.22 mmol) was dissolved in DMF (5 mL) and (E)-3-(6-aminopyridin-3-yl) acrylic acid (35 mg, 0.22 mmol) was added at 0° C. EDCl (61 mg, 0.32 mmol) and HOBt (44 mg, 0.32 mmol) were added to this reaction mixture at 0° C., followed by DIPEA (55 mg, 0.43 mmol) dropwise. The reaction mixture was allowed to warm to room temperature and stirred for further 2 h. The reaction mixture was transferred into water (20 mL) and extracted with EtOAc (25 mL×3). The combined organic layers were washed with brine, dried over anhydrous $Na_2SO_4$ and concentrated under reduced pressure to give crude product, which was purified by silica gel chromatography to afford 63 mg (E)-3-(6-aminopyridin-3-yl)-N-(3-(3-chloro-4'-(morpholine-4-carbonyl)biphenyl-4-yloxy)-2,2-difluoropropyl)acrylamide (349). Yield (54%). $^1$H NMR (400 MHz, DMSO-$d_6$) δ 8.19-8.17 (m, 1H), 8.03 (d, J=2 Hz, 1H), 7.74-7.70 (m, 3H), 7.62-7.60 (m, 1H), 7.54-7.52 (m, 2H), 7.46 (d, J=16 Hz, 1H), 7.24 (d, J=9 Hz, 1H), 7.05 (d, J=10 Hz, 1H), 6.65 (d, J=16 Hz, 1H), 4.47-4.41 (m, 2H), 4.11-4.03 (m, 2H), 3.78-3.54 (m, 8H). LCMS: m/z 556.8 $[M+H]^+$; $t_R$=1.34 min.

Synthesis of (3'-chloro-4'-(3-hydroxy-2,2-dimethyl-propoxy)biphenyl-4-yl)(morpholino)methanone (350)

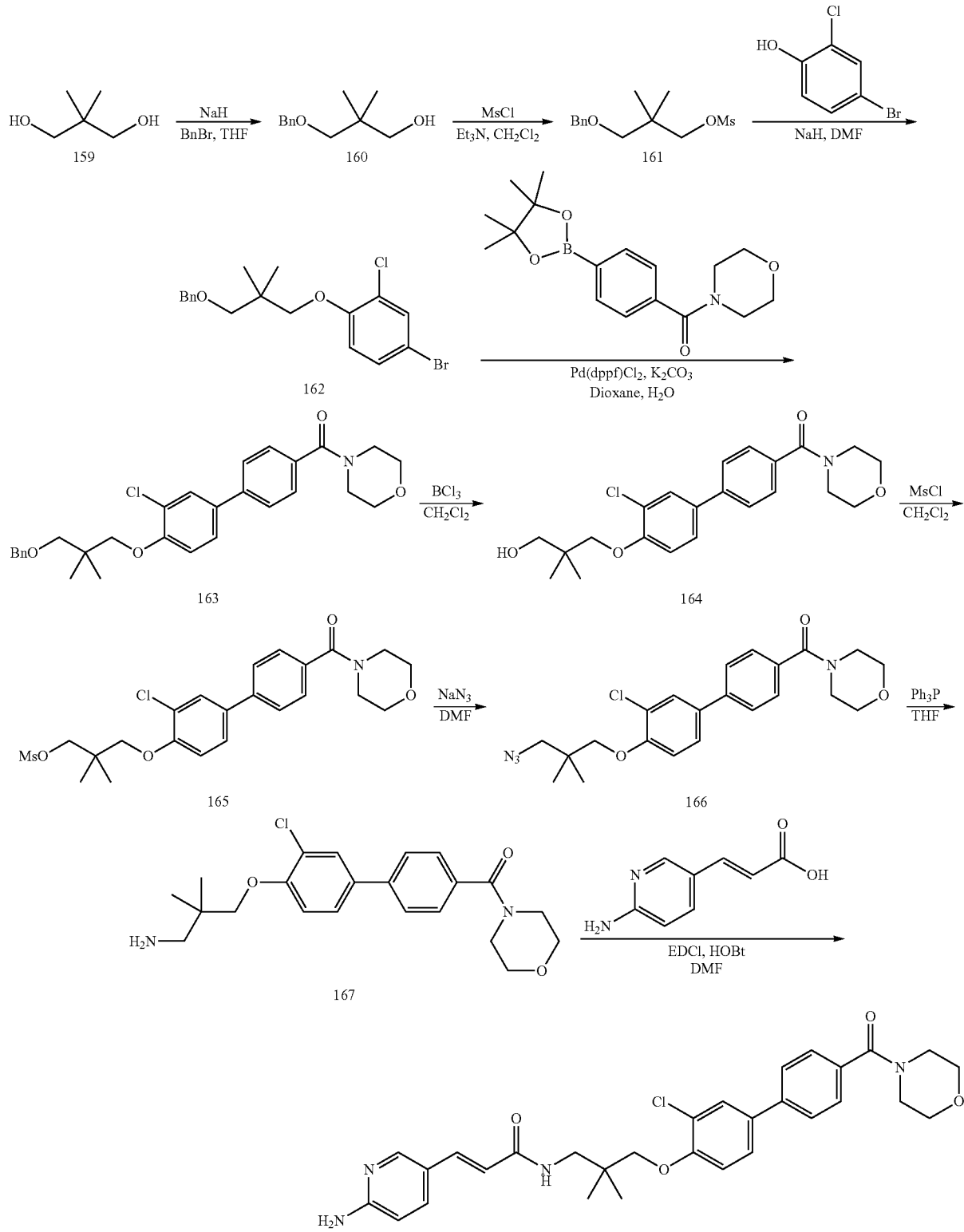

2,2-Dimethylpropane-1,3-diol 159 (4.24 g, 40 mmol) was dissolved in 120 mL of THF. To this mixture, was added NaH (1.92 g, 48 mmol, 60% in mineral oil) at 0° C. under nitrogen atmosphere. After stirring at 0° C. for 30 min, benzyl bromide (6.84 g, 40 mmol) was added to this mixture, and the resulting mixture was stirred at room temperature overnight. The reaction mixture was then transferred into iced water and extracted with ethyl acetate (50 mL×3). The combined organic layers were washed with brine, dried over anhydrous Na₂SO₄, and concentrated under reduced pressure to obtain crude product, which was purified by silica gel chromatography (10% ethyl acetate/petroleum ether) to give 4.5 g 3-(benzyloxy)-2,2-dimethylpropan-1-ol 160 (58% yield). LCMS: m/z 195.1 [M+H]⁺, $t_R$=1.70 min.

3-(Benzyloxy)-2,2-dimethylpropan-1-ol 160 (2.5 g, 12.9 mmol) was dissolved in dichloromethane (50 mL). Triethylamine (2.61 g, 25.8 mmol) and methane sulfonyl chloride (1.79 g, 15.5 mmol) were added at 0° C. and the reaction mixture was stirred at 0° C. for 2 h. The reaction mixture was transferred into iced water and extracted with dichloromethane (40 mL×3). The combined organic layers were washed with brine, dried over anhydrous Na₂SO₄, and concentrated under reduced pressure to give crude 3-(benzyloxy)-2,2-dimethylpropyl methanesulfonate 161, which was purified by silica gel chromatography (17% ethyl acetate/petroleum ether) to give 3.2 g of 3-(benzyloxy)-2,2-dimethylpropyl methanesulfonate 3 (91% yield). LCMS: m/z 294.9 [M+Na]⁺, $t_R$=1.78 min.

4-Bromo-2-chlorophenol (2.06 g, 10 mmol) was dissolved in 40 mL of DMF. NaH (800 mg, 20 mmol) and 3-(benzyloxy)-2,2-dimethylpropyl methanesulfonate 3 (3 g, 11 mmol) were added. The reaction mixture was heated to 110° C. and stirred overnight. After cooling to room temperature, the reaction mixture was transferred into iced water and extracted with ethyl acetate (20 mL×3). The combined organic layers were washed with brine, dried over anhydrous Na₂SO₄, and concentrated under reduced pressure to give crude product, which was purified by silica gel chromatography (5% ethyl acetate/petroleum ether) to give 1.5 g 1-(3-(benzyloxy)-2,2-dimethylpropoxy)-4-bromo-2-chlorobenzene 162 (40% yield).

A mixture of 1-(3-(benzyloxy)-2,2-dimethylpropoxy)-4-bromo-2-chlorobenzene 162 (1 g, 2.6 mmol), morpholino (4-(4,4,5,5-tetramethyl-1,3,2-dioxaborolan-2-yl)phenyl) methanone (989 mg, 3.18 mmol), Pd(dppf)Cl₂ (484 mg, 0.52 mmol) and K₂CO₃ (718 mg, 5.2 mmol) in 10 mL of dioxane and 1 mL of H₂O was stirred at 90° C. under nitrogen atmosphere for 3 h. The mixture was extracted with EtOAc (20 mL×3). The combined organic layers were washed with brine, dried over anhydrous Na₂SO₄, and the solvents were removed under reduced pressure to give crude product, which was purified by silica gel chromatography (33% EtOAc/petroleum ether) to give 890 mg (4'-(3-(benzyloxy)-2,2-dimethylpropoxy)-3'-chlorobiphenyl-4-yl)(morpholino) methanone 163 as oil (yield: 69%). LCMS: m/z 494.2 [M+H]⁺; $t_R$=2.09 min.

(4'-(3-(Benzyloxy)-2,2-dimethylpropoxy)-3'-chlorobiphenyl-4-yl)(morpholino)methanone 5 (500 mg, 1 mmol) was dissolved in dichloromethane (10 mL). BCl₃ (1 M in CH₂Cl₂, 4 mL) was added at −78° C. and the reaction mixture was stirred at −78° C. for 2 h. The reaction mixture was quenched with methanol and transferred into iced water and extracted with dichloromethane (20 mL×3). The combined organic layers were washed with brine, dried over anhydrous Na₂SO₄, and concentrated to give crude (3'-chloro-4'-(3-hydroxy-2,2-dimethylpropoxy)biphenyl-4-yl) (morpholino)methanone 164 (403 mg, 100% yield), which was used directly. LCMS: m/z 404.1 [M+H]⁺, $t_R$=1.73 min.

(3'-Chloro-4'-(3-hydroxy-2,2-dimethylpropoxy)biphenyl-4-yl)(morpholino)methanone 164 (403 mg, 1 mmol, crude mixture from previous step) was dissolved in dichloromethane (20 mL). Triethylamine (312 mg, 3 mmol) and methane sulfonyl chloride (228 mg, 2 mmol) were added at 0° C. and the reaction mixture was stirred at room temperature for 2 h. The reaction mixture was transferred into iced water and extracted with dichloromethane (10 mL×3). The combined organic layers were washed with brine, dried over anhydrous Na₂SO₄, and concentrated under reduced pressure to give crude product, which was purified by silica gel chromatography (25% ethyl acetate/petroleum ether) to give 340 mg 3-(3-chloro-4'-(morpholine-4-carbonyl)biphenyl-4-yloxy)-2,2-dimethylpropyl methanesulfonate 165 (97% yield). LCMS: m/z 482.1 [M+H]⁺, $t_R$=1.73 min.

(3'-Chloro-4'-(2,2-dimethyl-3-(methylsulfonyl)propoxy) biphenyl-4-yl)(morpholino)methanone 165 (340 mg, 0.7 mmol) was dissolved in DMF (10 mL). NaN₃ (91 mg, 1.4 mmol) was added at 25° C. and the reaction mixture was stirred at 100° C. overnight. The reaction mixture was transferred into iced water and extracted with ethyl acetate (30 mL×3). The combined organic layers were washed with brine, dried over anhydrous Na₂SO₄, and concentrated under reduced pressure to give 302 mg (4'-(3-azido-2,2-dimethylpropoxy)-3'-chlorobiphenyl-4-yl)(morpholino)methanone 166 (100% yield), which was used without further purification in the next step. LCMS: m/z 429.1 [M+H]⁺, $t_R$=1.27 min.

(4'-(3-Azido-2,2-dimethylpropoxy)-3'-chlorobiphenyl-4-yl)(morpholino)methanone 166 (302 mg, 0.7 mmol) was dissolved in tetrahydrofuran (10 mL). Triphenylphosphine (275 mg, 1.05 mmol) was added to the mixture and the mixture was stirred for 1 h under nitrogen atmosphere, then 1 mL of water was added to the reaction mixture. The mixture was stirred overnight. The mixture was concentrated and the residue was transferred into water and extracted with ethyl acetate (20 mL×3). The combined organic layers were washed with brine, dried over anhydrous Na₂SO₄, and concentrated under reduced pressure to give crude product, which was purified by silica gel chromatography (20% EtOAc/petroleum ether) to obtain 160 mg (4'-(3-amino-2,2-dimethylpropoxy)-3'-chlorobiphenyl-4-yl) (morpholino)methanone 167 (56% yield). LCMS: m/z 483.2 [M+H]⁺, $t_R$=0.88 min.

(E)-3-(6-Aminopyridin-3-yl)-N-(3-((3-chloro-4'-(morpholine-4-carbonyl)-[1,1'-biphenyl]-4-yl)oxy)-2,2-dimethylpropyl)acrylamide (350) was synthesized using the indicated reagents according to General Procedure 4. Yield (36%). ¹H NMR (400 MHz, CD₃OD) δ 8.05 (d, J=10 Hz, 1H), 7.83-7.69 (m, 4H), 7.59 (d, J=9 Hz, 1H), 7.52 (d, J=8 Hz, 2H), 7.42 (d, J=16 Hz, 1H), 7.17 (d, J=8 Hz, 1H), 6.70 (d, J=8.8 Hz, 1H), 6.53 (d, J=16 Hz, 1H), 3.89 (s, 2H), 3.78-3.33 (m, 8H), 3.32 (s, 2H), 1.14 (s, 6H). LCMS: m/z 549.3 [M+H]⁺; $t_R$=1.79 min.

Synthesis of (E)-3-(6-aminopyridin-3-yl)-N-(2-(2-chloro-4-(5-(morpholine-4-carbonyl)-1,3,4-oxadiazol-2-yl)phenoxy)ethyl)acrylamide (351)

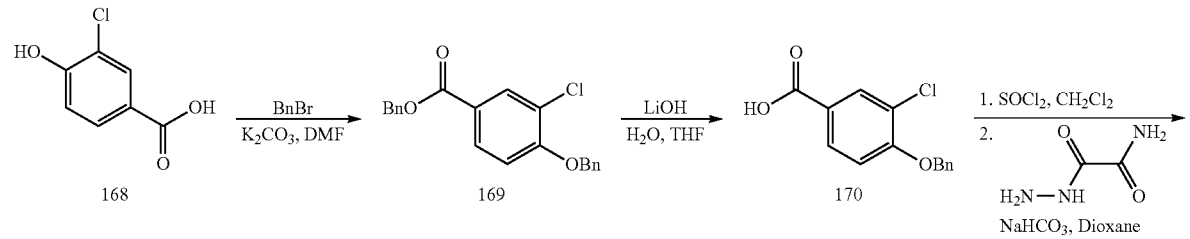

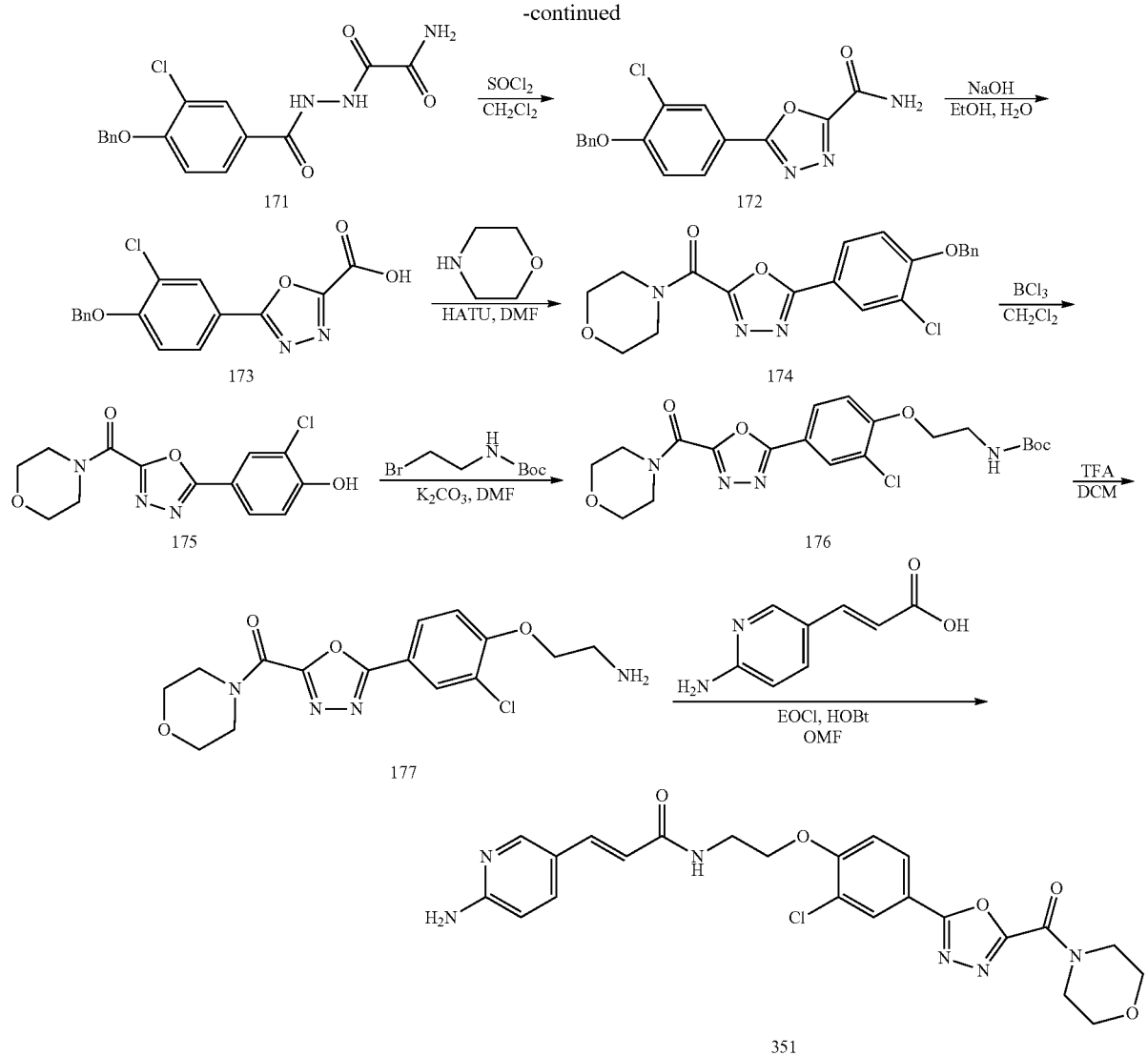

3-Chloro-4-hydroxybenzoic acid (2 g, 11.56 mmol) was dissolved in DMF (150 mL). Benzyl bromide (4.349 g, 25.4 mmol) and potassium carbonate (4 g, 28.9 mmol) were added to the reaction mixture and heated at 100° C. overnight. The reaction mixture was transferred into iced water and extracted with ethyl acetate (50 mL×3). The combined organic layers were washed with brine, dried over anhydrous $Na_2SO_4$, and concentrated under reduced pressure to give crude product, which was used directly in the next step without further purification (80% yield). LCMS: m/z 375.7 [M+H]$^+$; $t_R$=2.04 min.

Benzyl 4-(benzyloxy)-3-chlorobenzoate (169) (1 g, 2.67 mmol) was dissolved in THF (10 mL) LiOH (225 mg, 5.35 mmol) and water (1 mL) were added to the reaction mixture and the reaction mixture was stirred at room temperature for 12 h. 1N HCl solution was added (pH~6). The reaction mixture was transferred into iced water and extracted with ethyl acetate (15 mL×3). The combined organic layers were washed with brine, dried over anhydrous $Na_2SO_4$, and concentrated under reduced pressure to give crude product, which was used in the next step without further purification (71% yield). LCMS: m/z 263.7 [M+H]$^+$; $t_R$=1.77 min.

4-(Benzyloxy)-3-chlorobenzoic acid (170) (5 g, 19.1 mmol) was dissolved in dichloromethane (70 ml). Thionyl chloride (18.18 g, 152.8 mmol) was added dropwise and the reaction mixture was refluxed overnight. After cooling to room temperature, the mixture was concentrated to afford a crude oil, which was dissolved in dioxane (100 mL) 2-Hydrazinyl-2-oxoacetamide (1.63 g, 15.7 mmol) and sodium bicarbonate (3.6 g, 42.9 mmol) were added to the mixture. The mixture was refluxed overnight. The solid was removed by filtration, the filtrate was concentrated to afford crude 2-(2-(4-(benzyloxy)-3-chlorobenzoyl)hydrazinyl)-2-oxoacetamide 171 (3.5 g, 71% yield). LCMS: m/z 370 [M+H]$^+$; $t_R$=1.53 min.

A solution of 2-(2-(4-(benzyloxy)-3-chlorobenzoyl)hydrazinyl)-2-oxoacetamide 171 (500 mg, 1.44 mmol) in thionyl chloride (10 mL) was refluxed for 7 h. The mixture was concentrated to get 300 mg 5-(4-(benzyloxy)-3-chlorophenyl)-1,3,4-oxadiazole-2-carboxamide 172 (63% yield). LCMS: m/z 330.7 [M+H]$^+$; $t_R$=1.14 min.

5-(4-(Benzyloxy)-3-chlorophenyl)-1,3,4-oxadiazole-2-carboxamide (172) (500 mg, 1.52 mmol) was dissolved in ethanol (5 mL). 1.52 mL of 2N NaOH aqueous solution was added to the reaction mixture, and stirred overnight. The mixture was acidified with 1N hydrogen chloride (pH~6). The mixture was lyophilized to get 5-(4-(benzyloxy)-3-chlorophenyl)-1,3,4-oxadiazole-2-carboxylic acid 173 (70% yield). LCMS: m/z 331.7 [M+H]$^+$; $t_R$=1.47 min.

5-(4-(Benzyloxy)-3-chlorophenyl)-1,3,4-oxadiazole-2-carboxylic acid 173 (250 mg, 076 mmol) was dissolved in DMF (10 mL). Morpholine (66 mg, 0.76 mmol and HATU (289 mg, 0.76 mmol) were added and the mixture was stirred overnight. The reaction mixture was transferred into iced water and extracted with ethyl acetate (15 mL×3). The combined organic layers were washed with brine, dried over anhydrous $Na_2SO_4$, and concentrated under reduced pressure to give crude product, which was purified by silica gel chromatography (50% EtOAc/petroleum ether) to obtain 20 mg (5-(4-(benzyloxy)-3-chlorophenyl)-1,3,4-oxadiazol-2-yl)(morpholino)methanone 174 (25% yield). LCMS: m/z 400.7 [M+H]$^+$; $t_R$=1.84 min.

(5-(4-(Benzyloxy)-3-chlorophenyl)-1,3,4-oxadiazol-2-yl)(morpholino)methanone 174 (50 mg, 0.125 mmol) was dissolved in dichloromethane (5 mL). $BCl_3$ (0.5 mL, 0.5 mmol, 1N in $CH_2Cl_2$) was added at −78° C. After stirring for 1 h, the reaction mixture was transferred into iced water and extracted with ethyl acetate (5 mL×3). The combined organic layers were washed with brine, dried over anhydrous $Na_2SO_4$, and concentrated under reduced pressure to give crude product, which was purified by silica gel chromatography (50% EtOAc/petroleum ether) to obtain 25 mg (5-(3-chloro-4-hydroxyphenyl)-1,3,4-oxadiazol-2-yl)(morpholino)methanone 175 (64% yield). LCMS: m/z 310.7 [M+H]$^+$; $t_R$=1.41 min.

tert-Butyl 2-bromoethylcarbamate (43 mg, 0.194 mmol) was dissolved in DMF (5 mL). Potassium carbonate (45 mg, 0.324 mmol), (5-(3-chloro-4-hydroxyphenyl)-1,3,4-oxadiazol-2-yl)(morpholino)methanone 175 (50 mg, 0.162 mmol) and potassium iodide (33 mg, 0.194 mmol) were added at 25° C. and the reaction mixture was stirred overnight. The reaction mixture was transferred into iced water and extracted with ethyl acetate (8 mL×3). The combined organic layers were washed with brine, dried over anhydrous $Na_2SO_4$, and concentrated under reduced pressure to give crude product, which was purified by silica gel chromatography (30% EtOAc/petroleum ether) to obtain 30 mg tert-butyl 2-(2-chloro-4-(5-(morpholine-4-carbonyl)-1,3,4-oxadiazol-2-yl)phenoxy)ethylcarbamate (176) (41% yield). LCMS: m/z 474.8 [M+H]$^+$, $t_R$=1.67 min.

tert-Butyl 2-(2-chloro-4-(5-(morpholine-4-carbonyl)-1,3,4-oxadiazol-2-yl)phenoxy)ethylcarbamate (100 mg, 0.22 mmol) was dissolved in dichloromethane (5 mL). 2,2,2-trifluoroacetic acid (1 mL) was added at 0° C. The reaction mixture was stirred at room temperature for 2 h, and concentrated under reduced pressure to give crude (5-(4-(2-aminoethoxy)-3-chlorophenyl)-1,3,4-oxadiazol-2-yl)(morpholino)methanone 177, which was used without further purification in the next step. Yield (77%). LCMS: m/z 352.7 [M+H]$^+$; $t_R$=1.09 min.

(E)-3-(6-Aminopyridin-3-yl)-N-(2-(2-chloro-4-(5-(morpholine-4-carbonyl)-1,3,4-oxadiazol-2-yl)phenoxy)ethyl)acrylamide (351) was synthesized using the indicated reagents according to General Procedure 4 (20 mg, Yield: 24%). $^1$H NMR (400 MHz, DMSO-$d_6$) δ 8.41 (s, 1H), 8.19 (s, 3H), 8.03-7.96 (m, 3H), 7.45-7.36 (m, 2H), 6.94 (d, J=8 Hz, 1H), 6.57 (d, J=16 Hz, 1H), 4.27 (s, 2H), 3.98 (s, 2H), 3.69-3.63 (m, 8H). LCMS: m/z 499 [M+H]$^+$; $t_R$=1.19 min.

(E)-3-(6-aminopyridin-3-yl)-N-(4-(3-(5-(4,4-difluoropiperidin-1-carbonyl)pyridin-2-yl)-5-(trifluoromethyl)phenoxy)butan-2-yl)acrylamide (352)

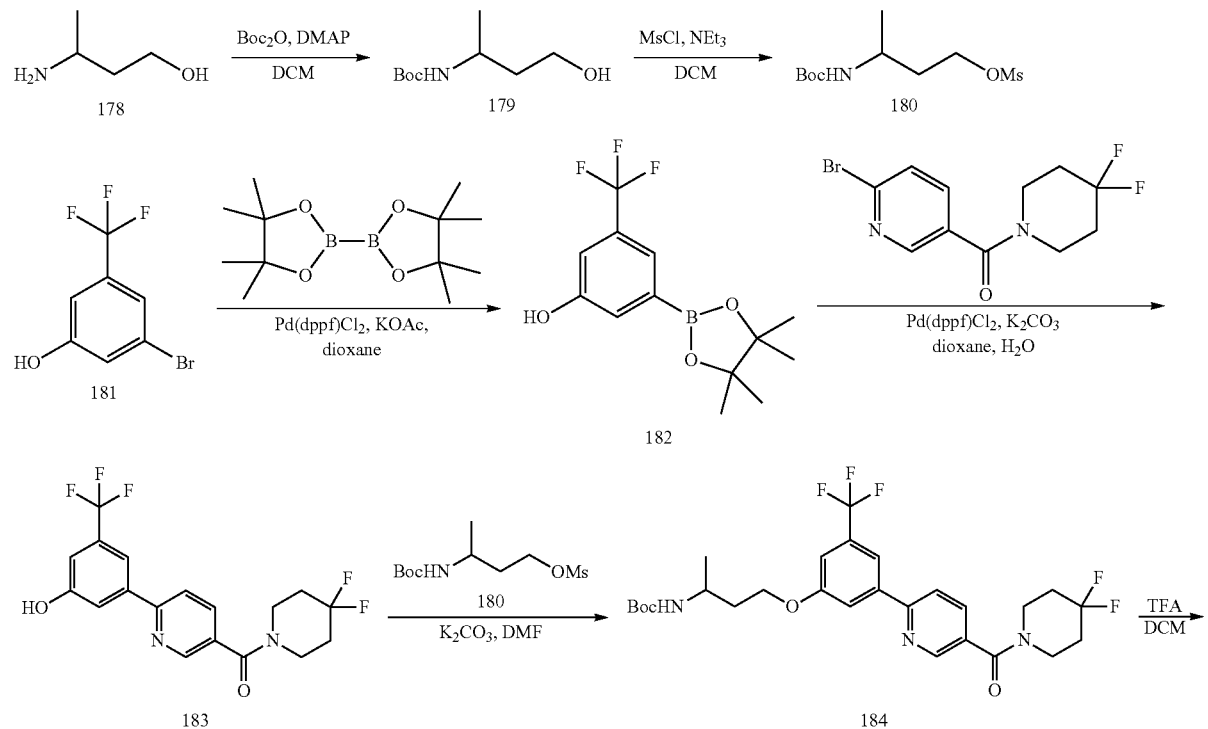

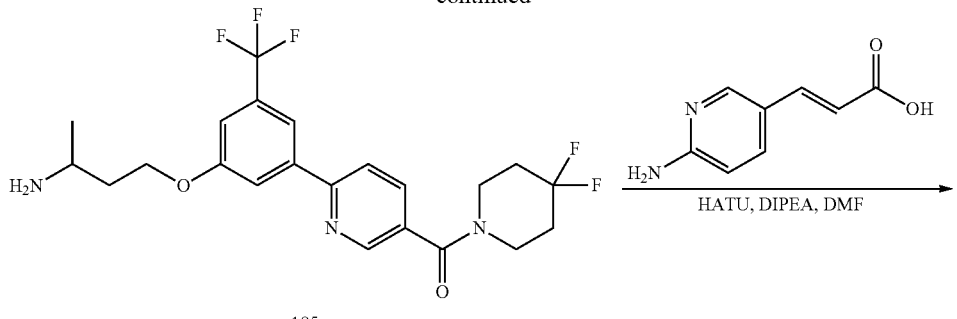

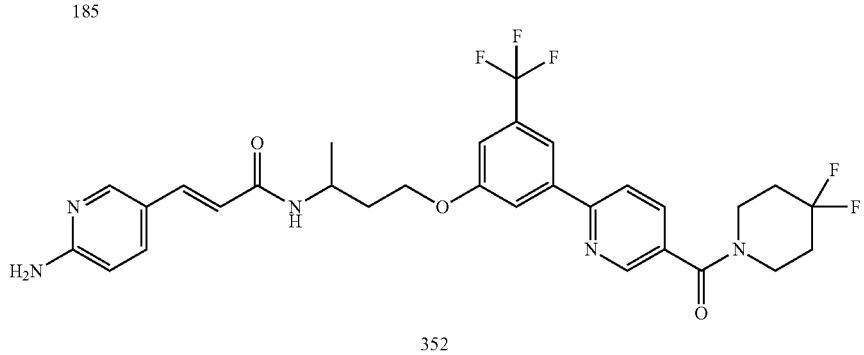

Synthesis of tert-butyl 4-hydroxybutan-2-ylcarbamate (179)

3-Aminobutan-1-ol (178; 2 g, 22.5 mmol) was dissolved in DCM (50 mL) DMAP (0.3 g, 2.3 mmol) and (Boc)$_2$O (5.4 g, 24.8 mmol) were added at room temperature. The reaction mixture was stirred at room temperature for 16 h. The reaction mixture was diluted with DCM (50 mL), washed with saturated NaHCO$_3$ (50 mL), water, brine, dried over anhydrous Na$_2$SO$_4$, and concentrated under reduced pressure to give 3 g of tert-butyl 4-hydroxybutan-2-ylcarbamate (179), which was used in next step without further purification (71% yield).

Synthesis of tert-butyl 4-hydroxybutan-2-ylcarbamate (180)

tert-butyl 4-hydroxybutan-2-ylcarbamate (180) was synthesized using the indicated reagents according to General Procedure 7. Yield 86%.

Synthesis of 3-(4,4,5,5-tetramethyl-1,3,2-dioxaborolan-2-yl)-5-(trifluoromethyl)phenol (182)

3-Bromo-5-(trifluoromethyl)phenol (181; 2.5 g, 10 mmol), 4,4,4',4',5,5,5',5'-octamethyl-2,2'-bi(1,3,2-dioxaborolane) (3.8 g, 15 mmol), Pd(dppf)Cl$_2$ (1.1 g, 1.5 mmol), and potassium acetate (2 g, 20 mmol) were added in 50 mL of dioxane and degassed. The reaction mixture was heated at 80° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 1.2 g of 3-(4,4,5,5-tetramethyl-1,3,2-dioxaborolan-2-yl)-5-(trifluoromethyl)phenol (182) as white solid (40% yield). LCMS: m/z 289.1, t$_R$=1.77 min.

Synthesis of (4,4-difluoropiperidin-1-yl)(6-(3-hydroxy-5-(trifluoromethyl)phenyl)pyridin-3-yl)methanone (183)

(4,4-difluoropiperidin-1-yl)(6-(3-hydroxy-5-(trifluoromethyl)phenyl)pyridin-3-yl)methanone (183) was synthesized using the indicated reagents according to General Procedure 1. Yield 10%. LCMS: m/z 387.1 [M+H]$^+$, t$_R$=1.60 min.

Synthesis of tert-butyl 4-(3-(5-(4,4-difluoropiperidine-1-carbonyl)pyridin-2-yl)-5-(trifluoromethyl)phenoxy)butan-2-ylcarbamate (184)

Tert-butyl 4-(3-(5-(4,4-difluoropiperidine-1-carbonyl)pyridin-2-yl)-5-(trifluoromethyl)phenoxy)butan-2-ylcarbamate (184) was synthesized using the indicated reagents according to General Procedure 8. Yield 20%. LCMS: m/z 558.1 [M+H]$^+$, t$_R$=1.80 min.

Synthesis of (6-(3-(3-aminobutoxy)-5-(trifluoromethyl)phenyl)pyridin-3-yl)(4,4-difluoropiperidin-1-yl)methanone (185)

(6-(3-(3-aminobutoxy)-5-(trifluoromethyl)phenyl)pyridin-3-yl)(4,4-difluoropiperidin-1-yl)methanone (185) was synthesized according to General Procedure 3. Yield 95%. LCMS: m/z 458.2 [M+H]$^+$, t$_R$=1.34 min.

Synthesis of (E)-3-(6-aminopyridin-3-yl)-N-(4-(3-(5-(4,4-difluoropiperidine-1-carbonyl)pyridin-2-yl)-5-(trifluoromethyl)phenoxy)butan-2-yl)acrylamide (352): (E)-3-(6-aminopyridin-3-yl)-N-(4-(3-(5-(4,4-difluoropiperidine-1-carbonyl)pyridin-2-yl)-5-(trifluoromethyl)phenoxy)butan-2-yl)acrylamide (352) was synthesized using the indicated reagents according to General Procedure 4. Yield 35%. $^1$H NMR (400 MHz, DMSO-d$_6$) δ 8.77 (s, 1H), 8.24 (d, J=8 Hz, 1H), 8.08-7.86 (m, 5H), 7.57 (d, J=8 Hz, 1H), 7.34 (s, 1H), 7.25 (d, J=16 Hz, 1H), 6.53-6.27 (m, 4H), 4.23-4.09 (m, 3H), 3.84-3.67 (m, 2H), 2.18-2.01 (m, 4H), 2.00-1.89 (m, 2H), 1.25-1.12 (m, 5H). LCMS: m/z 604.3 [M+H]$^+$; t$_R$=1.84 min.

Synthesis of (E)-N-((6-aminopyridin-3-yl)methyl)-4-(4-(5-(4,4-difluoropiperidine-1-carbonyl)pyridin-2-yl)-2-(trifluoromethyl)phenoxy)but-2-enamide (353)
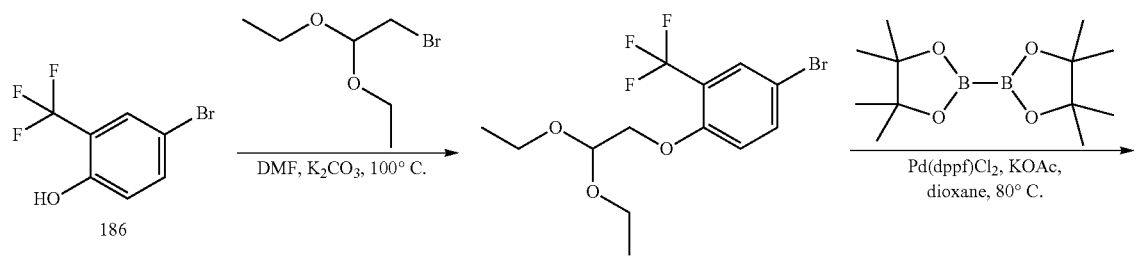
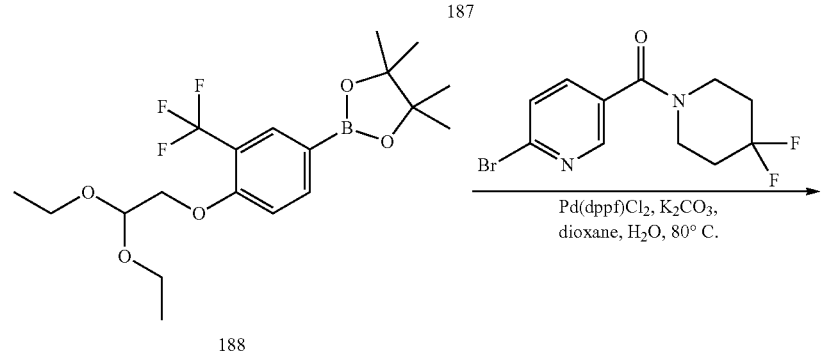
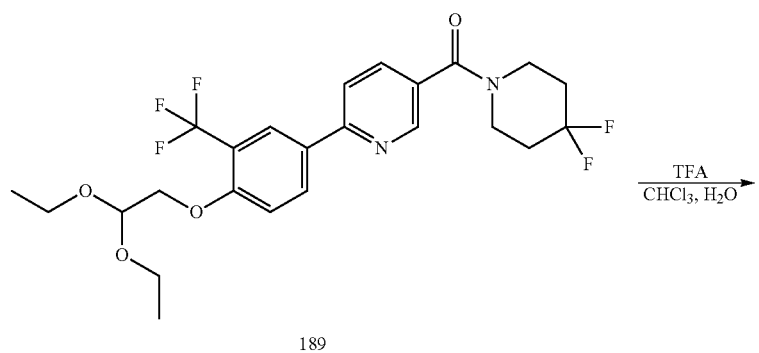
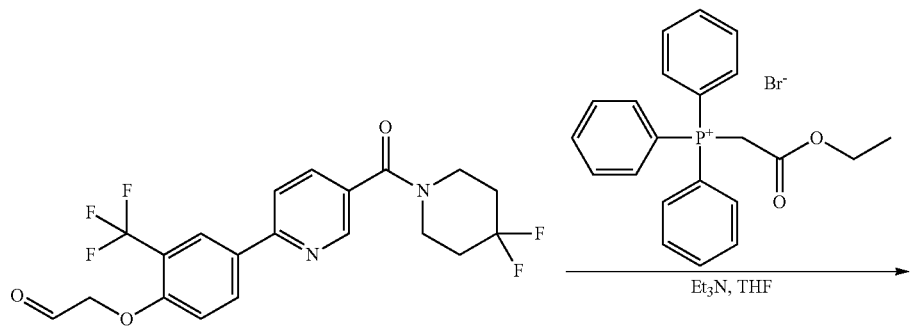
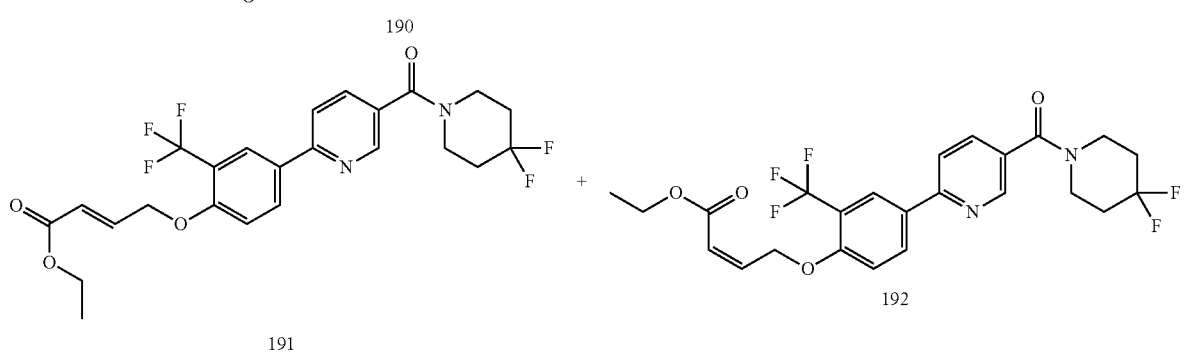

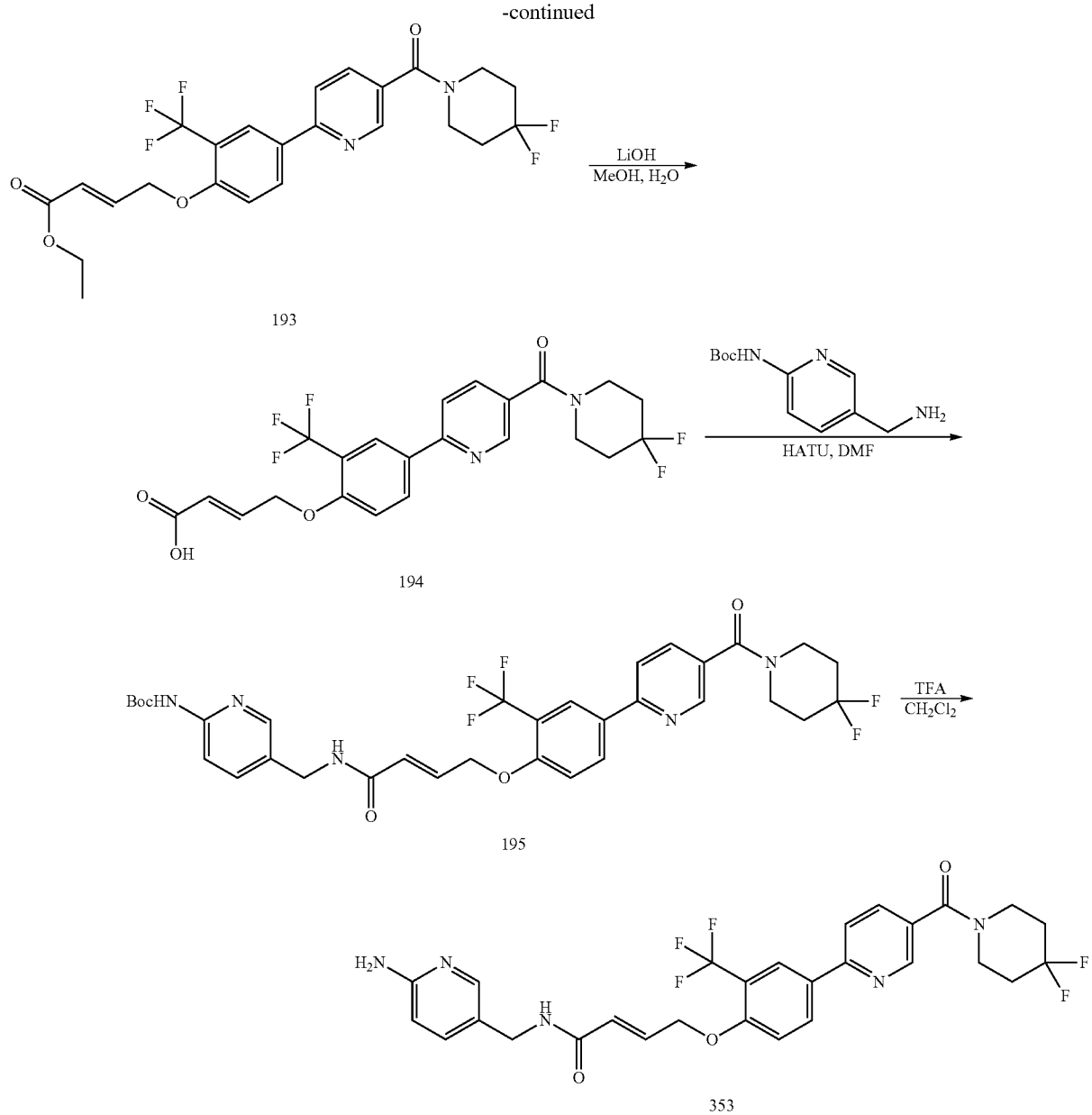

Synthesis of 4-bromo-1-(2,2-diethoxyethoxy)-2-(trifluoromethyl)benzene (187)

4-Bromo-2-(trifluoromethyl)phenol (186; 5 g, 20.7 mmol) was dissolved in 50 mL of DMF. $K_2CO_3$ (4.3 g, 31.1 mmol) and 2-bromo-1,1-diethoxyethane (4.5 g, 22.8 mmol) were added at room temperature. The reaction mixture was heated at 80° C. for 10 h. After cooled down to room temperature, water (100 mL) was added. The reaction mixture was extracted with EtOAc (100 mL×3). The combined organic layers were washed with brine, dried over anhydrous $Na_2SO_4$, and concentrated under reduced pressure to give crude product, which was purified by silica gel chromatography (5% EtOAc/petroleum ether) to yield 6.3 g of 4-bromo-1-(2,2-diethoxyethoxy)-2-(trifluoromethyl)benzene (187) as a pale yellow liquid (yield 85%).

Synthesis of 2-(4-(2,2-diethoxyethoxy)-3-(trifluoromethyl)phenyl)-4,4,5,5-tetramethyl-1,3,2-dioxaborolane (188)

4-Bromo-1-(2,2-diethoxyethoxy)-2-(trifluoromethyl)benzene (187; 6 g. 16.8 mmol), 4,4,4',4',5,5,5',5'-octamethyl-2,2'-bi(1,3,2-dioxaborolane) (5.1 g, 20.2 mmol), Pd(dppf)Cl$_2$ (1.5 g, 1.7 mmol), and potassium acetate (3.4 g, 33.6 mmol) were added in dioxane (50 mL) and degassed. The reaction mixture was heated at 100° C. under nitrogen atmosphere for 2 h. After cooling down to room temperature, the reaction mixture was filtered. The filtrate was concentrated under reduced pressure to give the crude product, which was purified by silica gel chromatography (5-20% EtOAc/petroleum ether) to yield 3 g of 2-(4-(2,2-diethoxyethoxy)-3-(trifluoromethyl)phenyl)-4,4,5,5-tetramethyl-1,3,2-dioxaborolane (188) as white solid (44% yield). LCMS: m/z 427.2 [M+Na]$^+$, $t_R$=1.97 min.

Synthesis of (6-(4-(2,2-diethoxyethoxy)-3-(trifluoromethyl)phenyl)pyridin-3-yl)(4,4-difluoropiperidin-1-yl)methanone (189)

(6-(4-(2,2-Diethoxyethoxy)-3-(trifluoromethyl)phenyl)pyridin-3-yl)(4,4-difluoropiperidin-1-yl)methanone 4 as white solid was synthesized using the indicated reagents according to General Procedure 1. Yield 70%. LCMS: m/z 503.2 [M+H]$^+$, $t_R$=1.77 min.

Synthesis of 2-(4-(5-(4,4-difluoropiperidine-1-carbonyl)pyridin-2-yl)-2-(trifluoromethyl)phenoxy)acetaldehyde (190)

(6-(4-(2,2-Diethoxyethoxy)-3-(trifluoromethyl)phenyl)pyridin-3-yl)(4,4-difluoropiperidin-1-yl)methanone (189; 700 mg, 1.4 mmol) was dissolved in 10 mL of CHCl$_3$. TFA (10 mL) and water (10 mL) were added to this mixture. The mixture was heated at 50° C. for 2 h, cooled down to room temperature and extracted with CH$_2$Cl$_2$ (20 mL×3). The combined organic layers were washed with NaHCO$_3$ aqueous solution, dried over anhydrous Na$_2$SO$_4$ and concentrated under reduced pressure to give the crude product, which was purified by silica gel chromatography (50% EtOAc/petroleum ether) to yield 500 mg of 2-(4-(5-(4,4-difluoropiperidine-1-carbonyl)pyridin-2-yl)-2-(trifluoromethyl)phenoxy)acetaldehyde (190) as white solid (yield 84%). LCMS: m/z 429.1 [M+H]$^+$, $t_R$=1.56 min.

Synthesis of (E)-ethyl 4-(4-(5-(4,4-difluoropiperidine-1-carbonyl)pyridin-2-yl)-2-(trifluoromethyl)phenoxy)but-2-enoate (191)

2-(4-(5-(4,4-difluoropiperidine-1-carbonyl)pyridin-2-yl)-2-(trifluoromethyl)phenoxy)acetaldehyde (190; 400 mg, 0.93 mmol) was dissolved in 10 mL of THF. (2-ethoxy-2-oxoethyl)triphenylphosphonium bromide (400 mg, 0.93 mmol) and Et$_3$N (94 mg, 0.93 mmol) were added in THF (10 mL) at 0° C. The reaction mixture was allowed to warm up to room temperature and stirred for 4 h. The reaction mixture was poured into iced water (10 mL), extracted with EtOAc (15 mL×3). The combined organic layers were washed with brine, dried over anhydrous Na$_2$SO$_4$, and concentrated under reduced pressure to give the crude product, which was purified by silica gel chromatography (10% EtOAc/petroleum ether) to yield 140 mg of (E)-ethyl 4-(4-(5-(4,4-difluoropiperidine-1-carbonyl)pyridin-2-yl)-2-(trifluoromethyl)phenoxy)but-2-enoate (191) as a white solid (yield 30%). LCMS: m/z 499.1 [M+H]$^+$, $t_R$=1.79 min. 220 mg of (Z)-ethyl 4-(4-(5-(4,4-difluoropiperidine-1-carbonyl)pyridin-2-yl)-2-(trifluoromethyl)phenoxy)but-2-enoate (192) was also obtained as a white solid (yield 48%). LCMS: m/z 499.1 [M+H]$^+$, $t_R$=1.73 min.

Synthesis of (E)-4-(4-(5-(4,4-difluoropiperidine-1-carbonyl)pyridin-2-yl)-2-(trifluoromethyl)phenoxy)but-2-enoic acid (193)

(E)-ethyl 4-(4-(5-(4,4-difluoropiperidine-1-carbonyl)pyridin-2-yl)-2-(trifluoromethyl)phenoxy)but-2-enoate (191; 100 mg, 0.2 mmol) and LiOH (84 mg, 2 mmol) were added in mixture of MeOH (10 mL) and H$_2$O (2 mL) The reaction mixture was stirred at room temperature for 1 h. The reaction mixture was concentrated under reduced pressure to remove MeOH, neutralized with HCl (conc.) until pH=6~7, extracted with EtOAc (10 mL×3). The combined organic layers were washed with brine, dried over anhydrous Na$_2$SO$_4$, and concentrated under reduced pressure to give 90 mg of the (E)-4-(4-(5-(4,4-difluoropiperidine-1-carbonyl)pyridin-2-yl)-2-(trifluoromethyl)phenoxy)but-2-enoic acid (193) as a white solid which was used directly (96% yield). LCMS: m/z 471.1 [M+H]$^+$, $t_R$=1.56 min.

Synthesis of (E)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (194)

(E)-4-(4-(5-(4,4-difluoropiperidine-1-carbonyl)pyridin-2-yl)-2-(trifluoromethyl)phenoxy)but-2-enoic acid (193; 90 mg, 0.19 mmol) was dissolved in DMF (3 mL) and tert-butyl 5-(aminomethyl)pyridin-2-ylcarbamate (42 mg, 0.19 mmol) was added at 0° C. (ice bath). HATU (87 mg, 0.23 mmol) was added to this reaction mixture. The reaction mixture was allowed to warm to room temperature and stirred further for 1 h. The reaction mixture was purified by Prep-HPLC to afford 30 mg of (E)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (194) (yield: 23%). LCMS: m/z 676.2 [M+H]$^+$, $t_R$ 1.56 min.

Synthesis of (E)-N-((6-aminopyridin-3-yl)methyl)-4-(4-(5-(4,4-difluoropiperidine-1-carbonyl)pyridin-2-yl)-2-(trifluoromethyl)phenoxy)but-2-enamide (353)

(E)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (194; 30 mg, 0.044 mmol) was dissolved in CH$_2$Cl$_2$ (6 mL). TFA (1 mL) was added dropwise at room temperature. The reaction mixture was stirred at room temperature for 1 h, and concentrated under reduced pressure to give the crude product, which was purified by silica gel chromatography (5% MeOH/EtOAc) to give 15 mg of (E)-N-((6-aminopyridin-3-yl)methyl)-4-(4-(5-(4,4-difluoropiperidine-1-carbonyl)pyridin-2-yl)-2-(trifluoromethyl)phenoxy)but-2-enamide (353) (yield 60%). $^1$H NMR (500 MHz, DMSO-d$_6$) δ 8.75 (s, 1H), 8.39 (d, J=2 Hz, 1H), 8.31-8.25 (m, 1H), 8.03-7.96 (m, 2H), 7.89 (s, 1H), 7.55-7.50 (m, 1H), 7.31 (d, J=9 Hz, 1H), 6.62 (d, J=9 Hz, 1H), 6.33-6.28 (m, 1H), 6.08-6.02 (m, 1H), 5.46-5.38 (m, 2H), 4.30 (s, 2H), 3.99-3.59 (m, 4H), 2.22-2.02 (m, 4H). LCMS: m/z 576.2 [M+H]$^+$; $t_R$=1.44 min.

Synthesis of (Z)—N-((6-aminopyridin-3-yl)methyl)-4-(4-(5-(4,4-difluoropiperidine-1-carbonyl)pyridin-2-yl)-2-(trifluoromethyl)phenoxy)but-2-enamide (354)

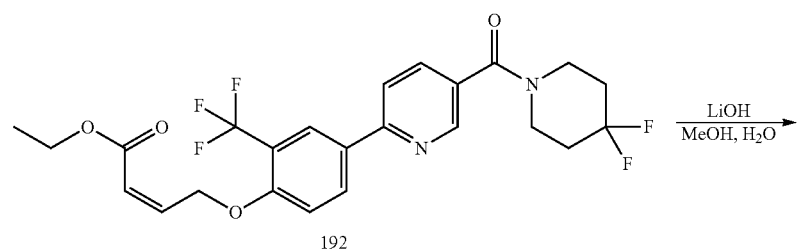

192

-continued

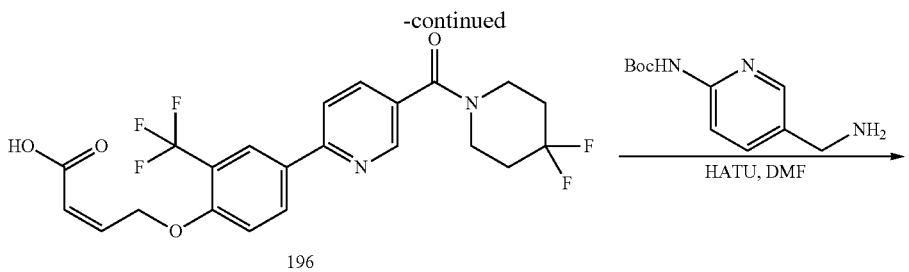
196

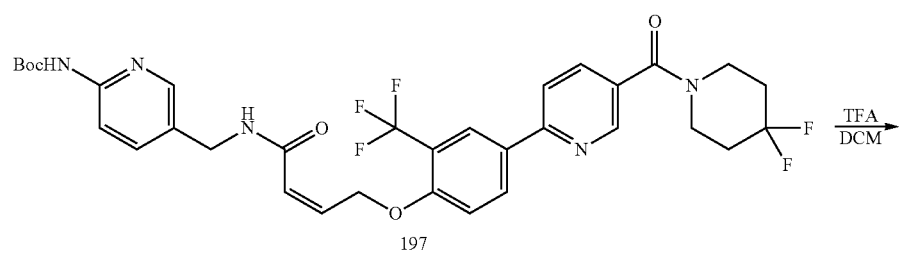
197

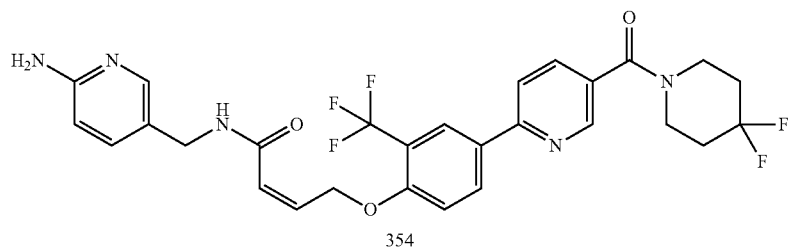
354

Synthesis of (Z)-4-(4-(5-(4,4-difluoropiperidine-1-carbonyl)pyridin-2-yl)-2-(trifluoromethyl)phenoxy)but-2-enoic acid (196)

(Z)-ethyl 4-(4-(5-(4,4-difluoropiperidine-1-carbonyl)pyridin-2-yl)-2-(trifluoromethyl)phenoxy)but-2-enoate (192; 150 mg, 0.3 mmol) and LiOH (126 mg, 3 mmol) were added in mixture of MeOH (15 mL) and H$_2$O (3 mL). The reaction mixture was stirred at room temperature for 1 h. The reaction mixture was concentrated under reduced pressure to remove MeOH, neutralized with HCl (conc.) until pH=6~7, extracted with EtOAc (10 mL×3). The combined organic layers were washed with brine, dried over anhydrous Na$_2$SO$_4$, and concentrated under reduced pressure to give 100 mg of (Z)-4-(4-(5-(4,4-difluoropiperidine-1-carbonyl)pyridin-2-yl)-2-(trifluoromethyl)phenoxy)but-2-enoic acid (196) as a white solid which was used directly (71% yield). LCMS: m/z 471.1 [M+H]$^+$, t$_R$=1.54 min.

Synthesis of (Z)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (197)

(Z)-4-(4-(5-(4,4-difluoropiperidine-1-carbonyl)pyridin-2-yl)-2-(trifluoromethyl)phenoxy)but-2-enoic acid (196; 100 mg, 0.21 mmol) was dissolved in DMF (3 mL) and tert-butyl 5-(aminomethyl)pyridin-2-ylcarbamate (47 mg, 0.21 mmol) was added at 0° C. (ice bath). HATU (96 mg, 0.25 mmol) was added to this reaction mixture. The reaction mixture was allowed to warm to room temperature and stirred further for 1 h. The reaction mixture was purified by Prep-HPLC to afford 40 mg of (Z)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (197) (yield: 28%). LCMS: m/z 676.3 [M+H]$^+$, t$_R$=1.94 min.

Synthesis of (Z)—N-((6-aminopyridin-3-yl)methyl)-4-(4-(5-(4,4-difluoropiperidine-1-carbonyl)pyridin-2-yl)-2-(trifluoromethyl)phenoxy)but-2-enamide (354)

(Z)-tert-butyl 5-((4-(4-(5-(4,4-difluoropiperidine-1-carbonyl)pyridin-2-yl)-2-(trifluoromethyl)phenoxy)but-2-enamido)methyl)pyridin-2-ylcarbamate (197; 40 mg, 0.06 mmol) was dissolved in CH$_2$Cl$_2$ (5 mL). TFA (1 mL) was added dropwise at room temperature. The reaction mixture was stirred at room temperature for 1 h, concentrated and purified by silica gel chromatography (5% MeOH/EtOAc) to give 20 mg of (Z)—N-((6-aminopyridin-3-yl)methyl)-4-(4-(5-(4,4-difluoropiperidine-1-carbonyl)pyridin-2-yl)-2-(trifluoromethyl)phenoxy)but-2-enamide (354) (yield 68%). $^1$H NMR (400 MHz, CD$_3$OD) δ 8.65 (s, 1H), 8.31 (s, 1H), 8.20 (d, J=9 Hz, 1H), 7.95-7.85 (m, 2H), 7.72 (s, 1H), 7.34-7.24 (m, 2H), 6.69 (d, J=6 Hz, 1H), 6.42 (d, J=8 Hz, 1H), 5.20-5.13 (m, 1H), 4.10 (s, 2H), 3.85-3.48 (m, 4H), 3.12 (d, J=7 Hz, 2H), 2.11-1.89 (m, 4H). LCMS: m/z 576.2 [M+H]$^+$; t$_R$=1.36 min.

Synthesis of (E)-3-(6-aminopyridin-3-yl)-N-(2-(4-(5-(4,4-difluoropiperidine-1-carbonyl)pyridin-2-yl)-2-(trifluoromethyl)phenoxy)ethyl)acrylamide (355)

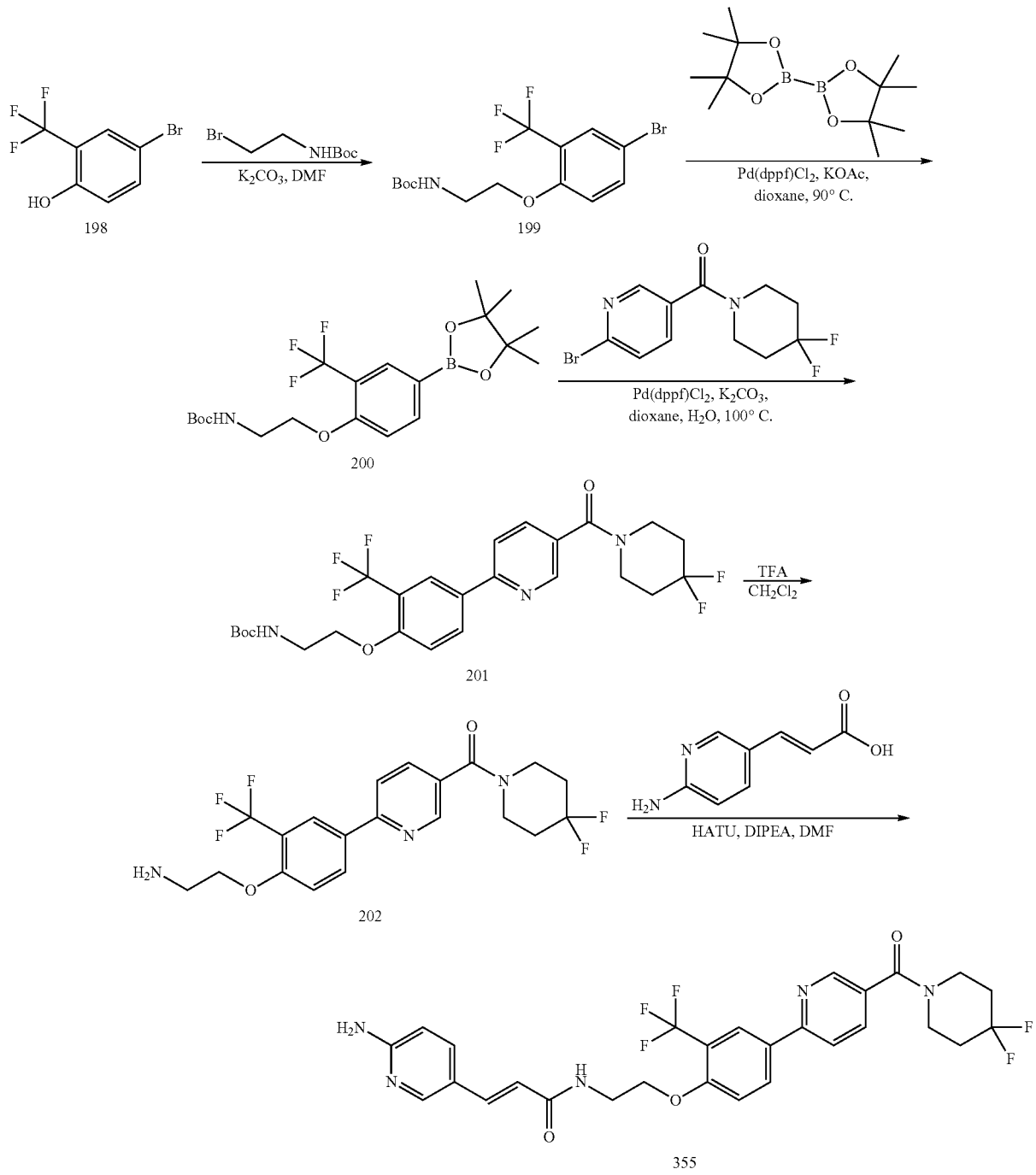

Synthesis of tert-butyl 2-(4-bromo-2-(trifluoromethyl)phenoxy)ethylcarbamate (199)

4-Bromo-2-(trifluoromethyl)phenol (198; 1.5 g, 6.2 mmol) was dissolved in DMF (20 mL) and $K_2CO_3$ (1.7 g, 12.4 mmol) was added. tert-Butyl 2-bromoethylcarbamate (2.1 g, 9.3 mmol) was added at room temperature. The reaction mixture was heated at 100° C. for 16 h. The reaction mixture was cooled down to room temperature, poured into iced water (50 mL), extracted with EtOAc (50 mL×3). The combined organic layers were washed with brine, dried over anhydrous $Na_2SO_4$, and concentrated under reduced pressure to give the crude product which was purified by silica gel chromatography (10% EtOAc/petroleum ether) to yield 1 g of tert-butyl 2-(4-bromo-2-(trifluoromethyl)phenoxy) ethylcarbamate 199 as white solid (42% yield). LCMS: 386.1 [M+H]$^+$, $t_R$=1.82 min.

Synthesis of tert-butyl 2-(4-(4,4,5,5-tetramethyl-1,3, 2-dioxaborolan-2-yl)-2-(trifluoromethyl)phenoxy) ethylcarbamate (200)

tert-Butyl 2-(4-bromo-2-(trifluoromethyl)phenoxy)ethylcarbamate (199; 1 g, 2.6 mmol), 4,4,4',4',5,5,5',5'-octamethyl-2,2'-bi(1,3,2-dioxaborolane) (1 g, 3.9 mmol), Pd(dppf)Cl$_2$ (0.4 g, 0.5 mmol), and potassium acetate (0.5 g, 5.2 mmol) were added in 50 mL of dioxane and degassed. The reaction mixture was heated at 90° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 0.66 g of tert-butyl 2-(4-(4,4,5,5-tetramethyl-1,3,2-dioxaborolan-2-yl)-2-(trifluoromethyl) phenoxy)ethylcarbamate 200 as a white solid (74% yield). LCMS: m/z 454.2 [M+Na]$^+$, $t_R$=1.91 min.

Synthesis of tert-butyl 2-(4-(5-(4,4-difluoropiperidine-1-carbonyl)pyridin-2-yl)-2-(trifluoromethyl) phenoxy)ethylcarbamate (201)

tert-Butyl 2-(4-(4,4,5,5-tetramethyl-1,3,2-dioxaborolan-2-yl)-2-(trifluoromethyl)phenoxy)ethylcarbamate (200; 500 mg, 1.2 mmol), (6-bromopyridin-3-yl)(4,4-difluoropiperidin-1-yl)methanone (400 mg, 1.3 mmol), Pd(dppf)Cl$_2$ (85 mg, 0.12 mmol), and K$_2$CO$_3$ (320 mg, 2.4 mmol) were added in a mixture of dioxane (10 mL) and water (1 mL) and degassed. The reaction mixture was heated at 100° C. under nitrogen atmosphere for 4 h. The reaction mixture was cooled down to room temperature, filtered and the filtrate was concentrated under reduced pressure to give the crude product, which was purified by silica gel chromatography (50% EtOAc/petroleum ether) to yield 130 mg of tert-butyl 2-(4-(5-(4,4-difluoropiperidine-1-carbonyl)pyridin-2-yl)-2-(trifluoromethyl)phenoxy)ethylcarbamate 201 as a white solid (21% yield). LCMS: m/z 474.2 [M-55]$^+$, $t_R$=1.72 min.

Synthesis of (6-(4-(2-aminoethoxy)-3-(trifluoromethyl)phenyl)pyridin-3-yl)(4,4-difluoropiperidin-1-yl)methanone (202)

tert-Butyl 2-(4-(5-(4,4-difluoropiperidine-1-carbonyl)pyridin-2-yl)-2-(trifluoromethyl)phenoxy)ethylcarbamate (201; 100 mg, 0.19 mmol) was dissolved in CH$_2$Cl$_2$ (5 mL) TFA (1 mL) was added dropwise at room temperature. The reaction mixture was stirred at room temperature for 2 h. The reaction mixture was concentrated under reduced pressure to give the crude (6-(4-(2-aminoethoxy)-3-(trifluoromethyl) phenyl)pyridin-3-yl)(4,4-difluoropiperidin-1-yl)methanone 202, which was used without further purification in the next step (81 mg, 100% yield). LCMS: m/z 430.1 [M+H]$^+$, $t_R$=1.24 min.

Synthesis of (E)-3-(6-aminopyridin-3-yl)-N-(2-(4-(5-(4,4-difluoropiperidine-1-carbonyl)pyridin-2-yl)-2-(trifluoromethyl)phenoxy)ethyl)acrylamide (355)

(6-(4-(2-Aminoethoxy)-3-(trifluoromethyl)phenyl)pyridin-3-yl)(4,4-difluoropiperidin-1-yl)methanone (202; 80 mg, 0.18 mmol) was dissolved in DMF (2 mL) and (E)-3-(6-aminopyridin-3-yl)acrylic acid (34 mg, 0.21 mmol) was added at 0° C. HATU (142 mg, 0.37 mmol) was added to this reaction mixture at 0° C. followed by DIPEA (48 mg, 0.37 mmol) dropwise. The reaction mixture was allowed to warm to room temperature and stirred further for 2 h. The reaction mixture was purified Prep-HPLC to afford 51 mg of (E)-3-(6-aminopyridin-3-yl)-N-(2-(4-(5-(4,4-difluoropiperidine-1-carbonyl)pyridin-2-yl)-2-(trifluoromethyl)phenoxy)ethyl) acrylamide (355) (50% yield). $^1$H NMR (500 MHz, DMSO-d$_6$) δ 8.74 (d, J=2 Hz, 1H), 8.42-8.37 (m, 2H), 8.34-8.30 (m, 1H), 8.20-8.07 (m, 5H), 7.98 (dd, J$_1$=8 Hz, J$_2$=2 Hz, 1H), 7.46 (d, J=9 Hz, 1H), 7.40 (d, J=16 Hz, 1H), 6.98 (d, J=9 Hz, 1H), 6.56 (d, J=16 Hz, 1H), 4.30 (t, J=6 Hz, 2H), 3.78-3.70 (m, 2H), 3.63-3.58 (m, 2H), 3.52-3.44 (m, 2H), 2.15-2.01 (m, 4H). LCMS: m/z 576.2 [M+H]$^+$; $t_R$=1.31 min.

Example 2. MTT Cell Proliferation Assay

The MTT cell proliferation assay was used to study the cytotoxic properties of the compounds. The assay was performed according to the method described by Roche Molecular Biochemicals, with minor modifications. The assay is based on the cleavage of the tetrazolium salt, MTT, in the presence of an electron-coupling reagent. The water-insoluble formazan salt produced must be solubilized in an additional step. Cells grown in a 96-well tissue culture plate were incubated with the MTT solution for approximately 4 hours. After this incubation period, a water-insoluble formazan dye formed. After solubilization, the formazan dye was quantitated using a scanning multi-well spectrophotometer (ELISA reader). The absorbance revealed directly correlates to the cell number. The cells were seeded at 5,000-10,000 cells in each well of 96-well plate in 100 μL of fresh culture medium and were allowed to attach overnight. The stock solutions of the compounds were diluted in 100 μL cell culture medium to obtain eight concentrations of each test compound, ranging from 1 nM to 30 μM. After incubation for approximately 64-72 hours, 20 uL of CellTiter 96 Aqueous One Solution Reagent (Promega, G358B) was added to each well and the plate was returned to the incubator (37° C.; 5% CO$_2$) until an absolute OD of 1.5 was reached for the control cells. All optical densities were measured at 490 nm using a Vmax Kinetic Microplate Reader (Molecular Devices). In most cases, the assay was performed in duplicate and the results were presented as a mean percent inhibition to the negative control±SE. The following formula was used to calculate the percent of inhibition. Inhibition (%)=(1−(OD$_c$/OD))×100.

The compounds were tested against MS751, Z138 and 3T3 cells. The MS751 cell line is derived from a metastasis to lymph node of human cervix from a patient diagnosed with squameous cell carcinoma of the cervix. The 2138 cell line is a mature B-cell acute lymphoblastic leukemia cell line derived from a patient with chronic lymphocytic leukemia. 3T3 cells are standard fibroblast cells; they were originally isolated from Swiss mouse embryo tissue.

The results of the MTT assay are reported in Table 1.

TABLE 1

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 300 | 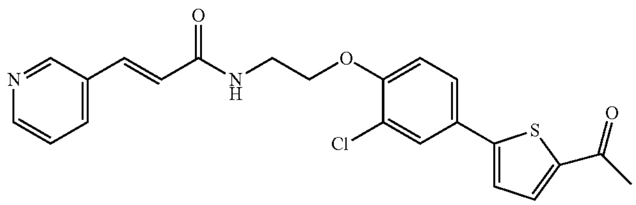 [SMILES: CC(=O)c1ccc(-c2ccc(OCCNC(=O)/C=C/c3cccnc3)c(Cl)c2)s1] | B | B | D | (E)-N-(2-(4-(5-acetylthiophen-2-yl)-2-chlorophenoxy)ethyl)-3-(pyridin-3-yl)acrylamide |
| 301 | 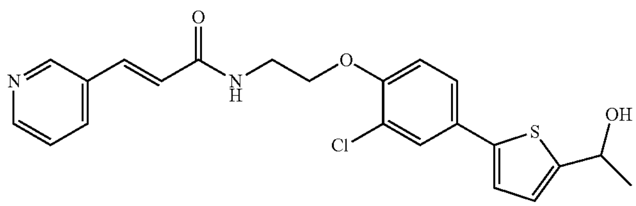 [SMILES: CC(O)c1ccc(-c2ccc(OCCNC(=O)/C=C/c3cccnc3)c(Cl)c2)s1] | B | A | B | (E)-N-(2-(2-chloro-4-(5-(1-hydroxyethyl)thiophen-2-yl)phenoxy)ethyl)-3-(pyridin-3-yl)acrylamide |
| 302 | 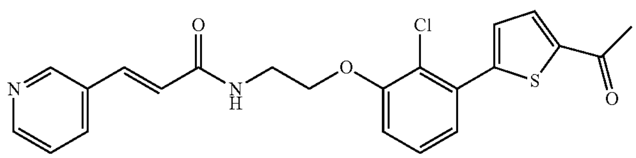 [SMILES: CC(=O)c1ccc(-c2cccc(OCCNC(=O)/C=C/c3cccnc3)c2Cl)s1] | B | A | B | (E)-N-(2-(3-(5-acetylthiophen-2-yl)-2-chlorophenoxy)ethyl)-3-(pyridin-3-yl)acrylamide |
| 303 | 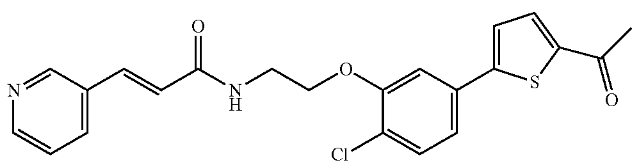 [SMILES: CC(=O)c1ccc(-c2ccc(Cl)c(OCCNC(=O)/C=C/c3cccnc3)c2)s1] | B | B | D | (E)-N-(2-(5-(5-acetylthiophen-2-yl)-2-chlorophenoxy)ethyl)-3-(pyridin-3-yl)acrylamide |
| 304 | 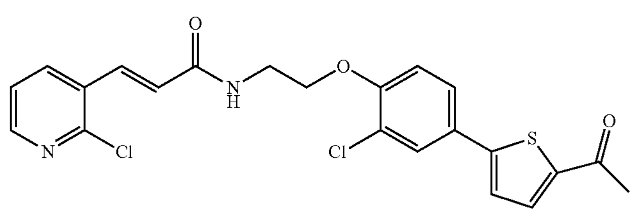 [SMILES: CC(=O)c1ccc(-c2ccc(OCCNC(=O)/C=C/c3cccnc3Cl)c(Cl)c2)s1] | D | C | D | (E)-N-(2-(4-(5-acetylthiophen-2-yl)-2-chlorophenoxy)ethyl)-3-(2-chloropyridin-3-yl)acrylamide |
| 305 | 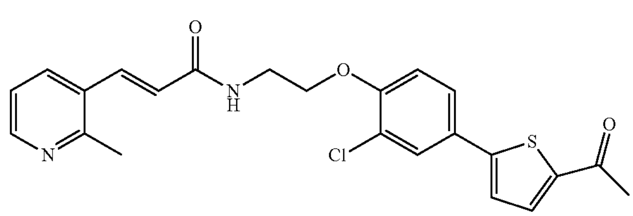 [SMILES: CC(=O)c1ccc(-c2ccc(OCCNC(=O)/C=C/c3cccnc3C)c(Cl)c2)s1] | D | D | D | (E)-N-(2-(4-(5-acetylthiophen-2-yl)-2-chlorophenoxy)ethyl)-3-(2-methylpyridin-3-yl)acrylamide |
| 306 | 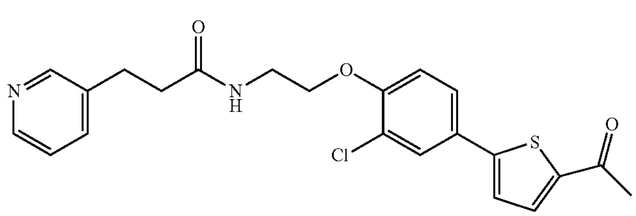 [SMILES: CC(=O)c1ccc(-c2ccc(OCCNC(=O)CCc3cccnc3)c(Cl)c2)s1] | D | C | D | N-(2-(4-(5-acetylthiophen-2-yl)-2-chlorophenoxy)ethyl)-3-(pyridin-3-yl)propanamide |

TABLE 1-continued

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 307 | 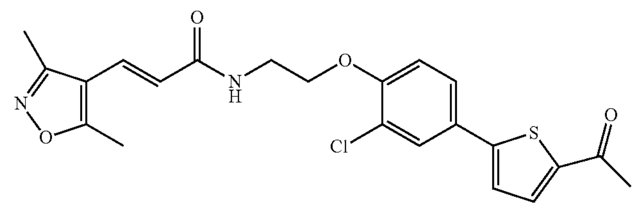 [SMILES: CC(=O)c1ccc(-c2ccc(OCCNC(=O)/C=C/c3c(C)noc3C)c(Cl)c2)s1] | D | D | D | (E)-N-(2-(4-(5-acetylthiophen-2-yl)-2-chlorophenoxy)ethyl)-3-(3,5-dimethylisoxazol-4-yl)acrylamide |
| 308 | 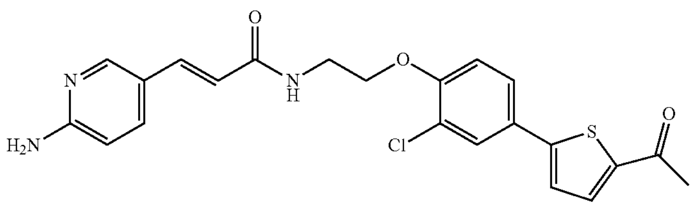 [SMILES: CC(=O)c1ccc(-c2ccc(OCCNC(=O)/C=C/c3ccc(N)nc3)c(Cl)c2)s1] | B | B | D | (E)-N-(2-(4-(5-acetylthiophen-2-yl)-2-chlorophenoxy)ethyl)-3-(6-aminopyridin-3-yl)acrylamide |
| 309 | 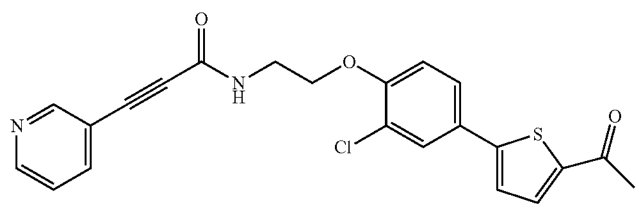 [SMILES: CC(=O)c1ccc(-c2ccc(OCCNC(=O)C#Cc3cccnc3)c(Cl)c2)s1] | D | D | D | N-(2-(4-(5-acetylthiophen-2-yl)-2-chlorophenoxy)ethyl)-3-(pyridin-3-yl)propiolamide |
| 310 | 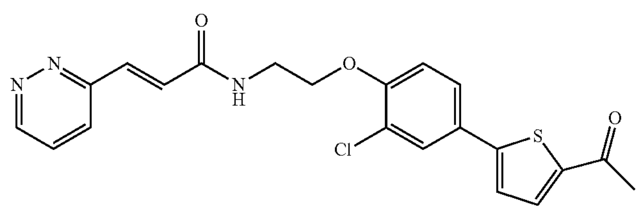 [SMILES: CC(=O)c1ccc(-c2ccc(OCCNC(=O)/C=C/c3cccnn3)c(Cl)c2)s1] | D | D | D | (E)-N-(2-(4-(5-acetylthiophen-2-yl)-2-chlorophenoxy)ethyl)-3-(pyridazin-3-yl)acrylamide |
| 311 | 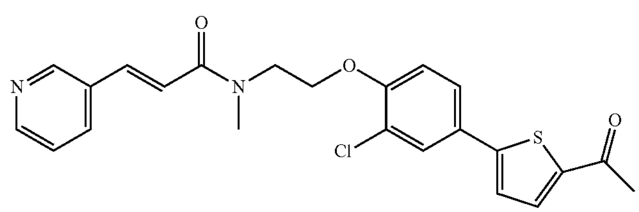 [SMILES: CC(=O)c1ccc(-c2ccc(OCCN(C)C(=O)/C=C/c3cccnc3)c(Cl)c2)s1] | B | B | B | (E)-N-(2-(4-(5-acetylthiophen-2-yl)-2-chlorophenoxy)ethyl)-N-methyl-3-(pyridin-3-yl)acrylamide |
| 312 | 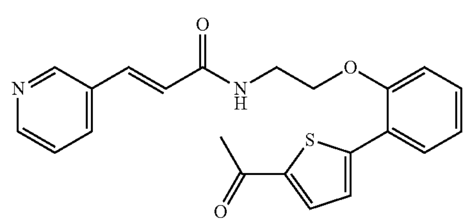 [SMILES: CC(=O)c1ccc(-c2ccccc2OCCNC(=O)/C=C/c2cccnc2)s1] | B | B | B | (E)-N-(2-(2-(5-acetylthiophen-2-yl)phenoxy)ethyl)-3-(pyridin-3-yl)acrylamide |
| 313 | 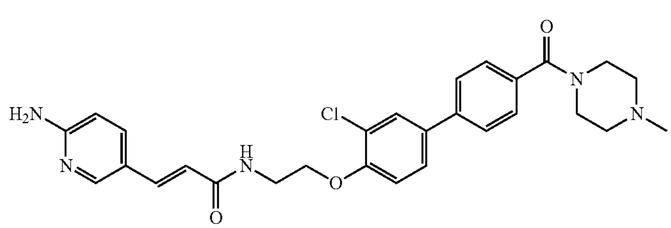 [SMILES: CN1CCN(C(=O)c2ccc(-c3ccc(OCCNC(=O)/C=C/c4ccc(N)nc4)c(Cl)c3)cc2)CC1] | A | A | B | (E)-3-(6-aminopyridin-3-yl)-N-(2-((3-chloro-4'-(4-methylpiperazine-1-carbonyl)-[1,1'-biphenyl]-4-yl)oxy)ethyl)acrylamide |

TABLE 1-continued

MTT Assay (IC$_{50}$: A = <100 nM; B = 100 nM to <5 µM; C = 5 µM to 10 µM; D = >10 µM).

| Cpd. No. | Compound Structure | Z138 | MS751 | 3T3 | Compound Name |
|---|---|---|---|---|---|
| 314 | 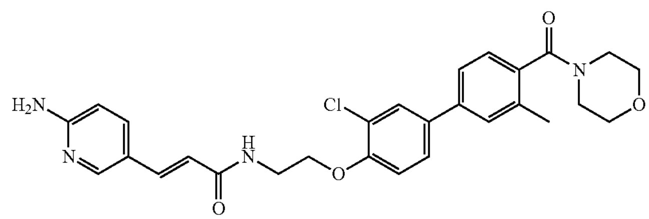 [SMILES: Cc1cc(-c2ccc(OCCNC(=O)/C=C/c3ccc(N)nc3)c(Cl)c2)ccc1C(=O)N1CCOCC1] | A | A | B | (E)-3-(6-aminopyridin-3-yl)-N-(2-((3-chloro-3'-methyl-4'-(morpholine-4-carbonyl)-[1,1'-biphenyl]-4-yl)oxy)ethyl)acrylamide |
| 315 | 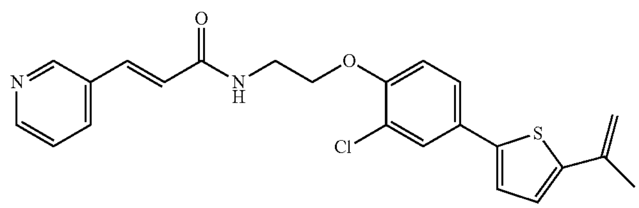 [SMILES: C=C(C)c1ccc(-c2ccc(OCCNC(=O)/C=C/c3cccnc3)c(Cl)c2)s1] | B | C | C | (E)-N-(2-(2-chloro-4-(5-(prop-1-en-2-yl)thiophen-2-yl)phenoxy)ethyl)-3-(pyridin-3-yl)acrylamide |
| 316 | 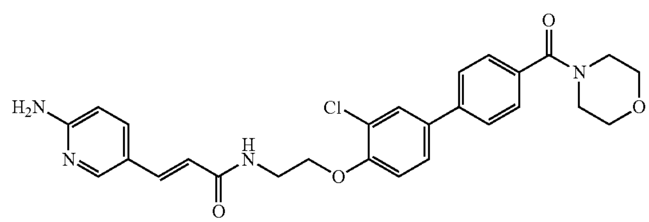 [SMILES: Nc1ccc(/C=C/C(=O)NCCOc2ccc(-c3ccc(C(=O)N4CCOCC4)cc3)cc2Cl)cn1] | A | A | B | (E)-3-(6-aminopyridin-3-yl)-N-(2-((3-chloro-4'-(morpholine-4-carbonyl)-[1,1'-biphenyl]-4-yl)oxy)ethyl)acrylamide |
| 317 | 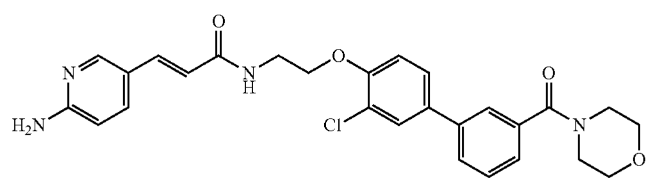 [SMILES: Nc1ccc(/C=C/C(=O)NCCOc2ccc(-c3cccc(C(=O)N4CCOCC4)c3)cc2Cl)cn1] | A | A | D | (E)-3-(6-aminopyridin-3-yl)-N-(2-((3-chloro-3'-(morpholine-4-carbonyl)-[1,1'-biphenyl]-4-yl)oxy)ethyl)acrylamide |
| 318 | 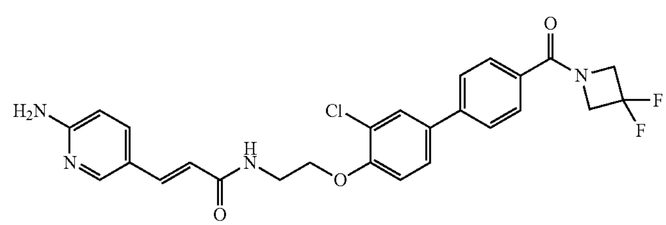 [SMILES: Nc1ccc(/C=C/C(=O)NCCOc2ccc(-c3ccc(C(=O)N4CC(F)(F)C4)cc3)cc2Cl)cn1] | A | A | B | (E)-3-(6-aminopyridin-3-yl)-N-(2-((3-chloro-4'-(3,3-difluoroazetidine-1-carbonyl)-[1,1'-biphenyl]-4-yl)oxy)ethyl)acrylamide |
| 319 | 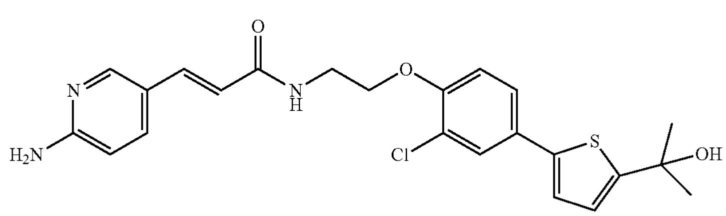 [SMILES: CC(C)(O)c1ccc(-c2ccc(OCCNC(=O)/C=C/c3ccc(N)nc3)c(Cl)c2)s1] | B | B | D | (E)-3-(6-aminopyridin-3-yl)-N-(2-(2-chloro-4-(5-(2-hydroxypropan-2-yl)thiophen-2-yl)phenoxy)ethyl)acrylamide |
| 320 | 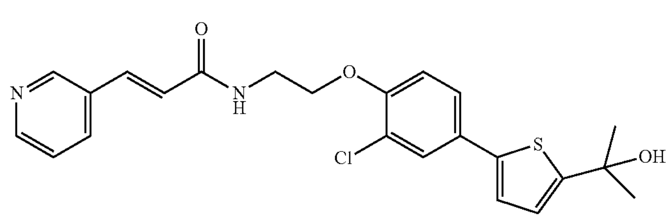 [SMILES: CC(C)(O)c1ccc(-c2ccc(OCCNC(=O)/C=C/c3cccnc3)c(Cl)c2)s1] | B | B | C | (E)-N-(2-(2-chloro-4-(5-(2-hydroxypropan-2-yl)thiophen-2-yl)phenoxy)ethyl)-3-(pyridin-3-yl)acrylamide |

TABLE 1-continued

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 321 | 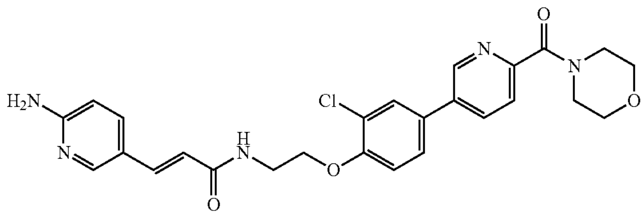 [SMILES: Nc1ccc(/C=C/C(=O)NCCOc2ccc(-c3ccc(C(=O)N4CCOCC4)nc3)cc2Cl)cn1] | A | A | D | (E)-3-(6-aminopyridin-3-yl)-N-(2-(2-chloro-4-(6-(morpholine-4-carbonyl)pyridin-3-yl)phenoxy)ethyl)acrylamide |
| 322 | 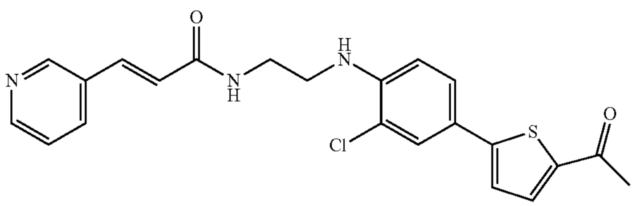 [SMILES: CC(=O)c1ccc(-c2ccc(NCCNC(=O)/C=C/c3cccnc3)c(Cl)c2)s1] | B | B | D | (E)-N-(2-((4-(5-acetylthiophen-2-yl)-2-chlorophenyl)amino)ethyl)-3-(pyridin-3-yl)acrylamide |
| 323 | 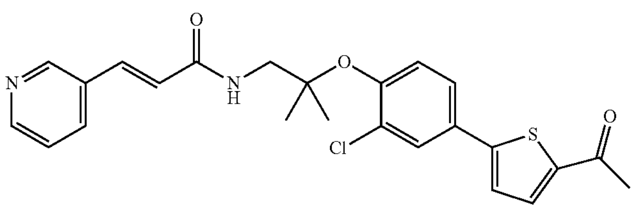 [SMILES: CC(=O)c1ccc(-c2ccc(OC(C)(C)CNC(=O)/C=C/c3cccnc3)c(Cl)c2)s1] | B | C | D | (E)-N-(2-(4-(5-acetylthiophen-2-yl)-2-chlorophenoxy)-2-methylpropyl)-3-(pyridin-3-yl)acrylamide |
| 325 | 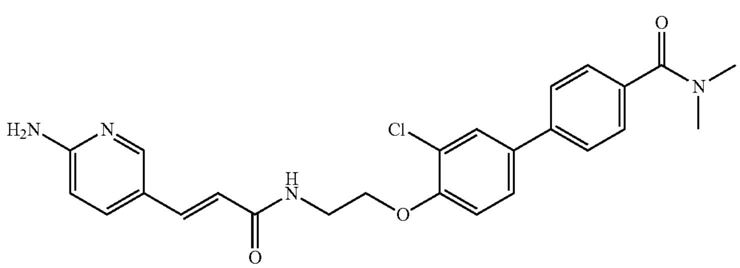 [SMILES: CN(C)C(=O)c1ccc(-c2ccc(OCCNC(=O)/C=C/c3ccc(N)nc3)c(Cl)c2)cc1] | B | B | D | (E)-4'-(2-(3-(6-aminopyridin-3-yl)acrylamido)ethoxy)-3'-chloro-N,N-dimethyl-[1,1'-biphenyl]-4-carboxamide |
| 326 | 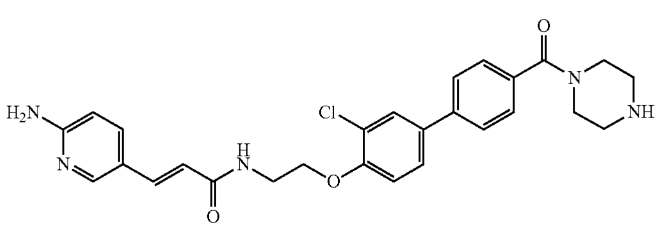 [SMILES: Nc1ccc(/C=C/C(=O)NCCOc2ccc(-c3ccc(C(=O)N4CCNCC4)cc3)cc2Cl)cn1] | A | A | B | (E)-3-(6-aminopyridin-3-yl)-N-(2-((3-chloro-4'-(piperazine-1-carbonyl)-[1,1'-biphenyl]-4-yl)oxy)ethyl)acrylamide |
| 327 | 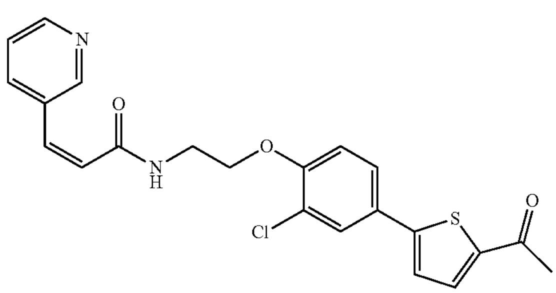 [SMILES: CC(=O)c1ccc(-c2ccc(OCCNC(=O)/C=C\c3cccnc3)c(Cl)c2)s1] | B | C | D | (Z)-N-(2-(4-(5-acetylthiophen-2-yl)-2-chlorophenoxy)ethyl)-3-(pyridin-3-yl)acrylamide |

TABLE 1-continued

MTT Assay (IC$_{50}$: A = <100 nM; B = 100 nM to <5 µM; C = 5 µM to 10 µM; D = >10 µM).

| Cpd. No. | Compound Structure | Z138 | MS751 | 3T3 | Compound Name |
|---|---|---|---|---|---|
| 328 | 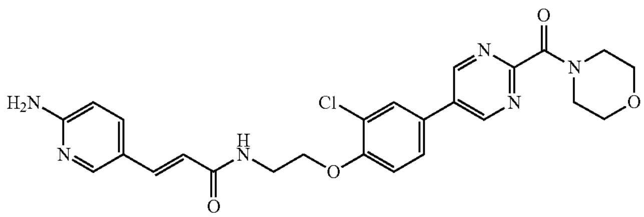 | B | B | D | (E)-3-(6-aminopyridin-3-yl)-N-(2-(2-chloro-4-(2-(morpholine-4-carbonyl)pyrimidin-5-yl)phenoxy)ethyl)acrylamide |
| 329 | 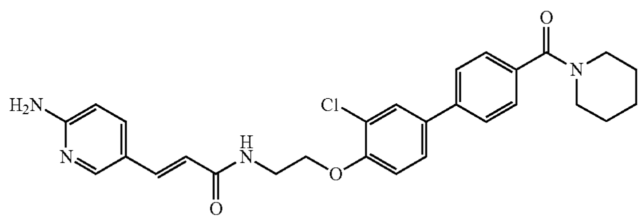 [SMILES: Nc1ccc(/C=C/C(=O)NCCOc2ccc(-c3ccc(C(=O)N4CCCCC4)cc3)cc2Cl)cn1] | A | A | D | (E)-3-(6-aminopyridin-3-yl)-N-(2-((3-chloro-4'-(piperidine-1-carbonyl)-[1,1'-biphenyl]-4-yl)oxy)ethyl)acrylamide |
| 330 | 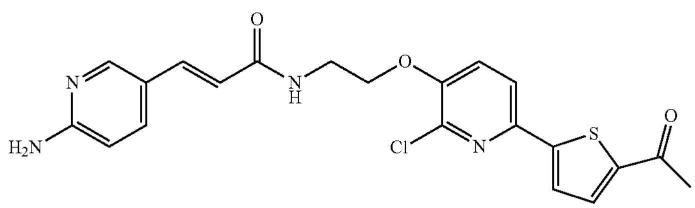 [SMILES: CC(=O)c1ccc(-c2ccc(OCCNC(=O)/C=C/c3ccc(N)nc3)c(Cl)n2)s1] | B | B | D | (E)-N-(2-((6-(5-acetylthiophen-2-yl])-2-chloropyridin-3-yl)oxy)ethy])-3-(6-aminopyridin-3-yl)acrylamide |
| 331 | 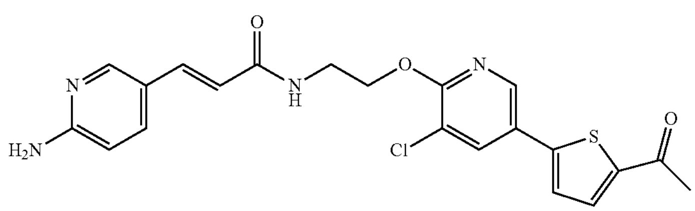 [SMILES: CC(=O)c1ccc(-c2cnc(OCCNC(=O)/C=C/c3ccc(N)nc3)c(Cl)c2)s1] | D | D | D | (E)-N-(2-((5-(5-acetylthiophen-2-yl)-3-chloropyridin-2-yl)oxy)ethyl)-3-(6-aminopyridin-3-yl)acrylamide |
| 332 | 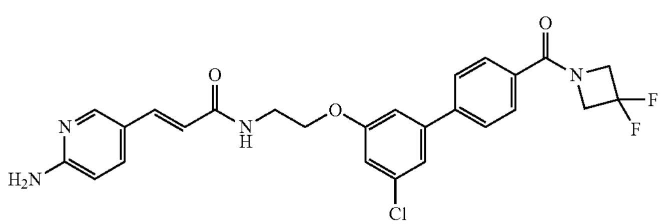 [SMILES: Nc1ccc(/C=C/C(=O)NCCOc2cc(Cl)cc(-c3ccc(C(=O)N4CC(F)(F)C4)cc3)c2)cn1] | A | A | B | (E)-3-(6-aminopyridin-3-yl)-N-(2-((5-chloro-4'-(3,3-difluoroazetidine-1-carbonyl)-[1,1'-biphenyl]-3-yl)oxy)ethyl)acrylamide |
| 333 | 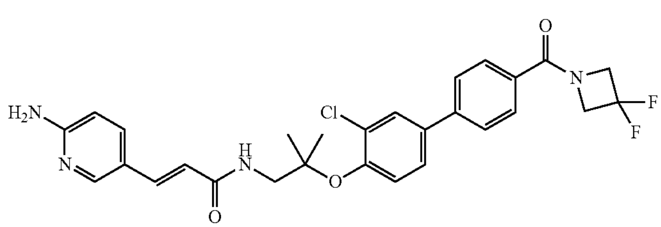 [SMILES: CC(C)(CNC(=O)/C=C/c1ccc(N)nc1)Oc1ccc(-c2ccc(C(=O)N3CC(F)(F)C3)cc2)cc1Cl] | B | B | D | (E)-3-(6-aminopyridin-3-yl)-N-(2-((3-chloro-4'-(3,3-difluoroazetidine-1-carbonyl)-[1,1'-biphenyl]-4-yl)oxy)-2-methylpropyl)acrylamide |
| 334 | 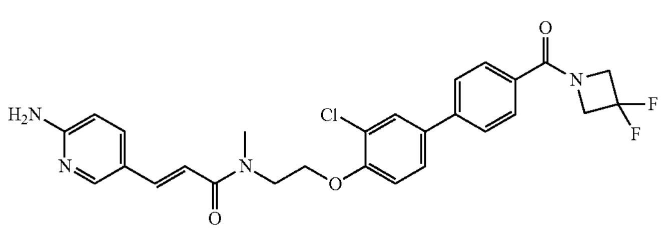 [SMILES: CN(CCOc1ccc(-c2ccc(C(=O)N3CC(F)(F)C3)cc2)cc1Cl)C(=O)/C=C/c1ccc(N)nc1] | A | B | C | (E)-3-(6-aminopyridin-3-yl)-N-(2-((3-chloro-4'-(3,3-difluoroazetidine-1-carbonyl)-[1,1'-biphenyl]-4-yl)oxy)ethyl)-N-methylacrylamide |

TABLE 1-continued

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 335 | 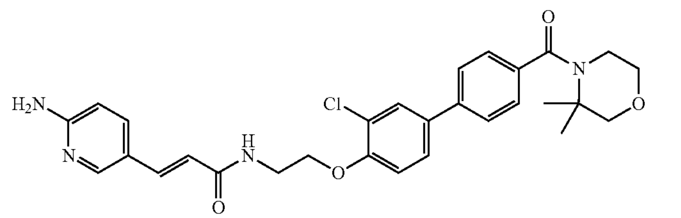 [SMILES: CC1(C)COCCN1C(=O)c1ccc(-c2ccc(OCCNC(=O)/C=C/c3ccc(N)nc3)c(Cl)c2)cc1] | A | A | B | (E)-3-(6-aminopyridin-3-yl)-N-(2-((3-chloro-4'-(3,3-dimethylmorpholine-4-carbonyl)-[1,1'-biphenyl]-4-yl)oxy)ethyl)acrylamide |
| 336 | 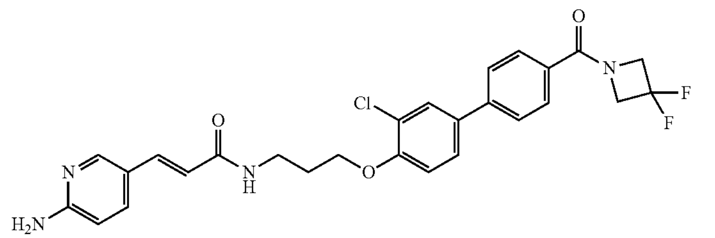 [SMILES: Nc1ccc(/C=C/C(=O)NCCCOc2ccc(-c3ccc(C(=O)N4CC(F)(F)C4)cc3)cc2Cl)cn1] | A | A | B | (E)-3-(6-aminopyridin-3-yl)-N-(3-((3-chloro-4'-(3,3-difluoroazetidine-1-carbonyl)-[1,1'-biphenyl]-4-yl)oxy)propyl)acrylamide |
| 337 | 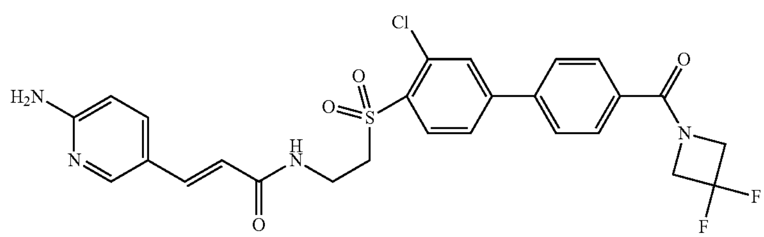 [SMILES: Nc1ccc(/C=C/C(=O)NCCS(=O)(=O)c2ccc(-c3ccc(C(=O)N4CC(F)(F)C4)cc3)cc2Cl)cn1] | D | D | D | (E)-3-(6-aminopyridin-3-yl)-N-(2-((3-chloro-4'-(3,3-difluoroazetidine-1-carbonyl)-[1,1'-biphenyl]-4-yl)sulfonyl)ethyl)acrylamide |
| 338 | 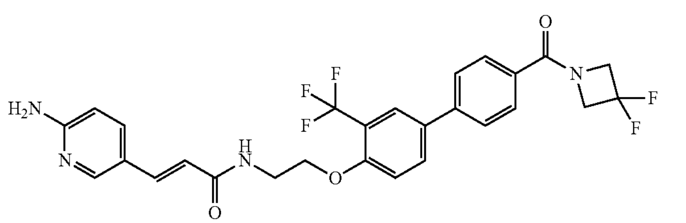 [SMILES: Nc1ccc(/C=C/C(=O)NCCOc2ccc(-c3ccc(C(=O)N4CC(F)(F)C4)cc3)cc2C(F)(F)F)cn1] | A | A | A | (E)-3-(6-aminopyridin-3-yl)-N-(2-((4'-(3,3-difluoroazetidine-1-carbonyl)-3-(trifluoromethyl)-[1,1'-biphenyl]-4-yl)oxy)ethyl)acrylamide |
| 339 | 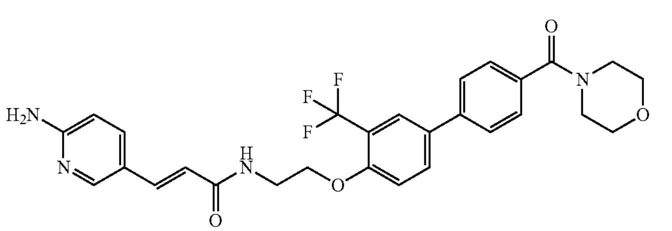 [SMILES: Nc1ccc(/C=C/C(=O)NCCOc2ccc(-c3ccc(C(=O)N4CCOCC4)cc3)cc2C(F)(F)F)cn1] | A | A | B | (E)-3-(6-aminopyridin-3-yl)-N-(2-((4'-(morpholine-4-carbonyl)-3-(trifluoromethyl)-[1,1'-biphenyl]-4-yl)oxy)ethyl)acrylamide |
| 340 | 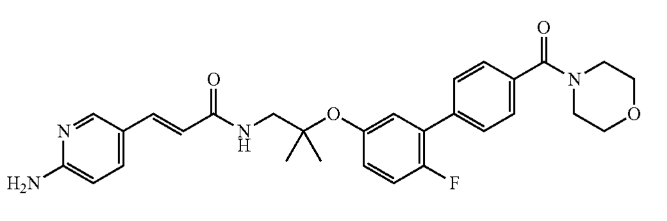 [SMILES: CC(C)(CNC(=O)/C=C/c1ccc(N)nc1)Oc1ccc(F)c(-c2ccc(C(=O)N3CCOCC3)cc2)c1] | A | B | D | (E)-3-(6-aminopyridin-3-yl)-N-(2-((6-fluoro-4'-(morpholine-4-carbonyl)-[1,1'-biphenyl]-3-yl)oxy)-2-methylpropyl)acrylamide |

TABLE 1-continued

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 342 | 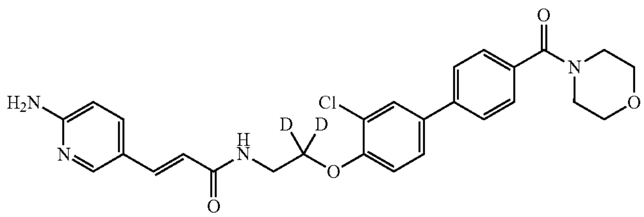 [SMILES: [2H]C([2H])(CNC(=O)/C=C/c1ccc(N)nc1)Oc1ccc(-c2ccc(C(=O)N3CCOCC3)cc2)cc1Cl] | A | A | B | (E)-3-(6-aminopyridin-3-yl)-N-(2-((3-chloro-4'-(morpholine-4-carbonyl)-[1,1'-biphenyl]-4-yl)oxy)ethyl-2,2-d2)acrylamide |
| 343 | 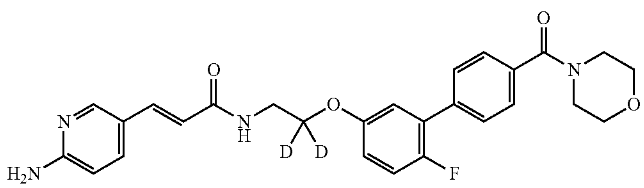 [SMILES: [2H]C([2H])(CNC(=O)/C=C/c1ccc(N)nc1)Oc1ccc(F)c(-c2ccc(C(=O)N3CCOCC3)cc2)c1] | B | B | D | (E)-3-(6-aminopyridin-3-yl)-N-(2-((6-fluoro-4'-(morpholine-4-carbonyl)-[1,1'-biphenyl]-3-yl)oxy)ethyl-2,2-d2)acrylamide |
| 344 | 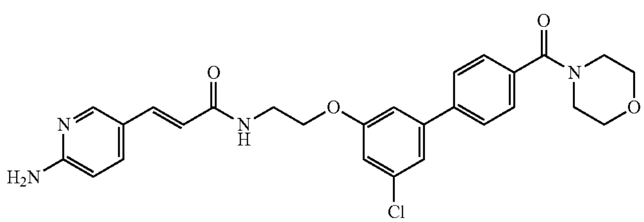 [SMILES: Nc1ccc(/C=C/C(=O)NCCOc2cc(Cl)cc(-c3ccc(C(=O)N4CCOCC4)cc3)c2)cn1] | A | A | B | (E)-3-(6-aminopyridin-3-yl)-N-(2-((5-chloro-4'-(morpholine-4-carbonyl)-[1,1'-biphenyl]-3-yl)oxy)ethyl)acrylamide |
| 345 | 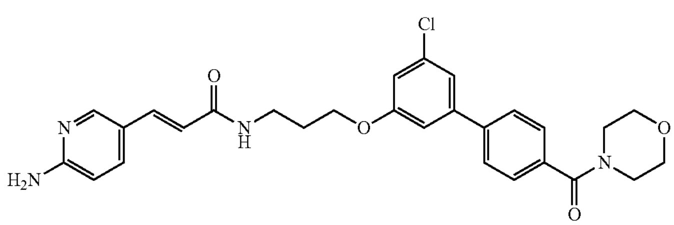 [SMILES: Nc1ccc(/C=C/C(=O)NCCCOc2cc(Cl)cc(-c3ccc(C(=O)N4CCOCC4)cc3)c2)cn1] | A | A | B | (E)-3-(6-aminopyridin-3-yl)-N-(3-((5-chloro-4'-(morpholine-4-carbonyl)-[1,1'-biphenyl]-3-yl)oxy)propyl)acrylamide |
| 346 | 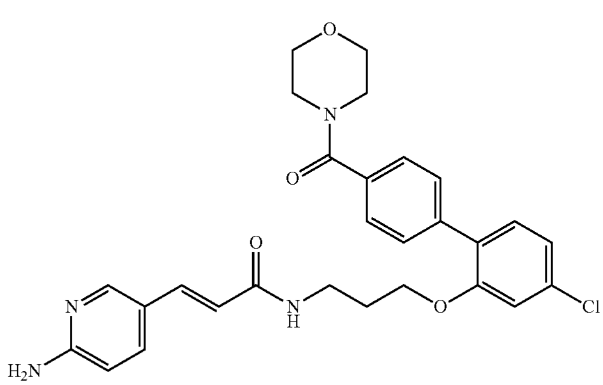 [SMILES: Nc1ccc(/C=C/C(=O)NCCCOc2cc(Cl)ccc2-c2ccc(C(=O)N3CCOCC3)cc2)cn1] | A | B | C | (E)-3-(6-aminopyridin-3-yl)-N-(3-((4-chloro-4'-(morpholine-4-carbonyl)-[1,1'-biphenyl]-2-yl)oxy)propyl)acrylamide |

TABLE 1-continued

MTT Assay (IC$_{50}$: A = <100 nM; B = 100 nM to <5 μM; C = 5 μM to 10 μM; D = >10 μM).

| Cpd. No. | Compound Structure | Z138 | MS751 | 3T3 | Compound Name |
|---|---|---|---|---|---|
| 347 | 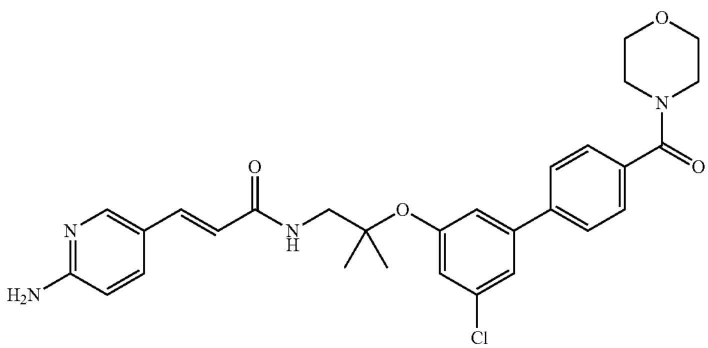 [SMILES: CC(C)(CNC(=O)/C=C/c1ccc(N)nc1)Oc1cc(Cl)cc(-c2ccc(C(=O)N3CCOCC3)cc2)c1] | A | B | D | (E)-3-(6-aminopyridin-3-yl)-N-(2-((5-chloro-4'-(morpholine-4-carbonyl)-[1,1'-biphenyl]-3-yl)oxy)-2-methylpropyl)acrylamide |
| 348 | 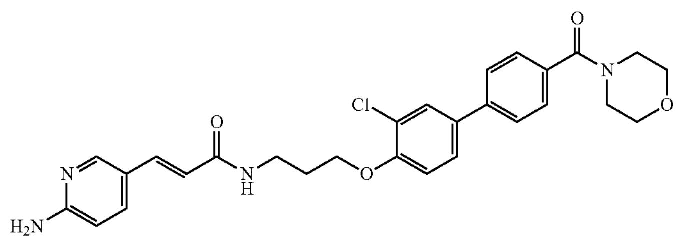 [SMILES: Nc1ccc(/C=C/C(=O)NCCCOc2ccc(-c3ccc(C(=O)N4CCOCC4)cc3)cc2Cl)cn1] | A | A | B | (E)-3-(6-aminopyridin-3-yl)-N-(3-((3-chloro-4'-(morpholine-4-carbonyl)-[1,1'-biphenyl]-4-yl)oxy)propyl)acrylamide |
| 349 | 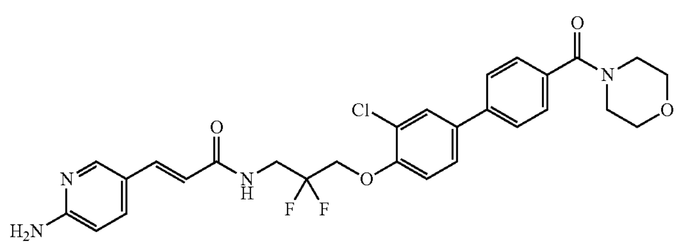 [SMILES: Nc1ccc(/C=C/C(=O)NCC(F)(F)COc2ccc(-c3ccc(C(=O)N4CCOCC4)cc3)cc2Cl)cn1] | A | A | B | (E)-3-(6-aminopyridin-3-yl)-N-(3-chloro-4'-(morpholine-4-carbonyl)-[1,1'-biphenyl]-4-yl)oxy)-2,2-difluoropropyl)acrylamide |
| 350 | 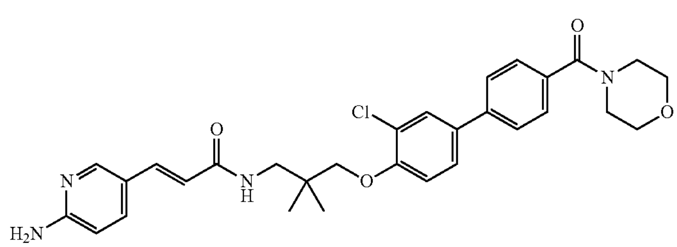 [SMILES: CC(C)(CNC(=O)/C=C/c1ccc(N)nc1)COc1ccc(-c2ccc(C(=O)N3CCOCC3)cc2)cc1Cl] | A | B | B | (E)-3-(6-aminopyridin-3-yl)-N-(3-((3-chloro-4'-(morpholine-4-carbonyl)-[1,1'-biphenyl]-4-yl)oxy)-2,2-dimethylpropyl)acrylamide |
| 351 | 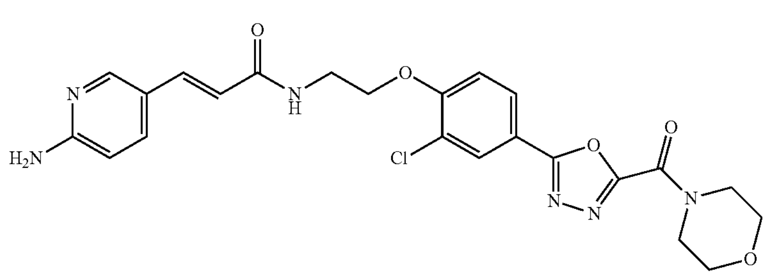 [SMILES: Nc1ccc(/C=C/C(=O)NCCOc2ccc(-c3nnc(C(=O)N4CCOCC4)o3)cc2Cl)cn1] | B | B | D | (E)-3-(6-aminopyridin-3-yl)-N-(2-(2-chloro-4-(5-(morpholine-4-carbonyl)-1,3,4-oxadiazol-2-yl)phenoxy)ethyl)acrylamide |

TABLE 1-continued

MTT Assay (IC$_{50}$: A = <100 nM; B = 100 nM to <5 µM; C = 5 µM to 10 µM; D = >10 µM).

| Cpd. No. | Compound Structure | Z138 | MS751 | 3T3 | Compound Name |
|---|---|---|---|---|---|
| 352 | 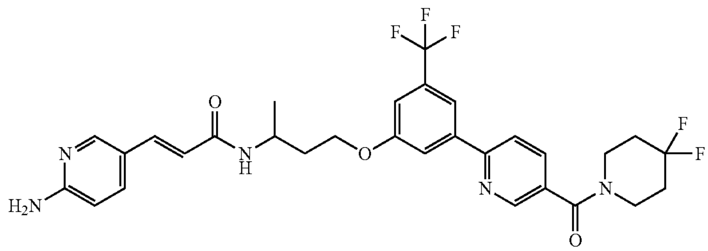 [SMILES: CC(CCOc1cc(-c2ccc(C(=O)N3CCC(F)(F)CC3)cn2)cc(C(F)(F)F)c1)NC(=O)/C=C/c1ccc(N)nc1] | B | B | D | (E)-3-(6-aminopyridin-3-yl)-N-(4-(3-(5-(4,4-difluoropiperidine-1-carbonyl)pyridin-2-yl)-5-(trifluoromethyl)phenoxy)butan-2-yl)acrylamide |
| 353 | 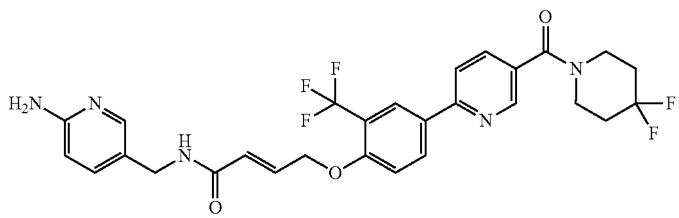 [SMILES: Nc1ccc(CNC(=O)/C=C/COc2ccc(-c3ccc(C(=O)N4CCC(F)(F)CC4)cn3)cc2C(F)(F)F)cn1] | B | B | D | (E)-N-((6-aminopyridin-3-yl)methyl)-4-(4-(5-(4,4-difluoropiperidine-1-carbonyl)pyridin-2-yl)-2-(trifluoromethyl)phenoxy)but-2-enamide |
| 354 | 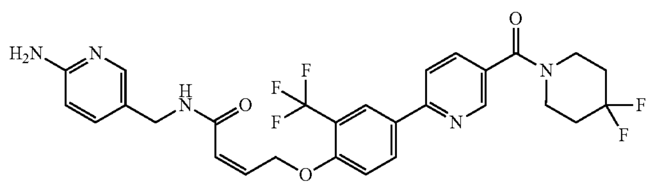 [SMILES: Nc1ccc(CNC(=O)/C=C\COc2ccc(-c3ccc(C(=O)N4CCC(F)(F)CC4)cn3)cc2C(F)(F)F)cn1] | D | D | D | (Z)-N-((6-aminopyridin-3-yl)methyl)-4-(4-(5-(4,4-difluoropiperidine-1-carbonyl)pyridin-2-yl)-2-(trifluoromethyl)phenoxy)but-2-enamide |
| 355 | 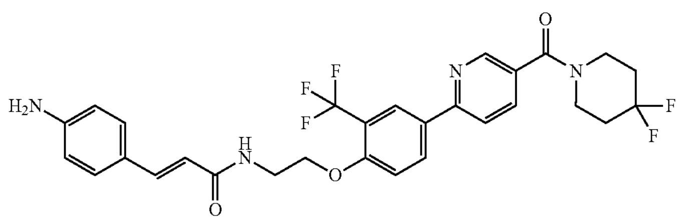 [SMILES: Nc1ccc(/C=C/C(=O)NCCOc2ccc(-c3ccc(C(=O)N4CCC(F)(F)CC4)cn3)cc2C(F)(F)F)cc1] | A | A | B | (E)-3-(6-aminopyridin-3-yl)-N-(2-(4-(5-(4,4-difluoropiperidine-1-carbonyl)pyridin-2-yl)-2-(trifluoromethyl)phenoxy)ethyl)acrylamide |

Selected compounds were further tested in the MTT cell proliferation assay against the cell lines listed in Table 2. NHDF cells are normal human dermal fibroblast cells. Hep G2 cells are human hepatocellular carcinoma cells. HEP 3B cells are human hepatocellular carcinoma cells. The UCH-2 cell line is a chordoma cell line. The SNU-182 cell line is a human hepatoma cell line. The L3.6pl cell line is a pancreatic cancer cell line.

Further results of the MTT assay are reported in Table 2.

TABLE 2

MTT Assay

| Compound Number | NHDF | Hep G2 | HEP 3B | UCH-2 | SNU-182 | L3.6pl |
|---|---|---|---|---|---|---|
| 318 | A | A | A | D | A | A |

(IC$_{50}$: A = <100 nM; B = 100 nM to <5 µM; C = 5 µM to 30 µM; D = >30 µM)

Example 3. Target Identification

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is modulated. For example, PAK1 is modulated, PAK2 is modulated, PAK3 is modulated or a combination of PAK1, PAK2 and PAK3, such as PAK1 and PAK2, PAK1 and PAK3, PAK2 and PAK3, or PAK1, PAK2 and PAK3 is modulated. In a particular embodiment, one or more of the group II PAKs (e.g., PAK4, PAK5, PAK6) is modulated. For example, PAK4 is modulated, PAK5 is modulated, PAK6 is modulated or a combination of PAK4, PAK5 and PAK6, such as PAK4 and PAK5, PAK4 and PAK6, PAK5 and PAK6 or PAK4, PAK5 and PAK6 is modulated. Therefore, the compounds described herein can be useful for treating PAK-mediated disorders.

In another particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

PAKs are a family of serine/threonine kinases that are involved in multiple intracellular signaling pathways. Six human PAKs have been identified to date (PAKs 1-6). The PAKs can be classified into two subfamilies based on domain structure, sequence homology, and regulation: Group 1, which includes PAKs 1-3, and Group 2, which includes PAKs 4-6 (1).

Group I PAKs are characterized by an N-terminal region that includes a conserved p21 binding domain (PBD) that overlaps with an autoinhibitory domain (AID), and a C-terminal kinase domain. Group I PAKs are known to be involved in regulating normal cellular activities and can play a role in disease progression. For example, PAK1 plays an important role in cytoskeleton dynamics, cell adhesion, migration, proliferation, apoptosis, mitosis and vesicle-mediated transport processes, and has been shown to be up-regulated in breast, ovary and thyroid cancer. PAK1 activity has also been shown to be suppressed in brain lysates from Alzheimer's disease patients. PAK2 plays a role in a variety of different signaling pathways including cytoskeleton regulation, cell motility, cell cycle progression, apoptosis and proliferation. PAK3 plays a role in cytoskeleton regulation, cell migration, and cell cycle regulation.

Group II PAKs are characterized by an N-terminal PBD and a C-terminal kinase domain, but lack other motifs found in the group I PAKs. PAK4 is a pluripotent kinase known to mediate cell motility and morphology, proliferation, embryonic development, cell survival, immune defense, and oncogenic transformation (2), and is a key effector for Cdc42, a subset of the Rho GTPase family, which has been shown to be required for Ras driven tumorigenesis (3). PAK5 is unique amongst the PAK family, as it is constitutively localized to the mitochondria, and its localization is independent of kinase activity and Cdc42 binding. The mitochondrial localization of PAK5 is required for it to exert its anti-apoptotic effects and to promote cell survival. One report suggests that PAK5 is overexpressed in colorectal cancer and promotes cancer cell invasion. Both PAK4 and PAK5 have been linked to the regulation of neurite outgrowth; whereas PAK5 induces neurite outgrowth, PAK4 inhibits neurite outgrowth. The link of PAK4 and PAK5 to neuronal development suggests that PAK4 and PAK5 may be involved in the progression of neurological disorders, such as Parkinson's disease, dementia and brain atrophy. PAK6 has been found to specifically bind to androgen receptor (AR) and estrogen receptor α (ERα), and co-translocates into the nucleus with AR in response to androgen. PAK6 expression in adult tissue is mainly restricted to the prostrate and testis. However, PAK6 has been found to be overexpressed in many cancer cell lines, particularly breast and prostate cancers.

Since the PAKs and, in particular, PAK4, are critical hubs of signaling cascades, inhibiting their function can be beneficial for the treatment of cancers, neurodegenerative diseases, and immune system diseases as described herein.

Target Identification Using SILAC (Stable Isotope Labeling of Amino Acids in Cells)

MS751 cellular proteins are labeled with non-radioactive heavy lysine (L-Lysine-2HCl, $^{13}C_6$, $^{15}N_2$) and arginine (L-Arginine-HCl, $^{13}C_6$, $^{15}N_4$) for 7 to 8 doublings. The heavy isotopes are incorporated efficiently with greater than 95% heavy proteins identified by LC-MS. Separate plates of cells are maintained in light amino acids. FIG. 1 is a schematic representation of a SILAC experiment, and shows the experimental design.

After successful isotope labeling, heavy and light plates of MS751 cells are collected and lysed in ModRIPA buffer (50 mM Tris-HCl, pH 7.8, 150 mM NaCl, 1% NP-40, 0.1% sodium deoxycholate, 1 mM EDTA), and the protein quantified using Pierce 660 reagent. Two milligrams of light total protein are mixed with a 50-fold excess of soluble competitor (for example, a compound of the invention or a PEGylated compound of the invention) while two milligrams of heavy protein lysate are mixed with an equal amount of vehicle (DMSO). In the second replicate, the heavy and light proteins are flipped. The mixture is incubated at 4° C. for 1 h with constant rotation. 30 μL of slurry (for example, 15 μL of 12.5% PEGylated compound of the invention immobilized on resin in 15 μL of PBS) is added to separate tubes with the protein mixtures of DMSO or soluble competitor, and incubated for 16 to 24 h with constant rotation.

The following day, the beads are collected by quick centrifugation and the supernatant removed. The resin is washed separately twice in ModRIPA buffer with spins after washes. The light (PEGylated compound of the invention) and heavy (DMSO) resins are mixed together then washed twice with ModRIPA, with spins after washes, and prepared for SDS-PAGE.

The lysates are run on a gradient SDS-PAGE gel and stained with Coomassie blue. Six bands from each replicate are cut from the gel, digested with trypsin, desalted, and prepared for LC-MS proteomics.

Samples are run on a Q-Exactive, and the heavy and light peptides are identified using MaxQuan and R Moderated T Test for statistical analysis. The statistical analysis shows the enrichment of PAK4 in DMSO samples compared to the soluble competitor samples.

Pull-Down of Proteins Using Immobilized Inhibitor

MS751, U2OS, or HeLa cells are collected and lysed in ModRIPA buffer, and the protein content quantified using Pierce 660 reagent. Two milligrams of total protein is mixed with a 50-fold excess of soluble competitor (for example, a compound of the invention or a PEGylated compound of the invention) or an equal amount of DMSO in three separate tubes. The mixture is incubated at 4° C. for 1 h with constant rotation. 30 μl, of slurry (for example, 15 μL of 12.5% PEGylated compound of the invention immobilized on resin in 15 μl, of PBS) is added to separate tubes with the protein mixtures of DMSO or soluble competitor and incubated for 16 to 24 h with constant rotation.

The following day, the beads are collected by quick centrifugation and the supernatant removed. The resin is washed separately three times in ModRIPA buffer with spins after each wash. Each sample along with input lysate is prepared for SDS-PAGE.

Samples are boiled, run on a 4-20% SDS-PAGE gel and transferred to nitrocellulose membranes for Western blotting. Anti-PAK4 primary antibody is incubated on the membrane overnight and detected with fluorescent secondary antibody. The Western blot shows that PAK4 binds to the resin pre-treated with DMSO but not the resin corresponding to samples pre-treated with soluble competitor.

REFERENCES

1. Arias-Romano, L. E.; Chernoff, J. Biol. Cell, 2008, 100, 97-108.
2. a) Dart, A. E.; Wells, C. M. *European Journal of Cell Biology*, 2013, 92, 129-138. b) Clairvoyant, F.; Zhu. S. et al. *J Biol Chem*, 2002, 277, 550-8. c) Cammarano, M. S. et al. *Mol Cell Biol.*, 2005, 21, 9532-42. d) Wells, C. M. et al, *J Cell Sci.*, 2010, 123, 1663-73. d) Siu, M. K. et al. *Proc. Natl. Acad. Sci. USA*, 2010, 107(43), 18622-7.
3. a) Guo, C. et al.; *J. Med. Chem.*, 2012, 55, 4728-4739 b) Deacon, S. W. et al. *Chemistry & Biology*, 2008, 15, 322-331 c) Wells, C. M.; Jones, G. E. *Biochem. J.*, 2010, 425, 465-473.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Structural Formula (XI) or (XII):

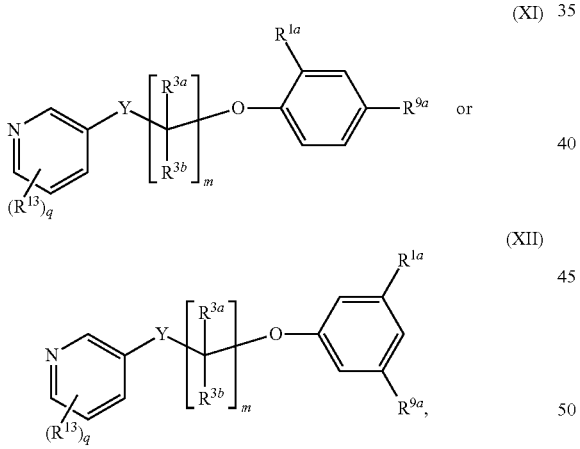

or a pharmaceutically acceptable salt thereof, wherein:
Y is —C($R^8$)=C($R^6$)—$R^5$—N($R^7$)-*, wherein "*" represents a portion of Y directly adjacent to —[C($R^{3a}$)($R^{3b}$)]$_m$—;
$R^{1a}$ is selected from hydroxyl, halogen, halo($C_1$-$C_4$) alkyl, ($C_1$-$C_4$)alkyl, ($C_1$-$C_4$)alkoxy and halo($C_1$-$C_4$) alkoxy; and
$R^{9a}$ is a 6-15-member aryl or a 5-15-member heteroaryl, optionally substituted with one or more substituents independently selected from halogen, ($C_1$-$C_4$)alkyl optionally substituted with hydroxyl, ($C_2$-$C_4$)alkenyl, ($C_1$-$C_4$)haloalkyl, —C(O)($C_1$-$C_4$) alkyl and —C(O)N$R^{11}R^{12}$, wherein:
$R^{11}$ and $R^{12}$ are each independently hydrogen, $C_1$-$C_4$ alkyl, 3-15-member carbocyclyl, or a 3-15-member heterocyclyl; or $R^{11}$ and $R^{12}$ are taken together with the nitrogen atom to which they are commonly attached to form a 3-7-member heterocyclyl, optionally substituted with 1 or 2 substituents independently selected from halogen, ($C_1$-$C_4$)alkyl and ($C_1$-$C_4$) haloalkyl;
each of $R^{3a}$ and $R^{3b}$ is independently selected from hydrogen, deuterium, halo, and ($C_1$-$C_4$)alkyl;
$R^5$ is —C(O)—;
$R^6$ and $R^8$ is each independently selected from hydrogen, halo, CN, and ($C_1$-$C_4$)alkyl;
$R^7$ is selected from hydrogen and ($C_1$-$C_4$)alkyl;
each $R^{13}$ is independently selected from amino, halogen, ($C_1$-$C_4$)alkyl and ($C_1$-$C_4$)haloalkyl;
m is 1, 2, or 3; and
q is 0, 1, 2, or 3.

2. The compound of claim 1, wherein $R^{9a}$ is selected from phenyl, thiophenyl, pyridinyl and pyrimidinyl.

3. The compound of claim 1 or 2, wherein q is 0, 1 or 2.

4. The compound of claim 1 or 2, wherein q is 1.

5. The compound of claim 1 or 2, wherein q is 0.

6. The compound of claim 1 or claim 2, wherein $R^{1a}$ is selected from halogen and halo($C_1$-$C_4$)alkyl.

7. The compound of claim 1 or claim 2, wherein $R^{1a}$ is selected from fluoro, chloro, —$CF_3$ and —$CHF_2$.

8. The compound of claim 1 or 2, wherein $R^{9a}$ is phenyl or a 5-6-membered heteroaryl having 1, 2 or 3 heteroatoms independently selected from nitrogen, oxygen and sulfur.

9. The compound of claim 1 or claim 2, wherein $R^{9a}$ is substituted with 1 or 2 substituents.

10. The compound of claim 1 or 2, wherein $R^{9a}$ is substituted with one substituent selected from:
halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; and —C(O)N$R^{11}R^{12}$, wherein $R^{11}$ and $R^{12}$ are taken together with the nitrogen atom to which they are commonly attached to form a 3-7-member heterocyclyl, optionally substituted with 1 or 2 substituents independently selected from halogen, ($C_1$-$C_4$) alkyl and ($C_1$-$C_4$)haloalkyl;
and is further optionally substituted with one substituent selected from halogen, ($C_1$-$C_4$)alkyl and ($C_1$-$C_4$)haloalkyl.

11. The compound of claim 1 or 2, wherein $R^{9a}$ is substituted with at least one substituent independently selected from —C(O)($C_1$-$C_4$)alkyl, —C(O)—N($R^{11}$)($R^{12}$), hydroxy-substituted ($C_1$-$C_4$)alkyl, and ($C_2$-$C_4$)alkenyl, wherein $R^{11}$ and $R^{12}$ are each independently selected from ($C_1$-$C_4$)alkyl; or $R^{11}$ and $R^{12}$ are taken together with the nitrogen to which they are bound to form a saturated 3-7-member heterocyclyl comprising 0 or 1 additional heteroatoms selected from N, O and S, and wherein the saturated 3-7-member heterocyclyl is optionally substituted with 1 or 2 substituents independently selected from halogen, ($C_1$-$C_4$)alkyl and ($C_1$-$C_4$)haloalkyl.

12. The compound of claim 11, wherein $R^{9a}$ is selected from phenyl, thiophen-2-yl, pyridin-3-yl and pyrimidin-3-yl.

13. The compound of claim 12, wherein $R^{9a}$ is selected from 4-dimethylaminocarbonylphenyl, 5-acetylthiophen-2-yl, 5-(1-hydroxyethyl)thiophen-2-yl, 5-(2-hydroxypropan-2-yl)thiophen-2-yl, 5-(prop-1-en-2-yl)thiophen-2-yl, 4-(4-methylpiperazin-1-ylcarbonyl)phenyl, 4-(morpholin-4-ylcarbonyl)phenyl, difluoroazetidin-1-ylcarbonyl)phenyl, 4-(piperazin-1-ylcarbonyl)phenyl, 4-(piperidin-1-ylcarbonyl)phenyl, 4-(3,3-dimethylmorpholin-4-ylcarbonyl)phenyl, 2-(morpholin-1-ylcarbonyl)pyrimidin-5-yl or (4,4-difluoropiperidine-1-carbonyl)pyridin-2-yl.

14. The compound of claim 1 represented by the following structural formula:

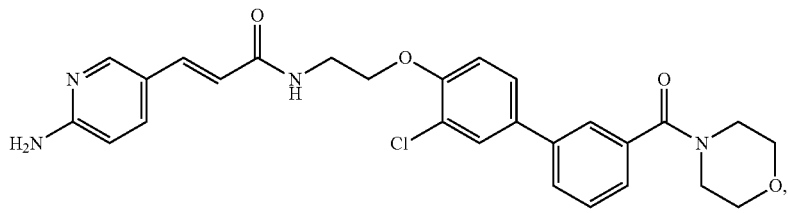 [SMILES: Nc1ccc(/C=C/C(=O)NCCOc2ccc(-c3cccc(C(=O)N4CCOCC4)c3)cc2Cl)cn1]

or a pharmaceutically acceptable salt thereof.

15. The compound of claim 1, represented by the following structural formula:

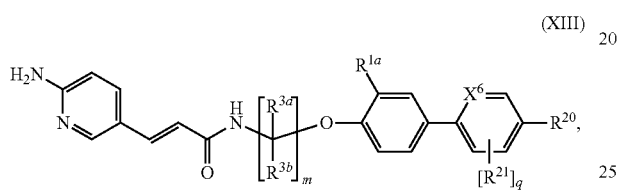

(XIII)

or a pharmaceutically acceptable salt thereof, wherein:
$X^6$ is —N— or —C(H)—;
$R^{20}$ is halogen, $(C_1\text{-}C_4)$alkyl optionally substituted with hydroxyl, $(C_2\text{-}C_4)$alkenyl, $(C_1\text{-}C_4)$haloalkyl, —C(O)$(C_1\text{-}C_4)$alkyl and —C(O)NR$^{11a}$R$^{12a}$, wherein:

$R^{11a}$ and $R^{12a}$ are each independently hydrogen, $C_1\text{-}C_4$ alkyl, 3-15-member carbocyclyl, or a 3-15-member heterocyclyl; or $R^{11a}$ and $R^{12a}$ are taken together with the nitrogen atom to which they are commonly attached to form a 3-7-member heterocyclyl, optionally substituted with 1 or 2 substituents independently selected from halogen, $(C_1\text{-}C_4)$alkyl and $(C_1\text{-}C_4)$ haloalkyl;

each $R^{21}$, if present, is independently fluoro, chloro, bromo or iodo; and $q^1$ is 0, 1, 2, 3 or 4.

16. The compound of claim 1, represented by any one of the following structural formulas, or a pharmaceutically acceptable salt thereof:

| Cpd. No. | Compound Structure |
|---|---|
| 300 | 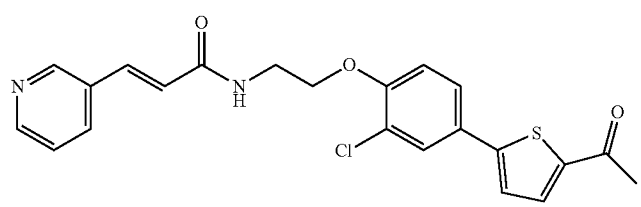 [SMILES: CC(=O)c1ccc(-c2ccc(OCCNC(=O)/C=C/c3cccnc3)c(Cl)c2)s1] |
| 301 | 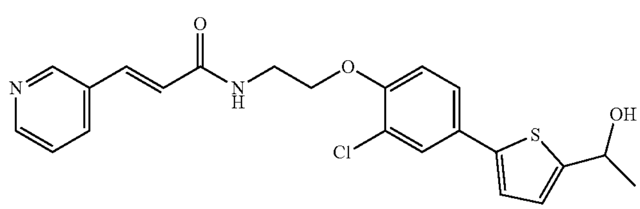 [SMILES: CC(O)c1ccc(-c2ccc(OCCNC(=O)/C=C/c3cccnc3)c(Cl)c2)s1] |
| 304 | 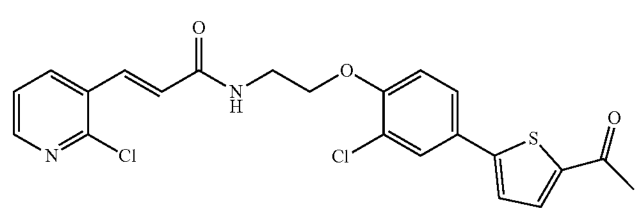 [SMILES: CC(=O)c1ccc(-c2ccc(OCCNC(=O)/C=C/c3cccnc3Cl)c(Cl)c2)s1] |

| Cpd. No. | Compound Structure |
|---|---|
| 305 | 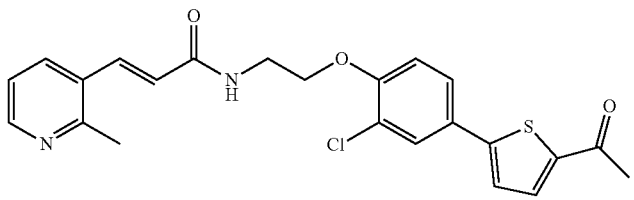 [SMILES: CC(=O)c1ccc(-c2ccc(OCCNC(=O)/C=C/c3cccnc3C)c(Cl)c2)s1] |
| 306 | 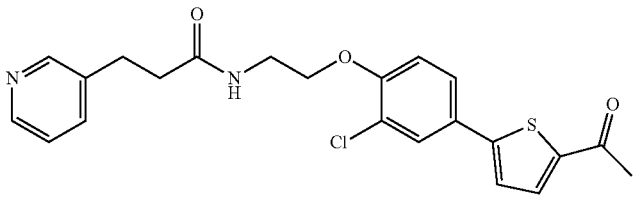 [SMILES: CC(=O)c1ccc(-c2ccc(OCCNC(=O)CCc3cccnc3)c(Cl)c2)s1] |
| 308 | 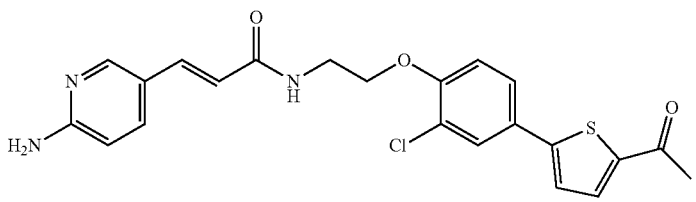 [SMILES: CC(=O)c1ccc(-c2ccc(OCCNC(=O)/C=C/c3ccc(N)nc3)c(Cl)c2)s1] |
| 311 | 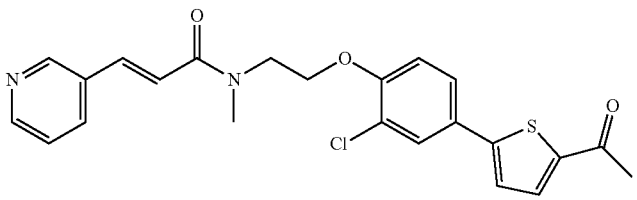 [SMILES: CC(=O)c1ccc(-c2ccc(OCCN(C)C(=O)/C=C/c3cccnc3)c(Cl)c2)s1] |
| 313 | 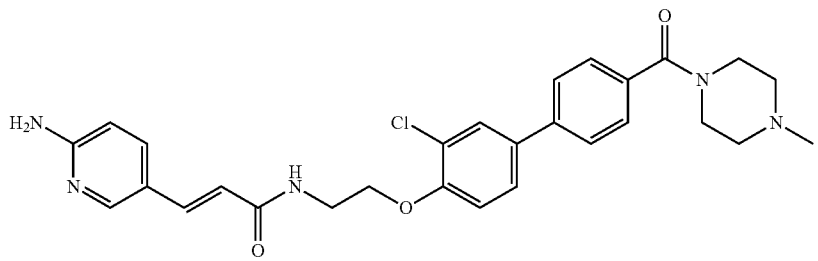 [SMILES: CN1CCN(C(=O)c2ccc(-c3ccc(OCCNC(=O)/C=C/c4ccc(N)nc4)c(Cl)c3)cc2)CC1] |
| 314 | 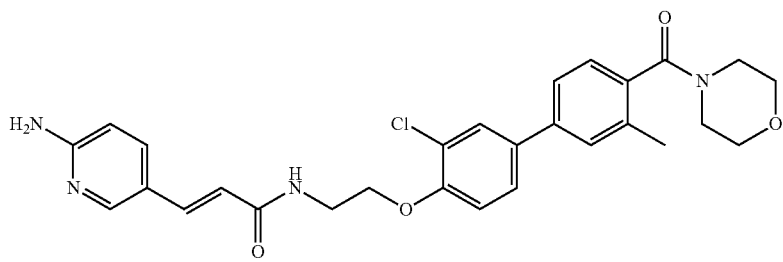 [SMILES: Cc1cc(-c2ccc(OCCNC(=O)/C=C/c3ccc(N)nc3)c(Cl)c2)ccc1C(=O)N1CCOCC1] |
| 315 | 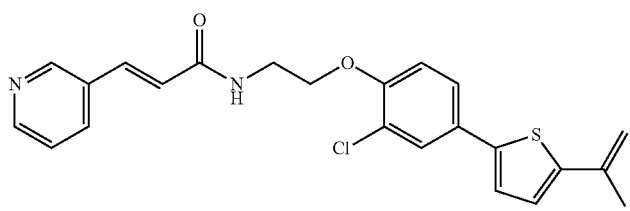 [SMILES: C=C(C)c1ccc(-c2ccc(OCCNC(=O)/C=C/c3cccnc3)c(Cl)c2)s1] |

| Cpd. No. | Compound Structure |
|---|---|
| 316 | 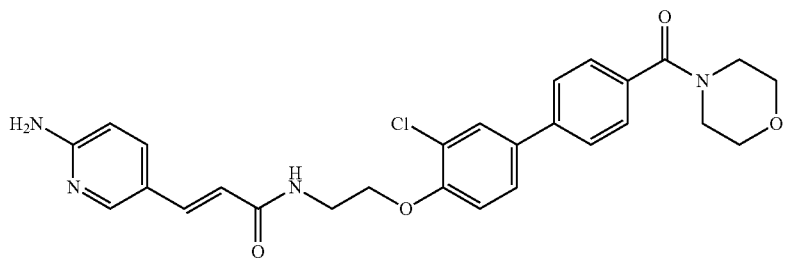 [SMILES: Nc1ccc(/C=C/C(=O)NCCOc2ccc(-c3ccc(C(=O)N4CCOCC4)cc3)cc2Cl)cn1] |
| 317 | 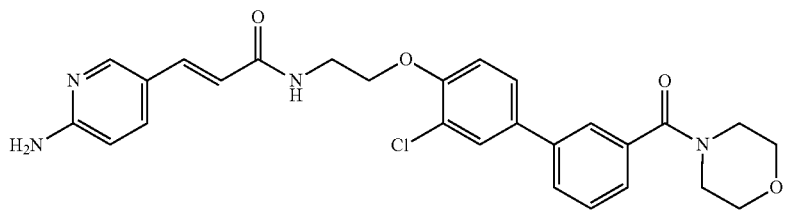 [SMILES: Nc1ccc(/C=C/C(=O)NCCOc2ccc(-c3cccc(C(=O)N4CCOCC4)c3)cc2Cl)cn1] |
| 318 | 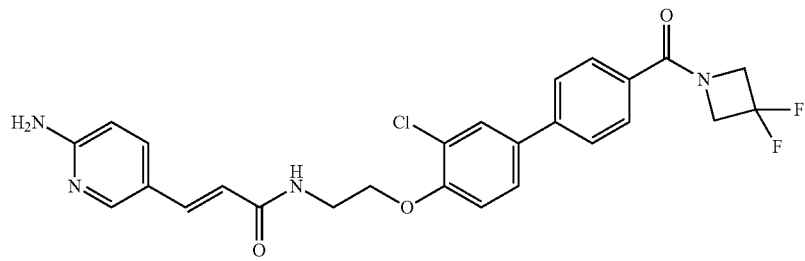 [SMILES: Nc1ccc(/C=C/C(=O)NCCOc2ccc(-c3ccc(C(=O)N4CC(F)(F)C4)cc3)cc2Cl)cn1] |
| 319 | 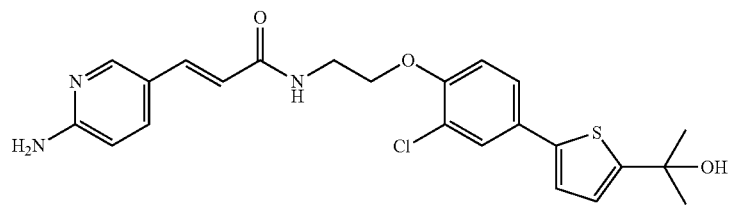 [SMILES: CC(C)(O)c1ccc(-c2ccc(OCCNC(=O)/C=C/c3ccc(N)nc3)c(Cl)c2)s1] |
| 320 | 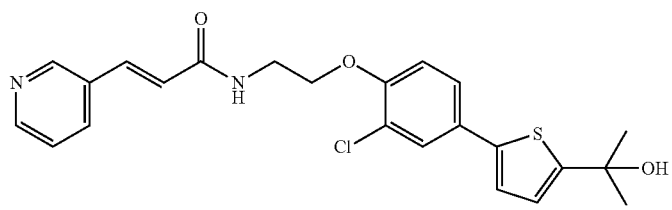 [SMILES: CC(C)(O)c1ccc(-c2ccc(OCCNC(=O)/C=C/c3cccnc3)c(Cl)c2)s1] |
| 321 | 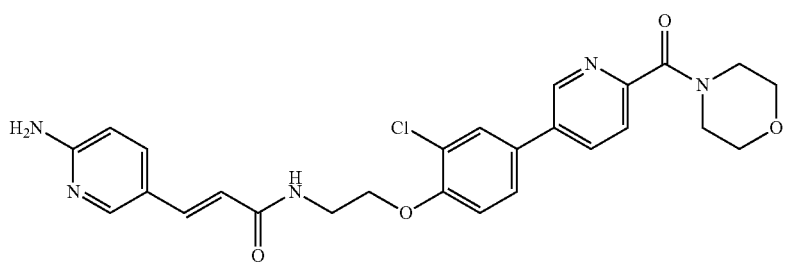 [SMILES: Nc1ccc(/C=C/C(=O)NCCOc2ccc(-c3ccc(C(=O)N4CCOCC4)nc3)cc2Cl)cn1] |

-continued

| Cpd. No. | Compound Structure |
|---|---|
| 323 | 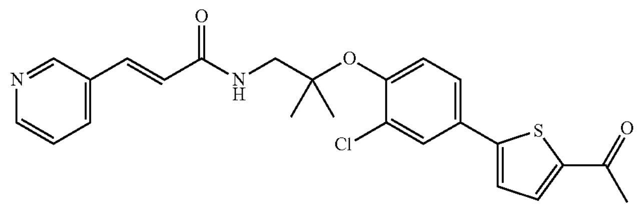 [SMILES: CC(=O)c1ccc(-c2ccc(OC(C)(C)CNC(=O)/C=C/c3cccnc3)c(Cl)c2)s1] |
| 325 | 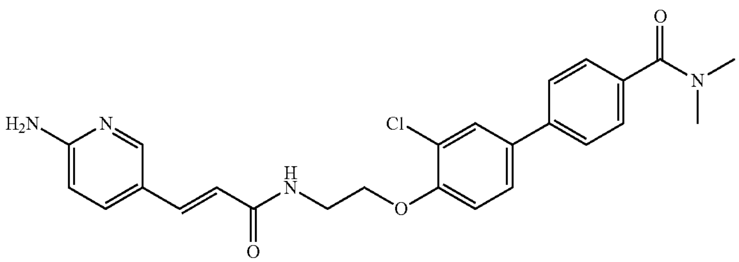 [SMILES: CN(C)C(=O)c1ccc(-c2ccc(OCCNC(=O)/C=C/c3ccc(N)nc3)c(Cl)c2)cc1] |
| 326 | 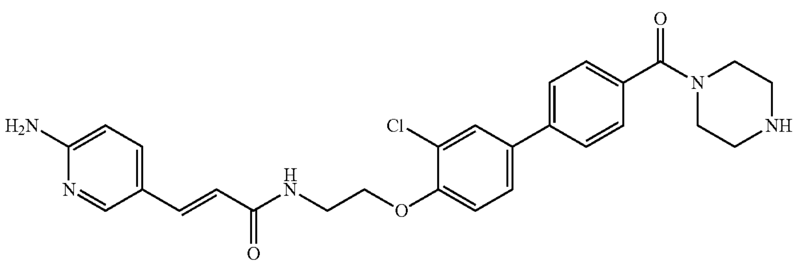 [SMILES: Nc1ccc(/C=C/C(=O)NCCOc2ccc(-c3ccc(C(=O)N4CCNCC4)cc3)cc2Cl)cn1] |
| 327 | 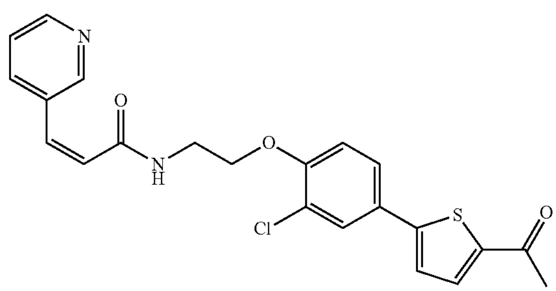 [SMILES: CC(=O)c1ccc(-c2ccc(OCCNC(=O)/C=C\c3cccnc3)c(Cl)c2)s1] |
| 328 | 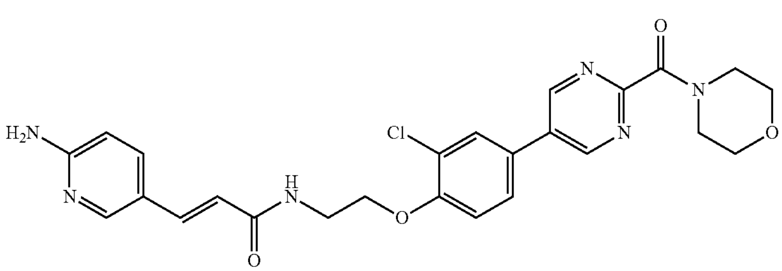 [SMILES: Nc1ccc(/C=C/C(=O)NCCOc2ccc(-c3cnc(C(=O)N4CCOCC4)nc3)cc2Cl)cn1] |
| 329 | 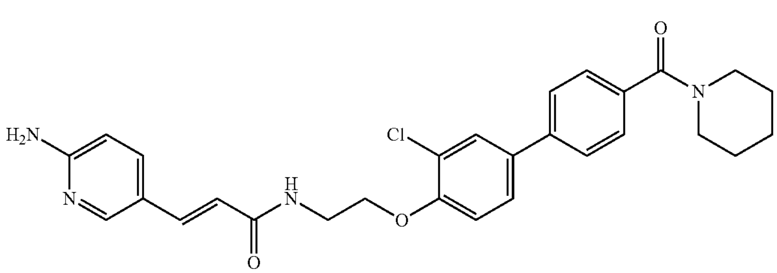 [SMILES: Nc1ccc(/C=C/C(=O)NCCOc2ccc(-c3ccc(C(=O)N4CCCCC4)cc3)cc2Cl)cn1] |

| Cpd. No. | Compound Structure |
|---|---|
| 332 | 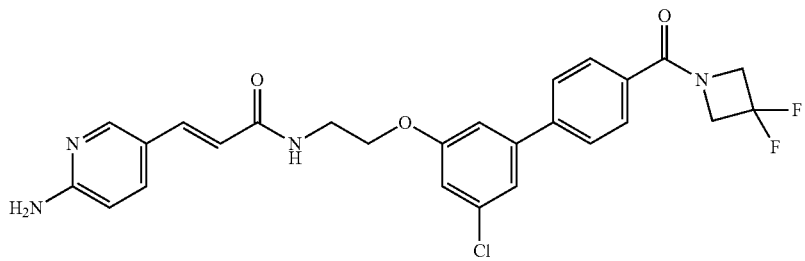 [SMILES: Nc1ccc(/C=C/C(=O)NCCOc2cc(Cl)cc(-c3ccc(C(=O)N4CC(F)(F)C4)cc3)c2)cn1] |
| 333 | 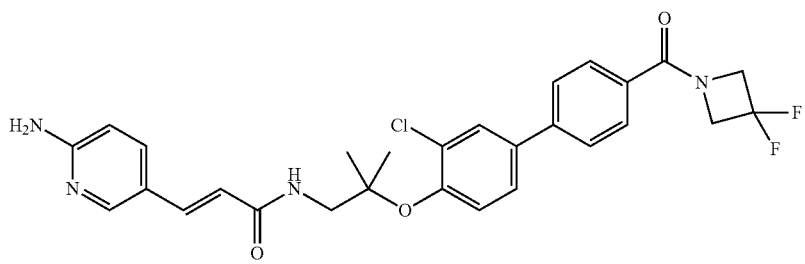 [SMILES: CC(C)(CNC(=O)/C=C/c1ccc(N)nc1)Oc1ccc(-c2ccc(C(=O)N3CC(F)(F)C3)cc2)cc1Cl] |
| 334 | 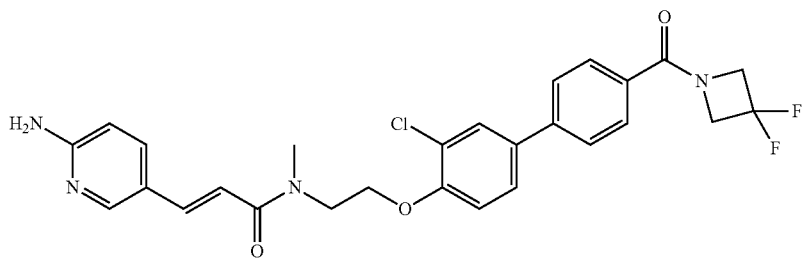 [SMILES: CN(CCOc1ccc(-c2ccc(C(=O)N3CC(F)(F)C3)cc2)cc1Cl)C(=O)/C=C/c1ccc(N)nc1] |
| 335 | 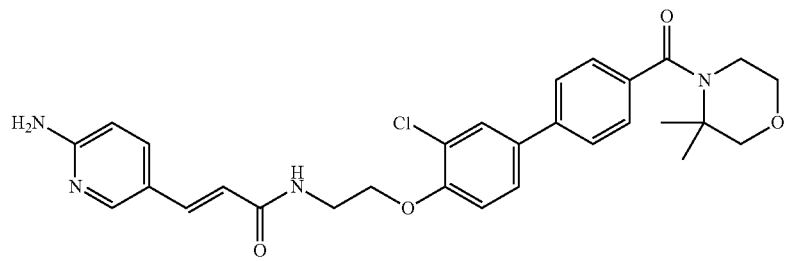 [SMILES: CC1(C)COCCN1C(=O)c1ccc(-c2ccc(OCCNC(=O)/C=C/c3ccc(N)nc3)c(Cl)c2)cc1] |
| 336 | 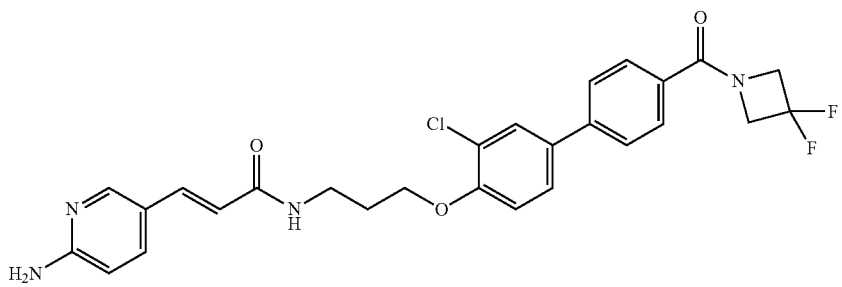 [SMILES: Nc1ccc(/C=C/C(=O)NCCCOc2ccc(-c3ccc(C(=O)N4CC(F)(F)C4)cc3)cc2Cl)cn1] |

| Cpd. No. | Compound Structure |
|---|---|
| 338 | 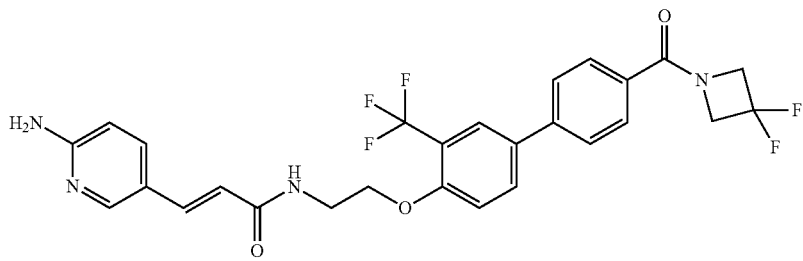 [SMILES: Nc1ccc(/C=C/C(=O)NCCOc2ccc(-c3ccc(C(=O)N4CC(F)(F)C4)cc3)cc2C(F)(F)F)cn1] |
| 339 | 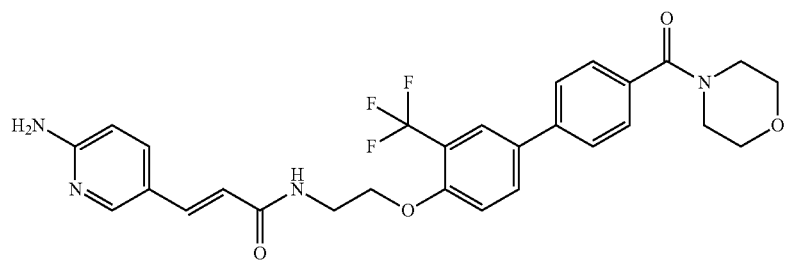 [SMILES: Nc1ccc(/C=C/C(=O)NCCOc2ccc(-c3ccc(C(=O)N4CCOCC4)cc3)cc2C(F)(F)F)cn1] |
| 342 | 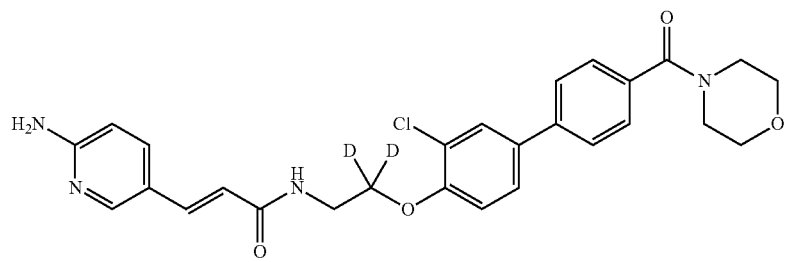 [SMILES: [2H]C([2H])(CNC(=O)/C=C/c1ccc(N)nc1)Oc1ccc(-c2ccc(C(=O)N3CCOCC3)cc2)cc1Cl] |
| 344 | 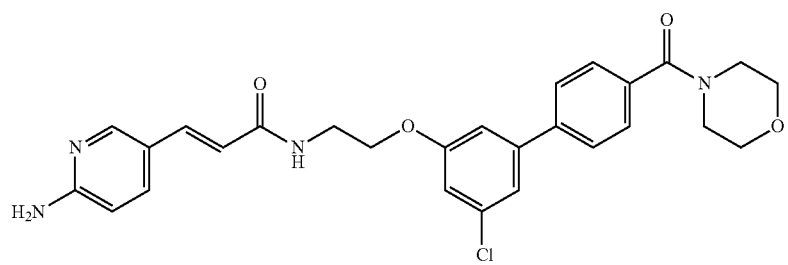 [SMILES: Nc1ccc(/C=C/C(=O)NCCOc2cc(Cl)cc(-c3ccc(C(=O)N4CCOCC4)cc3)c2)cn1] |
| 345 | 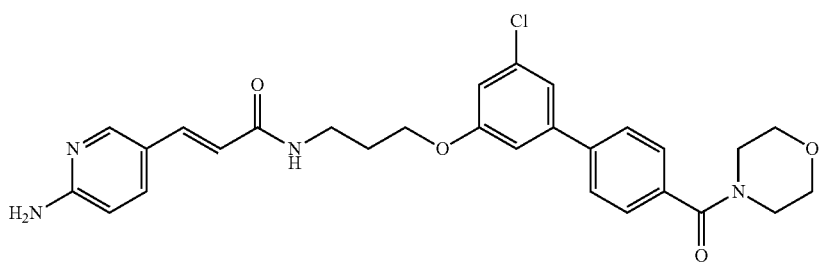 [SMILES: Nc1ccc(/C=C/C(=O)NCCCOc2cc(Cl)cc(-c3ccc(C(=O)N4CCOCC4)cc3)c2)cn1] |

| Cpd. No. | Compound Structure |
|---|---|
| 347 | 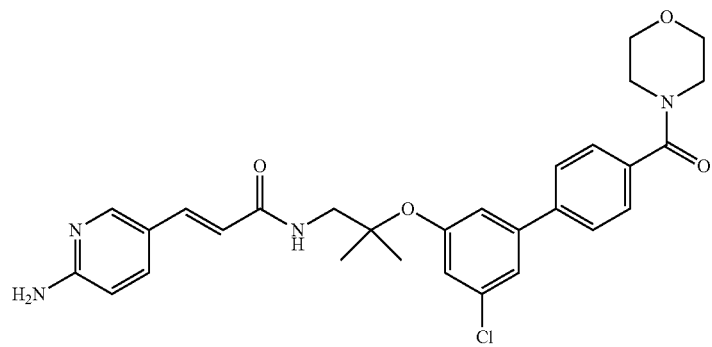 [SMILES: CC(C)(CNC(=O)/C=C/c1ccc(N)nc1)Oc1cc(Cl)cc(-c2ccc(C(=O)N3CCOCC3)cc2)c1] |
| 348 | 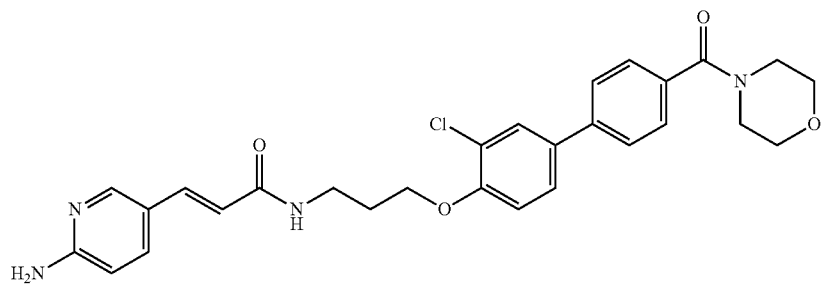 [SMILES: Nc1ccc(/C=C/C(=O)NCCCOc2ccc(-c3ccc(C(=O)N4CCOCC4)cc3)cc2Cl)cn1] |
| 349 | 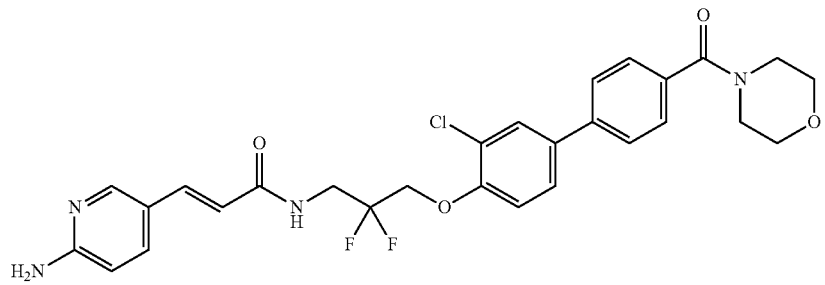 |
| 350 | 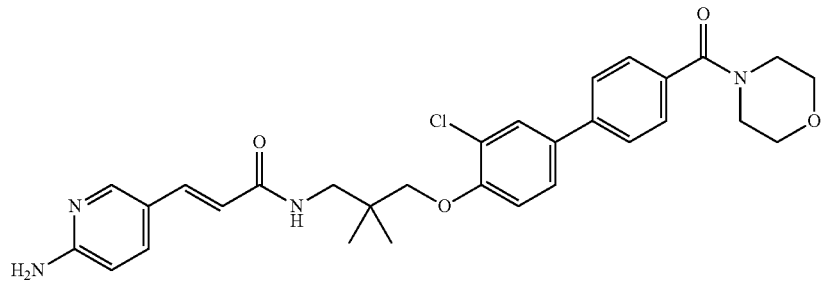 [SMILES: CC(C)(CNC(=O)/C=C/c1ccc(N)nc1)COc1ccc(-c2ccc(C(=O)N3CCOCC3)cc2)cc1Cl] |
| 351 | 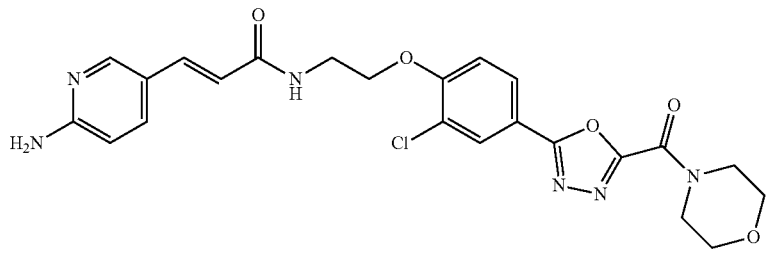 [SMILES: Nc1ccc(/C=C/C(=O)NCCOc2ccc(-c3nnc(C(=O)N4CCOCC4)o3)cc2Cl)cn1] |

-continued
| Cpd. No. | Compound Structure |
|---|---|
| 352 | 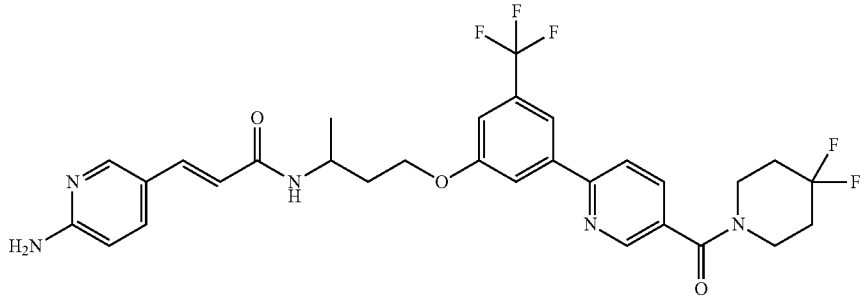 [SMILES: CC(CCOc1cc(-c2ccc(C(=O)N3CCC(F)(F)CC3)cn2)cc(C(F)(F)F)c1)NC(=O)/C=C/c1ccc(N)nc1] |
| 355 | 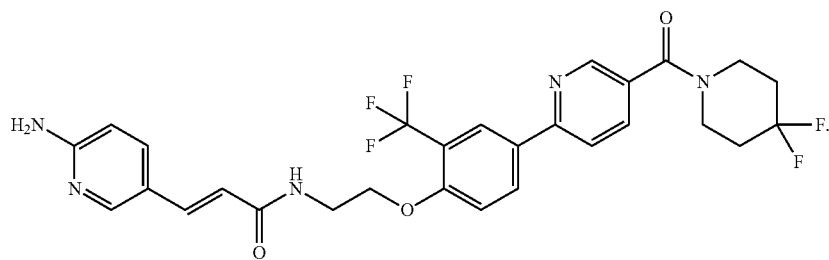 [SMILES: Nc1ccc(/C=C/C(=O)NCCOc2ccc(-c3ccc(C(=O)N4CCC(F)(F)CC4)cn3)cc2C(F)(F)F)cn1] |
17. A pharmaceutical composition comprising:
(a) a compound of claim 1, or a pharmaceutically acceptable salt thereof; and
(b) a pharmaceutically acceptable carrier.
* * * * *